(12) United States Patent
Abe et al.

(10) Patent No.: US 7,056,710 B2
(45) Date of Patent: Jun. 6, 2006

(54) METHODS FOR PRODUCING ML-236B, A PRAVASTATIN PRECURSOR, USING A HOST CELL TRANSFORMED WITH MLCR, A TRANSCRIPTION FACTOR

(75) Inventors: Yuki Abe, Iwaki (JP); Chiho Ono, Iwaki (JP); Hiroji Yoshikawa, Iwaki (JP)

(73) Assignee: Sankyo Company, Limited, Tokyo (JP)

( * ) Notice: Subject to any disclaimer, the term of this patent is extended or adjusted under 35 U.S.C. 154(b) by 218 days.

(21) Appl. No.: 09/836,705

(22) Filed: Apr. 17, 2001

(65) Prior Publication Data

US 2003/0078395 A1    Apr. 24, 2003

(30) Foreign Application Priority Data

Apr. 18, 2000  (JP)  ............................. 2000-116591
Apr. 19, 2000  (JP)  ............................. 2000-117458

(51) Int. Cl.
    *C12P 7/22*    (2006.01)
(52) U.S. Cl. ..................................................... 435/156
(58) Field of Classification Search ................. 435/156
    See application file for complete search history.

(56) References Cited

U.S. PATENT DOCUMENTS 5,179,013 A    1/1993    Matsuoka et al.

FOREIGN PATENT DOCUMENTS

| JP | 57-2240 | 1/1982 |
| WO | WO 95/12661 | 5/1995 |
| WO | WO 00/37629 | 6/2000 |
| WO | WO 01/12814 | 2/2001 |

OTHER PUBLICATIONS

Abe et al. Molecular cloning and characterization of an ML-236B (compactin) biosynthetic gene cluster in *Penicillium citrinum*. Mol Genet Genomics Jul. 2002;267(5):636-46.*
Abe et al. Effect of increased dosage of the ML-236B (compactin) biosynthetic gene cluster on ML-236B production in *Penicillium citrinum*. Mol Genet Genomics Sep. 2002;268(1):130-7.*
Abe et al. Functional analysis of mlcR, a regulatory gene for ML-236B (compactin) biosynthesis in *Penicillium citrinum*. Mol Genet Genomics Nov. 2002;268(3):352-61.*
Yu et al. Comparative Mapping of Aflatoxin Pathway Gene Clusters in *Aspergillus parasiticus* and *Aspergillus flavus*. Applied and Environmental Microbiology (1995) 61 (6): 2365-2371.*
Chang et al. Increased Expression of *Aspergillus parasiticus* aflR, Encoding a Sequence-Specific DNA-Binding Protein, Relieves Nitrate Inhibition of Aflatoxin Biosynthesis. Applied and Environmental Microbiology (1995) 61 (6): 2372-2377.*
J. Kennedy et al., Database EMBL 'Online!, Nov. 1, 1999 retrieved from EBI, Database accession No. Q9Y7C8 XP002184089.
J. Kennedy et al., Database EMBL 'Online!, Jun. 3, 1999 retrieved from EBI, Database accession No. AF141925 XP002184086.
J. Kennedy et al., Database EMBL 'Online!, Nov. 1, 1999 retrieved from EBI, Database accession No. Q9Y7D5 XP002184087.
J. Kennedy et al., Database EMBL 'Online!, Jun. 3, 1999 retrieved from EBI, Database accession No. AF141924 XP002184129.
J. Kennedy et al., Database EMBL 'Online!, Nov. 1, 1999 retrieved from EBI, Database accession No. Q9Y7D3 XP002184088.
Akira Endo et al., ML-236A, ML-236B, and ML-236C, "New Inhibitors of Cholesterogenesis Produced By *Penicillum citrinum*", The Journal of Antibiotics, 29, 1346-1348 (1976).
Richard Moore et al., "Biosynthesis of the Hypocholesterolemic Agent Mevinolin By *Aspergillus terreus*. Determination of the Origin of Carbon, Hydrogen, and Oxygen Atoms by $^{13}C$ NMR and Mass Spectrometry", *J. Am. Chem. Soc.*, 107, 3694-3701 (1985).

(Continued)

*Primary Examiner*—Kathleen Kerr
(74) *Attorney, Agent, or Firm*—Frishauf, Holtz, Goodman & Chick, P.C.

(57) ABSTRACT

Polynucleotides, such as DNA, are provided which accelerate the biosynthesis of a HMG-CoA reductase inhibitor, ML-236B, in an ML-236B producing micro-organism when introduced in the ML-236B producing micro-organism. Pravastatin, which is an HM-CoA reductase inhibitor, can be obtained using *Streptomyces carbophilus* by microbial conversion of ML-236B produced by *Pencillium citrinum*. The polynucleotides encode a gene (such as micA (polyketide synthase), mlcB (polyketide synthase), micE (efflux pump) or mlcR (transcription factor). Provided are vectors into which such polynucleotides are incorporated; host cells transformed by such vectors; and proteins expressed by such vectors. A method for producing ML-236B using such polynucleotides and/or proteins which comprises recovering ML-236B from a culture of the host cell.

26 Claims, 5 Drawing Sheets

OTHER PUBLICATIONS

David A. Hopwood and David H. Sherman, "Molecular Genetics of Polyketides and its Comparison to Fatty Acid Biosynthesis", *Annu. Rev. Genet.*, 24, 37-66 (1990).

C. Richard Hutchinson and Isao Fujii, "Polyketide Synthase Gene Manipulation: A Structure-Function Approach in Engineering Novel Antibiotics", *Annu. Rev. Microbiol.*, 49, 201-238 (1995).

Guo Hong Feng and Thomas J. Leonard, "Characterization of the Polyketide Synthase Gene (pksL1) Required for Aflatoxin Biosynthesis in *Aspergillus parasiticus*", *Journal of Bacteriology*, 177, 6246-6254 (1995).

Yoshitaka Takano et al., "Structural Analysis of PKS1, a Polyketide Synthase Gene Involved in Melanin Biosynthesis in *Colletotrichum lagenarium*", *Mol. Gen. Genet.*, 249, 162-167 (1995).

Jiujiang Yu et al., "Comparative Mapping of Aflatoxin Pathway Gene Clusters in *Aspergillus parasiticus* and *Aspergillus flavus*", *Applied and Environmental Microbiology*, 61, 2365-2371 (1995).

D. W. Brown et al., "Twenty-five Coregulated Transcripts Define a Sterigmatocystin Gene Cluster in *Aspergillus nidulans*", *Proc. Natl. Acad. Sci. USA*, 93, 1418-1422 (1996).

Jonathan Kennedy et al., "Modulation of Polyketide Synthase Activity by Accessory Proteins During Lovastatin Biosynthesis", *Science*, 284, 1368-1372 (1999).

Lee Hendrickson et al., "Lovastatin Biosynthesis in *Aspergillus terreus*: Characterization of Blocked Mutants, Enzyme Activities and a Multifuctional Polyketide Synthase Gene", *Chem. Biol.*, 6(7), 429-439 (1999).

Nobufusa Serizawa, "Development of Two-step Fermentation-based Production of Pravastatin, an HMG-CoA Reductase", *J. Synthe. Organ. Chem.*, 55(4), 334-338 (1997), Non-english.

I. Fujii, "Cloning of Polyketide Antibiotics Biosynthesising Genes", *Mochida Kinen Zaidan Kenku Seika Hokokusha*, 5, 256-257 (1989).

Isao Fujii et al., "Structures and Functional Analyses of Fungal Polyketide Synthase Genes", *Actinomycetol*, 12(1), 1-14 (1998).

Joachim Beck et al., "The Multifunctional 6-methylsalicylic Acid Synthase Gene of *Penicillium patulum*", *Eur. J. Biochem.*, 192, (2), 487-498 (1990).

Yoshio Tsujita, "Discovery and Development of Hypolipidemic Drug, Pravastatin Sodium", *Tiss. Cult. Res. Commun.*, 12(4), 279-289, (1993).

C. Richard Hutchinson et al., "Aspects of the Biosynthesis of non-aromatic Fungal Polyketides by Iterative Polyketide Synthases", *Antonie van Leeuwenhoek*, 78(3-4), 287-295, (2000).

Jonathan Kennedy et al., "Hypothetical 57.6 kDa Protein", DATABASE EMBL, Online, Nov. 1, 1999, retrieved from EBI, accession No. Q9Y7D4.

Futoshi Nara et al., "Development of a Transformation System for the Filamentous, MLO-236B (compactin) -Producing Fungus *Penicillium citrinum*", *Current Genetics*, vol. 23, No. 1, 1993, pp. 28-32, XP001018104.

Masahiko Hosobuchi. et al., "Production of ML-236B, and Inhibitor of 3-Hydroxy-3-Methylglutaryl CoA Reductase by *Penicillium citrinum*: Improvements of Strain and Culture Conditions", *Bioscience Biotechnology Biochemistry*, Japan Soc. For Bioscience, Biotechnology and Agrochem., Tokyo, Japan, vol. 57, No. 9, 1993, pp. 1414-1419.

Tatsuji Matsuoka et al., "Purification and Characterization of Cytochome P-450$_{sca}$ from *Streptomyces carbophilus*", *Eur. J. Biochem.*, 184, 707-713 (1989).

Ming-Shi Shiao and Hsiao-Shek Don, "Biosynthesis of Mevinolin, A Hypocholesterolemic Fungal Metabolite, in *Aspergillus terreus*", *Proc. Natl. Sci. Counc. Repub. China B. ROC*, 11, 223-231 (1987).

J. E. Flaherty and G. A. Payne; "Overexpression of aflR Leads to Upregulation of Pathway Gene Transcription and Increased Aflatoxin Production in *Aspergillus flavus*", *Applied and Environmental Microbiology*, Oct. 1997, pp. 3395-4000, vol. 63, No. 10.

Solveig Woitek et al., "3-Hydroxy-3-methylglutaryl-CoA reductase gene of *Gibberella fujikuroi*: isolation and characterization", *Current Genetics*, vol. 31, No. 1, 1997, pp. 38-47.

* cited by examiner

SEQUENCE LISTING

<160> NUMBER OF SEQ ID NOS: 62

<210> SEQ ID NO 1
<211> LENGTH: 34203
<212> TYPE: DNA
<213> ORGANISM: Penicillium citrinum

<400> SEQUENCE: 1

| | | | | | |
|---|---|---|---|---|---|
| gatcaatact | acgtcgttgt | tatttccttg | tcagtaatga | ctaacaaatt | ccccagaaca | 60 |
| gacgaagtca | cagctcacac | cacaagagaa | aatgagtcca | gcgaggatta | cagatttctc | 120 |
| gccaggcaaa | ccgagaaaag | ctctcttatg | catccacggt | gccgggtgct | cagcagccat | 180 |
| attccgcgtc | cagatctcta | aactgcgcgt | ggcgttgaaa | aacgagtttg | aattcgtata | 240 |
| tgcgaccgcg | ccgtttagct | ccagcccgg | acccggcgtg | cttcctgtct | tccaaggcat | 300 |
| gggtccatac | tacacctggt | tccaaaagca | tcatgacgcc | gttacaaaca | cgacaacccc | 360 |

-continued

```
cacggtgggc gatagagtag cggctgtgat cgggcctgtg caaaagaccg tccaagattg    420
gtctataact aacccacagg cacccattgt cggcatagtg gccttctctg agggcgcatt    480
ggtcgccact ttgctgctcc atcaacagca aatgggaaaa ctgccatggt ttccgaaaat    540
gagcattgct gttttgattt gctgtttcta tagcgatgaa gccagagatt acatgagagc    600
cgaggcgcaa gacgacgacg acaagctaat aatcaacgtg ccgacactgc atcttcacgg    660
tcgtcaagat tttgctctcc aagggtcgag acagatggtt gaaacacatt acctgcctca    720
gaatgcagat gtactcgagt ttcagggaaa gcataatttt cccaacagac cgagtgatgt    780
ccaggagacg gtcaagcgct tccaacagct atatcaaaag gtcaagatgt caggttcatt    840
tgtctaggtg agacaacagg gtatatagca aggctctggc tctcatgcct agtccatacc    900
acatttttac tgaacaaatt tgaatagttc taatcttaca cggtttgaat gctcaccttc    960
caagggtgat ttagttatag tggtcgcgac catctcataa atatttcgtg aacatatttt   1020
ggatagatca tggaaggctc gttctgaaca ggcatgacag acatctaaaa ccactcgatc   1080
accacaacaa ggcactaaac cagtaactat ggaactattt gcaatggcgt cgaatttata   1140
tacaggatgg attgaaatca attccaagcc ttggaggttt caccttcctc acagagtctt   1200
tcgaaacgcg ctaccgaggt atatttatca ccgttacggt actctgaacc gcgctatcta   1260
acttgatgtt acgattgctg caataaagaa gagcaacgaa ggtagaagta attttgacaa   1320
agatacaaga cgaattcgct atttgtagat gaatatgcgt gtgtcaattg acgccgaatt   1380
caggatagat ttgccatctg ctctattgcc aatttctaat ccatctttat catgaacaac   1440
actcaaacca cacatctgaa ttcacggcgc tgaacgatct aggccaactt cagagccggg   1500
ttcatcgaga acatagtgag gattgaagaa agtggtctca caaaggcctg agcgtgctca   1560
gggccataca gcgagctctg aagtttgaca tgaatgagtg ggtccttggt agggtcatcc   1620
cacatctcga gaacgatgtc ataaggagtg cgctcacggg aagcgagaac actcgtcatt   1680
ttggcattgc caattgagcc actctccgct tgaccctgct tgtaatcaaa gacagcctgg   1740 aacaagggggg cgtgtgtctg agtcttgggt tcctcgcctg aggtagggag attcaggcct   1800
agacagtcga ggatgacgcc atacggcacc cgcgcgtgtt gcatggcctc acgcacactg   1860
tccttggtgg ctacaaggtg ctcgccgaat gtcttgctgc cgacgaactc atcaaagcgc   1920
aggggaagca cgttagcgaa aaagcccatc gccgaaattt cttccatggt ggatcggttg   1980
gtttcggcga ggccgatggt tatgtctttg ctgccggtaa gacgcgccaa caaaacgtgg   2040
taggcggcca ggtagaactg catgggggtt gccttgtgct tgcggctccg ctctttgatt   2100
cggaaggcga ccatgggatc taaacgagca attgcttcat actgctgcca cgtgaatggc   2160
tgtatttgct gctgctctga attggcagca gggtcattga tcagattcat gatgggaagc   2220
acggttggcg cagatgacga gactttgcta tgcatggact tccagaacgc gatatcgtcc   2280
cccattcgcc cattttccag gttttcccgc tgttggacgg ctagatcaga gaattgggtc   2340
gatggtcgct gcattttcac cccgctgtaa atctgcccga tctcattgaa caggttttct   2400
gttgttgagc catcaccaac taatctgtgg tagccgatta ccaacaggtg gtcatctgtg   2460
ccccagtaga aatcaacgag tctgagagtg tcacctgtgg agatgctata gtttgtcttc   2520
tcgagtttcc ggtactcttc ctctgcctcc gcagcgttgt tcacctgaac aaagtgcact   2580
ctgttctccg ggttcttgag aaccacttgg acgggaccat ttaaatcgct gctatagtca   2640
tcgccagtaa caaagcacgt acggaagatc tcgtgacggc gcaatgaggc tttcagagcc   2700
cgcctcaacc ggtcgaggtc aatggtaccc ttcatgaaca tgccaatagt gttgttgaag   2760
```

```
atggtatgat cttttaccat ttgttgctgc ctccaggaat actcctggcc aagggacaac    2820
ctctcgcgac gaagaatctt acggcctccc tgctcattat cgtcctcttg ctcttcatcc    2880
tcttcggctg acgacgcatc tgtgctggta gcagagcttg cttcatcatg gctgtctgtt    2940
ggtgtcggag aagccccgct gtccgaggtt cccgtggaat caccaatttg caacagcagc    3000
ggaatggatg tagctgggag tcgggtggcc gcgtcgtcgg caagatcagc gacagaagca    3060
ccgccaagta ccctcaagag tgggaggtca aggtagagtt gctttgagaa ccatgagccg    3120
acagtcactg cacccaagga gtcgacacct tgatcaatga gaggaatggt tgggtccacg    3180
ctctccccgt ccgaaacttg gagggtaaca cggagtttct cagatagacc atctgcaact    3240
ttgttagttt gaactcgata tcaggaaacg catgagagat aacttaccaa tcacgatttg    3300
ccgaacttgg tctaaagttg ttgcttgttt gagctggtcg gcaatggagc ctttagaccc    3360
tgatccattg tcgccaccgt ctccgcgttg accgggaatt ttgaagtttc gaaacgagg    3420
gtcgttgaag taaataattc gatcttgaag cgcagggtca agatctggga tacccgtggt    3480
aagctcaagg tccgccatgt caatgaccgt cttgcgctgt ggttgctgcc gggcacgctg    3540
gtcagacacg accgcttcgg cgaaaagcgt gtgcagctca tgctcttcaa ctgagtcaaa    3600
catgaaacgg atagcatcaa agtcctcctc catctcggcc ctcgtgacaa acccacacc    3660
gtaaacggca ccaatatcga tggttgatcc ctgtggttgt gcgttagtaa cttgacgtcg    3720
atgcatgata attcagggt agaaaatacc gccaatcctc tggcgcaccg ttgctgggcc    3780
agagcctgta ggtaggcatt cgcagcgcca tagttggact ggccaggatt gccataact    3840
gcaacaatgg acgaaaacat gatgaagaag tcgagcgcct tgctgcccgt ctgttcggag    3900
aaccgttcat gaagaatgcg tgctccttgt accttgggct tcaacaccat gtccatcatc    3960
tggtggtcca tgttcttcag catgacatcc tgcagcacca aggcccgaa cgcgatgccg    4020
gcaacaggtg gcaacttcat atcgacaagc ttgccaaggc cagcatcgac tgaatcctca    4080
ttggcaacat ccctaaagaa agtaattgga taagtaaacg aggatgtggt agcaaggtgt    4140
gatgtgatat caatcaactt acattgacag aacggtgatg tcaccaccaa gtgcctccat    4200
gttggcgatc catttgggat caagtcgagg gttccggcta gtgagcacaa catggcgggc    4260
gccatgcaag atcatccagc gacagagaga gcgaccaagg tccccggtaa gaccaacaag    4320
caaatacgtc ttcttgttgg aaaataagtt accagagtcg atgggcaaa tcctagcgga    4380
cacctcattt tccttccagt cgatgacggt ggccagattg aagcgttggt cattgtggtt    4440
gacagagagc tgaccaggca agagaatttg tgtggctgta ataactttct cagtgtcgtc    4500
gacagtcgac gcagagacgg tattttttgc cattgccaca gagtgctcga ggattggaat    4560
atcctcaaca tgactaactt tgtatgtgga agctgtactt cggataagat agtcaccact    4620
gtacatgaag caactgggtg gtagcaactt ggccaaacgg ttggttatcc ggcagcagt    4680
ccggtcggta gacaagtcaa agaatgccat catgtttgtc ggcaggctgt gtttcagccg    4740
agcgtcggtt tccttggcat gtaatcggat ccaaggagcc ggaatagttt tgacgtcgga    4800
cagagttgtt gccaaatgaa cctgaacacc gtaggttttg gccgactcca gaattgcttt    4860
gacgcagaag attggggct ccataatcag aattgatgca tcagagccaa aggactgagc    4920
gctagagaga attgtttcgg caaggagggc tgcagctgtg gacaacaaga aggaactatc    4980
ctcgccttcc gccatgttat cgggcagact atgcatgtag tttctcggta catgcagtat    5040
agatccattc ttctcagcca gggcgactac aggcacctca catgtattct ccagaatact    5100
```

```
gccctgcacg acatggaagt atccgagatg gcccacgcga attgcctggg aagagcgta    5160
gcgaacacga acagttgctt ttccagcatg acgagcgtct tctaacgaat cacacgtctc    5220
ggttgactca agatagtaca tcgatgagga tgctcccctc gcctctttca gtgcaatggc    5280
cgtcttggac gaattaaagt taccgaaaat tggacgacga gacgagttca tacggtcgtt    5340
cctagcaata tcctgcttca aacgagggac ccaggcacga cccttgcacc agtacacttc    5400
gggctcatga gtccatgtta ttgattccaa aagctgatca tcgctctcct cgaagcgcaa    5460
aagttgctca acgaagaatt tggtgtctag gttctccaca gtatcgacat cgaagacgtg    5520
cgttcccaag tcagggttct cgagcttgat tgtcctcaac attccgatgg tgctggcctg    5580
gtggggatga tcaatccagg cattctctgt cagccacatc atgcgtccgg cgtagaagag    5640
aagagacttg actgcctcaa acttgtcctc ttcaaggttg caaaacactt catcatcaag    5700
ttccgagagg atgacaaaag tcgacttagg ctgcaaggcc gggtcgtcga aacactttc     5760
cagccgcttg acgagtgga tgtgtctatg cggtagggca gctttcatgt cgttcaaaat    5820
gcgttcggtt tttgtcgatt cgccaccgat aaccactaat ggcgggtatg agtccttcaa    5880
tggagcagaa agtggatcat acaaacgctc aacggtggca tccacagcat gtgtactgaa    5940
gacagacggg atcaaatcat cctctcgatc aagtgtccga ctatcgacgc cagagaaccc    6000
aactctcttg agggtatgct cccattggtc aacggacccc gaggcactca aagcacgagt    6060
ttcgtcttct ccagtccatc gatcagcgaa agcccagag atgaaggcga ggcgagcagg     6120
ctcgcgatgg gtgaccccga agtaaccaa gtgaccaccc ggcttgagca aggaccttat     6180
gtgagccaat ttttcctcga agttggagct ggcatggagg acatcggatg caataatcag    6240
atcgtaggag tgaggcttga atccttgctc tgctgggctt ctgttgatgt ctagtgcctc    6300
aaactgcatg agaccgtcga attcggaaag ttgttcacgg gccttgccaa taacatccgc    6360
cgagatgtca gtgcaagtgt aactgttgaa accaagttga ggtgatgcaa gaacgcgctt    6420
cgtggcgatg cctgtaccca agcctaaaaa gcgaacgaca gattagcaaa ctgcctagtt    6480
acttacattt cagattcgac ttaccgatct caaggatatc aatggattgg tagcgatgag    6540
caatttggct aaccagatcc tgaacgacgt gtattgctga gccaaaggcg agcttgttgg    6600
tatagtactc ggtgaacaac ccatcgcggt tcatgatatc caaaggatcc ccgttcccgc    6660
gaacaattga aattaattct ttgcctaccc tttggatcag gcgcacatgt gggtgggacg    6720
agttgcttca agtaaaaggt taatataaaa gaatgaaaaa acacggaaca gctttgggtg    6780
tacctttcac acatttgctc aatgtgaaca gaagtgtcct cctcccaaga ctcctggtac    6840
cactgatggt ggccagcccg agcatcggcc tgaacctggt cacaccattc aatgtacttc    6900
tgggaatgga ggtcggcatt ttgacggtcg tcggggggtta tctgggctag gaaggatttg    6960
atgtagaagt aaacgattcg ctcgatggtc agaatgtcct ccttgtcccg agctatgatc    7020
aacgtcgcag ggtcctccag cagttttcg ggcgtgaggg gtcccagac ccactttgcg      7080
aagattcggt ggtcggtcga agcagtcggg ggagagaaag gcttaaagac aatgttatca    7140
acttggaaaa gcgttgtctt ggtcgaatcg tacaccgtga tgtcgccgct caggaaatca    7200
cccttgtcgt gtgtgttgat tgtgtcaaac gcaagctcgg tttcaccaga attacccgcc    7260
gatatacaga gcgatggaat cagagtcact ctgtcaacgt gagtaggcac gtacaatgag    7320
cgtaggcgac gatctcctgg agaggaatac gctccaatga cagtctggaa cgcgatgtcc    7380
agggcgctg gtggagcaa gagggctca ttgcgcaatt catccttaag tggaaggaaa        7440
gccaaggtgc cgctagcttt ggagtcggcc cttctcatgg tctgcaaacg acggaagtct    7500
```

```
ttgctgtagt catacccaag gaggtcaagt tcccgataga agaaatcgat gttgacattg   7560
ttcatctggg ggtactcttc ctcaggtggc ggcaaaagct gcgatgacgg tgatgcctcg   7620 ccaaggggtta tgacgatttg gcctttggcg gatgtcgaaa gctcactctc ctttgccaga   7680
caggaatcaa taacaaattt gaccgtgact tggccatccg catcattgtc actggtgact   7740
tcggctgtca agttcagctc cacggaggtg ttttcatctt caaacacgat ggctttgttg   7800
atgctcatgt ccaagatttc caggagctga acttgggcgg cacgctcacc agccaccttc   7860
atggcagctt ccatggccat aattatgtac ccagcagcgg ggaacacagt ctggccttgt   7920
agcgcatgac cgtcgagcca ttccagatcc cggggcctga tgaagtttgt ccactggaag   7980
gtcgatgctg tgctgtaaga agaaagcttt ccaagcagaa gatggggcgc acctccacga   8040
agatgctggc gggtggagcg agattctgcc cagtattgac gagtatgatc caagagtat   8100 gtgggcaatg actttgacag gttttgaacg gcacgatcgg gccggacttg ttgtacgaag   8160
ccctcggcgt cgatactccg aactccgaaa cgctcccaaa tgtatcccag acctccagca   8220
aaagcgtcca catcgtcaac gtttcgtgcc aagcacccgg tataggcag ctccacaccg   8280 gcaagagcat ccttgatggt ggctagacac ggacccttga gagcagggtg ggcgccaatt   8340
tcgatggcga cgtcgattag acgatgagtg atgactgctt tctgcacagc ctgcgagaac   8400
aagaccggag agacgagatt gtcttttccaa taagcgggca tcacatcctg tacagtcatt   8460
tgcttgctgg tctcgtggac ggcagagaac caagcaacac tatcgttacc ttggccatcg   8520
gcaacagcac agtcgcactc cagcaatgcc ttgacatatg gagctgcgca tgggtgcatg   8580
tgatgcgaat ggtaggcctt gtcaactctc aagattctgg caaaagtgga ttcatcctcc   8640
aagacacctt caacgtgctg gatagcatcc atgtcgccgg agaaggtcac actatccggt   8700
gaattgctag cggcgacgca gacccgaccc tcaaaggctt cgagctcgca tagttccttt   8760
gcgtcatcgt acgacatacc tgccgctagc atagcgcctg tctggccgct tggagaagag   8820
gcatgctccg cggacacaac tccacgcaga tgcgcaatac ggatagcttg agtggcactg   8880
atgaatcctg ccgcaaaggc acaggcaatc tcacctgaac tgtggccgac aattgcactg   8940
aactcgatac cagctgcagc gagaagtcgg accagaacga tttgtacggc gcagcataga   9000
ggctgggaga agctggcgag tctgacgttt gaggcatccc cttcaagcat gagctggtca   9060
tacagtgtcc acgtaggccg atactttca ggcagtgttt gcagtgaatt atccagctct   9120
tcgagaatgc ctctcacaaa tggcataccc accatgagct tcttcagcat gcccggccac   9180
tgtgcacctt ggccagtaaa gacacctagt acgcgagggt tgtcattcgc gtcggtgcgg   9240
aagtcggtga cgacctcacc gtccgcgatg gcagcctcca gtgccgcgcg ggctacttcc   9300
ttgttgtgtg ctgcaatcgc acgacggaag ggcaagatag accgtttctc aagtaaggta   9360
tatgcgatat catgcatgtc cacgtcatca tgcgtttcca gaaattggag catattttct   9420
agcgttgcct tcatggagcg ctgcgacttc gatgaaagca caaggggcaa gctgcatgca   9480
tctgcatctg aggtcacctc tgttaccact gctgtcggct tgtgtggagg agccatatac   9540
tcttcgataa tagcatgggc atttgtacca ccaaatcctg atgtgtttat atgtttagct   9600
aacttcactt tcgttctcaa gaagtgcagt tgaatcctta ccaaatgaat taacgctgac   9660
tctgcgaggc tgcccgggcg caacaatcgg ccattctgtg gcctccgttg caattttcaa   9720
gtgcgtatag aacggagcga cacgggact gatcttctca aacagcaggt ttggcgggat   9780
cacgccattt cgtacagcaa acgatgcctt cattaagccc gcaataccag cagtgccttc   9840
```

-continued

```
cgtgtgaccg agaactgtct tgatgctgcc gacaaaaagc tcatctttct cgccgtcgct    9900
gtcgattgtt ccatccttgt gtccgaagaa ggctgttgca atagcctcag cttcctgtgg    9960
gtcaccggct ggtgtaccag ttcctgggat cttcgtgtta gggagagaga gactttctgc    10020
aacttccata aggctgatac ttccaggaa taccacttac catgggcttc aaagaactgg     10080
cagcgttcct gggggttggt aatatcaaga ccagccttgg catatgtggc ccgaatgagg    10140
gcttcttgtg cgctatggtt tggcattgtg atacctgtcg ttcggccatc ttggttgata    10200
ccggtctctc ggataacaca ctcgatactg tccccgtcgc gcagtgcctg gctcagcgtt    10260
ttcaggacaa tagagcaaac accttcctaa aaagcagtta caggaggtca gtgccatctt    10320
gcttttttg aaaggaattg atgcattgtc aacttactcc tctggcatat ccatcggcag     10380
cagcatccca cattcgagat ctaccattgg gggacagcat gttcaatttg ctctccatta    10440
caaaggtcat ggggcccaat atcagattcg caccggctgc aaccgccatg gtactctcgc    10500
ccgttctaag ctgttggacg gccagatgca cggcagctaa ggatgaacta caggctgtgt    10560
cgatcgtcat ctgcagaatc agtcaggaat ctgtcagcac ttgacgaagt cgggctcgct    10620
caatgagtgg cactcacact cggcccatgc cagtcgaaga agtatgatac acggttggag    10680
gccacactga cagctacccc cgtggcagag tatgtaggaa tactatccaa ttcacgcgtc    10740
acgatagtct catagtcatg cgtcatcata ccgacgtaca cagcagtaga ggatccttga    10800
aggccttgga tccgtaggcc tgcgttggat acagcttcat agaccgtctc cagcagcagc    10860
ctttgctgtg ggtcaatcgt ttcggcctct ccagcttgga tgttgaagaa agaggcatca    10920
aaaccgcgta gatcctcctg cagcaagtat gcaaagggtg cgttcgtgcg cccggggtga    10980
gtgccatcgg ggctgtaaaa tgtatcgacg tcaaatctct ccttagggat cttggtctgt    11040
acatcccggg gctctttgag cagctcccaa agttttgatg gtgtgttgac accacctgga    11100
aaccgacaac cgcttcccac taccacaatt ggctcgtttg gatagttggc ttgatccata    11160
actgctgatc ctgttttttgg gcgataggat tgggattaaa ccttgtcttg cgtcagtaga    11220
tcttctcact gcatgccggg cacaacattt gttcttacag aatcgcagag ttgaatctct    11280
gagcgaacaa gccggccttg caaccgatac cgtcgttata tttacttgca cgtatcagta    11340
ctcatctaga ttcggacaat ttcaagatcc attctagtac tcaaatgccc ccacttccca    11400
gcaatgcaag ctcggcacct agcaaaccct cccggcgtca ttcggtgcac gaatagccat    11460
tcctccatac ggcgttattc ggtcacacga ggctgaatga atcaaacgtg aatatcaatt    11520
ggctgtatca aggtgaaacc gagttttca ctcggattgt tcttgtgctg ctcggtgaag     11580
ctgctcctaa aggaaacaac cgaactgccc catccaggta aacttcgatt ggggggggg     11640
tttttttttt ttcaaggttg actggaagag tgctctcggc cacaaaatcc cagaagcatt    11700
agtgctgtta ttcgattata aaccgtcgca gcgctctcat tcttcgctct ttcttcttt     11760
ccactggtgt gcataggtcc tatctgtctc acgcaatgct cggccaggtt cttctgaccg    11820
tcgaatcgta ccaatgggta tcgacccctc aagcccttgt ggcggtcgca gtgcttctta    11880
gtctcatcgc ctaccgtttg cggggcgcc agtccgaact gcaagtctat aatcccaaaa     11940
aatggtggga gttgacgacc atgagggcta ggcaggactt cgatacgtat ggtccgagct    12000
ggatcgaagc ttggttctcg aaaaacgaca agccctgcg cttcattgtt gattccggct     12060
attgcaccat cctcccatcg tccatggccg acgagtttcg gaaaatcaaa gatatgtgca    12120
tgtacaagtt ttggcggat gtatgacctc tgaattttcc attgttgtaa ctcaatgacg     12180
tctctaagat tctgatgaat gtataggact ttcactctca tctccctgga ttcgacgggt    12240
```

```
tcaaggaaat ctgccaggat gcacatcttg tcaacaaagt tgttttgaac cagttacaaa      12300
cccaagcccc caagtacaca aagccattgg ctaccttggc cgacgctact attgccaagt      12360
tgttcggtaa aagcgagggt aagtgtcaat ttttctgtct tgagcattga gcctctggct      12420
gacataccgc gaatatacta gagtggcaaa ccgcacctgt ctattccaat ggattggacc      12480
ttgtcacacg aacagtcaca ctcattatgg tcggcgacaa aatctgccac aatgaggagt      12540
ggctggatat tgcaaagaac catgccgtga gtgtggcggt acaagctcgc caacttcgcg      12600
tatggcccat gctactgcga ccgctcgctc actggtttca accgcaagga cgcaaattgc      12660
gtgaccaagt gcgccgcgca cgaaagatca ttgatcctga gattcagcga cgacgtgctg      12720
aaaaggccgc atgtgtagcg aagggcgtgc agccgcccca gtacgtcgat accatgcaat      12780
ggtttgaaga caccgccgac ggccgctggt acgatgtggc gggtgctcag ctcgctatgg      12840
atttcgccgg catctacgcc tcgacggatc ttttcgtcgg tgcccttgtg acattgcca       12900 ggcacccaga ccttattcag cctctccgcc aagagatccg cactgtaatc ggagaagggg      12960
gctggacgcc tgcctctctg ttcaagctga agctcctcga cagctgcatg aaagagacgc      13020
agcgaatcaa gccggtcgag tgcgccacta tgcgcagtac cgctctcaga gacatcactc      13080
tatccaatgg cctcttcatt cccaaggggcg agttggccgc tgtggctgca gaccgcatga      13140
acaaccctga tgtgtgggaa aaccccgaaa attatgatcc ctaccgattt atgcgcatgc      13200
gcgaggatcc agacaaggcc ttcaccgctc aattggagaa taccaacggt gatcacatcg      13260
gcttcggctg gaacccacgc gcttgtcccg ggcggttctt cgcctcgaag gaaatcaaga      13320
ttctcctcgc tcatatactg attcagtatg atgtgaagcc tgtaccagga gacgatgaca      13380
aatactaccg tcacgctttt agcgttcgta tgcatccaac cacaaagctc atggtacgcc      13440
ggcgcaacga ggacatcccg ctccctcatg accggtgcta agatataaca cgcaaactaa      13500
aacaaatatg catccgtccc caggcttatt ccaatagttt ccgtcccaga gaaactaggt      13560
gctgtattag tcgagtaggt tagtaaaata aaacgcattt tattcgattg tgatgccttc      13620
tttgtaatcg aacgtggtgt agactttggc tatgtgcgag agacagaaac acagagagag      13680
agaagggaga gagtgtgtat tcctgctacg cagagcggcc atctgcttct ataccgccag      13740
ctacaccgcc acgtagggaa gtcggcagta atgaagcttt tctcccggta caatcaccga      13800 tctcccccatt ctctcaggcg ttgactggcg cttacgatga cgagggctta ggctctgtta      13860
agtcttgatt ttcctactca acatccccga ctaggcgaaa gagaggacgg cgcaacgacg      13920
tggacacaag tactccctcc cgccttccga ctacatatcc acaatctgta cccactgccc      13980
gtgccaacgc ctttcgaccg ttcaacgcgc atttacaagg cttgcgggaa tcataatgga      14040
gagaaaaaga gagaactttt gacagtcaag cctccgaggt gctaagacag cttccctggt      14100
agtataaaaa gcattcactc ttccgacttc gagaacgagt gcacatgtgt actttgttgc      14160
ttctcagggc cactgtaatg gtatttcagg tatctctatt tactgctatc cagaagtcag      14220
gcattaaata gtcaggctca gcccaggctc gattcagatt ggattcaggc ttcagaccat      14280
ggccgctatg ctccttcgta ctataccctcc gtcgagctat acccgcttgg ccagacaaaa      14340
ggcttcactg aacccttcaa cttaactgca tttcgccaca actaactcga cgaggccggc      14400
gatggtgtta ccattcatga gctcaaagat cgacacatca acatggattt cagatgtgat      14460
ccagtttcga agttcaatgg cgacgagtga gtctacgccg acacctgcca ggttttttgga     14520 cgaggacatg tcgtcttctg ccagaccaaa cattcgcatc agcttttccg tcattgcttt      14580
```

```
gaggacgata gaaatggcct cgtcgtgaga ggtgaccctg cttagttggg cccgcacgcc    14640
atctggtcct ttttatgcg aagagacaaa ggattggtct gcatgaagga cttggcggta    14700
tttaagtccc acaaaccgct gttcctgtat ccagtttgcc tcggtccagt gagcacccgg    14760
ggatgtgttg attcctgtaa ccacagctgc gggaggtgat ggaaattgag gggaagaaca    14820
caggattgcc ttctccaaca catccatgac gtccttttca tgcataggct tgtaacctat    14880
tctagcgagc cggtcggcca caccacggcc agtttcagcc acgtatccaa cagacttgac    14940
catgcccaag tcaatggtga cagccggcat gccatgggct ctccggtggt gcgcaagtgc    15000
gtcctggaat gcaccagcag ctgcgtaatt ggcctggcct gccccaccca tgaccccaac    15060
aagggatgag agcatcacga agaagtcaac atcctgtgcg atcttgtgaa gataccaact    15120
accctgtact tttgggcgtg ttgctgcatt aaattcatcc aatgtcattc gcatagaag    15180 cgcgtccttg agaaccatgg caccttgtat gatacctcga attggcggtg catgtgcttc    15240
ttcgcacaac cggagcacct tggtgacctg atcttgatct gagatgtcac atgcgtgtag    15300
atagacagcg cactgttgat tttgcaagct ggttatgaat ggactggcct ttgcacttct    15360
cgataggata atcaagtgct tcgcgccatg atcaacaagc cactgacaga tctgctttcc    15420 aattccccc agcccaccag caactaggta agaactgtca ggcttcagct tcagcgagaa    15480
ccctccatcg ccgactggga ccagttcgtc cccagataca ttgaccacaa ctttgccaac    15540
atgctgacca ctctgcatcg tacggaaggc cttctcgatg tttgacaagg agtgctgctg    15600
gattggacca atcaagccaa tcgcttttgt ctcgaggagt tttgtgacat ggttcaacgc    15660
ttcggatact tcttcacttt tggctctttg ccacgagaga agatcaattg atgtgaaaga    15720
gacgtcccgg gtgaatggca gcatgtcaag tctgctgttt tgctccaggt cctttttttcc    15780 aatctcaaca aatctgccga attcggccat gcagtcaaag cttgcttgga ggagttgacc    15840
tgccaatgag tttagaacga catgaacgcc aagtccgccc gtgtaggctt tgatgccgtc    15900
gacgaataag tcattcctgc tcgagaagat atgatccgga ttgatgccga atttatcgcc    15960
gacaaagtca cgcttggctt gagttcccgc tgtgacgaag acctcggcac ccgcaagctg    16020
ggacaaaatg atcgctgctt gaccgacgcc tccagctcca ctgtggatca agactctttc    16080
gcctcgtcgt agctttgccg tggtataaag cgcaatatat gcggtagtga aagccagggg    16140
gaccgaagcg gcttctggga agcccatttc gtccggaata cggacgacat tagtgtacgg    16200
cgtctgtgtt ctggtcgccc aatggccttt cagtagtgca catacgcggt cccctaatct    16260
gaggccttgg ctagcggcag cagctccacc gagctttgtg atcactccgg cgcattcgaa    16320
gcccatcaca cggttggcct ccaattgacc catggcaacc atgacatccc gaaaattgag    16380
accgaaagct ttgggttcga tttctaccca atcatccgga agatccttgc cttcacgtcc    16440
ttcgtcgtct cgaaattgca gggagtctaa gagccctggc gtctcaacct ccatccgcag    16500
acgacgcccg ggttgctcga acggctgcag tgtgacctca accgcttctt ggtccttcca    16560
gtgcgggtca ttgaaaagtc gcggtacgtg gatgacgccg tttctctctg caaattcaaa    16620
ctccttgtct tcgaaaggt cgccgaggcg gccattgaag atattgcaga tagcatacag    16680
ggactcgtgg gtgtatgcgt ttcgagaagg atcgagatcc aacgatacat attccttccc    16740
gttattttcg ttgcggatgg tacgcagcag accaatatgt agagctttcc atggatcctc    16800
ggagctcatg gctgctcctc tagacaccca gagaagtgcg ttgcagttat tcagcatcgc    16860
ggtgatggat ttgaaggtct cgcttccac ctctccaagg agcgaggact ccatttccc    16920 aagaaaaatg catgtccttc cagtggtatc tacctcgccc agagcgttga tcgatgggct    16980
```

-continued

```
agaactggtc ttttcacaaa ttgctgcctg gagactttcc agccaagatg aaggaggtcg   17040
gagcgctccg tgcagcaaaa gcacctccga ttctgccact gtatccgggg ttgtattctc   17100
ttttctagcc gtcgatagca ttgtgctgat catgtaaaac tcatcgtctt cacaatcacg   17160
aacctccaat tccacaccgt tgaaaccgct cgtgtccaac atggtgttcc aaagatcggt   17220
agtgagcgat ggcgtcgact tccgctcagg ctcctcactg agccaccaac ctggcaacag   17280
tccgaaggta agaacaaat cgagctgatc cctggtagtc tcaaccaaaa tcaagttgcc   17340
cccaggcttg agcaattttc gaacgttact cagtgttcgt ttcatgcatc gagttgcatg   17400
caggacctgg caagccacga ccacatcgta ggtggcacat tcaaaccctt gttgctcggg   17460
atcgctttca atatccaatt ttttgaaagt catcacgtct tgccaatccg caaattgctc   17520
acgcgccgac tcgaaaaacc cggcagacac atcggtgaag tcataacgat cgatcggctt   17580
ggtgtttccc aatgcattga caataagctt tgtgcagccg cccgtgcctc cgccaatctc   17640
caaaatgcga gaacgcgggt tcttgtgggc gcaaagtcgg atcagctcgc tggcttgtgc   17700
gtttgatcgg ctccatttga ttgcgttgac gtagtatctg cttagcagct gatcttgcat   17760
catcaactca agtggctctg tttcgcggcg tagcattgct attaactgag gtcctagacg   17820
agaaatcatc tcgccattga cgctttctcc agcgactctg gcctgtaggc atttcttctg   17880
ctcagcatcg tcacttagcc agtcgcaact ggctgggctg agcttgtttt gtctcgcaag   17940
gtccaattgg acattcatcc aatcgaaata cttctgaagg tggccatcca gatgttggat   18000
atcagaattt gtcaaatcag tgacagcctc ctgtataaag ttgatcgtgc atcttcggag   18060
gtccatcatg agttccgttt ctttcgtctc agcctcagtg ctcaactttt ctttgagcca   18120
agtggagtca cccaagctga tgtcaggggc ccaaacccag gagctgcagg catttctgt   18180
gtcgttggag tctgactttt ggtcagagaa gctgcttcca accgactgga aaacaaggcc   18240
ttcaatctct atgactggga ttccgtccga gggagaagaa ccgctatcat agtcatcaaa   18300
cactgccaag tcggtagaga aggattgaga gttgcgatcc ttgatgctgg cctgtgcgtc   18360
cagagcatca ccagcctcca agtcagccag gctagaggat attttgacat tcttagcct   18420
ccttggtacc atggccgttt tcatacgtgt tcccgcgtag ggtaacaccg tgtatgccgc   18480
ctggatcacc gagtccagag tagtaggatg gacgatgtgt cgattctcgt acgagtgagg   18540
catagccgag gcagtgtcag caatggaaaa tctgcaaaac gagccctgtc cattgttttg   18600
aattcgctga atgttctgaa aaatgggtcc gtggcatatc ccattcgcgt gtaaggactc   18660
ccagagatcg ttgggatcaa tgctccggtt atctgagcct agattcaacc tgcgtgaggc   18720
ttccacagtt gaacagtcaa ggtggcttct ttcgctctcc gaacgtatta atccggtgca   18780
gtgttctgtc caggtattat tttcgcccga aattgagtgc acagaaaatt gatgccagtt   18840
ctttgtgccg agggaccttt cctcacatga acggatcgtt aggcgcaggt caacctctgc   18900
ttctgcatca gcgggtatta tgagagcctg cgcgagttca acgtcacgca agttgtagtt   18960
gatgctagcc cccgcaactg gtgggcagac ttgtgaaaac ccctcgatgg ccatgctgat   19020
gaagccagct cccggaaaga tgatgctcga accaacgacg tgatctcgta tccatggaat   19080
atctgacaga cggagaacat gtttccattt aggcgcgaaa tgaggagaga gagattcccg   19140
tgagcctatc aaagtgtgag gcggatgggt tctctgtttg gactcacgac tgccgcgagg   19200
ctctctccaa taacgggttt ggtgattcca cgggtacgcc ggcaaatcgc tcagtacctt   19260
cactctgggc tcttttcttc catgaggaaa gtttatagcg tccatttga gcccataacc   19320
```

```
cttgcttatc aactccgtag cagcacgata cattgtctcc aacgagcttc tgccgcgaga   19380
aaggcaactg agatagttta tatctgttcc tttcagaccc agatcctgca tgacttggtt   19440
gattggacca ccaagcgctc cgtgaggccc tatttcaata atcacatcga cggctttctc   19500
tttggtgttg ggatcaaagc acatctcgcg gagtgaggac tcgaactcta ccggctgtag   19560
catactatcc atccagtgtg tgggatccaa tagcaattta agatcggtca tgcgactacc   19620
agtcttaggt gatgaatata atacacccTt tgaggtgtca gcattgggat tgtcgttgtt   19680
gttatccgag ttgaacagat ctctcagtga cgccccaaag gcatctgcca ttggtcgcat   19740
gtggcttgaa tggaaggctt cagtgacttt cagtttcctg gtaaagatgc catcggcgtg   19800
taacaacttt tcaagtttct cgattgcacc caaatctccc gacaccgtca cactacattg   19860
actgttgata catccaacca ccacacagcc gtcctcctgg ttgagacgcg aaatgtaaac   19920
attggtctca ctgcgaccaa gacccaccgc catcattcct cctttggctg ccaatgcggg   19980
cttgggctta gtggtcaata caccgcgtat ataagtgatc ccaatggccg accgcgcgga   20040
taaagcccca gctgcgtagg cagcagcagc ctctccactt gagtgactgg ttatccccgt   20100
tggccgaatt ccccatgacc aaaggagacg cacaagtgca atttggatag cggttgacag   20160
tggtagactg tattcggcat catttacccg agtcgtcagc tcatcacggt ggagctcctc   20220
tgtgcaattg aatgttagta cctcaagctt gatacagtat tacttttccc gggctcgcaa   20280
cttacccata aaattccaac tcgcgcccag ttgcttgatg tagccatcac attcaagaat   20340
cgcctgtttg aatactggga atgtattgac cagctctctg cccattgcat gccactgcgc   20400
cccctgaccg gtgaatacaa atccgagccg tactttctca ttcgctcgtt ttggttgatt   20460
ggactcatcg ctgagggcag aaacaaggcc gccaaggctg tctgctacat acactgacgt   20520
ccatggcaga atggaacggc gagagcctag tgtataggcg aggctggcga ggaagggttc   20580
cccgtcaatg tcagcgacgg atttaatgta gtctcgcagg cttgctatcg ttcgccgaca   20640
agcttgctcg tccttggcac gcacaacgta tatgcggctc tgtttggaac catcctcaac   20700
cctaccatgc tcagagttac cattgacatg cacttgatcc tctggcaggg ccaatgatgc   20760
gcgatcatat gattccaaaa tgacgtgagc attcgaacca ccaaagccga agttattgac   20820
agatgcgcga cgagtcccat cttTcacagg ccagtcttga gcagacatgg ggatctttga   20880
aacattaacc tttgaaacat ataactgaat ctgcgaatgc gcaaagcctt accttgatgt   20940
tcttttggtc aagcatcagc ttgctgttct tttgcaggaa ccgcgcatta ggggggaatca   21000 agcccttctc caaggccaag gccaccttga ttatactggc caggccactg gcggcttctg   21060
tatggccaat atttgctttc acagagccaa ggtgcagagg atgtcccttta aaagctgctg   21120 aaaattgctga gatttcaagg gggtcaccag ttggtgttcc agttccgtgg gcctccacgt   21180
acgaggtcaa cgacatatct agcccagcct tatcgtaaca ctcctggatc agacttttct   21240
gcgccacatc actcggcgca gtaattgcgg gtgttttgcc atcctggttc agcgctgtct   21300
ctcgaatgac ggctcggata gggtcttggt ctcgcaacgc gttagggagg gcctttatta   21360
ccagagcggc aattccttcc ccgcgaccat atccattcgc tcgaggatca aaagagtacg   21420
agataccatc cggggacaaa aatctgtcat tgagcaacaa ggattgctta gttcaagact   21480
ctcgatctgg aatcttcttc ggaaaactca ccccaggttt gacatcgtaa caaaaacatc   21540
gggattgagc agaagatttg caccgataac gatggctgta tctgactccc cagtacgtaa   21600
gctctggcac gccaagtgca gtgcggtcaa tgtcgtcgaa caggccgtgt caaccgtcac   21660
gctgggacca cgtaagtcgt agaagtgtga tatccggttc gaaagcattg ttcctgagtt   21720
```

```
gccagttatg aaataacgcg gaactgtctc ggggtcacga ttgagcgaat cctgatagtc   21780
gtggtacatg acaccccaa acaccgacgt attagagcct gccataccat cgatggtgat    21840
accggctgga tgatggtcag tgacgtttgc ttacagtgag gatgacccac actacatacc   21900
actctccagc gattcgtaga ccacctcaag cataagccga tactgcggat ccatgcactg   21960
tccaatatta gatctctgcg tcccgggtta gatcaattga ataatcata cgctggcgac    22020 ctctgtggtc atgttgaaga acgcggcgtc aaataaagca ggatcctcgt cgatgaagtg   22080
tccacccttt acgtgggtct atccagtcat ccttggagtc agtaaccaag cttcagtgat   22140
gctcaaatct tgtgtcaaat attcaaaaca agatataaat gcatgcatgt tagatactca   22200
cggacccgac cctttcgcca ttcggtggt atactcctct cacattgaat cgcgaggagg    22260
ggaccttaga ccaggcactg cctcctcttt caaccatttc ccaaagcttc tgtggactcg   22320
ttgcatctcc agcaaatcga catcccattc caactatggc aatgggcgtg gatgtgttag   22380
agcaagccga gcctgccatt gcggttgcgg ttgcggttgc ggttgcggtt gcggttacgg   22440
cgggggtatt gttcattcca acgttgtttc attgactgat atatcagtcg ccctggtgat   22500
aaaaccgttg atagtcttcc aacagtctac aggtccctgg catagctata gatgcataag   22560
ctgcccccga cacgtgattc atagttcggg gtttgttttc atcttggacg tgacacgata   22620
ttcgctctgt gcccatggga aaccccggac caccatgcta tgctcggggc aatacctttag   22680 aggtaccggt tcgggaggca ttgtctgtcg tcacgataat cccgagtcaa acgccgatg    22740 ggaaaccgtc gaacaagacg aaacaggtca ggccggccag gtagttttcg ggtataatgg    22800
aggctgtcag aatccgatac tccgtacaca gatgcgaaat acgcatacga gctatcaaac   22860
caaacgaatc caaaagcctt ggaaaagctt ggaaaggctt agtgggtaat cctgtcccaa   22920
ggtttgttga gggcctgagc gcagggtggg tcctgtaagc agttggtaat tcaatttcca   22980
acaatacaca atccccaaaa tttgcattat cggttgacta agacaagcaa acaaaatata   23040
tgcaggaagc gcaattcatc gcgagcaaac gatcatcatg agcatgtgac cctttcctct   23100
tttttctact tcggaaggcg gcatgatcat ctgtcagaac tcccaatcgg gagcaatacc   23160
ataccttacg gcaccccact cagacccatg cacaaagaaa atccatgcgc cgaatattga   23220
agccttggca acaaagcccc gtgtaactcc gaaggtatcc aaagaccgag agacgccgat   23280
ttgagagaca cgtacggagg tccacacaaa atgttcccga gtctatacac tatactccaa   23340
actgacttct tgtctacctg ggtatcttgt tcaggttgct gtttactgag ataaatgata   23400 ccggggggg gggggggggg ggggttgac actggctttt cgtggacaga ataatccca    23460 tacatccctg cgtaagtagt cgtttcgaga agaatgtgtt tcgtggtgca ttactccgta   23520
ggcacaatat atttccattc ctcacgaagt ggcctcgtcc gggcgtgatc gatgcagctt   23580
gccgccccac caaaaaagga ccacaatacg agtcagatta gaaacgtcta acaggacgtc   23640
tatgtaagag gacgctcctt tgtatgtcgg atctaggcat gacaaaataa ctatacctag   23700
gtagtgttct gtcttattgg tcatttggcc tactttcgga acaatcttgg aagttcacat   23760
tcctaggtat cagggcaatt gattggtgtc cccagaattc ttttttctcg aataaaggat   23820
aaatttatgc ataaaaacct tggaaactga gcatagttat gagcacaaat actagttttc   23880
agtgcaattg gtcctactat cctttgcttg gtaccccttta ccaattatac cctaggcagc   23940
agttgacacc ggtcatgaat ccattcataa aggtggacca gatgcaggga taaggaagcg   24000
aatctttccg ctgcctcagc ctcagggggcg cgcgccattt gttatttttct tctactcatt   24060
```

```
tcccgtacct aggaactgtt cagttgtccc tcccaacccc ttgggccgaa caaccttcct    24120
ccaatctacg acggcagatt atacctaggc gcctaaccga ttaggttgct cattcgattt    24180
tggaggtatg cactttatct caagccctaa ttcccaattg aagtgctttt ccgtccccat    24240
ttgcagagct gactagattc ttttctcaga gactacctag ctataggtac cactccaagc    24300
tgtagcacag acctttcagc atggtcgctt cgttgctacc ctctcgcttt cgcggtaggg    24360
aatcaatgaa tcagcagcac cctctacgct cgggaaatcg ggcattgacc tccacactcc    24420
aatttctatc caaaacggcg tgtctacacc cgatccatac cgtttgcacc atagctattc    24480
tagctagtac cacatacgtt ggactactca aagacagctt cttccatggc cccgcaaacg    24540
ttgataaagc agaatggggc tctttggtcg aaggaagtcg aagcttgatc accggcccac    24600
agaatggctg gaagtggcag agcttcgacg gggatgcaga tgttctcgga gatttcaacc    24660
atcaagcact aatgaccttg gtattcccgg ggtcatatgg ggttgcatct caagcagcct    24720
caccattcct tgctcccctc cctgtgaacc tatctgtgat tgaccttccc tcaacgtcga    24780
gcccttaaac cgcctattcg aaagataaag ttttcgcctt ctctgtggaa tacagcagcg    24840
cgccggaact cgtggctgct gttcaagaaa tccccaacaa cagtgccgac ctgaaattgc    24900
aggagacgca attgatcgag atggaacgcc agatgtggat catgaaggct gccagggctc    24960
acacaaaacg cagccttgct caatgggtgc acgatacctg gacagagtct cttgatctta    25020
tcaagagcgc tcaaacgctc gacgtggttg tcatggtgct aggttatata tcaatgcact    25080
tgactttcgt ctcactcttc ctcagcatga aaaaattggg atcgaaggtt tggctggcta    25140
caagcgtcct tttgtcgtca acatttgcct ttctcctcgg tctcgacgtg gccataagac    25200 tagggggttcc gatgagcatg aggttgctat ccgaaggcct ccccttcttg gtggtgatcg    25260
ttggctttga gaagagcatc actctgacca gggctgtttt gtcctatgct gtgcagcacc    25320
gaaagcccca gaagatacag tctgaccagg gtagcgtgac agccattgct gaaagtacca    25380
tcaattacgc cgtacgaagc gccattcggg agaagggtta caatatcgtg tgccactacg    25440
tggtcgagat cctgctccta gttatcggtg ctgtcttagg catccaaggt gggctacagc    25500
acttctgtgt tctagctgca ttgatcctgt tctttgactg tctgctgctg tttacattct    25560
acactgcgat tctgtctatc aagctcgagg taaaccgcct caaacgtcat atcaacatgc    25620
ggtacgcgtt ggaagatgag ggtctcagtc agcggacggc ggagagtgtc gcgaccagca    25680
atgatgccca agacagtgca cgtacatatc tgtttggcaa tgatatgaaa ggcagcagtg    25740
ttccgaagtt caaattctgg atggtcgttg gtttccttat cgtcaacctc gtcaacatcg    25800
gctccaccct tttccaagcc tcttctagtg atcgttgtc cagtatatca tcttggaccg    25860
aaagtctgag cggatcggcc attaaacccc gcttgagcc cttcaaggta gctggaagtg    25920
gactagatga actacttttc caggcaagag ggcgcggtca atcgactatg gtcactgtcc    25980
tcgcccccat caagtacgaa ctagagtatc cttccattca ccgtggtacc tcgcagctac    26040
acgagtatgg agttggtgga aaaatggtcg gtagcctgct caccagcctg aagatcccg    26100 tcctctccaa atgggtgttt gtggcacttg ccctaagtgt cgctctgaac agctatctgt    26160
tcaaggccgc cagactggga atcaaagatc ctaatctccc gagtcaccca gttgatccag    26220
ttgagcttga ccaggccgaa agcttcaacg ctgcccagaa ccagacccct cagattcaat    26280
caagtctcca agctcctcag accagagtgt tcactcctac caccaccgac agtgacagtg    26340
atgcctcatt agtcttaatt aaagcatctc taaaggtcac taagcgagca gaaggaaaga    26400
cagccactag tgaacttccc gtgtctcgca cacaaatcga actggacaat ttgctgaagc    26460
```

-continued

```
agaacacaat cagcgagttg aacgatgagg atgtcgttgc cttgtctttg cggggaaagg    26520
ttcccgggta tgccctagag aagagtctca aagactgcac tcgtgccgtc aaggttcgcc    26580
gctctatcat ttcgaggaca ccggctaccg cagagcttac aagtatgctg gagcactcga    26640
agctgccgta cgaaaactac gcctgggaac gcgtgctcgg tgcatgttgc gagaacgtta    26700
ttggctatat gccagtccct gttggcgtcg ccggtcctat tgttatcgac ggcaagagtt    26760
atttcattcc tatggcaacc accgagggcg tcctcgtcgc tagtgctagc cgtggcagta    26820
aggcaatcaa cctcggtggc ggtgccgtga cagtcctgac tggcgacggt atgacacgag    26880
gcccgtgtgt gaagtttgat gtccttgaac gagctggtgc tgctaagatc tggctcgatt    26940
cggacgtcgg ccagaccgta atgaaagaag ccttcaattc aaccagcaga tttgcgcgct    27000
tacaaagtat gcggacaact atcgccggta ctcacttata tattcgattt aagactacta    27060
ctggcgacgc tatgggaatg aatatgattt ctaagggcgt ggagcatgca ctgaatgtta    27120
tggcgacaga ggcaggtttc agcgatatga atattattac cctatcagga aattactgta    27180
cggataagaa accttcagct ttgaattgga tcgatggacg gggcaagggc attgtggccg    27240
aagccatcat accggcgaac gttgtcaggg atgtcttaaa gagcgatgtg gatagcatgg    27300
ttcagctcaa catatcgaaa aatctgattg ggtccgctat ggctggctca gttggcggct    27360
tcaacgccca agctgccaat cttgcggcag ccatttttcat tgccacaggt caggatccgg    27420
cgcaagttgt ggagagcgct aactgcatca ctctcatgaa caagtaagtt gaaagcggcc    27480
gcttacttgg aaacattcac taatcctgtt tagtcttcgc ggatcgcttc aaatctctgt    27540
ctccatgccg tctattgagg ttggaacgtt gggcggtggt acgattctgg agccccaggg    27600
cgcaatgctt gacatgcttg tgtccgcgcg atcacacccg accactcccg gtgagaatgc    27660
acgtcaactt gcgcgcatca tcggaagcgc tgttttggct ggggagctct cgctatgtgc    27720
tgccctagcc gccggtcacc tggtcaaggc gcacatggcg cacaaccgtt ctgccccggc    27780
atcttcagcc ccttctcgaa gtgtctcccc gtcaggcgga accaggacag tccctgttcc    27840
taacaatgca ctgaggccga gtgctgcagc tactgatcgg gctcgacgct gattaggtcg    27900
gaatcttagg agcattccaa gctccgtacc ccctccagtg gattcattgc aggaggatca    27960 tatttttttct cattggttgt tattgtcata attttcaaaa gcacaatgca atgagacagg    28020
caggtggtag agtgaacggc cagaaagggt atctcatgtt tatatgttgt gaaatttac    28080 gatgcaagta gtagggaaga agaatatata aagagatggt cctttttccag agagtgttta    28140 ggtctgatcc ctcataatta tttaatgagt gaaagctttg ttcaagctat aacttactga    28200
gtaggttgaa tgttgatctg attcattcct gaggtatcag gattgatgcc tgaaacatca    28260
atcatccatt gtcagatgcc gtaactaact aactatgaat ctcaacatag ttatatgttg    28320
ccaatctagc cacggtgact agaaccttga gatggactta actagacat gggtcgcggg    28380 caatgacata tagaatcttt gaaatcgaca ttaattaagt atgtggagat tctttgtgga    28440
ggcacggtaa tgtgtctatc tagcaacgcg gtcaagcatc agtctcaggc acagcccggg    28500
tgtcgttttt ggttgcaatc ttccgccatc ccattccaaa ggcaaacaca acgtgcacg    28560 ccgtagctcc cactgctaag taaaaagtat gatcaacggc gagactgtaa gcttttacaa    28620
cccctggaag gttattcttg ctgaccacat ctctgaagcc agtcgcccct gctgccgtca    28680
cggcctgcgt gtcgacagtg ggcgcatact tgctcaggcc agttctcaaa ccggacccaa    28740
agacaaggtt agcaaagtcc aggaagagcg atcctccaaa cgtctgtcca aacacggcga    28800
```

```
gagaaattcc gagggcacct tgttcgggcg aaagcgtgct ttggatggcg atgataggct    28860
ggccattgag tattgatgtc agcgtctagc ggttgcatgc tcttcttgct ttgatacaaa    28920
gccgaaagcg tgagagatga tcaaaggttt catagcttac cgtttgcatg ccacaaccac    28980
gaccgaagcc cgcgataaat tggtacatga cccatttcac agttgatgta tggggctgga    29040
aggtggatac cagacctgcg cctatgcgca cgagaacagc gctgcctagg gcccaaggca    29100
aatagtatcc tgtcttttcca actggtgcgt catatgtcag tatacacgat atccaagccc    29160
gatgtcagac ggttgtggca agaaaggagc catagaaatg gacggggtgg agaaaaatgt    29220
gtacgcgagt ttcacttact tgcgaagcca gaaaccatag ccataatgac ttgtccaaga    29280
attccaggca acatgtacac accactcagt gtgggagaaa catccttcac agcctggaag    29340
tagatcggta gatagtagga aaagacaagc aaggagccag agaaaagcc cataaataaa    29400
caagagcacc acacttgtcg tttaccagcc actgagccag gaatcatggc aacagcatcg    29460
ccaacatgac gctcccatag cacgaacgca atcagagcaa accctccgcc acagaacagg    29520
ccgatgatga cggaacttcg ccaggtgtag gtcgaccctc cccattctag tgcgagggaa    29580
atcatggttg cgaaggctgc aaagaccaca agcctacaa ggtccagttt gcgaagtgtg    29640
gattttatgt tggccattgg tttgtcggtc gagagttcgc tgtccgtgga tgaaattcgg    29700
tcgggtatgg tgatgacgag aaggaggaat gcagcgacag cgccgatggg gagattgata    29760
taaaagcctg aattccaagt gagaacatgg acaacaatca taaaaggcc aaggtcaac    29820
atacaccatc gccaagtggc gtgttgagtg aaagcacctc cgagcagtgg tccacagaca    29880
atggcaatct gactaactga aaacatattg tcagacgacg aaccgttcgt ttgggtaca    29940
tcagatcttg agatgacata cgacccatca tcactccaat caaaacttca tatgcgaggt    30000
cagcgtgtac acggcaccca gcagacttcc aaaaatcggt tcccttacct ggttgcttgt    30060
gcttaggagc agctgttgag aggattgtga gggctccgtt gacaagacct gagcctccca    30120
ttccagcaac ggcccgccca acaatcaaca tggtggaaga tcttgcggca ccgcatagca    30180
ccgagcctag ttcaaaaata cagaggaagg caaagaaagt gtacttcaag cccaagagtg    30240
tatacaattt accggccagg ggctggagag cacagctaaa tatgatgtta gctaatctgt    30300
tcgtacaatg aacaaggtca aggagaacag agccatactt agccagaaga taagcactgc    30360
cgtaccaccc tacatcgttc agagagtgga actcgcttgt gatatgtggg attgcctgtg    30420
gctggagtca attgactgtg ctgcgctctg ttctgaggta gccaccatct taccgtgacg    30480
ataatggaca tatcaaggag catcaaaaat gctacgaaag taactgaagc aaccaccagc    30540
ccgagcttga ggcctgtgat gtgctgggac ttggactcag tcgcttcgag cgtgtcattt    30600
tgactttctt ccttctgtgg ccttggttcc ccttctttag ggggtagagg ttctgacatc    30660
gcgcaattcc ttccgacttt tgcttcaagg ggcggtgtga atctctactg cgcggcgctt    30720
ctatagtacc tgtgttttgg tgtatgaatg atctcgctct cgttgtttcg ttaaggtccg    30780
ctagcctgaa gtcagattga tggatgggga tcaggggaaa ttggcgacgt ctttaatttt    30840
gcttttcttt gttaccggaa gtgttgcggt attagcgtgt ctgggcttat ttacgacgca    30900
caagatgcat tgaactggcc ccactgctag atctcactag tattgtggtt gtaatttacc    30960
tatactccat attgactggg caggttttga acacaaccca caccccccca tactacacat    31020
tagttttgca tattttcctg ggggccaaaa aaaccccaaa aggcttcaat attttgcggc    31080
caatggagag tgtaactaat ttggcccaca ctccggtggt atcaatcgga tctcactgca    31140
tatatgatga aagcaagagg gggcaggaga tacgctcttt attggctgtc tgcgcgaagc    31200
```

```
tgggcaaatg caaataaaaa gacaaacaac cagctggaag accgggcgac aaacatggtt   31260
tacctaacac cctcgatccc aacaatgtgc atgttaatca atgtgctccg tggggagtat   31320
gaactataac atacgaagca gccattcatg tcaaaaaaaa aaccaggcga atgggcgtcg   31380
tcaacggttt cacataagta ctatattgta ctaactaccc gtgagactgg agagaacagt   31440
ctcgcgcgaa gaaacgataa gagcatcggt catatcggtc catctcggtc taagtgtatg   31500
agaatattcc gacgtgaatc catccgtcag tgatcaatgt ctccaagtaa ttcatcattt   31560
caattaccct cgctttactc cgtagaatac aagaccttac tagcgcaaac aagtgggggc   31620
taacggtgtg atctccttcc gttgcggccg ccacctcggt tccagccgta atacgacgac   31680
ccgtctatcg cgaccccta gccttggcca tttttggcgt tacagtaaag ctttggagag   31740
aaacgccaag ggaaaatgct agccaccaat tctataaatt actcttcaca tgcagctagt   31800
atcactggta agtctacggg gcacatgtaa aatttttatt actttctaat aatctttcca   31860
agttcttttc cacggggccc caatgcttaa aatactcaaa agacgtgaaa aacctgcaag   31920
ccgccagtga tatcacacgt aatgcctcaa cagcctgatt ccgagccatt atatgctgtt   31980
tgatgatctc aaattgagat ggcgagcgct ggatctggga aattggtagt gggattggta   32040
tagaaacgta agtgcagaag accatgtaat aagtacatat ggaggctatg tgatggcccg   32100
atctagtttc ttcaatatag cgctgggtat aaaaaaaagc aggggctttc tcagggtaat   32160
gtcgcagtct acaacgagtg gcgtccactg acagggaaag gcgagcgggg ctatgctacc   32220
ttcaatttcc atagagggg gatgcaccat ctccgacaat ctatagttac tcaaacaggt   32280
acggtactaa gcaatattgt gtttcttcgc taatgcgaat atttccttat agcaacgtcg   32340
caacacattt atcgtcttcc ctgaggcctt tgttgacttg ggctcttcgt ctccggcttc   32400
gtcactccaa agcacagata ggagacgaga ggccggcgtt atggttttat tttcagcgcc   32460
aaggatttgc cacgatgtgc ttggcatatc tgataggacc tattcccct ctccggtca   32520
gcgcattgct gatgtatgca agggaagaaa agactggtgg ttatcggtcc cacttactag   32580
acgaatagat gccgcagccc cgtgctcctg tgctatcccc aaagcagtct caatctcact   32640
caatagtcga aggcttacac gcaatgtcgt gcatgcagaa gataaggcgt gcatgaatgg   32700
gtcgagatgt gaaatgagct cgccgatatg aagattagag tgaaacgagg gaagtgcttc   32760
ggctcttcca ttgtcatttc tagtggttga gccagaccag taccaatcca ttcgtgtgct   32820
ttgcttttgt ccacaaggtt gggctttcat cacctcggat agtagcagct gggaaagtga   32880
tgtcatgatt ttgacagaca acatgtagca atgcaccgcc atgaacaagt tcttggtttg   32940
cagacaccca tctaacatgc tgctattgct gctcgtgatc acacgttctt gaagatgtag   33000
tagcaatcta ccaaaggcat tcaaaaagtc ccctatcggg tctaggaaga agctttagcg   33060
acaatcaaga ggcagtaaac aggcagaatt gaaaatctca cagcttaaaa ttttttgctt   33120
gggccattcc acagtcaccc cgtggagtat tacctctagg tcctgtgaca catccgacag   33180
actttcgaaa aggtctcgtt gcgtgttgct tgtgttggat tgtccggatg acgagttccc   33240
ctctacttcg aggtcaaaca gcgatggcga gacaggcgcc gttgcatcca aagggccttc   33300
aaagtcgtag cctagatctg gtatccccga agattcattg ctgttggcat cgtcgcgaaa   33360
tgtatttggc tgaggccagc cgccgggaaa cgactcggga tcatcaaagt tgattgatgt   33420
atcatagaat tgcagggttg ccgctgatgg ttctgataat gtttccttga gtgccgaggt   33480
gccaatatgc gtaggtggtg agcagtaagg tggaggagtc tctgccaatg atgagaagac   33540
```

```
cgtagaagat gtcgcggtca tcggttgtga ggtttctgtg gctcttgtag ttccagctgc    33600
ggcttcttta tgtaaattgc gcttgggtag cctttcgctg tacacacacc ttaatccggc    33660
ttgttgacaa cgttgacact gagcacggac taaattggca ttgctaccgg tacatttgag    33720
cttttgtgca tgacaccggt cacatgagcg tcgaaacgcg cgacggcgta ggttcgtcgg    33780
aatcgttgca tgcggcaggg acataattat tggattaaga tcaaataatg tgaggtgaga    33840 cttttgcatgt tcctggatct ttatgtattg gaattggaga gtaagctcgt gcaggagata    33900
agttcaggtc gtcttgctgg aagacttact aagttatatg caaacaagtg ttttcgagcg    33960
gacaccaaaa gccaatagtc ttactatgaa tgtcttttca gtcacccgga gaaatactct    34020
tagcctctgc tcttatgcga gctcatcaaa gctgggcata catacccat ccagcgccac      34080 gtattacact agaaagagtt ctaaaagaaa tagattcggc cccccatctg gctatcatat    34140
atgccagatg aaatacctgt aacgtggggc ataaaaaggc aggctctagt ctaccagcag    34200
atc                                                                  34203

<210> SEQ ID NO 2
<211> LENGTH: 34203
<212> TYPE: DNA
<213> ORGANISM: Penicillium citrinum

<400> SEQUENCE: 2
gatctgctgg tagactagag cctgcctttt tatgccccac gttacaggta tttcatctgg      60
catatatgat agccagatgg ggggccgaat ctatttcttt tagaactctt tctagtgtaa     120
tacgtggcgc tggatggggt atgtatgccc agctttgatg agctcgcata agagcagagg     180
ctaagagtat ttctccgggt gactgaaaag acattcatag taagactatt ggcttttggt     240
gtccgctcga aaacacttgt ttgcatataa cttagtaagt cttccagcaa gacgacctga     300
acttatctcc tgcacgagct tactctccaa ttccaataca taaagatcca ggaacatgca     360
aagtctcacc tcacattatt tgatcttaat ccaataatta tgtccctgcc gcatgcaacg     420
attccgacga acctacgccg tcgcgcgttt cgacgctcat gtgaccggtg tcatgcacaa     480
aagctcaaat gtaccggtag caatgccaat ttagtccgtg ctcagtgtca acgttgtcaa     540
caagccggat taaggtgtgt gtacagcgaa aggctaccca agcgcaattt acataaagaa     600
gccgcagctg gaactacaag agccacagaa acctcacaac cgatgaccgc gacatcttct     660
acggtcttct catcattggc agagactcct ccaccttact gctcaccacc tacgcatatt     720
ggcacctcgg cactcaagga aacattatca gaaccatcag cggcaaccct gcaattctat     780
gatacatcaa tcaactttga tgatcccgag tcgtttcccg gcggctggcc tcagccaaat     840
acatttcgcg acgatgccaa cagcaatgaa tcttcgggga taccagatct aggctacgac     900
tttgaaggcc ctttggatgc aacggcgcct gtctcgccat cgctgtttga cctcgaagta     960
gaggggaact cgtcatccgg acaatccaac acaagcaaca cgcaacgaga ccttttcgaa    1020
agtctgtcgg atgtgtcaca ggacctagag gtaatactcc acggggtgac tgtggaatgg    1080
cccaagcaaa aaatttttaag ctgtgagatt ttcaattctg cctgtttact gcctcttgat    1140
tgtcgctaaa gcttcttcct agacccgata ggggacttt tgaatgcctt tggtagattg     1200
ctactacatc ttcaagaacg tgtgatcacg agcagcaata gcagcatgtt agatgggtgt    1260
ctgcaaacca agaacttgtt catggcggtg cattgctaca tgttgtctgt caaaatcatg    1320
acatcacttt cccagctgct actatccgag gtgatgaaag cccaaccttg tggacaaaag    1380
caaagcacac gaatggattg gtactggtct ggctcaacca ctagaaatga caatggaaga    1440
```

```
gccgaagcac ttccctcgtt tcactctaat cttcatatcg gcgagctcat ttcacatctc   1500
gacccattca tgcacgcctt atcttctgca tgcacgacat tgcgtgtaag ccttcgacta   1560
ttgagtgaga ttgagactgc tttggggata gcacaggagc acggggctgc ggcatctatt   1620
cgtctagtaa gtgggaccga taaccaccag tcttttcttc ccttgcatac atcagcaatg   1680
cgctgaccgg gagaggggga ataggtccta tcagatatgc caagcacatc gtggcaaatc   1740
cttggcgctg aaaataaaac cataacgccg gcctctcgtc tcctatctgt gctttggagt   1800
gacgaagccg gagacgaaga gcccaagtca acaaaggcct cagggaagac gataaatgtg   1860
ttgcgacgtt gctataagga aatattcgca ttagcgaaga aacacaatat tgcttagtac   1920
cgtacctgtt tgagtaacta tagattgtcg gagatggtgc atccccctc tatggaaatt   1980
gaaggtagca tagcccgct cgcctttccc tgtcagtgga cgccactcgt tgtagactgc   2040
gacattaccc tgagaaagcc cctgcttttt tttataccca gcgctatatt gaagaaacta   2100
gatcgggcca tcacatagcc tccatatgta cttattacat ggtcttctgc acttacgttt   2160
ctataccaat cccactacca atttcccaga tccagcgctc gccatctcaa tttgagatca   2220
tcaaacagca tataatggct cggaatcagg ctgttgaggc attacgtgtg atatcactgg   2280
cggcttgcag gttttttcacg tcttttgagt attttaagca ttggggcccc gtggaaaaga   2340
acttggaaag attattagaa agtaataaaa attttacatg tgccccgtag acttaccagt   2400
gatactagct gcatgtgaag agtaatttat agaattggtg gctagcattt tcccttggcg   2460
tttctctcca aagctttact gtaacgccaa aaatggccaa ggctagggggg tcgcgataga   2520
cgggtcgtcg tattacggct ggaaccgagg tggcggccgc aacggaagga gatcacaccg   2580
ttagccccca cttgtttgcg ctagtaaggt cttgtattct acgagtaaa gcgagggtaa   2640
ttgaaatgat gaattacttg gagacattga tcactgacgg atggattcac gtcggaatat   2700
tctcatacac ttagaccgag atggaccgat atgaccgatg ctcttatcgt ttcttcgcgc   2760
gagactgttc tctccagtct cacgggtagt tagtacaata tagtacttat gtgaaaccgt   2820
tgacgacgcc cattcgcctg gtttttttttt tgacatgaat ggctgcttcg tatgttatag   2880
ttcatactcc ccacggagca cattgattaa catgcacatt gttgggatcg agggtgttag   2940
gtaaaccatg tttgtcgccc ggtcttccag ctggttgttt gtcttttttat ttgcatttgc   3000
ccagcttcgc gcagacagcc aataaagagc gtatctcctg ccccctcttg ctttcatcat   3060
atatgcagtg agatccgatt gataccaccg gagtgtgggc caaattagtt acactctcca   3120
ttggccgcaa aatattgaag ccttttgggg ttttttttggc ccccaggaaa atatgcaaaa   3180
ctaatgtgta gtatggggggg gtgtgggttg tgttcaaaac ctgcccagtc aatatggagt   3240
ataggtaaat tacaaccaca atactagtga gatctagcag tggggccagt tcaatgcatc   3300
ttgtgcgtcg taaataagcc cagacacgct aataccgcaa cacttccggt aacaaagaaa   3360
agcaaaatta aagacgtcgc caatttcccc tgatcccat ccatcaatct gacttcaggc   3420
tagcggacct taacgaaaca acgagagcga gatcattcat acaccaaaac acaggtacta   3480
tagaagcgcc gcgcagtaga gattcacacc gccccttgaa gcaaaagtcg gaaggaattg   3540
cgcgatgtca gaacctctac cccctaaaga aggggaacca aggccacaga aggaagaaag   3600
tcaaaatgac acgctcgaag cgactgagtc caagtcccag cacatcacag gcctcaagct   3660
cgggctggtg gttgcttcag ttactttcgt agcatttttg atgctccttg atatgtccat   3720
tatcgtcacg gtaagatggt ggctacctca gaacagagcg cagcacagtc aattgactcc   3780
```

```
agccacaggc aatcccacat atcacaagcg agttccactc tctgaacgat gtagggtggt    3840
acggcagtgc ttatcttctg gctaagtatg gctctgttct ccttgacctt gttcattgta    3900
cgaacagatt agctaacatc atatttagct gtgctctcca gccctggcc ggtaaattgt     3960
atacactctt gggcttgaag tacactttct ttgccttcct ctgtattttt gaactaggct    4020
cggtgctatg cggtgccgca agatcttcca ccatgttgat tgttgggcgg gccgttgctg    4080
gaatgggagg ctcaggtctt gtcaacggag ccctcacaat cctctcaaca gctgctccta    4140
agcacaagca accaggtaag ggaaccgatt tttggaagtc tgctgggtgc cgtgtacacg    4200
ctgacctcgc atatgaagtt tgattggag tgatgatggg tcgtatgtca tctcaagatc      4260
tgatgtaccc caaacgaacg gttcgtcgtc tgacaatatg ttttcagtta gtcagattgc    4320
cattgtctgt ggaccactgc tcggaggtgc tttcactcaa cacgccactt ggcgatggtg    4380
tatgttgacc tttggccttt ttatgattgt tgtccatgtt ctcacttgga attcaggctt    4440
ttatatcaat ctccccatcg gcgctgtcgc tgcattcctc cttctcgtca tcaccatacc    4500
cgaccgaatt tcatccacgg acagcgaact ctcgaccgac aaaccaatgg ccaacataaa    4560
atccacactt cgcaaactgg accttgtagg ctttgtggtc tttgcagcct cgcaaccat     4620
gatttccctc gcactagaat ggggagggtc gacctacacc tggcgaagtt ccgtcatcat    4680
cggcctgttc tgtggcggag ggtttgctct gattgcgttc gtgctatggg agcgtcatgt    4740
tggcgatgct gttgccatga ttcctggctc agtggctggt aaacgacaag tgtggtgctc    4800
ttgtttattt atgggctttt tctctggctc cttgcttgtc ttttcctact atctaccgat    4860
ctacttccag gctgtgaagg atgtttctcc cacactgagt ggtgtgtaca tgttgcctgg    4920
aattcttgga caagtcatta tggctatggt ttctggcttc gcaagtaagt gaaactcgcg    4980
tacacatttt tctccacccc gtccatttct atggctcctt tcttgccaca accgtctgac    5040
atcgggcttg gatatcgtgt atactgacat atgacgcacc agttggaaag acaggatact    5100
atttgccttg ggccctaggc agcgctgttc tcgtcgccat aggcgcaggt ctggtatcca    5160
ccttccagcc ccatacatca actgtgaaat gggtcatgta ccaatttatc gcgggcttcg    5220
gtcgtggttg tggcatgcaa acggtaagct atgaaacctt tgatcatctc tcacgctttc    5280
ggctttgtat caaagcaaga agagcatgca accgctagac gctgacatca atactcaatg    5340
gccagcctat catcgccatc caaagcacgc tttcgcccga acaaggtgcc ctcggaattt    5400
ctctcgccgt gtttggacag acgtttggag gatcgctctt cctggacttt gctaaccttg    5460
tctttgggtc cggtttgaga actggcctga gcaagtatgc gcccactgtc gacacgcagg    5520
ccgtgacggc agcaggggcg actggcttca gagatgtggt cagcaagaat aaccttccag    5580
gggttgtaaa agcttacagt ctcgccgttg atcatacttt ttacttagca gtgggagcta    5640
cggcgtgcac gtttgtgttt gccttttgga tgggatggcg aagattgca accaaaaacg      5700
acacccgggc tgtgcctgag actgatgctt gaccgcgttg ctagatagac acattaccgt    5760
gcctccacaa agaatctcca catacttaat taatgtcgat ttcaaagatt ctatatgtca    5820
ttgcccgcga cccatgtcta gtctaagtcc atctcaaggt tctagtcacc gtggctagat    5880
tggcaacata taactatgtt gagattcata gttagttagt tacggcatct gacaatggat    5940
gattgatgtt tcaggcatca atcctgatac ctcaggaatg aatcagatca acattcaacc    6000
tactcagtaa gttatagctt gaacaaagct ttcactcatt aaataattat gagggatcag    6060
acctaaaaac tctctggaaa aggaccatct ctttatatat tcttcttccc tactacttgc    6120
atcgtaaatt tcaacaacat ataaacatga gatacccttt ctggccgttc actctaccac    6180
```

-continued

```
ctgcctgtct cattgcattg tgcttttgaa aattatgaca ataacaacca atgagaaaaa    6240
atatgatcct cctgcaatga atccactgga gggggtacgg agcttggaat gctcctaaga    6300
ttccgaccta atcagcgtcg agcccgatca gtagctgcag cactcggcct cagtgcattg    6360
ttaggaacag ggactgtcct ggttccgcct gacggggaga cacttcgaga agggctgaa     6420 gatgccgggg cagaacggtt gtgcgccatg tgcgccttga ccaggtgacc ggcggctagg    6480
gcagcacata gcgagagctc cccagccaaa acagcgcttc cgatgatgcg cgcaagttga    6540
cgtgcattct caccgggagt ggtcgggtgt gatccgcgga caccaagcat gtcaagcatt    6600
gcgccctggg gctccagaat cgtaccaccg cccaacgttc caacctcaat agacggcatg    6660
gagacagaga tttgaagcga tccgcgaaga ctaaacagga ttagtgaatg tttccaagta    6720
agcggccgct ttcaacttac ttgttcatga gagtgatgca gttagcgctc tccacaactt    6780
gcgccggatc ctgacctgtg gcaatgaaaa tggctgccgc aagattggca gcttgggcgt    6840
tgaagccgcc aactgagcca gccatagcgg acccaatcag attttcgat atgttgagct      6900 gaaccatgct atccacatcg ctctttaaga catccctgac aacgttcgcc ggtatgatgg    6960
cttcggccac aatgcccttg ccccgtccat cgatccaatt caaagctgaa ggtttcttat    7020
ccgtacagta atttcctgat agggtaataa tattcatatc gctgaaacct gcctctgtcg    7080
ccataacatt cagtgcatgc tccacgccct tagaaatcat attcattccc atagcgtcgc    7140
cagtagtagt cttaaatcga atatataagt gagtaccggc gatagttgtc cgcatacttt    7200
gtaagcgcgc aaatctgctg gttgaattga aggcttcttt cattacggtc tggccgacgt    7260
ccgaatcgag ccagatctta gcagcaccag ctcgttcaag gacatcaaac ttcacacacg    7320
ggcctcgtgt cataccgtcg ccagtcagga ctgtcacggc accgccaccg aggttgattg    7380
ccttactgcc acggctagca ctagcgacga ggacgccctc ggtggttgcc ataggaatga    7440
aataactctt gccgtcgata acaataggac cggcgacgcc aacagggact ggcatatagc    7500
caataacgtt ctcgcaacat gcaccgagca gcgttccca ggcgtagttt tcgtacggca     7560
gcttcgagtg ctccagcata cttgtaagct ctgcggtagc cggtgtcctc gaaatgatag    7620
agcggcgaac cttgacggca cgagtgcagt cttttgagact cttctctagg gcatacccgg   7680 gaaccttttcc ccgcaaagac aaggcaacga catcctcatc gttcaactcg ctgattgtgt   7740
tctgcttcag caaattgtcc agttcgattt gtgtgcgaga cacgggaagt tcactagtgg    7800
ctgtctttcc ttctgctcgc ttagtgacct ttagagatgc tttaattaag actaatgagg    7860
catcactgtc actgtcggtg gtggtaggag tgaacactct ggtctgagga gcttggagac    7920
ttgattgaat ctgagggtc tggttctggg cagcgttgaa gctttcggcc tggtcaagct     7980
caactggatc aactgggtga ctcgggagat taggatcttt gattcccagt ctggcggcct    8040
tgaacagata gctgttcaga gcgacactta gggcaagtgc cacaaacacc catttggaga    8100
ggacgggatc ttccaggctg gtgagcaggc taccgaccat ttttccacca actccatact    8160
cgtgtagctg cgaggtacca cggtgaatgg aaggatactc tagttcgtac ttgatggggg    8220
cgaggacagt gaccatagtc gattgaccgc gccctcttgc ctggaaaagt agttcatcta    8280
gtccacttcc agctaccttg aagggctcaa gcggggggttt aatggccgat ccgctcagac   8340
tttcggtcca agatgatata ctggacaacg atccactaga agaggcttgg aaaagggtgg    8400
agccgatgtt gacgaggttg acgataagga aaccaacgac catccagaat ttgaacttcg    8460
gaacactgct gcctttcata tcattgccaa acagatatgt acgtgcactg tcttgggcat    8520
```

```
cattgctggt cgcgacactc tccgccgtcc gctgactgag accctcatct tccaacgcgt    8580
accgcatgtt gatatgacgt ttgaggcggt ttacctcgag cttgatagac agaatcgcag    8640
tgtagaatgt aaacagcagc agacagtcaa agaacaggat caatgcagct agaacacaga    8700
agtgctgtag cccaccttgg atgcctaaga cagcaccgat aactaggagc aggatctcga    8760
ccacgtagtg gcacacgata ttgtaaccct tctcccgaat ggcgcttcgt acggcgtaat    8820
tgatggtact ttcagcaatg gctgtcacgc taccctggtc agactgtatc ttctgggggct   8880 ttcggtgctg cacagcatag gacaaaacag ccctggtcag agtgatgctc ttctcaaagc    8940
caacgatcac caccaagaag gggaggcctt cggatagcaa cctcatgctc atcggaaccc    9000
ctagtcttat ggccacgtcg agaccgagga gaaaggcaaa tgttgacgac aaaaggacgc    9060
ttgtagccag ccaaaccttc gatcccaatt ttttcatgct gaggaagagt gagacgaaag    9120
tcaagtgcat tgatatataa cctagcacca tgacaaccac gtcgagcgtt tgagcgctct    9180
tgataagatc aagagactct gtccaggtat cgtgcaccca ttgagcaagg ctgcgttttg    9240
tgtgagccct ggcagccttc atgatccaca tctggcgttc catctcgatc aattgcgtct    9300
cctgcaattt caggtcggca ctgttgttgg ggatttcttg aacagcagcc acgagttccg    9360
gcgcgctgct gtattccaca gagaaggcga aaactttatc tttcgaatag gcggttaaag    9420
ggctcgacgt tgagggaagg tcaatcacag ataggttcac aggggaggga gcaaggaatg    9480
gtgaggctgc ttgagatgca accccatatg accccgggaa taccaaggtc attagtgctt    9540
gatggttgaa atctccgaga acatctgcat ccccgtcgaa gctctgccac ttccagccat    9600
tctgtgggcc ggtgatcaag cttcgacttc cttcgaccaa agagccccat tctgctttat    9660
caacgtttgc ggggccatgg aagaagctgt ctttgagtag tccaacgtat gtggtactag    9720
ctagaatagc tatggtgcaa acggtatgga tcgggtgtag acacgccgtt ttggatagaa    9780
attggagtgt ggaggtcaat gcccgatttc ccgagcgtag agggtgctgc tgattcattg    9840
attccctacc gcgaaagcga gagggtagca acgaagcgac catgctgaaa ggtctgtgct    9900
acagcttgga gtggtaccta tagctaggta gtctctgaga aaagaatcta gtcagctctg    9960
caaatgggga cggaaaagca cttcaattgg gaattagggc ttgagataaa gtgcatacct   10020
ccaaaatcga atgagcaacc taatcggtta ggcgcctagg tataatctgc cgtcgtagat   10080
tggaggaagg ttgttcggcc caaggggttg ggagggacaa ctgaacagtt cctaggtacg   10140
ggaaatgagt agaagaaaat aacaaatggc gcgcgcccct gaggctgagg cagcggaaag   10200
attcgcttcc ttatccctgc atctggtcca cctttatgaa tggattcatg accggtgtca   10260
actgctgcct agggtataat tggtaagggg taccaagcaa aggatagtag gaccaattgc   10320
actgaaaact agtatttgtg ctcataacta tgctcagttt ccaaggtttt tatgcataaa   10380
tttatccttt attcgagaaa aagaattct ggggacacca atcaattgcc ctgataccta    10440
ggaatgtgaa cttccaagat tgttccgaaa gtaggccaaa tgaccaataa dacagaacac   10500
tacctaggta tagttatttt gtcatgccta gatccgacat acaaggagc gtcctcttac   10560 atagacgtcc tgttagacgt ttctaatctg actcgtattg tggtccttttt ttggtggggc   10620 ggcaagctgc atcgatcacg cccggacgag gccacttcgt gaggaatgga aatatattgt   10680
gcctacggag taatgcacca cgaaacacat tcttctcgaa acgactactt acgcagggat   10740
gtatgggtat tattctgtcc acgaaaagcc agtgtcaacc cccccccccc cccccccccc   10800
cggtatcatt tatctcagta aacagcaacc tgaacaagat acccaggtag acaagaagtc   10860
agtttggagt atagtgtata gactcgggaa cattttgtgt ggacctccgt acgtgtctct   10920
```

```
caaatcggcg tctctcggtc tttggatacc ttcggagtta cacggggctt tgttgccaag    10980
gcttcaatat tcggcgcatg gattttcttt gtgcatgggt ctgagtgggg tgccgtaagg    11040
tatggtattg ctcccgattg ggagttctga cagatgatca tgccgccttc cgaagtagaa    11100
aaaagaggaa agggtcacat gctcatgatg atcgtttgct cgcgatgaat tgcgcttcct    11160
gcatatattt tgtttgcttg tcttagtcaa ccgataatgc aaattttggg gattgtgtat    11220
tgttggaaat tgaattacca actgcttaca ggacccaccc tgcgctcagg ccctcaacaa    11280
accttgggac aggattaccc actaagcctt tccaagcttt tccaaggctt ttggattcgt    11340
ttggtttgat agctcgtatg cgtatttcgc atctgtgtac ggagtatcgg attctgacag    11400
cctccattat acccgaaaac tacctggccg gcctgacctg tttcgtcttg ttcgacggtt    11460
tcccatcggc gttttgactc gggattatcg tgacgacaga caatgcctcc cgaaccggta    11520
cctctaaggt attgccccga gcatagcatg gtggtccggg gtttcccatg ggcacagagc    11580
gaatatcgtg tcacgtccaa gatgaaaaca acccccgaac tatgaatcac gtgtcggggg    11640
cagcttatgc atctatagct atgccaggga cctgtagact gttggaagac tatcaacggt    11700
tttatcacca gggcgactga tatatcagtc aatgaaacaa cgttggaatg aacaataccc    11760
ccgccgtaac cgcaaccgca accgcaaccg caaccgcaac cgcaatggca ggctcggctt    11820
gctctaacac atccacgccc attgccatag ttggaatggg atgtcgattt gctggagatg    11880
caacgagtcc acagaagctt tgggaaatgg ttgaaagagg aggcagtgcc tggtctaagg    11940 tccctcctc gcgattcaat gtgagaggag tataccaccc gaatggcgaa agggtcgggt    12000
ccgtgagtat ctaacatgca tgcatttata tcttgttttg aatatttgac acaagatttg    12060
agcatcactg aagcttggtt actgactcca aggatgactg gatagaccca cgtaaagggt    12120
ggacacttca tcgacgagga tcctgcttta tttgacgccg cgttcttcaa catgaccaca    12180
gaggtcgcca gcgtatgatt atttcaattg atctaacccg ggacgcagag atctaatatt    12240
ggacagtgca tggatccgca gtatcggctt atgcttgagg tggtctacga atcgctggag    12300
agtggtatgt agtgtgggtc atcctcactg taagcaaacg tcactgacca tcatccagcc    12360
ggtatcacca tcgatggtat ggcaggctct aatacgtcgg tgtttggggg tgtcatgtac    12420
cacgactatc aggattcgct caatcgtgac cccgagacag ttccgcgtta tttcataact    12480
ggcaactcag gaacaatgct ttcgaaccgg atatcacact tctacgactt acgtggtccc    12540
agcgtgacgg ttgacacggc ctgttcgacg acattgaccg cactgcactt ggcgtgccag    12600
agcttacgta ctggggagtc agatacagcc atcgttatcg gtgcaaatct tctgctcaat    12660
cccgatgttt ttgttacgat gtcaaacctg gggtgagttt tccgaagaag attccagatc    12720
gagagtcttg aactaagcaa tccttgttgc tcaatgacag attttttgtcc ccggatggta    12780 tctcgtactc ttttgatcct cgagcgaatg gatatggtcg cggggaagga attgccgctc    12840
tggtaataaa ggccctccct aacgcgttgc gagaccaaga ccctatccga gccgtcattc    12900
gagagacagc gctgaaccag gatggcaaaa caccgcaat tactgcgccg agtgatgtgg    12960
cgcagaaaag tctgatccag gagtgttacg ataaggctgg gctagatatg tcgttgacct    13020
cgtacgtgga ggcccacgga actgaacac caactggtga ccccctttgaa atctcagcaa    13080 tttcagcagc ttttaaagga catcctctgc accttggctc tgtgaaagca aatattggcc    13140
atacagaagc cgccagtggc ctggccagta taatcaaggt ggccttggcc ttggagaagg    13200
gcttgattcc ccctaatgcg cggttcctgc aaaagaacag caagctgatg cttgaccaaa    13260
```

```
agaacatcaa ggtaaggctt tgcgcattcg cagattcagt tatatgtttc aaaggttaat   13320
gtttcaaaga tccccatgtc tgctcaagac tggcctgtga agatgggac tcgtcgcgca    13380 tctgtcaata acttcggctt tggtggttcg aatgctcacg tcattttgga atcatatgat   13440
cgcgcatcat tggccctgcc agaggatcaa gtgcatgtca atggtaactc tgagcatggt   13500
agggttgagg atggttccaa acagagccgc atatacgttg tgcgtgccaa ggacgagcaa   13560
gcttgtcggc gaacgatagc aagcctgcga gactacatta aatccgtcgc tgacattgac   13620
ggggaaccct tcctcgccag cctcgcctat acactaggct ctcgccgttc cattctgcca   13680
tggacgtcag tgtatgtagc agacagcctt ggcggccttg tttctgccct cagcgatgag   13740
tccaatcaac caaaacgagc gaatgagaaa gtacggctcg gatttgtatt caccggtcag   13800
ggggcgcagt ggcatgcaat gggcagagag ctggtcaata cattcccagt attcaaacag   13860
gcgattcttg aatgtgatgg ctacatcaag caactgggcg cgagttggaa ttttatgggt   13920
aagttgcgag cccgggaaaa gtaatactgt atcaagcttg aggtactaac attcaattgc   13980
acagaggagc tccaccgtga tgagctgacg actcgggtaa atgatgccga atacagtcta   14040
ccactgtcaa ccgctatcca aattgcactt gtgcgtctcc tttggtcatg gggaattcgg   14100
ccaacgggga taaccagtca ctcaagtgga gaggctgctg ctgcctacgc agctggggct   14160
ttatccgcgc ggtcggccat gggatcact tatatacgcg gtgtattgac cactaagccc    14220
aagcccgcat tggcagccaa aggaggaatg atggcggtgg gtcttggtcg cagtgagacc   14280
aatgtttaca tttcgcgtct caaccaggag gacggctgtg tggtggttgg atgtatcaac   14340
agtcaatgta gtgtgacggt gtcgggagat ttgggtgcaa tcgagaaact tgaaaagttg   14400
ttacacgccg atggcatctt taccaggaaa ctgaaagtca ctgaagcctt ccattcaagc   14460
cacatgcgac caatggcaga tgcctttggg gcgtcactga gagatctgtt caactcggat   14520
aacaacaacg acaatcccaa tgctgacacc tcaaagggtg tattatattc atcacctaag   14580
actggtagtc gcatgaccga tcttaaattg ctattggatc ccacacactg gatggatagt   14640
atgctacagc cggtagagtt cgagtcctca ctccgcgaga tgtgctttga tcccaacacc   14700
aaagagaaag ccgtcgatgt gattattgaa atagggcctc acggagcgct tggtggtcca   14760
atcaaccaag tcatgcagga tctgggtctg aaaggaacag atataaacta tctcagttgc   14820 cttttctcgcg gcagaagctc gttggagaca atgtatcgtg ctgctacgga gttgataagc   14880
aagggttatg ggctcaaaat ggacgctata aactttcctc atggaagaaa agagcccaga   14940
gtgaaggtac tgagcgattt gccggcgtac ccgtggaatc accaaacccg ttattggaga   15000
gagcctcgcg gcagtcgtga gtccaaacag agaacccatc cgcctcacac tttgataggc   15060
tcacgggaat ctctctctcc tcatttcgcg cctaaatgga acatgttct ccgtctgtca    15120 gatattccat ggatacgaga tcacgtcgtt ggttcgagca tcatctttcc gggagctggc   15180
ttcatcagca tggccatcga gggtttttca caagtctgcc caccagttgc gggggctagc   15240
atcaactaca acttgcgtga cgttgaactc gcgcaggctc tcataatacc cgctgatgca   15300
gaagcagagg ttgacctgcg cctaacgatc cgttcatgtg aggaaaggtc cctcggcaca   15360
aagaactggc atcaattttc tgtgcactca atttcgggcg aaaataatac ctggacagaa   15420
cactgcaccg gattaatacg ttcggagagc gaaagaagcc accttgactg ttcaactgtg   15480
gaagcctcac gcaggttgaa tctaggctca gataaccgga gcattgatcc caacgatctc   15540
tgggagtcct tacacgcgaa tgggatatgc cacggaccca tttttcagaa cattcagcga   15600
attcaaaaca atggacaggg ctcgttttgc agattttcca ttgctgacac tgcctcggct   15660
```

```
atgcctcact cgtacgagaa tcgacacatc gtccatccta ctactctgga ctcggtgatc   15720
caggcggcat acacggtgtt accctacgcg ggaacacgta tgaaaacggc catggtacca   15780
aggaggctaa gaaatgtcaa aatatcctct agcctggctg acttggaggc tggtgatgct   15840
ctggacgcac aggccagcat caaggatcgc aactctcaat ccttctctac cgacttggca   15900
gtgtttgatg actatgatag cggttcttct ccctcggacg gaatcccagt catagagatt   15960
gaaggccttg ttttccagtc ggttggaagc agcttctctg accaaaagtc agactccaac   16020
gacacagaaa atgcctgcag ctcctgggtt tgggcccctg acatcagctt gggtgactcc   16080
acttggctca agaaaagtt gagcactgag gctgagacga agaaacgga actcatgatg    16140 gacctccgaa gatgcacgat caactttata caggaggctg tcactgattt gacaaattct   16200
gatatccaac atctggatgg ccaccttcag aagtatttcg attggatgaa tgtccaattg   16260
gaccttgcga gacaaaacaa gctcagccca gccagttgcg actggctaag tgacgatgct   16320
gagcagaaga aatgcctaca ggccagagtc gctggagaaa gcgtcaatgg cgagatgatt   16380
tctcgtctag gacctcagtt aatagcaatg ctacgccgcg aaacagagcc acttgagttg   16440
atgatgcaag atcagctgct aagcagatac tacgtcaacg caatcaaatg gagccgatca   16500
aacgcacaag ccagcgagct gatccgactt gcgcccaca agaacccgcg ttctcgcatt    16560
ttggagattg gcggaggcac gggcggctgc acaaagctta ttgtcaatgc attgggaaac   16620
accaagccga tcgatcgtta tgacttcacc gatgtgtctg ccgggttttt cgagtcggcg   16680
cgtgagcaat ttgcggattg gcaagacgtg atgactttca aaaaattgga tattgaaagc   16740
gatcccgagc aacaagggtt tgaatgtgcc acctacgatg tggtcgtggc ttgccaggtc   16800
ctgcatgcaa ctcgatgcat gaaacgaaca ctgagtaacg ttcgaaaatt gctcaagcct   16860
gggggcaact tgattttggt tgagactacc agggatcagc tcgatttgtt ctttaccttc   16920
ggactgttgc caggttggtg gctcagtgag gagcctgagc ggaagtcgac gccatcgctc   16980
actaccgatc tttggaacac catgttggac acgagcggtt tcaacggtgt ggaattggag   17040
gttcgtgatt gtgaagacga tgagttttac atgatcagca aatgctatc gacggctaga    17100 aaagagaata caaccccgga tacagtggca gaatcggagg tgcttttgct gcacggagcg   17160
ctccgacctc cttcatcttg gctggaaagt ctccaggcag caatttgtga aaagaccagt   17220
tctagcccat cgatcaacgc tctgggcgag gtagatacca ctggaaggac atgcattttt   17280
cttggggaaa tggagtcctc gctccttgga gaggtgggaa gcgagacctt caaatccatc   17340
accgcgatgc tgaataactg caacgcactt ctctggtgt ctagaggagc agccatgagc    17400
tccgaggatc catggaaagc tctacatatt ggtctgctgc gtaccatccg caacgaaaat   17460
aacgggaagg aatatgtatc gttggatctc gatccttctc gaaacgcata cacccacgag   17520
tccctgtatg ctatctgcaa tatcttcaat ggccgcctcg cgaccttttc gaagacaag    17580 gagtttgaat ttgcagagag aaacggcgtc atccacgtac cgcgactttt caatgacccg   17640
cactggaagg accaagaagc ggttgaggtc acactgcagc cgttcgagca acccgggcgt   17700
cgtctgcgga tggaggttga gacgccaggg ctcttagact ccctgcaatt cgagacgac    17760 gaaggacgtg aaggcaagga tcttccggat gattgggtag aaatcgaacc caaagctttc   17820
ggtctcaatt ttcgggatgt catggttgcc atgggtcaat tggaggccaa ccgtgtgatg   17880
ggcttcgaat gcgccggagt gatcacaaag ctcggtggag ctgctgccgc tagccaaggc   17940
ctcagattag gggaccgcgt atgtgcacta ctgaaaggcc attgggcgac cagaacacag   18000
```

```
acgccgtaca ctaatgtcgt ccgtattccg gacgaaatgg gcttcccaga agccgcttcg   18060 gtcccctgg ctttcactac cgcatatatt gcgctttata ccacggcaaa gctacgacga    18120
ggcgaaagag tcttgatcca cagtggagct ggaggcgtcg gtcaagcagc gatcattttg   18180
tcccagcttg cgggtgccga ggtcttcgtc acagcgggaa ctcaagccaa gcgtgacttt   18240
gtcggcgata aattcggcat caatccggat catatcttct cgagcaggaa tgacttattc   18300
gtcgacggca tcaaagccta cacgggcgga cttggcgttc atgtcgttct aaactcattg   18360
gcaggtcaac tcctccaagc aagctttgac tgcatggccg aattcggcag atttgttgag   18420
attggaaaaa aggacctgga gcaaaacagc agacttgaca tgctgccatt cacccgggac   18480
gtctctttca catcaattga tcttctctcg tggcaaagag ccaaaagtga agaagtatcc   18540
gaagcgttga accatgtcac aaaactcctc gagacaaaag cgattggctt gattggtcca   18600
atccagcagc actccttgtc aaacatcgag aaggccttcc gtacgatgca gagtggtcag   18660
catgttggca aagttgtggt caatgtatct ggggacgaac tggtcccagt cggcgatgga   18720
gggttctcgc tgaagctgaa gcctgacagt tcttacctag ttgctggtgg gctgggggga   18780
attggaaagc agatctgtca gtggcttgtt gatcatggcg cgaagcactt gattatccta   18840
tcgagaagtg caaaggccag tccattcata accagcttgc aaaatcaaca gtgcgctgtc   18900
tatctacacg catgtgacat ctcagatcaa gatcaggtca ccaaggtgct ccggttgtgc   18960
gaagaagcac atgcaccgcc aattcgaggt atcatacaag gtgccatggt tctcaaggac   19020
gcgcttctat cgcgaatgac attggatgaa tttaatgcag caacacgccc aaaagtacag   19080
ggtagttggt atcttcacaa gatcgcacag gatgttgact tcttcgtgat gctctcatcc   19140
cttgttgggg tcatgggtgg ggcaggccag gccaattacg cagctgctgg tgcattccag   19200
gacgcacttg cgcaccaccg gagagcccat ggcatgccgg ctgtcaccat tgacttgggc   19260
atggtcaagt ctgttggata cgtggctgaa actggccgtg gtgtggccga ccggctcgct   19320
agaataggtt acaagcctat gcatgaaaag gacgtcatgg atgtgttgga gaaggcaatc   19380
ctgtgttctt cccctcaatt tccatcacct cccgcagctg tggttacagg aatcaacaca   19440
tccccgggtg ctcactggac cgaggcaaac tggatacagg aacagcggtt tgtgggactt   19500
aaataccgcc aagtccttca tgcagaccaa tcctttgtct cttcgcataa aaaaggacca   19560
gatggcgtgc gggcccaact aagcagggtc acctctcacg acgaggccat ttctatcgtc   19620
ctcaaagcaa tgacggaaaa gctgatgcga atgtttggtc tggcagaaga cgacatgtcc   19680
tcgtccaaaa acctggcagg tgtcggcgta gactcactcg tcgccattga acttcgaaac   19740
tggatcacat ctgaaatcca tgttgatgtg tcgatctttg agctcatgaa tggtaacacc   19800
atcgccggcc tcgtcgagtt agttgtggcg aaatgcagtt aagttgaagg gttcagtgaa   19860
gccttttgtc tggccaagcg ggtatagctc gacggaggta tagtacgaag gagcatagcg   19920
gccatggtct gaagcctgaa tccaatctga atcgagcctg gctgagcct gactatttaa    19980 tgcctgactt ctggatagca gtaaatagag atacctgaaa taccattaca gtggccctga   20040
gaagcaacaa agtacacatg tgcactcgtt ctcgaagtcg gaagagtgaa tgctttttat   20100
actaccaggg aagctgtctt agcacctcgg aggcttgact gtcaaaagtt ctctcttttt   20160
ctctccatta tgattcccgc aagccttgta aatgcgcgtt gaacggtcga aaggcgttgg   20220
cacgggcagt gggtacagat tgtggatatg tagtcggaag gcgggaggga gtacttgtgt   20280
ccacgtcgtt gcgccgtcct ctctttcgcc tagtcgggga tgttgagtag gaacatcaag   20340
acttaacaga gcctaagccc tcgtcatcgt aagcgccagt caacgcctga gagaatgggg   20400
```

```
agatcggtga ttgtaccggg agaaaagctt cattactgcc gacttcccta cgtggcggtg    20460
tagctggcgg tatagaagca gatggccgct ctgcgtagca ggaatacaca ctctctccct    20520
tctctctctc tgtgtttctg tctctcgcac atagccaaag tctacaccac gttcgattac    20580
aaagaaggca tcacaatcga ataaaatgcg tttttatttta ctaacctact cgactaatac    20640
agcacctagt ttctctggga cggaaactat tggaataagc ctggggacgg atgcatattt    20700
gttttagttt gcgtgttata tcttagcacc ggtcatgagg gagcgggatg tcctcgttgc    20760
gccggcgtac catgagcttt gtggttggat gcatacgaac gctaaaagcg tgacggtagt    20820
atttgtcatc gtctcctggt acaggcttca catcatactg aatcagtata tgagcgagga    20880
gaatcttgat ttccttcgag gcgaagaacc gcccgggaca gcgcgtggg ttccagccga    20940 agccgatgtg atcaccgttg gtattctcca attgagcggt gaaggccttg tctggatcct    21000
cgcgcatgcg cataaatcgg tagggatcat aattttcggg gttttcccac acatcagggt    21060
tgttcatgcg gtctgcagcc acagcggcca actcgcccct gggaatgaag aggccattgg    21120
atagagtgat gtctctgaga gcggtactgc gcatagtggc gcactcgacc ggcttgattc    21180
gctgcgtctc tttcatgcag ctgtcgagga gcttcagctt gaacagagag gcaggcgtcc    21240 agccccttc tccgattaca gtgcggatct cttggcggag aggctgaata aggtctgggt    21300
gcctggcaat gtccacaagg gcaccgacga aagatccgt cgaggcgtag atgccggcga    21360
aatccatagc gagctgagca cccgccacat cgtaccagcg gccgtcggcg gtgtcttcaa    21420
accattgcat ggtatcgacg tactggggcg gctgcacgcc cttcgctaca catgcggcct    21480
tttcagcacg tcgtcgctga atctcaggat caatgatctt tcgtgcgcgg cgcacttggt    21540
cacgcaattt gcgtccttgc ggttgaaacc agtgagcgag cggtcgcagt agcatgggcc    21600
atacgcgaag ttggcgagct tgtaccgcca cactcacggc atggttcttt gcaatatcca    21660
gccactcctc attgtggcag attttgtcgc cgaccataat gagtgtgact gttcgtgtga    21720
caaggtccaa tccattggaa tagacaggtg cggtttgcca ctctagtata ttcgcggtat    21780
gtcagccaga ggctcaatgc tcaagacaga aaaattgaca cttaccctcg cttttaccga    21840
acaacttggc aatagtagcg tcggccaagg tagccaatgg cttttgtgtac ttgggggctt    21900 gggtttgtaa ctggttcaaa acaactttgt tgacaagatg tgcatcctgg cagatttcct    21960
tgaacccgtc gaatccaggg agatgagagt gaaagtccta tacattcatc agaatcttag    22020
agacgtcatt gagttacaac aatggaaaat tcagaggtca tacatccgcc aaaaacttgt    22080
acatgcacat atctttgatt ttccgaaact cgtcggccat ggacgatggg aggatggtgc    22140
aatagccgga atcaacaatg aagcgcaggg gcttgtcgtt tttcgagaac caagcttcga    22200
tccagctcgg accatacgta tcgaagtcct gcctagccct catggtcgtc aactcccacc    22260
attttttggg attatagact tgcagttcgg actggcgccc ccgcaaacgg taggcgatga    22320
gactaagaag cactgcgacc gccacaaggg cttgaggggt cgatacccat tggtacgatt    22380
cgacggtcag aagaacctgg ccgagcattg cgtgagacag ataggaccta tgcacaccag    22440
tggaaaagaa gaaagagcga agaatgagag cgctgcgacg gtttataatc gaataacagc    22500
actaatgctt ctgggatttt gtggccgaga gcactcttcc agtcaacctt gaaaaaaaaa    22560 aaacccccc cccaatcgaa gtttacctgg atggggcagt tcggttgttt cctttaggag    22620
cagcttcacc gagcagcaca agaacaatcc gagtgaaaaa ctcggtttca ccttgataca    22680
gccaattgat attcacgttt gattcattca gcctcgtgtg accgaataac gccgtatgga    22740
```

-continued

```
ggaatggcta ttcgtgcacc gaatgacgcc gggagggttt gctaggtgcc gagcttgcat    22800
tgctgggaag tgggggcatt tgagtactag aatggatctt gaaattgtcc gaatctagat    22860
gagtactgat acgtgcaagt aaatataacg acggtatcgg ttgcaaggcc ggcttgttcg    22920
ctcagagatt caactctgcg attctgtaag aacaaatgtt gtgcccggca tgcagtgaga    22980
agatctactg acgcaagaca aggtttaatc ccaatcctat cgcccaaaaa caggatcagc    23040
agttatggat caagccaact atccaaacga gccaattgtg gtagtgggaa gcggttgtcg    23100
gtttccaggt ggtgtcaaca caccatcaaa actttgggag ctgctcaaag agccccggga    23160
tgtacagacc aagatcccta aggagagatt tgacgtcgat acattttaca gccccgatgg    23220
cactcacccc gggcgcacga acgcacccct tgcatacttg ctgcaggagg atctacgcgg    23280
ttttgatgcc tctttcttca acatccaagc tggagaggcc gaaacgattg acccacagca    23340
aaggctgctg ctggagacgg tctatgaagc tgtatccaac gcaggcctac ggatccaagg    23400
ccttcaagga tcctctactg ctgtgtacgt cggtatgatg acgcatgact atgagactat    23460
cgtgacgcgt gaattggata gtattcctac atactctgcc acggggtag ctgtcagtgt    23520 ggcctccaac cgtgtatcat acttcttcga ctggcatggg ccgagtgtga gtgccactca    23580
ttgagcgagc ccgacttcgt caagtgctga cagattcctg actgattctg cagatgacga    23640
tcgacacagc ctgtagttca tccttagctg ccgtgcatct ggccgtccaa cagcttagaa    23700
cgggcgagag taccatggcg gttgcagccg gtgcgaatct gatattgggc cccatgacct    23760
ttgtaatgga gagcaaattg aacatgctgt cccccaatgg tagatctcga atgtgggatg    23820
ctgctgccga tggatatgcc agaggagtaa gttgacaatg catcaattcc tttcaaaaaa    23880
agcaagatgg cactgacctc ctgtaactgc tttttaggaa ggtgtttgct ctattgtcct    23940
gaaaacgctg agccaggcac tgcgcgacgg ggacagtatc gagtgtgtta ccgagagac    24000 cggtatcaac caagatggcc gaacgacagg tatcacaatg ccaaaccata gcgcacaaga    24060
agccctcatt cgggccacat atgccaaggc tggtcttgat attaccaacc cccaggaacg    24120
ctgccagttc tttgaagccc atggtaagtg gtattccctg gaagtatcag ccttatggaa    24180
gttgcagaaa gtctctctct ccctaacacg aagatcccag gaactggtac accagccggt    24240
gacccacagg aagctgaggc tattgcaaca gccttcttcg gacacaagga tggaacaatc    24300
gacagcgacg gcgagaaaga tgagcttttt gtcggcagca tcaagacagt tctcggtcac    24360
acggaaggca ctgctggtat tgcgggctta atgaaggcat cgtttgctgt acgaaatggc    24420
gtgatcccgc caaacctgct gtttgagaag atcagtcccc gtgtcgctcc gttctatacg    24480
cacttgaaaa ttgcaacgga ggccacagaa tggccgattg ttgcgcccgg gcagcctcgc    24540
agagtcagcg ttaattcatt tggtaaggat tcaactgcac ttcttgagaa cgaaagtgaa    24600
gttagctaaa catataaaca catcaggatt tggtggtaca aatgcccatg ctattatcga    24660
agagtatatg gctcctccac acaagccgac agcagtggta acagaggtga cctcagatgc    24720
agatgcatgc agcttgcccc ttgtgctttc atcgaagtcg cagcgctcca tgaaggcaac    24780
gctagaaaat atgctccaat ttctggaaac gcatgatgac gtggacatgc atgatatcgc    24840 ataccctta cttgagaaac ggtctatctt gcccttccgt cgtgcgattg cagcacacaa    24900
caaggaagta gcccgcgcgg cactggaggc tgccatcgcg gacggtgagg tcgtcaccga    24960
cttccgcacc gacgcgaatg acaaccctcg cgtactaggt gtctttactg gccaaggtgc    25020
acagtggccg ggcatgctga agaagctcat ggtgggtatg ccatttgtga gaggcattct    25080
cgaagagctg gataattcac tgcaaacact gcctgaaaag tatcggccta cgtggacact    25140
```

```
gtatgaccag ctcatgcttg aagggatgc ctcaaacgtc agactcgcca gcttctccca    25200
gcctctatgc tgcgccgtac aaatcgttct ggtccgactt ctcgctgcag ctggtatcga    25260
gttcagtgca attgtcggcc acagttcagg tgagattgcc tgtgcctttg cggcaggatt    25320
catcagtgcc actcaagcta tccgtattgc gcatctgcgt ggagttgtgt ccgcggagca    25380
tgcctcttct ccaagcggcc agacaggcgc tatgctagcg gcaggtatgt cgtacgatga    25440
cgcaaaggaa ctatgcgagc tcgaagcctt tgagggtcgg gtctgcgtcg ccgctagcaa    25500
ttcaccggat agtgtgacct ctccggcga catggatgct atccagcacg ttgaaggtgt     25560
cttggaggat gaatccactt ttgccagaat cttgagagtt gacaaggcct accattcgca    25620
tcacatgcac ccatgcgcag ctccatatgt caaggcattg ctggagtgcg actgtgctgt    25680
tgccgatggc caaggtaacg atagtgttgc ttggttctct gccgtccacg agaccagcaa    25740
gcaaatgact gtacaggatg tgatgcccgc ttattggaaa acaatctcg tctctccggt     25800
cttgttctcg caggctgtgc agaaagcagt catcactcat cgtctaatcg acgtcgccat    25860
cgaaattggc gccccacctg ctctcaaggg tccgtgtcta gccaccatca aggatgctct    25920
tgccggtgtg gagctgccgt ataccgggtg cttggcacga aacgttgacg atgtggacgc    25980
ttttgctgga ggtctgggat acatttggga gcgtttcgga gttcggagta tcgacgccga    26040
gggcttcgta caacaagtcc ggcccgatcg tgccgttcaa aacctgtcaa agtcattgcc    26100
cacatactct tgggatcata ctcgtcaata ctgggcagaa tctcgctcca cccgccagca    26160
tcttcgtgga ggtgcgcccc atcttctgct tggaaagctt tcttcttaca gcacagcatc    26220
gaccttccag tggacaaact tcatcaggcc ccgggatctg gaatggctcg acggtcatgc    26280
gctacaaggc cagactgtgt tccccgctgc tgggtacata attatggcca tggaagctgc    26340
catgaaggtg gctggtgagc gtgccgccca agttcagctc ctggaaatct tggacatgag    26400
catcaacaaa gccatcgtgt ttgaagatga aaacacctcc gtggagctga acttgacagc    26460
cgaagtcacc agtgacaatg atgcggatgg ccaagtcacg gtcaaatttg ttattgattc    26520
ctgtctggca aaggagagtg agcttttcga catccgccaa aggccaaatcg tcataaccct    26580
tggcgaggca tcaccgtcat cgcagctttt gccgccacct gaggaagagt accccagat     26640
gaacaatgtc aacatcgatt tcttctatcg ggaacttgac ctccttgggt atgactacag    26700
caaagacttc cgtcgtttgc agaccatgag aagggccgac tccaaagcta gcggcacctt    26760
ggctttcctt ccacttaagg atgaattgcg caatgagccc ctcttgctcc acccagcgcc    26820
cctggacatc gcgttccaga ctgtcattgg agcgtattcc tctccaggag atcgtcgcct    26880
acgctcattg tacgtgccta ctcacgttga cagagtgact ctgattccat cgctctgtat    26940
atcggcgggt aattctggtg aaaccgagct tgcgtttgac acaatcaaca cacacgacaa    27000
gggtgatttc ctgagcggcg acatcacggt gtacgattcg accaagacaa cgcttttcca    27060
agttgataac attgtcttta agcctttctc tcccccgact gcttcgaccg accaccgaat    27120
cttcgcaaag tgggtctggg acccctcac gcccgaaaaa ctgctggagg accctgcgac    27180
gttgatcata gctcgggaca aggaggacat tctgaccatc gagcgaatcg tttacttcta    27240
catcaaatcc ttcctagccc agataacccc cgacgaccgt caaaatgccg acctccattc    27300
ccagaagtac attgaatggt gtgaccaggt tcaggccgat gctcgggctg gccaccatca    27360
gtggtaccag gagtcttggg aggaggacac ttctgttcac attgagcaaa tgtgtgaaag    27420
gtacacccaa agctgttccg tgtttttca ttcttttata ttaacctttt acttgaagca     27480
```

```
actcgtccca cccacatgtg cgcctgatcc aaagggtagg caaagaatta atttcaattg    27540
ttcgcgggaa cggggatcct ttggatatca tgaaccgcga tgggttgttc accgagtact    27600
ataccaacaa gctcgccttt ggctcagcaa tacacgtcgt tcaggatctg gttagccaaa    27660
ttgctcatcg ctaccaatcc attgatatcc ttgagatcgg taagtcgaat ctgaaatgta    27720
agtaactagg cagtttgcta atctgtcgtt cgcttttag gcttgggtac aggcatcgcc     27780
acgaagcgcg ttcttgcatc acctcaactt ggtttcaaca gttacacttg cactgacatc    27840
tcggcggatg ttattggcaa ggcccgtgaa caactttccg aattcgacgg tctcatgcag    27900
tttgaggcac tagacatcaa cagaagccca gcagagcaag gattcaagcc tcactcctac    27960
gatctgatta ttgcatccga tgtcctccat gccagctcca acttcgagga aaaattggct    28020
cacataaggt ccttgctcaa gccgggtggt cacttggtta ctttcggggt cacccatcgc    28080
gagcctgctc gcctcgcctt catctctggg cttttcgctg atcgatggac tggagaagac    28140
gaaactcgtg ctttgagtgc ctcggggtcc gttgaccaat gggagcatac cctcaagaga    28200
gttgggttct ctggcgtcga tagtcggaca cttgatcgag aggatgattt gatcccgtct    28260
gtcttcagta cacatgctgt ggatgccacc gttgagcgtt tgtatgatcc actttctgct    28320
ccattgaagg actcataccc gccattagtg gttatcggtg gcgaatcgac aaaaaccgaa    28380
cgcattttga cgacatgaa agctgcccta ccgcatagac acatccactc cgtcaagcgg     28440
ctggaaagtg ttctcgacga cccggccttg cagcctaagt cgacttttgt catcctctcg    28500
gaacttgatg atgaagtgtt ttgcaacctt gaagaggaca gtttgaggc agtcaagtct     28560 cttctcttct acgccggacg catgatgtgg ctgacagaga atgcctggat tgatcatccc    28620
caccaggcca gcaccatcgg aatgttgagg acaatcaagc tcgagaaccc tgacttggga    28680
acgcacgtct tcgatgtcga tactgtggag aacctagaca ccaaattctt cgttgagcaa    28740
cttttgcgct tcgaggagag cgatgatcag cttttggaat caataacatg gactcatgag    28800
cccgaagtgt actggtgcaa gggtcgtgcc tgggtccctc gtttgaagca ggatattgct    28860
aggaacgacc gtatgaactc gtctcgtcgt ccaattttcg gtaactttaa ttcgtccaag    28920
acggccattg cactgaaaga ggcgagggga gcatcctcat cgatgtacta tcttgagtca    28980
accgagacgt gtgattcgtt agaagacgct cgtcatgctg aaaagcaac tgttcgtgtt     29040 cgctacgctc ttccccaggc aattcgcgtg ggccatctcg atacttcca tgtcgtgcag     29100 ggcagtattc tggagaatac atgtgaggtg cctgtagtcg ccctggctga gaagaatgga    29160
tctatactgc atgtaccgag aaactacatg catagtctgc ccgataacat ggcggaaggc    29220
gaggatagtt ccttcttgtt gtccacagct gcagccctcc ttgccgaaac aattctctct    29280
agcgctcagt cctttggctc tgatgcatca attctgatta tggagccccc aatcttctgc    29340
gtcaaagcaa ttctggagtc ggccaaaacc tacggtgttc aggttcattt ggcaacaact    29400
ctgtccgacg tcaaaactat tccggctcct tggatccgat tacatgccaa ggaaaccgac    29460
gctcggctga acacagcct gccgacaaac atgatggcat tctttgactt gtctaccgac     29520
cggactgctg ccgggataac caaccgtttg gccaagttgc taccacccag ttgcttcatg    29580
tacagtggtg actatcttat ccgaagtaca gcttccacat acaaagttag tcatgttgag    29640
gatattccaa tcctcgagca ctctgtggca atggcaaaaa ataccgtctc tgcgtcgact    29700
gtcgacgaca ctgagaaagt tattacagcc acacaaattc tcttgcctgg tcagctctct    29760
gtcaaccaca atgaccaacg cttcaatctg gccaccgtca tcgactggaa ggaaaatgag    29820
gtgtccgcta ggatttgccc catcgactct ggtaacttat tttccaacaa gaagacgtat    29880
```

```
ttgcttgttg gtcttaccgg ggaccttggt cgctctctct gtcgctggat gatcttgcat    29940
ggcgcccgcc atgttgtgct cactagccgg aaccctcgac ttgatcccaa atggatcgcc    30000
aacatggagg cacttggtgg tgacatcacc gttctgtcaa tgtaagttga ttgatatcac    30060
atcacacctt gctaccacat cctcgtttac ttatccaatt actttcttta gggatgttgc    30120
caatgaggat tcagtcgatg ctggccttgg caagcttgtc gatatgaagt tgccacctgt    30180
tgccggcatc gcgttcgggc ctttggtgct gcaggatgtc atgctgaaga acatggacca    30240
ccagatgatg gacatggtgt tgaagcccaa ggtacaagga gcacgcattc ttcatgaacg    30300
gttctccgaa cagacgggca gcaaggcgct cgacttcttc atcatgtttt cgtccattgt    30360
tgcagttatt ggcaatcctg gccagtccaa ctatggcgct gcgaatgcct acctacaggc    30420
tctggcccag caacggtgcg ccagaggatt ggcggtattt tctacccctg aattatcatg    30480
catcgacgtc aagttactaa cgcacaacca caggatcaa ccatcgatat tggtgccgtt    30540
tacggtgtag ggtttgtcac gagggccgag atggaggagg actttgatgc tatccgtttc    30600
atgtttgact cagttgaaga gcatgagctg cacacgcttt tcgccgaagc ggtcgtgtct    30660
gaccagcgtg cccggcagca accacagcgc aagacggtca ttgacatggc ggaccttgag    30720
cttaccacgg gtatcccaga tcttgaccct gcgcttcaag atcgaattat ttacttcaac    30780
gacctcgtt tcggaaactt caaaattccc ggtcaacgcg gagacggtgg cgacaatgga    30840
tcagggtcta aaggctccat tgccgaccag ctcaaacaag caacaacttt agaccaagtt    30900
cggcaaatcg tgattggtaa gttatctctc atgcgtttcc tgatatcgag ttcaaactaa    30960
caaagttgca gatggtctat ctgagaaact ccgtgttacc ctccaagttt cggacgggga    31020
gagcgtggac ccaaccattc ctctcattga tcaaggtgtc gactccttgg gtgcagtgac    31080
tgtcggctca tggttctcaa agcaactcta ccttgacctc ccactcttga gggtacttgg    31140
cggtgcttct gtcgctgatc ttgccgacga cgcggccacc cgactcccag ctacatccat    31200
tccgctgctg ttgcaaattg gtgattccac gggaacctcg acagcgggg cttctccgac    31260
accaacagac agccatgatg aagcaagctc tgctaccagc acagatgcgt cgtcagccga    31320
agaggatgaa gagcaagagg acgataatga gcagggaggc cgtaagattc ttcgtcgcga    31380
gaggttgtcc cttggccagg agtattcctg gaggcagcaa caaatggtaa aagatcatac    31440
catcttcaac aacactattg gcatgttcat gaagggtacc attgacctcg accggttgag    31500
gcgggctctg aaagcctcat tgcgccgtca cgagatcttc cgtacgtgct tgttactggg    31560
cgatgactat agcagcgatt taaatggtcc cgtccaagtg gttctcaaga acccggagaa    31620
cagagtgcac tttgttcagg tgaacaacgc tgcggaggca gaggaagagt accggaaact    31680
cgagaagaca aactatagca tctccacagg tgacactctc agactcgttg atttctactg    31740
gggcacagat gaccacctgt tggtaatcgg ctaccacaga ttagttggtg atggctcaac    31800
aacagaaaac ctgttcaatg agatcgggca gatttacagc ggggtgaaaa tgcagcgacc    31860
atcgacccaa ttctctgatc tagccgtcca acagcgggaa aacctggaaa atgggcgaat    31920
gggggacgat atcgcgttct ggaagtccat gcatagcaaa gtctcgtcat ctgcgccaac    31980
cgtgcttccc atcatgaatc tgatcaatga ccctgctgcc aattcagagc agcagcaaat    32040
acagccattc acgtggcagc agtatgaagc aattgctcgt ttagatccca tggtcgcctt    32100
ccgaatcaaa gagcggagcc gcaagcacaa ggcaaccccc atgcagttct acctggccgc    32160
ctaccacgtt ttgttggcgc gtcttaccgg cagcaaagac ataaccatcg gcctcgccga    32220
```

```
aaccaaccga tccaccatgg aagaaatttc ggcgatgggc ttttcgcta acgtgcttcc      32280 cctgcgcttt gatgagttcg tcggcagcaa gacattcggc gagcaccttg tagccaccaa      32340
ggacagtgtg cgtgaggcca tgcaacacgc gcgggtgccg tatggcgtca tcctcgactg      32400
tctaggcctg aatctcccta cctcaggcga ggaacccaag actcagacac acgccccctt      32460
gttccaggct gtctttgatt acaagcaggg tcaagcggag agtggctcaa ttggcaatgc      32520
caaaatgacg agtgttctcg cttcccgtga gcgcactcct tatgacatcg ttctcgagat      32580
gtgggatgac cctaccaagg acccactcat tcatgtcaaa cttcagagct cgctgtatgg      32640
ccctgagcac gctcaggcct ttgtagacca cttttcttca atcctcacta tgttctcgat      32700
gaacccggct ctgaagttgg cctagatcgt tcagcgccgt gaattcagat gtgtggtttg      32760
agtgttgttc atgataaaga tggattagaa attggcaata gagcagatgg caaatctatc      32820
ctgaattcgg cgtcaattga cacacgcata ttcatctaca aatagcgaat tcgtcttgta      32880
tctttgtcaa aattacttct accttcgttg ctcttcttta ttgcagcaat cgtaacatca      32940
agttagatag cgcggttcag agtaccgtaa cggtgataaa tatacctcgg tagcgcgttt      33000
cgaaagactc tgtgaggaag gtgaaacctc caaggcttgg aattgatttc aatccatcct      33060
gtatataaat tcgacgccat tgcaaatagt tccatagtta ctggtttagt gccttgttgt      33120
ggtgatcgag tggttttaga tgtctgtcat gcctgttcag aacgagcctt ccatgatcta      33180
tccaaaatat gttcacgaaa tatttatgag atggtcgcga ccactataac taaatcaccc      33240
ttggaaggtg agcattcaaa ccgtgtaaga ttagaactat tcaaatttgt tcagtaaaaa      33300
tgtggtatgg actaggcatg agagccagag ccttgctata taccctgttg tctcacctag      33360
acaaatgaac ctgacatctt gacctttga tatagctgtt ggaagcgctt gaccgtctcc      33420
tggacatcac tcggtctgtt gggaaaatta tgctttccct gaaactcgag tacatctgca      33480
ttctgaggca ggtaatgtgt ttcaaccatc tgtctcgacc cttggagagc aaaatcttga      33540
cgaccgtgaa gatgcagtgt cggcacgttg attattagct tgtcgtcgtc gtcttgcgcc      33600
tcggctctca tgtaatctct ggcttcatcg ctatagaaac agcaaatcaa acagcaatg       33660 ctcattttcg gaaaccatgg cagtttttccc atttgctgtt gatggagcag caaagtggcg      33720
accaatgcgc cctcagagaa ggccactatg ccgacaatgg gtgcctgtgg gttagttata      33780
gaccaatctt ggacggtctt ttgcacaggc ccgatcacag ccgctactct atcgcccacc      33840
gtgggggttg tcgtgtttgt aacggcgtca tgatgctttt ggaaccaggt gtagtatgga      33900
cccatgcctt ggaagacagg aagcacgccg ggtccggggc tggagctaaa cggcgcggtc      33960
gcatatacga attcaaactc gttttcaac gccacgcgca gtttagagat ctggacgcgg       34020
aatatggctg ctgagcaccc ggcaccgtgg atgcataaga gagctttct cggtttgcct       34080 ggcgagaaat ctgtaatcct cgctggactc attttctctt gtggtgtgag ctgtgacttc      34140
gtctgttctg gggaatttgt tagtcattac tgacaaggaa ataacaacga cgtagtattg      34200
atc                                                                    34203
```

<210> SEQ ID NO 3
<211> LENGTH: 17
<212> TYPE: DNA
<213> ORGANISM: Artificial Sequence
<220> FEATURE:
<221> NAME/KEY: misc_feature
<223> OTHER INFORMATION: Description of Artificial Sequence: A mixed
      primer which has a DNA sequence decuced from the amino
      acid sequence of PKS of Aspergillus flavus.
<220> FEATURE:

```
<221> NAME/KEY: modified_base
<222> LOCATION: (6)..(6)
<223> OTHER INFORMATION: i
<220> FEATURE:
<221> NAME/KEY: modified_base
<222> LOCATION: (9)..(9)
<223> OTHER INFORMATION: i

<400> SEQUENCE: 3
gayacngcnt gyasttc                                                    17

<210> SEQ ID NO 4
<211> LENGTH: 17
<212> TYPE: DNA
<213> ORGANISM: Artificial Sequence
<220> FEATURE:
<221> NAME/KEY: misc_feature
<223> OTHER INFORMATION: Description of Artificial Sequence: A mixed
      primer which has a DNA sequence deduced from the amino
      acid sequence of PKS of Aspergillus flavus.
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (6)..(6)
<223> OTHER INFORMATION: i
<220> FEATURE:
<221> NAME/KEY: modified_base
<222> LOCATION: (8)..(8)
<223> OTHER INFORMATION: i
<220> FEATURE:
<221> NAME/KEY: modified_base
<222> LOCATION: (15)..(15)
<223> OTHER INFORMATION: i

<400> SEQUENCE: 4
tcnccnknrc wgtgncc                                                    17

<210> SEQ ID NO 5
<211> LENGTH: 19
<212> TYPE: DNA
<213> ORGANISM: Penicillium citrinum

<400> SEQUENCE: 5
gcatgttcaa tttgctctc                                                  19

<210> SEQ ID NO 6
<211> LENGTH: 19
<212> TYPE: DNA
<213> ORGANISM: Penicillium citrinum

<400> SEQUENCE: 6
ctggatcaga cttttctgc                                                  19

<210> SEQ ID NO 7
<211> LENGTH: 18
<212> TYPE: DNA
<213> ORGANISM: Penicillium citrinum

<400> SEQUENCE: 7
gtcgcagtag catgggcc                                                   18

<210> SEQ ID NO 8
<211> LENGTH: 20
<212> TYPE: DNA
<213> ORGANISM: Penicillium citrinum
```

-continued

```
<400> SEQUENCE: 8
gtcagagtga tgctcttctc                                              20

<210> SEQ ID NO 9
<211> LENGTH: 20
<212> TYPE: DNA
<213> ORGANISM: Penicillium citrinum

<400> SEQUENCE: 9
gttgagagga ttgtgagggc                                              20

<210> SEQ ID NO 10
<211> LENGTH: 19
<212> TYPE: DNA
<213> ORGANISM: Penicillium citrinum

<400> SEQUENCE: 10
ttgcttgtgt tggattgtc                                               19

<210> SEQ ID NO 11
<211> LENGTH: 20
<212> TYPE: DNA
<213> ORGANISM: Penicillium citrinum

<400> SEQUENCE: 11
catggtactc tcgcccgttc                                              20

<210> SEQ ID NO 12
<211> LENGTH: 19
<212> TYPE: DNA
<213> ORGANISM: Penicillium citrinum

<400> SEQUENCE: 12
ctccccagta cgtaagctc                                               19

<210> SEQ ID NO 13
<211> LENGTH: 21
<212> TYPE: DNA
<213> ORGANISM: Penicillium citrinum

<400> SEQUENCE: 13
ccataatgag tgtgactgtt c                                            21

<210> SEQ ID NO 14
<211> LENGTH: 19
<212> TYPE: DNA
<213> ORGANISM: Penicillium citrinum

<400> SEQUENCE: 14
gaacatctgc atccccgtc                                               19

<210> SEQ ID NO 15
<211> LENGTH: 20
<212> TYPE: DNA
<213> ORGANISM: Penicillium citrinum

<400> SEQUENCE: 15
ggaaggcaaa gaaagtgtac                                              20

<210> SEQ ID NO 16
<211> LENGTH: 21
<212> TYPE: DNA
<213> ORGANISM: Penicillium citrinum
```

<400> SEQUENCE: 16
agattcattg ctgttggcat c                                           21

<210> SEQ ID NO 17
<211> LENGTH: 722
<212> TYPE: DNA
<213> ORGANISM: Penicillium citrinum

<400> SEQUENCE: 17
ggccacgcgt cgactagtac gggggggggg gggggggggg gcttgttcgc tcagagattc    60
aactctgcga ttctgtttaa tcccaatcct atcgcccaaa acaggatca gcagttatgg   120
atcaagccaa ctatccaaac gagccaattg tggtagtggg aagcggttgt cggtttccag   180
gtggtgtcaa cacaccatca aaactttggg agctgctcaa agagcccgg gatgtacaga   240
ccaagatccc taaggagaga tttgacgtcg atacatttta cagccccgat ggcactcacc   300
ccgggcgcac gaacgcaccc tttgcatact tgctgcagga ggatctacgc ggttttgatg   360
cctctttctt caacatccaa gctggagagg ccgaaacgat tgacccacag caaaggctgc   420
tgctggagac ggtctatgaa gctgtatcca acgcaggcct acggatccaa ggccttcaag   480
gatcctctac tgctgtgtac gtcggtatga tgacgcatga ctatgagact atcgtgacgc   540
gtgaattgga tagtattcct acatactctg ccacggggt agctgtcagt gtggcctcca   600
accgtgtatc atacttcttc gactggcatg ggccgagtat gacgatcgac acagcctgta   660
gttcatcctt agctgccgtg catctggccg tccaacagct tagaacgggc gagagtacca   720
tg                                                                722

<210> SEQ ID NO 18
<211> LENGTH: 760
<212> TYPE: DNA
<213> ORGANISM: Penicillium citrinum

<400> SEQUENCE: 18
ggccacgcgt cgactagtac gggggggggg gggggggggg gactatcaac ggttttatca    60
ccagggcgac tgatatatca gtcaatgaaa caacgttgga atgaacaata ccccgccgt   120
aaccgcaacc gcaaccgcaa ccgcaaccgc aaccgcaatg gcaggctcgg cttgctctaa   180
cacatccacg cccattgcca tagttggaat gggatgtcga tttgctggag atgcaacgag   240
tccacagaag ctttgggaaa tggttgaaag aggaggcagt gcctggtcta aggtcccctc   300
ctcgcgattc aatgtgagag gagtatacca cccgaatggc gaaagggtcg ggtccaccca   360
cgtaaagggt ggacacttca tcgacgagga tcctgcttta tttgacgccg cgttcttcaa   420
catgaccaca gaggtcgcca gctgcatgga tccgcagtat cggcttatgc ttgaggtggt   480
ctacgaatcg ctggagagtg ccggtatcac catcgatgat atggcaggct ctaatacgtc   540
ggtgttggg ggtgtcatgt accacgacta tcaggattcg ctcaatcgtg accccgagac   600
agttccgcgt tatttcataa ctggcaactc aggaacaatg ctttcgaacc ggatatcaca   660
cttctacgac ttacgtggtc ccagcgtgac ggttgacacg gcctgttcga cgacattgac   720
cgcactgcac ttggcgtgcc agagcttacg tactggggag                        760

<210> SEQ ID NO 19
<211> LENGTH: 773
<212> TYPE: DNA
<213> ORGANISM: Penicillium citrinum -continued

```
<400> SEQUENCE: 19
ggccacgcgt cgactagtac gggggggggg ggttttttttt ttttcaaggt tgactggaag    60
agtgctctcg gccacaaaat cccagaagca ttagtgctgt tattcgatta taaaccgtcg   120
cagcgctctc attcttcgct ctttcttctt ttccactggt gtgcataggt cctatctgtc   180
tcacgcaatg ctcggccagg ttcttctgac cgtcgaatcg taccaatggg tatcgacccc   240
tcaagccctt gtggcggtcg cagtgcttct tagtctcatc gcctaccgtt tgcggggcg    300 ccagtccgaa ctgcaagtct ataatcccaa aaaatggtgg gagttgacga ccatgagggc   360
taggcaggac ttcgatacgt atggtccgag ctggatcgaa gcttggttct cgaaaaacga   420
caagcccctg cgcttcattg ttgattccgg ctattgcacc atcctcccat cgtccatggc   480
cgacgagttt cggaaaatca agatatgtg catgtacaag tttttggcgg atgactttca    540
ctctcatctc cctggattcg acgggttcaa ggaaatctgc caggatgcac atcttgtcaa   600
caaagttgtt ttgaaccagt acaaaccca gcccccaag tacacaaagc cattggctac    660
cttggccgac gctactattg ccaagttgtt cggtaaaagc gaggagtggc aaaccgcacc   720
tgtctattcc aatggattgg accttgtcac acgaacagtc acactcatta tgg          773

<210> SEQ ID NO 20
<211> LENGTH: 527
<212> TYPE: DNA
<213> ORGANISM: Penicillium citrinum

<400> SEQUENCE: 20
ggccacgcgt cgactagtac gggggggggg gtacctagga actgttcagt tgtccctccc    60
aaccccttgg gccgaacaac cttcctccaa tctacgacgg cagattatac ctaggcgcct   120
aaccgattag gttgctcatt cgattttgga gagactacct agctataggt accactccaa   180
gctgtagcac agacctttca gcatggtcgc ttcgttgcta ccctctcgct ttcgcggtag   240
ggaatcaatg aatcagcagc accctctacg ctcgggaaat cgggcattga cctccacact   300
ccaatttcta tccaaaacgg cgtgtctaca cccgatccat accgtttgca ccatagctat   360
tctagctagt accacatacg ttggactact caaagacagc ttcttccatg gccccgcaaa   420
cgttgataaa gcagaatggg gctctttggt cgaaggaagt cgaagcttga tcaccggccc   480
acagaatggc tggaagtggc agagcttcga cggggatgca gatgttc                  527

<210> SEQ ID NO 21
<211> LENGTH: 522
<212> TYPE: DNA
<213> ORGANISM: Penicillium citrinum

<400> SEQUENCE: 21
ggccacgcgt cgactagtac gggggggggg gggggggggg ggatccatca atctgacttc    60
aggctagcgg accttaacga aacaacgaga gcgagatcat tcatacacca aaacacaggt   120
actatagaag cgccgcgcag tagagattca caccgcccct tgaagcaaaa gtcggaagga   180
attgcgcgat gtcagaacct ctacccccta agaagggga accaaggcca cagaaggaag    240
aaagtcaaaa tgacacgctc gaagcgactg agtccaagtc ccagcacatc acaggcctca   300
agctcgggct ggtggttgct tcagttactt tcgtagcatt tttgatgctc cttgatatgt   360
ccattatcgt cacggcaatc ccacatatca caagcgagtt ccactctctg aacgatgtag   420
ggtggtacgg cagtgcttat cttctggcta actgtgctct ccagcccctg gccggtaaat   480
tgtatacact cttgggcttg aagtacactt tctttgcctt cc                      522
```

<210> SEQ ID NO 22
<211> LENGTH: 541
<212> TYPE: DNA
<213> ORGANISM: Penicillium citrinum

<400> SEQUENCE: 22

| | | | | | |
|---|---|---|---|---|---|
| ggccacgcgt | cgactagtac | gggggggggg | ggctcacctc | acattatttg | atcttaatcc | 60 |
| aataattatg | tccctgccgc | atgcaacgat | tccgacgaac | ctacgccgtc | gcgcgtttcg | 120 |
| acgctcatgt | gaccggtgtc | atgcacaaaa | gctcaaatgt | accggtagca | atgccaattt | 180 |
| agtccgtgct | cagtgtcaac | gttgtcagca | agccggatta | aggtgtgtgt | acagcgaaag | 240 |
| gctacccaag | cgcaatttac | ataaagaagc | cgcagctgga | actacaagag | ccacagaaac | 300 |
| ctcacaaccg | atgaccgcga | catcttctac | ggtcttctca | tcattggcag | agactcctcc | 360 |
| accttactgc | tcaccaccta | cgcatattgg | cactcggca | ctcaaggaaa | cattatcaga | 420 |
| accatcagcg | gcaaccctgc | aattctatga | tacatcaatc | aactttgatg | atcccgagtc | 480 |
| gtttcccggc | ggctggcctc | agccaaatac | atttcgcgac | gatgccaaca | gcaatgaatc | 540 |
| t | | | | | | 541 |

<210> SEQ ID NO 23
<211> LENGTH: 20
<212> TYPE: DNA
<213> ORGANISM: Penicillium citrinum

<400> SEQUENCE: 23
atcataccat cttcaacaac                                               20

<210> SEQ ID NO 24
<211> LENGTH: 20
<212> TYPE: DNA
<213> ORGANISM: Penicillium citrinum

<400> SEQUENCE: 24
gctagaatag gttacaagcc                                               20

<210> SEQ ID NO 25
<211> LENGTH: 20
<212> TYPE: DNA
<213> ORGANISM: Penicillium citrinum

<400> SEQUENCE: 25
acattgccag gcacccagac                                               20

<210> SEQ ID NO 26
<211> LENGTH: 20
<212> TYPE: DNA
<213> ORGANISM: Penicillium citrinum

<400> SEQUENCE: 26
caacgcccaa gctgccaatc                                               20

<210> SEQ ID NO 27
<211> LENGTH: 20
<212> TYPE: DNA
<213> ORGANISM: Penicillium citrinum

<400> SEQUENCE: 27
gtcttttcct actatctacc                                               20

<210> SEQ ID NO 28
<211> LENGTH: 20
<212> TYPE: DNA
<213> ORGANISM: Penicillium citrinum

<400> SEQUENCE: 28
ctttcccagc tgctactatc                                               20

<210> SEQ ID NO 29
<211> LENGTH: 1524
<212> TYPE: DNA
<213> ORGANISM: Penicillium citrinum

<400> SEQUENCE: 29
aactggaaga attcgcggcc gcaggaattt tttttttttt ttttttttcaa cgaaggtaga    60 agtaattttg acaaagatac aagacgaatt cgctatttgt agatgaatat gcgtgtgtca   120
attgaagccg aattcaggat agatttgcca tctgctctat tgccaatttc taatccatct   180
ttatcatgaa caacactcaa accacacatc tgaattcacg gcgctgaacg atctaggcca   240
acttcagagc cgggttcatc gagaacatag tgaggattga agaaaagtgg tctacaaagg   300
cctgagcgtg ctcagggcca tacagcgagc tctgaagttt gacatgaatg agtgggtcct   360
tggtagggtc atcccacatc tcgagaacga tgtcataagg agtgcgctca cgggaagcga   420
gaacactcgt cattttggca ttgccaattg agccactctc cgcttgaccc tgcttgtaat   480
caaagacagc ctggaacaag ggggcgtgtg tctgagtctt gggttcctcg cctgaggtag   540
ggagattcag gcctagacag tcgaggatga cgccatacgg cacccgcgcg tgttgcatgg   600
cctcacgcac actgtccttg gtggctacaa ggtgctcgcc gaatgtcttg ctgccgacga   660
actcatcaaa gcgcagggga agcacgttag cgaaaaagcc catcgccgaa atttcttcca   720
tggtggatcg gttggtttcg gcgaggccga tggttatgtc tttgctgccg gtaagacgcg   780
ccaacaaaac gtggtaggcg ccaggtaga actgcatggg ggttgccttg tgcttgcggc    840
tccgctcttt gattcggaag cgaccatgg gatctaaacg agcaattgct tcatactgct   900
gccacgtgaa tggctgtatt tgctgctgct ctgaattggc agcagggtca ttgatcagat   960
tcatgatggg aagcacggtt ggcgcagatg acgagacttt gctatgcatg gacttccaga  1020
acgcgatatc gtcccccatt cgcccatttt ccaggttttc ccgctgttgg acggctagat  1080
cagagaattg ggtcgatggt cgctgcattt tcaccccgct gtaaatctgc ccgatctcat  1140
tgaacaggtt ttctgttgtt gagccatcac caactaatct gtggtagccg attaccaaca  1200
ggtggtcatc tgtgccccag tagaaatcaa cgagtctgag agtgtcacct gtggagatgc  1260
tatagtttgt cttctcgagt ttccggtact cttcctctgc ctccgcagcg ttgttcacct  1320
gaacaaagtg cactctgttc tccgggttct tgagaaccac ttggacggga ccatttaaat  1380
cgctgctata gtcatcgcca gtaacaaagc acgtacggaa gatctcgtga cggcgcaatg  1440
aggctttcag agcccgcctc aaccggtcga ggtcaatggt acccttcatg aacatgccaa  1500
tagtgttgtt gaagatggta tgat                                        1524

<210> SEQ ID NO 30
<211> LENGTH: 784
<212> TYPE: DNA
<213> ORGANISM: Penicillium citrinum

<400> SEQUENCE: 30
aactggaaga attcgcggcc gcaggaattt tttttttttt ttttttttc tttgttgctt     60

-continued

| | |
|---|---|
| ctcagggcca ctgtaatggt atttcaggta tctctattta ctgctatcca gaagtcaggc | 120 |
| attaaatagt caggctcagc ccaggctcga ttcagattgg attcaggctt cagaccatgg | 180 |
| ccgctatgct ccttcgtact ataccctccgt cgagctatac ccgcttggcc agacaaaagg | 240 |
| cttcactgaa cccttcaact taactgcatt tcgccacaac taactcgacg aggccggcga | 300 |
| tggtgttacc attcatgagc tcaaagatcg acacatcaac atggatttca gatgtgatcc | 360 |
| agtttcgaag ttcaatggcg acgagtgagt ctacgccgac acctgccagg ttttttggacg | 420 |
| aggacatgtc gtcttctgcc agaccaaaca ttcgcatcag cttttccgtc attgctttga | 480 |
| ggacgataga aatggcctcg tcgtgagagg tgaccctgct tagttgggcc cgcacgccat | 540 |
| ctggtccttt tttatgcgaa gagacaaagg attggtctgc atgaaggact tggcggtatt | 600 |
| taagtcccac aaaccgctgt tcctgtatcc agtttgcctc ggtccagtga gcacccgggg | 660 |
| atgtgttgat tcctgtaacc acagctgcgg gaggtgatgg aaattgaggg gaagaacaca | 720 |
| ggattgcctt ctccaacaca tccatgacgt ccttttcatg cataggcttg taacctattc | 780 |
| tagc | 784 |

<210> SEQ ID NO 31
<211> LENGTH: 764
<212> TYPE: DNA
<213> ORGANISM: Penicillium citrinum

<400> SEQUENCE: 31

| | |
|---|---|
| aactggaaga attcgcggcc gcaggaattt tttttttttt ttttttttc gaataaaatg | 60 |
| cgttttattt tactaaccta ctcgactaat acagcaccta gtttctctgg gacggaaacc | 120 |
| attggaataa gcctggggac ggatgcatat ttgttttagt ttgcgtgtta tatcttagca | 180 |
| ccggtcatga gggagcggga tgtcctcgtt gcgccggcgt accatgagct ttgtggttgg | 240 |
| atgcatacga acgctaaaag cgtgacggta gtatttgtca tcgtctcctg gtacaggctt | 300 |
| cacatcatac tgaatcagta tatgagcgag gagaatcttg atttccttcg aggcgaagaa | 360 |
| ccgcccggga caagcgcgtg ggttccagcc gaagccgatg tgatcaccgt tggtattctc | 420 |
| caattgagcg gtgaaggcct tgtctggatc ctcgcgcatg cgcataaatc ggtagggatc | 480 |
| ataattttcg gggttttccc acacatcagg gttgttcatg cggtctgcag ccacagcggc | 540 |
| caactcgccc ttgggaatga agaggccatt ggatagagtg atgtctctga gagcggtact | 600 |
| gcgcatagtg gcgcactcga ccggcttgat tcgctgcgtc tctttcatgc agctgtcgag | 660 |
| gagcttcagc ttgaacagag aggcaggcgt ccagcccct tctccgatta cagtgcggat | 720 |
| ctcttggcgg agaggctgaa taaggtctgg gtgcctggca atgt | 764 |

<210> SEQ ID NO 32
<211> LENGTH: 765
<212> TYPE: DNA
<213> ORGANISM: Penicillium citrinum

<400> SEQUENCE: 32

| | |
|---|---|
| aactggaaga attcgcggcc gcaggaattt tttttttttt ttttttctgg aaaaggacca | 60 |
| tctctttata tattcttctt ccctactact tgcatcgtaa atttcaacaa catataaaca | 120 |
| tgagatacccc tttctggccg ttcactctac cacctgcctg tctcattgca ttgtgctttt | 180 |
| gaaaattatg acaataacaa ccaatgagaa aaaatatgat cctcctgcaa tgaatccact | 240 |
| ggaggggta cggagcttgg aatgctccta agattccgac ctaatcagcg tcgagcccga | 300 |

| | |
|---|---|
| tcagtagctg cagcactcgg cctcagtgca ttgttaggaa cagggactgt cctggttccg | 360 |
| cctgacgggg agacacttcg agaagggct gaagatgccg gggcagaacg gttgtgcgcc | 420 |
| atgtgcgcct tgaccaggtg accgcggct agggcagcac atagcgagag ctccccagcc | 480 |
| aaaacagcgc ttccgatgat gcgcgcaagt tgacgtgcat tctcaccggg agtggtcggg | 540 |
| tgtgatccgc ggacaccaag catgtcaagc attgcgccct ggggctccag aatcgtacca | 600 |
| ccgcccaacg ttccaacctc aatagacggc atggagacag agatttgaag cgatccgcga | 660 |
| agattgttca tgagagtgat gcagttagcg ctctccacaa cttgcgccgg atcctgacct | 720 |
| gtggcaatga aatggctgc cgcaagattg gcagcttggg cgttg | 765 |

<210> SEQ ID NO 33
<211> LENGTH: 802
<212> TYPE: DNA
<213> ORGANISM: Penicillium citrinum

<400> SEQUENCE: 33

| | |
|---|---|
| aactggaaga attcgcggcc gcaggaattt tttttttttt tttttataga atctttgaaa | 60 |
| tcgacattaa ttaagtatgt ggagattctt tgtggaggca cggtaatgtg tctatctagc | 120 |
| aacgcggtca agcatcagtc tcaggcacag cccgggtgtc gttttggtt gcaatcttcc | 180 |
| gccatcccat tccaaaggca aacacaaacg tgcacgccgt agctcccact gctaagtaaa | 240 |
| aagtatgatc aacggcgaga ctgtaagctt ttacaacccc tggaaggtta ttcttgctga | 300 |
| ccacatctct gaagccagtc gcccctgctg ccgtcacggc ctgcgtgtcg acagtgggcg | 360 |
| catacttgct caggccagtt ctcaaaccgg acccaaagac aaggttagca aagtccagga | 420 |
| agagcgatcc tccaaacgtc tgtccaaaca cggcgagaga aattccgagg gcaccttgtt | 480 |
| cgggcgaaag cgtgctttgg atggcgatga taggcgtttg catgccacaa ccacgaccga | 540 |
| agcccgcgat aaattggtac atgacccatt tcacagttga tgtatggggc tggaaggtgg | 600 |
| ataccagacc tgcgcctatg gcgacgagaa cagcgctgcc tagggcccaa ggcaaatagt | 660 |
| atcctgtctt tccaattgcg aagccagaaa ccatagccat aatgacttgt ccaagaattc | 720 |
| caggcaacat gtacacacca ctcagtgtgg gagaaacatc cttcacagcc tggaagtaga | 780 |
| tcggtagata gtaggaaaag ac | 802 |

<210> SEQ ID NO 34
<211> LENGTH: 562
<212> TYPE: DNA
<213> ORGANISM: Penicillium citrinum

<400> SEQUENCE: 34

| | |
|---|---|
| aactggaaga attcgcggcc gcaggaattt tttttttttt tttttttac taagcaatat | 60 |
| tgtgtttctt cgctaatgcg aatatttcct tatagcaacg tcgcaacaca tttatcgtct | 120 |
| tccctgaggc ctttgttgac ttgggctctt cgtctccggc ttcgtcactc caaagcacag | 180 |
| ataggagacg agaggccggc gttatggttt tattttcagc gccaaggatt tgccacgatg | 240 |
| tgcttggcat atctgatagg actagacgaa tagatgccgc agccccgtgc tcctgtgcta | 300 |
| tccccaaagc agtctcaatc ccactcaata gtcgaaggct tacacgcaat gtcgtgcatg | 360 |
| cagaagataa ggcgtgcatg aatgggtcga gatgtgaaat gagctcgccg atatgaagat | 420 |
| tagagtgaaa cgagggaagt gcttcggctc ttccattgtc atttctagtg gttgagccag | 480 |
| accagtacca atccattcgt gtgctttgct tttgtccaca aggttgggct ttcatcacct | 540 |
| cggatagtag cagctgggaa ag | 562 |

```
<210> SEQ ID NO 35
<211> LENGTH: 26
<212> TYPE: DNA
<213> ORGANISM: Penicillium citrinum

<400> SEQUENCE: 35
gttaacatgt cagaacctct accccc                                            26

<210> SEQ ID NO 36
<211> LENGTH: 27
<212> TYPE: DNA
<213> ORGANISM: Penicillium citrinum

<400> SEQUENCE: 36
aatatttcaa gcatcagtct caggcac                                           27

<210> SEQ ID NO 37
<211> LENGTH: 1662
<212> TYPE: DNA
<213> ORGANISM: Penicillium citrinum
<220> FEATURE:
<221> NAME/KEY: CDS
<222> LOCATION: (1)..(1662)

<400> SEQUENCE: 37
```

| | | | | | | | | | | | | | | | | |
|---|---|---|---|---|---|---|---|---|---|---|---|---|---|---|---|---|
| atg | tca | gaa | cct | cta | ccc | cct | aaa | gaa | ggg | gaa | cca | agg | cca | cag | aag | 48 |
| Met | Ser | Glu | Pro | Leu | Pro | Pro | Lys | Glu | Gly | Glu | Pro | Arg | Pro | Gln | Lys | |
| 1 | | | 5 | | | | | 10 | | | | | 15 | | | |
| gaa | gaa | agt | caa | aat | gac | acg | ctc | gaa | gcg | act | gag | tcc | aag | tcc | cag | 96 |
| Glu | Glu | Ser | Gln | Asn | Asp | Thr | Leu | Glu | Ala | Thr | Glu | Ser | Lys | Ser | Gln | |
| | | | 20 | | | | | 25 | | | | | 30 | | | |
| cac | atc | aca | ggc | ctc | aag | ctc | ggg | ctg | gtg | gtt | gct | tca | gtt | act | ttc | 144 |
| His | Ile | Thr | Gly | Leu | Lys | Leu | Gly | Leu | Val | Val | Ala | Ser | Val | Thr | Phe | |
| | | 35 | | | | | 40 | | | | | 45 | | | | |
| gta | gca | ttt | ttg | atg | ctc | ctt | gat | atg | tcc | att | atc | gtc | acg | gca | atc | 192 |
| Val | Ala | Phe | Leu | Met | Leu | Leu | Asp | Met | Ser | Ile | Ile | Val | Thr | Ala | Ile | |
| | 50 | | | | | 55 | | | | | 60 | | | | | |
| cca | cat | atc | aca | agc | gag | ttc | cac | tct | ctg | aac | gat | gta | ggg | tgg | tac | 240 |
| Pro | His | Ile | Thr | Ser | Glu | Phe | His | Ser | Leu | Asn | Asp | Val | Gly | Trp | Tyr | |
| 65 | | | | | 70 | | | | | 75 | | | | | 80 | |
| ggc | agt | gct | tat | ctt | ctg | gct | aac | tgt | gct | ctc | cag | ccc | ctg | gcc | ggt | 288 |
| Gly | Ser | Ala | Tyr | Leu | Leu | Ala | Asn | Cys | Ala | Leu | Gln | Pro | Leu | Ala | Gly | |
| | | | | 85 | | | | | 90 | | | | | 95 | | |
| aaa | ttg | tat | aca | ctc | ttg | ggc | ttg | aag | tac | act | ttc | ttt | gcc | ttc | ctc | 336 |
| Lys | Leu | Tyr | Thr | Leu | Leu | Gly | Leu | Lys | Tyr | Thr | Phe | Phe | Ala | Phe | Leu | |
| | | | 100 | | | | | 105 | | | | | 110 | | | |
| tgt | att | ttt | gaa | cta | ggc | tcg | gtg | cta | tgc | ggt | gcc | gca | aga | tct | tcc | 384 |
| Cys | Ile | Phe | Glu | Leu | Gly | Ser | Val | Leu | Cys | Gly | Ala | Ala | Arg | Ser | Ser | |
| | | 115 | | | | | 120 | | | | | 125 | | | | |
| acc | atg | ttg | att | gtt | ggg | cgg | gcc | gtt | gct | gga | atg | gga | ggc | tca | ggt | 432 |
| Thr | Met | Leu | Ile | Val | Gly | Arg | Ala | Val | Ala | Gly | Met | Gly | Gly | Ser | Gly | |
| | 130 | | | | | 135 | | | | | 140 | | | | | |
| ctt | gtc | aac | gga | gcc | ctc | aca | atc | ctc | tca | aca | gct | gct | cct | aag | cac | 480 |
| Leu | Val | Asn | Gly | Ala | Leu | Thr | Ile | Leu | Ser | Thr | Ala | Ala | Pro | Lys | His | |
| 145 | | | | | 150 | | | | | 155 | | | | | 160 | |
| aag | caa | cca | gtt | ttg | att | gga | gtg | atg | atg | ggt | ctt | agt | cag | att | gcc | 528 |
| Lys | Gln | Pro | Val | Leu | Ile | Gly | Val | Met | Met | Gly | Leu | Ser | Gln | Ile | Ala | |
| | | | | 165 | | | | | 170 | | | | | 175 | | |
| att | gtc | tgt | gga | cca | ctg | ctc | gga | ggt | gct | ttc | act | caa | cac | gcc | act | 576 |
| Ile | Val | Cys | Gly | Pro | Leu | Leu | Gly | Gly | Ala | Phe | Thr | Gln | His | Ala | Thr | |
| | | | 180 | | | | | 185 | | | | | 190 | | | |

```
tgg cga tgg tgc ttt tat atc aat ctc ccc atc ggc gct gtc gct gca       624
Trp Arg Trp Cys Phe Tyr Ile Asn Leu Pro Ile Gly Ala Val Ala Ala
        195                 200                 205 ttc ctc ctt ctc gtc atc acc ata ccc gac cga att tca tcc acg gac       672
Phe Leu Leu Leu Val Ile Thr Ile Pro Asp Arg Ile Ser Ser Thr Asp
    210                 215                 220 agc gaa ctc tcg acc gac aaa cca atg gcc aac ata aaa tcc aca ctt       720
Ser Glu Leu Ser Thr Asp Lys Pro Met Ala Asn Ile Lys Ser Thr Leu
225                 230                 235                 240 cgc aaa ctg gac ctt gta ggc ttt gtg gtc ttt gca gcc ttc gca acc       768
Arg Lys Leu Asp Leu Val Gly Phe Val Val Phe Ala Ala Phe Ala Thr
                245                 250                 255 atg att tcc ctc gca cta gaa tgg gga ggg tcg acc tac acc tgg cga       816
Met Ile Ser Leu Ala Leu Glu Trp Gly Gly Ser Thr Tyr Thr Trp Arg
            260                 265                 270 agt tcc gtc atc atc ggc ctg ttc tgt ggc gga ggg ttt gct ctg att       864
Ser Ser Val Ile Ile Gly Leu Phe Cys Gly Gly Gly Phe Ala Leu Ile
        275                 280                 285 gcg ttc gtg cta tgg gag cgt cat gtt ggc gat gct gtt gcc atg att       912
Ala Phe Val Leu Trp Glu Arg His Val Gly Asp Ala Val Ala Met Ile
    290                 295                 300 cct ggc tca gtg gct ggt aaa cga caa gtg tgg tgc tct tgt tta ttt       960
Pro Gly Ser Val Ala Gly Lys Arg Gln Val Trp Cys Ser Cys Leu Phe
305                 310                 315                 320 atg ggc ttt ttc tct ggc tcc ttg ctt gtc ttt tcc tac tat cta ccg      1008
Met Gly Phe Phe Ser Gly Ser Leu Leu Val Phe Ser Tyr Tyr Leu Pro
                325                 330                 335 atc tac ttc cag gct gtg aag gat gtt tct ccc aca ctg agt ggt gtg      1056
Ile Tyr Phe Gln Ala Val Lys Asp Val Ser Pro Thr Leu Ser Gly Val
            340                 345                 350 tac atg ttg cct gga att ctt gga caa gtc att atg gct atg gtt tct      1104
Tyr Met Leu Pro Gly Ile Leu Gly Gln Val Ile Met Ala Met Val Ser
        355                 360                 365 ggc ttc gca att gga aag aca gga tac tat ttg cct tgg gcc cta ggc      1152
Gly Phe Ala Ile Gly Lys Thr Gly Tyr Tyr Leu Pro Trp Ala Leu Gly
    370                 375                 380 agc gct gtt ctc gtc gcc ata ggc gca ggt ctg gta tcc acc ttc cag      1200
Ser Ala Val Leu Val Ala Ile Gly Ala Gly Leu Val Ser Thr Phe Gln
385                 390                 395                 400 ccc cat aca tca act gtg aaa tgg gtc atg tac caa ttt atc gcg ggc      1248
Pro His Thr Ser Thr Val Lys Trp Val Met Tyr Gln Phe Ile Ala Gly
                405                 410                 415 ttc ggt cgt ggt tgt ggc atg caa acg cct atc atc gcc atc caa agc      1296
Phe Gly Arg Gly Cys Gly Met Gln Thr Pro Ile Ile Ala Ile Gln Ser
            420                 425                 430 acg ctt tcg ccc gaa caa ggt gcc ctc gga att tct ctc gcc gtg ttt      1344
Thr Leu Ser Pro Glu Gln Gly Ala Leu Gly Ile Ser Leu Ala Val Phe
        435                 440                 445 gga cag acg ttt gga gga tcg ctc ttc ctg gac ttt gct aac ctt gtc      1392
Gly Gln Thr Phe Gly Gly Ser Leu Phe Leu Asp Phe Ala Asn Leu Val
    450                 455                 460 ttt ggg tcc ggt ttg aga act ggc ctg agc aag tat gcg ccc act gtc      1440
Phe Gly Ser Gly Leu Arg Thr Gly Leu Ser Lys Tyr Ala Pro Thr Val
465                 470                 475                 480 gac acg cag gcc gtg acg gca gca ggg gcg act ggc ttc aga gat gtg      1488
Asp Thr Gln Ala Val Thr Ala Ala Gly Ala Thr Gly Phe Arg Asp Val
                485                 490                 495 gtc agc aag aat aac ctt cca ggg gtt gta aaa gct tac agt ctc gcc      1536
Val Ser Lys Asn Asn Leu Pro Gly Val Val Lys Ala Tyr Ser Leu Ala
```

```
                   500             505             510
gtt gat cat act ttt tac tta gca gtg gga gct acg gcg tgc acg ttt    1584
Val Asp His Thr Phe Tyr Leu Ala Val Gly Ala Thr Ala Cys Thr Phe
        515             520             525 gtg ttt gcc ttt gga atg gga tgg cgg aag att gca acc aaa aac gac    1632
Val Phe Ala Phe Gly Met Gly Trp Arg Lys Ile Ala Thr Lys Asn Asp
530             535             540 acc cgg gct gtg cct gag act gat gct tga                            1662
Thr Arg Ala Val Pro Glu Thr Asp Ala
545             550
```

<210> SEQ ID NO 38
<211> LENGTH: 553
<212> TYPE: PRT
<213> ORGANISM: Penicillium citrinum

<400> SEQUENCE: 38

```
Met Ser Glu Pro Leu Pro Pro Lys Gly Glu Pro Arg Pro Gln Lys
1               5                   10                  15

Glu Glu Ser Gln Asn Asp Thr Leu Glu Ala Thr Glu Ser Lys Ser Gln
            20                  25                  30

His Ile Thr Gly Leu Lys Leu Gly Leu Val Val Ala Ser Val Thr Phe
        35                  40                  45

Val Ala Phe Leu Met Leu Leu Asp Met Ser Ile Ile Val Thr Ala Ile
    50                  55                  60

Pro His Ile Thr Ser Glu Phe His Ser Leu Asn Asp Val Gly Trp Tyr
65                  70                  75                  80

Gly Ser Ala Tyr Leu Leu Ala Asn Cys Ala Leu Gln Pro Leu Ala Gly
                85                  90                  95

Lys Leu Tyr Thr Leu Leu Gly Leu Lys Tyr Thr Phe Phe Ala Phe Leu
            100                 105                 110

Cys Ile Phe Glu Leu Gly Ser Val Leu Cys Gly Ala Ala Arg Ser Ser
        115                 120                 125

Thr Met Leu Ile Val Gly Arg Ala Val Ala Gly Met Gly Gly Ser Gly
    130                 135                 140

Leu Val Asn Gly Ala Leu Thr Ile Leu Ser Thr Ala Ala Pro Lys His
145                 150                 155                 160

Lys Gln Pro Val Leu Ile Gly Val Met Met Gly Leu Ser Gln Ile Ala
                165                 170                 175

Ile Val Cys Gly Pro Leu Leu Gly Gly Ala Phe Thr Gln His Ala Thr
            180                 185                 190

Trp Arg Trp Cys Phe Tyr Ile Asn Leu Pro Ile Gly Ala Val Ala Ala
        195                 200                 205

Phe Leu Leu Val Ile Thr Ile Pro Asp Arg Ile Ser Ser Thr Asp
    210                 215                 220

Ser Glu Leu Ser Thr Asp Lys Pro Met Ala Asn Ile Lys Ser Thr Leu
225                 230                 235                 240

Arg Lys Leu Asp Leu Val Gly Phe Val Val Phe Ala Ala Phe Ala Thr
                245                 250                 255

Met Ile Ser Leu Ala Leu Glu Trp Gly Gly Ser Thr Tyr Thr Trp Arg
            260                 265                 270

Ser Ser Val Ile Ile Gly Leu Phe Cys Gly Gly Phe Ala Leu Ile
        275                 280                 285

Ala Phe Val Leu Trp Glu Arg His Val Gly Asp Ala Val Ala Met Ile
    290                 295                 300
```

Pro Gly Ser Val Ala Gly Lys Arg Gln Val Trp Cys Ser Cys Leu Phe
305                 310                 315                 320

Met Gly Phe Phe Ser Gly Ser Leu Leu Val Phe Ser Tyr Tyr Leu Pro
                325                 330                 335

Ile Tyr Phe Gln Ala Val Lys Asp Val Ser Pro Thr Leu Ser Gly Val
            340                 345                 350

Tyr Met Leu Pro Gly Ile Leu Gly Gln Val Ile Met Ala Met Val Ser
        355                 360                 365

Gly Phe Ala Ile Gly Lys Thr Gly Tyr Tyr Leu Pro Trp Ala Leu Gly
    370                 375                 380

Ser Ala Val Leu Val Ala Ile Gly Ala Gly Leu Val Ser Thr Phe Gln
385                 390                 395                 400

Pro His Thr Ser Thr Val Lys Trp Val Met Tyr Gln Phe Ile Ala Gly
                405                 410                 415

Phe Gly Arg Gly Cys Gly Met Gln Thr Pro Ile Ile Ala Ile Gln Ser
            420                 425                 430

Thr Leu Ser Pro Glu Gln Gly Ala Leu Gly Ile Ser Leu Ala Val Phe
        435                 440                 445

Gly Gln Thr Phe Gly Gly Ser Leu Phe Leu Asp Phe Ala Asn Leu Val
    450                 455                 460

Phe Gly Ser Gly Leu Arg Thr Gly Leu Ser Lys Tyr Ala Pro Thr Val
465                 470                 475                 480

Asp Thr Gln Ala Val Thr Ala Ala Gly Ala Thr Gly Phe Arg Asp Val
                485                 490                 495

Val Ser Lys Asn Asn Leu Pro Gly Val Val Lys Ala Tyr Ser Leu Ala
            500                 505                 510

Val Asp His Thr Phe Tyr Leu Ala Val Gly Ala Thr Ala Cys Thr Phe
        515                 520                 525

Val Phe Ala Phe Gly Met Gly Trp Arg Lys Ile Ala Thr Lys Asn Asp
530                 535                 540

Thr Arg Ala Val Pro Glu Thr Asp Ala
545                 550

<210> SEQ ID NO 39
<211> LENGTH: 31
<212> TYPE: DNA
<213> ORGANISM: Penicillium citrinum

<400> SEQUENCE: 39
ggatccatgt ccctgccgca tgcaacgatt c                                  31

<210> SEQ ID NO 40
<211> LENGTH: 30
<212> TYPE: DNA
<213> ORGANISM: Penicillium citrinum

<400> SEQUENCE: 40
ggatccctaa gcaatattgt gtttcttcgc                                    30

<210> SEQ ID NO 41
<211> LENGTH: 1380
<212> TYPE: DNA
<213> ORGANISM: Penicillium citrinum
<220> FEATURE:
<221> NAME/KEY: CDS
<222> LOCATION: (1)..(1380)

<400> SEQUENCE: 41

-continued

| | |
|---|---|
| atg tcc ctg ccg cat gca acg att ccg acg aac cta cgc cgt cgc gcg<br>Met Ser Leu Pro His Ala Thr Ile Pro Thr Asn Leu Arg Arg Arg Ala<br>1               5                  10                 15 | 48 |
| ttt cga cgc tca tgt gac cgg tgt cat gca caa aag ctc aaa tgt acc<br>Phe Arg Arg Ser Cys Asp Arg Cys His Ala Gln Lys Leu Lys Cys Thr<br>            20                 25                 30 | 96 |
| ggt agc aat gcc aat tta gtc cgt gct cag tgt caa cgt tgt caa caa<br>Gly Ser Asn Ala Asn Leu Val Arg Ala Gln Cys Gln Arg Cys Gln Gln<br>        35                 40                 45 | 144 |
| gcc gga tta agg tgt gtg tac agc gaa agg cta ccc aag cgc aat tta<br>Ala Gly Leu Arg Cys Val Tyr Ser Glu Arg Leu Pro Lys Arg Asn Leu<br>    50                 55                 60 | 192 |
| cat aaa gaa gcc gca gct gga act aca aga gcc aca gaa acc tca caa<br>His Lys Glu Ala Ala Ala Gly Thr Thr Arg Ala Thr Glu Thr Ser Gln<br>65                 70                 75                 80 | 240 |
| ccg atg acc gcg aca tct tct acg gtc ttc tca tca ttg gca gag act<br>Pro Met Thr Ala Thr Ser Ser Thr Val Phe Ser Ser Leu Ala Glu Thr<br>                85                 90                 95 | 288 |
| cct cca cct tac tgc tca cca cct acg cat att ggc acc tcg gca ctc<br>Pro Pro Pro Tyr Cys Ser Pro Pro Thr His Ile Gly Thr Ser Ala Leu<br>            100                105                110 | 336 |
| aag gaa aca tta tca gaa cca tca gcg gca acc ctg caa ttc tat gat<br>Lys Glu Thr Leu Ser Glu Pro Ser Ala Ala Thr Leu Gln Phe Tyr Asp<br>        115                120                125 | 384 |
| aca tca atc aac ttt gat gat ccc gag tcg ttt ccc ggc ggc tgg cct<br>Thr Ser Ile Asn Phe Asp Asp Pro Glu Ser Phe Pro Gly Gly Trp Pro<br>    130                135                140 | 432 |
| cag cca aat aca ttt cgc gac gat gcc aac agc aat gaa tct tcg ggg<br>Gln Pro Asn Thr Phe Arg Asp Asp Ala Asn Ser Asn Glu Ser Ser Gly<br>145                150                155                160 | 480 |
| ata cca gat cta ggc tac gac ttt gaa ggc cct ttg gat gca acg gcg<br>Ile Pro Asp Leu Gly Tyr Asp Phe Glu Gly Pro Leu Asp Ala Thr Ala<br>                165                170                175 | 528 |
| cct gtc tcg cca tcg ctg ttt gac ctc gaa gta gag ggg aac tcg tca<br>Pro Val Ser Pro Ser Leu Phe Asp Leu Glu Val Glu Gly Asn Ser Ser<br>            180                185                190 | 576 |
| tcc gga caa tcc aac aca agc aac acg caa cga gac ctt ttc gaa agt<br>Ser Gly Gln Ser Asn Thr Ser Asn Thr Gln Arg Asp Leu Phe Glu Ser<br>        195                200                205 | 624 |
| ctg tcg gat gtg tca cag gac cta gag gta ata ctc cac ggg gtg act<br>Leu Ser Asp Val Ser Gln Asp Leu Glu Val Ile Leu His Gly Val Thr<br>    210                215                220 | 672 |
| gtg gaa tgg ccc aag caa aaa att tta agc tac ccg ata ggg gac ttt<br>Val Glu Trp Pro Lys Gln Lys Ile Leu Ser Tyr Pro Ile Gly Asp Phe<br>225                230                235                240 | 720 |
| ttg aat gcc ttt ggt aga ttg cta cta cat ctt caa gaa cgt gtg atc<br>Leu Asn Ala Phe Gly Arg Leu Leu Leu His Leu Gln Glu Arg Val Ile<br>                245                250                255 | 768 |
| acg agc agc aat agc agc atg tta gat ggg tgt ctg caa acc aag aac<br>Thr Ser Ser Asn Ser Ser Met Leu Asp Gly Cys Leu Gln Thr Lys Asn<br>            260                265                270 | 816 |
| ttg ttc atg gcg gtg cat tgc tac atg ttg tct gtc aaa atc atg aca<br>Leu Phe Met Ala Val His Cys Tyr Met Leu Ser Val Lys Ile Met Thr<br>        275                280                285 | 864 |
| tca ctt tcc cag ctg cta cta tcc gag gtg atg aaa gcc caa cct tgt<br>Ser Leu Ser Gln Leu Leu Leu Ser Glu Val Met Lys Ala Gln Pro Cys<br>    290                295                300 | 912 |
| gga caa aag caa agc aca cga atg gat tgg tac tgg tct ggc tca acc<br>Gly Gln Lys Gln Ser Thr Arg Met Asp Trp Tyr Trp Ser Gly Ser Thr<br>305                310                315                320 | 960 |

```
act aga aat gac aat gga aga gcc gaa gca ctt ccc tcg ttt cac tct    1008
Thr Arg Asn Asp Asn Gly Arg Ala Glu Ala Leu Pro Ser Phe His Ser
            325                 330                 335 aat ctt cat atc ggc gag ctc att tca cat ctc gac cca ttc atg cac    1056
Asn Leu His Ile Gly Glu Leu Ile Ser His Leu Asp Pro Phe Met His
        340                 345                 350 gcc tta tct tct gca tgc acg aca ttg cgt gta agc ctt cga cta ttg    1104
Ala Leu Ser Ser Ala Cys Thr Thr Leu Arg Val Ser Leu Arg Leu Leu
            355                 360                 365 agt gag att gag act gct ttg ggg ata gca cag gag cac ggg gct gcg    1152
Ser Glu Ile Glu Thr Ala Leu Gly Ile Ala Gln Glu His Gly Ala Ala
    370                 375                 380 gca tct att cgt cta gtc cta tca gat atg cca agc aca tcg tgg caa    1200
Ala Ser Ile Arg Leu Val Leu Ser Asp Met Pro Ser Thr Ser Trp Gln
385                 390                 395                 400 atc ctt ggc gct gaa aat aaa acc ata acg ccg gcc tct cgt ctc cta    1248
Ile Leu Gly Ala Glu Asn Lys Thr Ile Thr Pro Ala Ser Arg Leu Leu
                405                 410                 415 tct gtg ctt tgg agt gac gaa gcc gga gac gaa gag ccc aag tca aca    1296
Ser Val Leu Trp Ser Asp Glu Ala Gly Asp Glu Glu Pro Lys Ser Thr
            420                 425                 430 aag gcc tca ggg aag acg ata aat gtg ttg cga cgt tgc tat aag gaa    1344
Lys Ala Ser Gly Lys Thr Ile Asn Val Leu Arg Arg Cys Tyr Lys Glu
        435                 440                 445 ata ttc gca tta gcg aag aaa cac aat att gct tag                    1380
Ile Phe Ala Leu Ala Lys Lys His Asn Ile Ala
    450                 455
```

<210> SEQ ID NO 42
<211> LENGTH: 459
<212> TYPE: PRT
<213> ORGANISM: Penicillium citrinum

<400> SEQUENCE: 42

```
Met Ser Leu Pro His Ala Thr Ile Pro Thr Asn Leu Arg Arg Arg Ala
1               5                   10                  15

Phe Arg Arg Ser Cys Asp Arg Cys His Ala Gln Lys Leu Lys Cys Thr
            20                  25                  30

Gly Ser Asn Ala Asn Leu Val Arg Ala Gln Cys Gln Arg Cys Gln Gln
        35                  40                  45

Ala Gly Leu Arg Cys Val Tyr Ser Glu Arg Leu Pro Lys Arg Asn Leu
    50                  55                  60

His Lys Glu Ala Ala Ala Gly Thr Thr Arg Ala Thr Glu Thr Ser Gln
65                  70                  75                  80

Pro Met Thr Ala Thr Ser Ser Thr Val Phe Ser Ser Leu Ala Glu Thr
                85                  90                  95

Pro Pro Pro Tyr Cys Ser Pro Pro Thr His Ile Gly Thr Ser Ala Leu
            100                 105                 110

Lys Glu Thr Leu Ser Glu Pro Ser Ala Ala Thr Leu Gln Phe Tyr Asp
        115                 120                 125

Thr Ser Ile Asn Phe Asp Asp Pro Glu Ser Phe Gly Gly Trp Pro
    130                 135                 140

Gln Pro Asn Thr Phe Arg Asp Ala Asn Ser Asn Glu Ser Ser Gly
145                 150                 155                 160

Ile Pro Asp Leu Gly Tyr Asp Phe Glu Gly Pro Leu Asp Ala Thr Ala
                165                 170                 175

Pro Val Ser Pro Ser Leu Phe Asp Leu Glu Val Glu Gly Asn Ser Ser
```

```
                  180                 185                 190
Ser Gly Gln Ser Asn Thr Ser Asn Thr Gln Arg Asp Leu Phe Glu Ser
            195                 200                 205

Leu Ser Asp Val Ser Gln Asp Leu Glu Val Ile Leu His Gly Val Thr
    210                 215                 220

Val Glu Trp Pro Lys Gln Lys Ile Leu Ser Tyr Pro Ile Gly Asp Phe
225                 230                 235                 240

Leu Asn Ala Phe Gly Arg Leu Leu Leu His Leu Gln Glu Arg Val Ile
                245                 250                 255

Thr Ser Ser Asn Ser Ser Met Leu Asp Gly Cys Leu Gln Thr Lys Asn
            260                 265                 270

Leu Phe Met Ala Val His Cys Tyr Met Leu Ser Val Lys Ile Met Thr
        275                 280                 285

Ser Leu Ser Gln Leu Leu Leu Ser Glu Val Met Lys Ala Gln Pro Cys
    290                 295                 300

Gly Gln Lys Gln Ser Thr Arg Met Asp Trp Tyr Trp Ser Gly Ser Thr
305                 310                 315                 320

Thr Arg Asn Asp Asn Gly Arg Ala Glu Ala Leu Pro Ser Phe His Ser
                325                 330                 335

Asn Leu His Ile Gly Glu Leu Ile Ser His Leu Asp Pro Phe Met His
            340                 345                 350

Ala Leu Ser Ser Ala Cys Thr Thr Leu Arg Val Ser Leu Arg Leu Leu
        355                 360                 365

Ser Glu Ile Glu Thr Ala Leu Gly Ile Ala Gln Glu His Gly Ala Ala
    370                 375                 380

Ala Ser Ile Arg Leu Val Leu Ser Asp Met Pro Ser Thr Ser Trp Gln
385                 390                 395                 400

Ile Leu Gly Ala Glu Asn Lys Thr Ile Thr Pro Ala Ser Arg Leu Leu
                405                 410                 415

Ser Val Leu Trp Ser Asp Glu Ala Gly Asp Glu Pro Lys Ser Thr
            420                 425                 430

Lys Ala Ser Gly Lys Thr Ile Asn Val Leu Arg Arg Cys Tyr Lys Glu
        435                 440                 445

Ile Phe Ala Leu Ala Lys Lys His Asn Ile Ala
    450                 455

<210> SEQ ID NO 43
<211> LENGTH: 9099
<212> TYPE: DNA
<213> ORGANISM: Penicillium citrinum
<220> FEATURE:
<221> NAME/KEY: CDS
<222> LOCATION: (1)..(9099)

<400> SEQUENCE: 43 atg gat caa gcc aac tat cca aac gag cca att gtg gta gtg gga agc      48
Met Asp Gln Ala Asn Tyr Pro Asn Glu Pro Ile Val Val Val Gly Ser
1               5                   10                  15 ggt tgt cgg ttt cca ggt ggt gtc aac aca cca tca aaa ctt tgg gag      96
Gly Cys Arg Phe Pro Gly Gly Val Asn Thr Pro Ser Lys Leu Trp Glu
                20                  25                  30 ctg ctc aaa gag ccc cgg gat gta cag acc aag atc cct aag gag aga     144
Leu Leu Lys Glu Pro Arg Asp Val Gln Thr Lys Ile Pro Lys Glu Arg
            35                  40                  45 ttt gac gtc gat aca ttt tac agc ccc gat ggc act cac ccc ggg cgc     192
Phe Asp Val Asp Thr Phe Tyr Ser Pro Asp Gly Thr His Pro Gly Arg
        50                  55                  60
```

```
acg aac gca ccc ttt gca tac ttg ctg cag gag gat cta cgc ggt ttt         240
Thr Asn Ala Pro Phe Ala Tyr Leu Leu Gln Glu Asp Leu Arg Gly Phe
 65                  70                  75                  80 gat gcc tct ttc ttc aac atc caa gct gga gag gcc gaa acg att gac         288
Asp Ala Ser Phe Phe Asn Ile Gln Ala Gly Glu Ala Glu Thr Ile Asp
                 85                  90                  95 cca cag caa agg ctg ctg ctg gag acg gtc tat gaa gct gta tcc aac         336
Pro Gln Gln Arg Leu Leu Leu Glu Thr Val Tyr Glu Ala Val Ser Asn
             100                 105                 110 gca ggc cta cgg atc caa ggc ctt caa gga tcc tct act gct gtg tac         384
Ala Gly Leu Arg Ile Gln Gly Leu Gln Gly Ser Ser Thr Ala Val Tyr
         115                 120                 125 gtc ggt atg atg acg cat gac tat gag act atc gtg acg cgt gaa ttg         432
Val Gly Met Met Thr His Asp Tyr Glu Thr Ile Val Thr Arg Glu Leu
     130                 135                 140 gat agt att cct aca tac tct gcc acg ggg gta gct gtc agt gtg gcc         480
Asp Ser Ile Pro Thr Tyr Ser Ala Thr Gly Val Ala Val Ser Val Ala
145                 150                 155                 160 tcc aac cgt gta tca tac ttc ttc gac tgg cat ggg ccg agt atg acg         528
Ser Asn Arg Val Ser Tyr Phe Phe Asp Trp His Gly Pro Ser Met Thr
                 165                 170                 175 atc gac aca gcc tgt agt tca tcc tta gct gcc gtg cat ctg gcc gtc         576
Ile Asp Thr Ala Cys Ser Ser Ser Leu Ala Ala Val His Leu Ala Val
             180                 185                 190 caa cag ctt aga acg ggc gag agt acc atg gcg gtt gca gcc ggt gcg         624
Gln Gln Leu Arg Thr Gly Glu Ser Thr Met Ala Val Ala Ala Gly Ala
         195                 200                 205 aat ctg ata ttg ggc ccc atg acc ttt gta atg gag agc aaa ttg aac         672
Asn Leu Ile Leu Gly Pro Met Thr Phe Val Met Glu Ser Lys Leu Asn
     210                 215                 220 atg ctg tcc ccc aat ggt aga tct cga atg tgg gat gct gct gcc gat         720
Met Leu Ser Pro Asn Gly Arg Ser Arg Met Trp Asp Ala Ala Ala Asp
225                 230                 235                 240 gga tat gcc aga gga gaa ggt gtt tgc tct att gtc ctg aaa acg ctg         768
Gly Tyr Ala Arg Gly Glu Gly Val Cys Ser Ile Val Leu Lys Thr Leu
                 245                 250                 255 agc cag gca ctg cgc gac ggg gac agt atc gag tgt gtt atc cga gag         816
Ser Gln Ala Leu Arg Asp Gly Asp Ser Ile Glu Cys Val Ile Arg Glu
             260                 265                 270 acc ggt atc aac caa gat ggc cga acg aca ggt atc aca atg cca aac         864
Thr Gly Ile Asn Gln Asp Gly Arg Thr Thr Gly Ile Thr Met Pro Asn
         275                 280                 285 cat agc gca caa gaa gcc ctc att cgg gcc aca tat gcc aag gct ggt         912
His Ser Ala Gln Glu Ala Leu Ile Arg Ala Thr Tyr Ala Lys Ala Gly
     290                 295                 300 ctt gat att acc aac ccc cag gaa cgc tgc cag ttc ttt gaa gcc cat         960
Leu Asp Ile Thr Asn Pro Gln Glu Arg Cys Gln Phe Phe Glu Ala His
305                 310                 315                 320 gga act ggt aca cca gcc ggt gac cca cag gaa gct gag gct att gca        1008
Gly Thr Gly Thr Pro Ala Gly Asp Pro Gln Glu Ala Glu Ala Ile Ala
                 325                 330                 335 aca gcc ttc ttc gga cac aag gat gga aca atc gac agc gac ggc gag        1056
Thr Ala Phe Phe Gly His Lys Asp Gly Thr Ile Asp Ser Asp Gly Glu
             340                 345                 350 aaa gat gag ctt ttt gtc ggc agc atc aag aca gtt ctc ggt cac acg        1104
Lys Asp Glu Leu Phe Val Gly Ser Ile Lys Thr Val Leu Gly His Thr
         355                 360                 365 gaa ggc act gct ggt att gcg ggc tta atg aag gca tcg ttt gct gta        1152
Glu Gly Thr Ala Gly Ile Ala Gly Leu Met Lys Ala Ser Phe Ala Val
```

-continued

|  |  |  |  |  |  |  |  |  |  |  |  |  |  |  |  |  |
|---|---|---|---|---|---|---|---|---|---|---|---|---|---|---|---|---|
|  | 370 |  |  |  | 375 |  |  |  |  | 380 |  |  |  |  |  |  |
| cga | aat | ggc | gtg | atc | ccg | cca | aac | ctg | ctg | ttt | gag | aag | atc | agt | ccc | 1200 |
| Arg | Asn | Gly | Val | Ile | Pro | Pro | Asn | Leu | Leu | Phe | Glu | Lys | Ile | Ser | Pro |  |
| 385 |  |  |  |  | 390 |  |  |  |  | 395 |  |  |  |  | 400 |  |
| cgt | gtc | gct | ccg | ttc | tat | acg | cac | ttg | aaa | att | gca | acg | gag | gcc | aca | 1248 |
| Arg | Val | Ala | Pro | Phe | Tyr | Thr | His | Leu | Lys | Ile | Ala | Thr | Glu | Ala | Thr |  |
|  |  |  |  | 405 |  |  |  |  | 410 |  |  |  |  | 415 |  |  |
| gaa | tgg | ccg | att | gtt | gcg | ccc | ggg | cag | cct | cgc | aga | gtc | agc | gtt | aat | 1296 |
| Glu | Trp | Pro | Ile | Val | Ala | Pro | Gly | Gln | Pro | Arg | Arg | Val | Ser | Val | Asn |  |
|  |  |  | 420 |  |  |  |  | 425 |  |  |  |  | 430 |  |  |  |
| tca | ttt | gga | ttt | ggt | ggt | aca | aat | gcc | cat | gct | att | atc | gaa | gag | tat | 1344 |
| Ser | Phe | Gly | Phe | Gly | Gly | Thr | Asn | Ala | His | Ala | Ile | Ile | Glu | Glu | Tyr |  |
|  |  | 435 |  |  |  |  | 440 |  |  |  |  | 445 |  |  |  |  |
| atg | gct | cct | cca | cac | aag | ccg | aca | gca | gtg | gta | aca | gag | gtg | acc | tca | 1392 |
| Met | Ala | Pro | Pro | His | Lys | Pro | Thr | Ala | Val | Val | Thr | Glu | Val | Thr | Ser |  |
| 450 |  |  |  |  | 455 |  |  |  |  | 460 |  |  |  |  |  |  |
| gat | gca | gat | gca | tgc | agc | ttg | ccc | ctt | gtg | ctt | tca | tcg | aag | tcg | cag | 1440 |
| Asp | Ala | Asp | Ala | Cys | Ser | Leu | Pro | Leu | Val | Leu | Ser | Ser | Lys | Ser | Gln |  |
| 465 |  |  |  |  | 470 |  |  |  |  | 475 |  |  |  |  | 480 |  |
| cgc | tcc | atg | aag | gca | acg | cta | gaa | aat | atg | ctc | caa | ttt | ctg | gaa | acg | 1488 |
| Arg | Ser | Met | Lys | Ala | Thr | Leu | Glu | Asn | Met | Leu | Gln | Phe | Leu | Glu | Thr |  |
|  |  |  |  | 485 |  |  |  |  | 490 |  |  |  |  | 495 |  |  |
| cat | gat | gac | gtg | gac | atg | cat | gat | atc | gca | tat | acc | tta | ctt | gag | aaa | 1536 |
| His | Asp | Asp | Val | Asp | Met | His | Asp | Ile | Ala | Tyr | Thr | Leu | Leu | Glu | Lys |  |
|  |  |  | 500 |  |  |  |  | 505 |  |  |  |  | 510 |  |  |  |
| cgg | tct | atc | ttg | ccc | ttc | cgt | cgt | gcg | att | gca | gca | cac | aac | aag | gaa | 1584 |
| Arg | Ser | Ile | Leu | Pro | Phe | Arg | Arg | Ala | Ile | Ala | Ala | His | Asn | Lys | Glu |  |
|  |  | 515 |  |  |  |  | 520 |  |  |  |  | 525 |  |  |  |  |
| gta | gcc | cgc | gcg | gca | ctg | gag | gct | gcc | atc | gcg | gac | ggt | gag | gtc | gtc | 1632 |
| Val | Ala | Arg | Ala | Ala | Leu | Glu | Ala | Ala | Ile | Ala | Asp | Gly | Glu | Val | Val |  |
| 530 |  |  |  |  | 535 |  |  |  |  | 540 |  |  |  |  |  |  |
| acc | gac | ttc | cgc | acc | gac | gcg | aat | gac | aac | cct | cgc | gta | cta | ggt | gtc | 1680 |
| Thr | Asp | Phe | Arg | Thr | Asp | Ala | Asn | Asp | Asn | Pro | Arg | Val | Leu | Gly | Val |  |
| 545 |  |  |  |  | 550 |  |  |  |  | 555 |  |  |  |  | 560 |  |
| ttt | act | ggc | caa | ggt | gca | cag | tgg | ccg | ggc | atg | ctg | aag | aag | ctc | atg | 1728 |
| Phe | Thr | Gly | Gln | Gly | Ala | Gln | Trp | Pro | Gly | Met | Leu | Lys | Lys | Leu | Met |  |
|  |  |  |  | 565 |  |  |  |  | 570 |  |  |  |  | 575 |  |  |
| gtg | ggt | atg | cca | ttt | gtg | aga | ggc | att | ctc | gaa | gag | ctg | gat | aat | tca | 1776 |
| Val | Gly | Met | Pro | Phe | Val | Arg | Gly | Ile | Leu | Glu | Glu | Leu | Asp | Asn | Ser |  |
|  |  |  | 580 |  |  |  |  | 585 |  |  |  |  | 590 |  |  |  |
| ctg | caa | aca | ctg | cct | gaa | aag | tat | cgg | cct | acg | tgg | aca | ctg | tat | gac | 1824 |
| Leu | Gln | Thr | Leu | Pro | Glu | Lys | Tyr | Arg | Pro | Thr | Trp | Thr | Leu | Tyr | Asp |  |
|  |  | 595 |  |  |  |  | 600 |  |  |  |  | 605 |  |  |  |  |
| cag | ctc | atg | ctt | gaa | ggg | gat | gcc | tca | aac | gtc | aga | ctc | gcc | agc | ttc | 1872 |
| Gln | Leu | Met | Leu | Glu | Gly | Asp | Ala | Ser | Asn | Val | Arg | Leu | Ala | Ser | Phe |  |
| 610 |  |  |  |  | 615 |  |  |  |  | 620 |  |  |  |  |  |  |
| tcc | cag | cct | cta | tgc | tgc | gcc | gta | caa | atc | gtt | ctg | gtc | cga | ctt | ctc | 1920 |
| Ser | Gln | Pro | Leu | Cys | Cys | Ala | Val | Gln | Ile | Val | Leu | Val | Arg | Leu | Leu |  |
| 625 |  |  |  |  | 630 |  |  |  |  | 635 |  |  |  |  | 640 |  |
| gct | gca | gct | ggt | atc | gag | ttc | agt | gca | att | gtc | ggc | cac | agt | tca | ggt | 1968 |
| Ala | Ala | Ala | Gly | Ile | Glu | Phe | Ser | Ala | Ile | Val | Gly | His | Ser | Ser | Gly |  |
|  |  |  |  | 645 |  |  |  |  | 650 |  |  |  |  | 655 |  |  |
| gag | att | gcc | tgt | gcc | ttt | gcg | gca | gga | ttc | atc | agt | gcc | act | caa | gct | 2016 |
| Glu | Ile | Ala | Cys | Ala | Phe | Ala | Ala | Gly | Phe | Ile | Ser | Ala | Thr | Gln | Ala |  |
|  |  |  | 660 |  |  |  |  | 665 |  |  |  |  | 670 |  |  |  |
| atc | cgt | att | gcg | cat | ctg | cgt | gga | gtt | gtg | tcc | gcg | gag | cat | gcc | tct | 2064 |
| Ile | Arg | Ile | Ala | His | Leu | Arg | Gly | Val | Val | Ser | Ala | Glu | His | Ala | Ser |  |
|  |  | 675 |  |  |  |  | 680 |  |  |  |  | 685 |  |  |  |  |
| tct | cca | agc | ggc | cag | aca | ggc | gct | atg | cta | gcg | gca | ggt | atg | tcg | tac | 2112 |

```
                Ser Pro Ser Gly Gln Thr Gly Ala Met Leu Ala Ala Gly Met Ser Tyr
                    690             695                 700 gat gac gca aag gaa cta tgc gag ctc gaa gcc ttt gag ggt cgg gtc           2160
Asp Asp Ala Lys Glu Leu Cys Glu Leu Glu Ala Phe Glu Gly Arg Val
705                 710                 715                 720 tgc gtc gcc gct agc aat tca ccg gat agt gtg acc ttc tcc ggc gac           2208
Cys Val Ala Ala Ser Asn Ser Pro Asp Ser Val Thr Phe Ser Gly Asp
                    725                 730                 735 atg gat gct atc cag cac gtt gaa ggt gtc ttg gag gat gaa tcc act           2256
Met Asp Ala Ile Gln His Val Glu Gly Val Leu Glu Asp Glu Ser Thr
                740                 745                 750 ttt gcc aga atc ttg aga gtt gac aag gcc tac cat tcg cat cac atg           2304
Phe Ala Arg Ile Leu Arg Val Asp Lys Ala Tyr His Ser His His Met
            755                 760                 765 cac cca tgc gca gct cca tat gtc aag gca ttg ctg gag tgc gac tgt           2352
His Pro Cys Ala Ala Pro Tyr Val Lys Ala Leu Leu Glu Cys Asp Cys
        770                 775                 780 gct gtt gcc gat ggc caa ggt aac gat agt gtt gct tgg ttc tct gcc           2400
Ala Val Ala Asp Gly Gln Gly Asn Asp Ser Val Ala Trp Phe Ser Ala
785                 790                 795                 800 gtc cac gag acc agc aag caa atg act gta cag gat gtg atg ccc gct           2448
Val His Glu Thr Ser Lys Gln Met Thr Val Gln Asp Val Met Pro Ala
                    805                 810                 815 tat tgg aaa gac aat ctc gtc tct ccg gtc ttg ttc tcg cag gct gtg           2496
Tyr Trp Lys Asp Asn Leu Val Ser Pro Val Leu Phe Ser Gln Ala Val
                    820                 825                 830 cag aaa gca gtc atc act cat cgt cta atc gac gtc gcc atc gaa att           2544
Gln Lys Ala Val Ile Thr His Arg Leu Ile Asp Val Ala Ile Glu Ile
                835                 840                 845 ggc gcc cac cct gct ctc aag ggt ccg tgt cta gcc acc atc aag gat           2592
Gly Ala His Pro Ala Leu Lys Gly Pro Cys Leu Ala Thr Ile Lys Asp
        850                 855                 860 gct ctt gcc ggt gtg gag ctg ccg tat acc ggg tgc ttg gca cga aac           2640
Ala Leu Ala Gly Val Glu Leu Pro Tyr Thr Gly Cys Leu Ala Arg Asn
865                 870                 875                 880 gtt gac gat gtg gac gct ttt gct gga ggt ctg gga tac att tgg gag           2688
Val Asp Asp Val Asp Ala Phe Ala Gly Gly Leu Gly Tyr Ile Trp Glu
                    885                 890                 895 cgt ttc gga gtt cgg agt atc gac gcc gag ggc ttc gta caa caa gtc           2736
Arg Phe Gly Val Arg Ser Ile Asp Ala Glu Gly Phe Val Gln Gln Val
                    900                 905                 910 cgg ccc gat cgt gcc gtt caa aac ctg tca aag tca ttg ccc aca tac           2784
Arg Pro Asp Arg Ala Val Gln Asn Leu Ser Lys Ser Leu Pro Thr Tyr
                915                 920                 925 tct tgg gat cat act cgt caa tac tgg gca gaa tct cgc tcc acc cgc           2832
Ser Trp Asp His Thr Arg Gln Tyr Trp Ala Glu Ser Arg Ser Thr Arg
        930                 935                 940 cag cat ctt cgt gga ggt gcg ccc cat ctt ctg ctt gga aag ctt tct           2880
Gln His Leu Arg Gly Gly Ala Pro His Leu Leu Leu Gly Lys Leu Ser
945                 950                 955                 960 tct tac agc aca gca tcg acc ttc cag tgg aca aac ttc atc agg ccc           2928
Ser Tyr Ser Thr Ala Ser Thr Phe Gln Trp Thr Asn Phe Ile Arg Pro
                    965                 970                 975 cgg gat ctg gaa tgg ctc gac ggt cat gcg cta caa ggc cag act gtg           2976
Arg Asp Leu Glu Trp Leu Asp Gly His Ala Leu Gln Gly Gln Thr Val
                    980                 985                 990 ttc ccc gct gct ggg tac ata att atg gcc atg gaa gct gcc atg aag           3024
Phe Pro Ala Ala Gly Tyr Ile Ile Met Ala Met Glu Ala Ala Met Lys
                995                 1000                1005
```

|  |  |
|---|---|
| gtg gct ggt gag cgt gcc gcc caa gtt cag ctc ctg gaa atc ttg<br>Val Ala Gly Glu Arg Ala Ala Gln Val Gln Leu Leu Glu Ile Leu<br>1010                    1015                    1020 | 3069 |
| gac atg agc atc aac aaa gcc atc gtg ttt gaa gat gaa aac acc<br>Asp Met Ser Ile Asn Lys Ala Ile Val Phe Glu Asp Glu Asn Thr<br>1025                    1030                    1035 | 3114 |
| tcc gtg gag ctg aac ttg aca gcc gaa gtc acc agt gac aat gat<br>Ser Val Glu Leu Asn Leu Thr Ala Glu Val Thr Ser Asp Asn Asp<br>1040                    1045                    1050 | 3159 |
| gcg gat ggc caa gtc acg gtc aaa ttt gtt att gat tcc tgt ctg<br>Ala Asp Gly Gln Val Thr Val Lys Phe Val Ile Asp Ser Cys Leu<br>1055                    1060                    1065 | 3204 |
| gca aag gag agt gag ctt tcg aca tcc gcc aaa ggc caa atc gtc<br>Ala Lys Glu Ser Glu Leu Ser Thr Ser Ala Lys Gly Gln Ile Val<br>1070                    1075                    1080 | 3249 |
| ata acc ctt ggc gag gca tca ccg tca tcg cag ctt ttg ccg cca<br>Ile Thr Leu Gly Glu Ala Ser Pro Ser Ser Gln Leu Leu Pro Pro<br>1085                    1090                    1095 | 3294 |
| cct gag gaa gag tac ccc cag atg aac aat gtc aac atc gat ttc<br>Pro Glu Glu Glu Tyr Pro Gln Met Asn Asn Val Asn Ile Asp Phe<br>1100                    1105                    1110 | 3339 |
| ttc tat cgg gaa ctt gac ctc ctt ggg tat gac tac agc aaa gac<br>Phe Tyr Arg Glu Leu Asp Leu Leu Gly Tyr Asp Tyr Ser Lys Asp<br>1115                    1120                    1125 | 3384 |
| ttc cgt cgt ttg cag acc atg aga agg gcc gac tcc aaa gct agc<br>Phe Arg Arg Leu Gln Thr Met Arg Arg Ala Asp Ser Lys Ala Ser<br>1130                    1135                    1140 | 3429 |
| ggc acc ttg gct ttc ctt cca ctt aag gat gaa ttg cgc aat gag<br>Gly Thr Leu Ala Phe Leu Pro Leu Lys Asp Glu Leu Arg Asn Glu<br>1145                    1150                    1155 | 3474 |
| ccc ctc ttg ctc cac cca gcg ccc ctg gac atc gcg ttc cag act<br>Pro Leu Leu Leu His Pro Ala Pro Leu Asp Ile Ala Phe Gln Thr<br>1160                    1165                    1170 | 3519 |
| gtc att gga gcg tat tcc tct cca gga gat cgt cgc cta cgc tca<br>Val Ile Gly Ala Tyr Ser Ser Pro Gly Asp Arg Arg Leu Arg Ser<br>1175                    1180                    1185 | 3564 |
| ttg tac gtg cct act cac gtt gac aga gtg act ctg att cca tcg<br>Leu Tyr Val Pro Thr His Val Asp Arg Val Thr Leu Ile Pro Ser<br>1190                    1195                    1200 | 3609 |
| ctc tgt ata tcg gcg ggt aat tct ggt gaa acc gag ctt gcg ttt<br>Leu Cys Ile Ser Ala Gly Asn Ser Gly Glu Thr Glu Leu Ala Phe<br>1205                    1210                    1215 | 3654 |
| gac aca atc aac aca cac gac aag ggt gat ttc ctg agc ggc gac<br>Asp Thr Ile Asn Thr His Asp Lys Gly Asp Phe Leu Ser Gly Asp<br>1220                    1225                    1230 | 3699 |
| atc acg gtg tac gat tcg acc aag aca acg ctt ttc caa gtt gat<br>Ile Thr Val Tyr Asp Ser Thr Lys Thr Thr Leu Phe Gln Val Asp<br>1235                    1240                    1245 | 3744 |
| aac att gtc ttt aag cct ttc tct ccc ccg act gct tcg acc gac<br>Asn Ile Val Phe Lys Pro Phe Ser Pro Pro Thr Ala Ser Thr Asp<br>1250                    1255                    1260 | 3789 |
| cac cga atc ttc gca aag tgg gtc tgg gga ccc ctc acg ccc gaa<br>His Arg Ile Phe Ala Lys Trp Val Trp Gly Pro Leu Thr Pro Glu<br>1265                    1270                    1275 | 3834 |
| aaa ctg ctg gag gac cct gcg acg ttg atc ata gct cgg gac aag<br>Lys Leu Leu Glu Asp Pro Ala Thr Leu Ile Ile Ala Arg Asp Lys<br>1280                    1285                    1290 | 3879 |
| gag gac att ctg acc atc gag cga atc gtt tac ttc tac atc aaa<br>Glu Asp Ile Leu Thr Ile Glu Arg Ile Val Tyr Phe Tyr Ile Lys<br>1295                    1300                    1305 | 3924 |

```
tcc ttc cta gcc cag ata acc ccc gac gac cgt caa aat gcc gac       3969
Ser Phe Leu Ala Gln Ile Thr Pro Asp Asp Arg Gln Asn Ala Asp
1310                1315                1320 ctc cat tcc cag aag tac att gaa tgg tgt gac cag gtt cag gcc       4014
Leu His Ser Gln Lys Tyr Ile Glu Trp Cys Asp Gln Val Gln Ala
    1325                1330                1335 gat gct cgg gct ggc cac cat cag tgg tac cag gag tct tgg gag       4059
Asp Ala Arg Ala Gly His His Gln Trp Tyr Gln Glu Ser Trp Glu
1340                1345                1350 gag gac act tct gtt cac att gag caa atg tgt gaa agc aac tcg       4104
Glu Asp Thr Ser Val His Ile Glu Gln Met Cys Glu Ser Asn Ser
    1355                1360                1365 tcc cac cca cat gtg cgc ctg atc caa agg gta ggc aaa gaa tta       4149
Ser His Pro His Val Arg Leu Ile Gln Arg Val Gly Lys Glu Leu
1370                1375                1380 att tca att gtt cgc ggg aac ggg gat cct ttg gat atc atg aac       4194
Ile Ser Ile Val Arg Gly Asn Gly Asp Pro Leu Asp Ile Met Asn
    1385                1390                1395 cgc gat ggg ttg ttc acc gag tac tat acc aac aag ctc gcc ttt       4239
Arg Asp Gly Leu Phe Thr Glu Tyr Tyr Thr Asn Lys Leu Ala Phe
1400                1405                1410 ggc tca gca ata cac gtc gtt cag gat ctg gtt agc caa att gct       4284
Gly Ser Ala Ile His Val Val Gln Asp Leu Val Ser Gln Ile Ala
    1415                1420                1425 cat cgc tac caa tcc att gat atc ctt gag atc ggc ttg ggt aca       4329
His Arg Tyr Gln Ser Ile Asp Ile Leu Glu Ile Gly Leu Gly Thr
1430                1435                1440 ggc atc gcc acg aag cgc gtt ctt gca tca cct caa ctt ggt ttc       4374
Gly Ile Ala Thr Lys Arg Val Leu Ala Ser Pro Gln Leu Gly Phe
    1445                1450                1455 aac agt tac act tgc act gac atc tcg gcg gat gtt att ggc aag       4419
Asn Ser Tyr Thr Cys Thr Asp Ile Ser Ala Asp Val Ile Gly Lys
1460                1465                1470 gcc cgt gaa caa ctt tcc gaa ttc gac ggt ctc atg cag ttt gag       4464
Ala Arg Glu Gln Leu Ser Glu Phe Asp Gly Leu Met Gln Phe Glu
    1475                1480                1485 gca cta gac atc aac aga agc cca gca gag caa gga ttc aag cct       4509
Ala Leu Asp Ile Asn Arg Ser Pro Ala Glu Gln Gly Phe Lys Pro
1490                1495                1500 cac tcc tac gat ctg att att gca tcc gat gtc ctc cat gcc agc       4554
His Ser Tyr Asp Leu Ile Ile Ala Ser Asp Val Leu His Ala Ser
    1505                1510                1515 tcc aac ttc gag gaa aaa ttg gct cac ata agg tcc ttg ctc aag       4599
Ser Asn Phe Glu Glu Lys Leu Ala His Ile Arg Ser Leu Leu Lys
1520                1525                1530 ccg ggt ggt cac ttg gtt act ttc ggg gtc acc cat cgc gag cct       4644
Pro Gly Gly His Leu Val Thr Phe Gly Val Thr His Arg Glu Pro
    1535                1540                1545 gct cgc ctc gcc ttc atc tct ggg ctt ttc gct gat cga tgg act       4689
Ala Arg Leu Ala Phe Ile Ser Gly Leu Phe Ala Asp Arg Trp Thr
1550                1555                1560 gga gaa gac gaa act cgt gct ttg agt gcc tcg ggg tcc gtt gac       4734
Gly Glu Asp Glu Thr Arg Ala Leu Ser Ala Ser Gly Ser Val Asp
    1565                1570                1575 caa tgg gag cat acc ctc aag aga gtt ggg ttc tct ggc gtc gat       4779
Gln Trp Glu His Thr Leu Lys Arg Val Gly Phe Ser Gly Val Asp
1580                1585                1590 agt cgg aca ctt gat cga gag gat gat ttg atc ccg tct gtc ttc       4824
Ser Arg Thr Leu Asp Arg Glu Asp Asp Leu Ile Pro Ser Val Phe
```

-continued

|  |  |  |  |  |  |  |  |  |  |  |  |  |  |  |  |
|---|---|---|---|---|---|---|---|---|---|---|---|---|---|---|---|
| | 1595 | | | | 1600 | | | | | 1605 | | | | | |
| agt | aca | cat | gct | gtg | gat | gcc | acc | gtt | gag | cgt | ttg | tat | gat | cca | 4869 |
| Ser | Thr | His | Ala | Val | Asp | Ala | Thr | Val | Glu | Arg | Leu | Tyr | Asp | Pro | |
| 1610 | | | | | 1615 | | | | | 1620 | | | | | |
| ctt | tct | gct | cca | ttg | aag | gac | tca | tac | ccg | cca | tta | gtg | gtt | atc | 4914 |
| Leu | Ser | Ala | Pro | Leu | Lys | Asp | Ser | Tyr | Pro | Pro | Leu | Val | Val | Ile | |
| 1625 | | | | | 1630 | | | | | 1635 | | | | | |
| ggt | ggc | gaa | tcg | aca | aaa | acc | gaa | cgc | att | ttg | aac | gac | atg | aaa | 4959 |
| Gly | Gly | Glu | Ser | Thr | Lys | Thr | Glu | Arg | Ile | Leu | Asn | Asp | Met | Lys | |
| 1640 | | | | | 1645 | | | | | 1650 | | | | | |
| gct | gcc | cta | ccg | cat | aga | cac | atc | cac | tcc | gtc | aag | cgg | ctg | gaa | 5004 |
| Ala | Ala | Leu | Pro | His | Arg | His | Ile | His | Ser | Val | Lys | Arg | Leu | Glu | |
| 1655 | | | | | 1660 | | | | | 1665 | | | | | |
| agt | gtt | ctc | gac | gac | ccg | gcc | ttg | cag | cct | aag | tcg | act | ttt | gtc | 5049 |
| Ser | Val | Leu | Asp | Asp | Pro | Ala | Leu | Gln | Pro | Lys | Ser | Thr | Phe | Val | |
| 1670 | | | | | 1675 | | | | | 1680 | | | | | |
| atc | ctc | tcg | gaa | ctt | gat | gat | gaa | gtg | ttt | tgc | aac | ctt | gaa | gag | 5094 |
| Ile | Leu | Ser | Glu | Leu | Asp | Asp | Glu | Val | Phe | Cys | Asn | Leu | Glu | Glu | |
| 1685 | | | | | 1690 | | | | | 1695 | | | | | |
| gac | aag | ttt | gag | gca | gtc | aag | tct | ctt | ctc | ttc | tac | gcc | gga | cgc | 5139 |
| Asp | Lys | Phe | Glu | Ala | Val | Lys | Ser | Leu | Leu | Phe | Tyr | Ala | Gly | Arg | |
| 1700 | | | | | 1705 | | | | | 1710 | | | | | |
| atg | atg | tgg | ctg | aca | gag | aat | gcc | tgg | att | gat | cat | ccc | cac | cag | 5184 |
| Met | Met | Trp | Leu | Thr | Glu | Asn | Ala | Trp | Ile | Asp | His | Pro | His | Gln | |
| 1715 | | | | | 1720 | | | | | 1725 | | | | | |
| gcc | agc | acc | atc | gga | atg | ttg | agg | aca | atc | aag | ctc | gag | aac | cct | 5229 |
| Ala | Ser | Thr | Ile | Gly | Met | Leu | Arg | Thr | Ile | Lys | Leu | Glu | Asn | Pro | |
| 1730 | | | | | 1735 | | | | | 1740 | | | | | |
| gac | ttg | gga | acg | cac | gtc | ttc | gat | gtc | gat | act | gtg | gag | aac | cta | 5274 |
| Asp | Leu | Gly | Thr | His | Val | Phe | Asp | Val | Asp | Thr | Val | Glu | Asn | Leu | |
| 1745 | | | | | 1750 | | | | | 1755 | | | | | |
| gac | acc | aaa | ttc | ttc | gtt | gag | caa | ctt | ttg | cgc | ttc | gag | gag | agc | 5319 |
| Asp | Thr | Lys | Phe | Phe | Val | Glu | Gln | Leu | Leu | Arg | Phe | Glu | Glu | Ser | |
| 1760 | | | | | 1765 | | | | | 1770 | | | | | |
| gat | gat | cag | ctt | ttg | gaa | tca | ata | aca | tgg | act | cat | gag | ccc | gaa | 5364 |
| Asp | Asp | Gln | Leu | Leu | Glu | Ser | Ile | Thr | Trp | Thr | His | Glu | Pro | Glu | |
| 1775 | | | | | 1780 | | | | | 1785 | | | | | |
| gtg | tac | tgg | tgc | aag | ggt | cgt | gcc | tgg | gtc | cct | cgt | ttg | aag | cag | 5409 |
| Val | Tyr | Trp | Cys | Lys | Gly | Arg | Ala | Trp | Val | Pro | Arg | Leu | Lys | Gln | |
| 1790 | | | | | 1795 | | | | | 1800 | | | | | |
| gat | att | gct | agg | aac | gac | cgt | atg | aac | tcg | tct | cgt | cgt | cca | att | 5454 |
| Asp | Ile | Ala | Arg | Asn | Asp | Arg | Met | Asn | Ser | Ser | Arg | Arg | Pro | Ile | |
| 1805 | | | | | 1810 | | | | | 1815 | | | | | |
| ttc | ggt | aac | ttt | aat | tcg | tcc | aag | acg | gcc | att | gca | ctg | aaa | gag | 5499 |
| Phe | Gly | Asn | Phe | Asn | Ser | Ser | Lys | Thr | Ala | Ile | Ala | Leu | Lys | Glu | |
| 1820 | | | | | 1825 | | | | | 1830 | | | | | |
| gcg | agg | gga | gca | tcc | tca | tcg | atg | tac | tat | ctt | gag | tca | acc | gag | 5544 |
| Ala | Arg | Gly | Ala | Ser | Ser | Ser | Met | Tyr | Tyr | Leu | Glu | Ser | Thr | Glu | |
| 1835 | | | | | 1840 | | | | | 1845 | | | | | |
| acg | tgt | gat | tcg | tta | gaa | gac | gct | cgt | cat | gct | gga | aaa | gca | act | 5589 |
| Thr | Cys | Asp | Ser | Leu | Glu | Asp | Ala | Arg | His | Ala | Gly | Lys | Ala | Thr | |
| 1850 | | | | | 1855 | | | | | 1860 | | | | | |
| gtt | cgt | gtt | cgc | tac | gct | ctt | ccc | cag | gca | att | cgc | gtg | ggc | cat | 5634 |
| Val | Arg | Val | Arg | Tyr | Ala | Leu | Pro | Gln | Ala | Ile | Arg | Val | Gly | His | |
| 1865 | | | | | 1870 | | | | | 1875 | | | | | |
| ctc | gga | tac | ttc | cat | gtc | gtg | cag | ggc | agt | att | ctg | gag | aat | aca | 5679 |
| Leu | Gly | Tyr | Phe | His | Val | Val | Gln | Gly | Ser | Ile | Leu | Glu | Asn | Thr | |
| 1880 | | | | | 1885 | | | | | 1890 | | | | | |
| tgt | gag | gtg | cct | gta | gtc | gcc | ctg | gct | gag | aag | aat | gga | tct | ata | 5724 |

```
                      -continued

Cys Glu Val Pro Val Val Ala Leu Ala Glu Lys Asn Gly Ser Ile
1895                1900                1905 ctg cat gta ccg aga aac tac atg cat agt ctg ccc gat aac atg      5769
Leu His Val Pro Arg Asn Tyr Met His Ser Leu Pro Asp Asn Met
1910                1915                1920 gcg gaa ggc gag gat agt tcc ttc ttg ttg tcc aca gct gca gcc      5814
Ala Glu Gly Glu Asp Ser Ser Phe Leu Leu Ser Thr Ala Ala Ala
1925                1930                1935 ctc ctt gcc gaa aca att ctc tct agc gct cag tcc ttt ggc tct      5859
Leu Leu Ala Glu Thr Ile Leu Ser Ser Ala Gln Ser Phe Gly Ser
1940                1945                1950 gat gca tca att ctg att atg gag ccc cca atc ttc tgc gtc aaa      5904
Asp Ala Ser Ile Leu Ile Met Glu Pro Pro Ile Phe Cys Val Lys
1955                1960                1965 gca att ctg gag tcg gcc aaa acc tac ggt gtt cag gtt cat ttg      5949
Ala Ile Leu Glu Ser Ala Lys Thr Tyr Gly Val Gln Val His Leu
1970                1975                1980 gca aca act ctg tcc gac gtc aaa act att ccg gct cct tgg atc      5994
Ala Thr Thr Leu Ser Asp Val Lys Thr Ile Pro Ala Pro Trp Ile
1985                1990                1995 cga tta cat gcc aag gaa acc gac gct cgg ctg aaa cac agc ctg      6039
Arg Leu His Ala Lys Glu Thr Asp Ala Arg Leu Lys His Ser Leu
2000                2005                2010 ccg aca aac atg atg gca ttc ttt gac ttg tct acc gac cgg act      6084
Pro Thr Asn Met Met Ala Phe Phe Asp Leu Ser Thr Asp Arg Thr
2015                2020                2025 gct gcc ggg ata acc aac cgt ttg gcc aag ttg cta cca ccc agt      6129
Ala Ala Gly Ile Thr Asn Arg Leu Ala Lys Leu Leu Pro Pro Ser
2030                2035                2040 tgc ttc atg tac agt ggt gac tat ctt atc cga agt aca gct tcc      6174
Cys Phe Met Tyr Ser Gly Asp Tyr Leu Ile Arg Ser Thr Ala Ser
2045                2050                2055 aca tac aaa gtt agt cat gtt gag gat att cca atc ctc gag cac      6219
Thr Tyr Lys Val Ser His Val Glu Asp Ile Pro Ile Leu Glu His
2060                2065                2070 tct gtg gca atg gca aaa aat acc gtc tct gcg tcg act gtc gac      6264
Ser Val Ala Met Ala Lys Asn Thr Val Ser Ala Ser Thr Val Asp
2075                2080                2085 gac act gag aaa gtt att aca gcc aca caa att ctc ttg cct ggt      6309
Asp Thr Glu Lys Val Ile Thr Ala Thr Gln Ile Leu Leu Pro Gly
2090                2095                2100 cag ctc tct gtc aac cac aat gac caa cgc ttc aat ctg gcc acc      6354
Gln Leu Ser Val Asn His Asn Asp Gln Arg Phe Asn Leu Ala Thr
2105                2110                2115 gtc atc gac tgg aag gaa aat gag gtg tcc gct agg att tgc ccc      6399
Val Ile Asp Trp Lys Glu Asn Glu Val Ser Ala Arg Ile Cys Pro
2120                2125                2130 atc gac tct ggt aac tta ttt tcc aac aag aag acg tat ttg ctt      6444
Ile Asp Ser Gly Asn Leu Phe Ser Asn Lys Lys Thr Tyr Leu Leu
2135                2140                2145 gtt ggt ctt acc ggg gac ctt ggt cgc tct ctc tgt cgc tgg atg      6489
Val Gly Leu Thr Gly Asp Leu Gly Arg Ser Leu Cys Arg Trp Met
2150                2155                2160 atc ttg cat ggc gcc cgc cat gtt gtg ctc act agc cgg aac cct      6534
Ile Leu His Gly Ala Arg His Val Val Leu Thr Ser Arg Asn Pro
2165                2170                2175 cga ctt gat ccc aaa tgg atc gcc aac atg gag gca ctt ggt ggt      6579
Arg Leu Asp Pro Lys Trp Ile Ala Asn Met Glu Ala Leu Gly Gly
2180                2185                2190
```

-continued

| | | |
|---|---|---|
| gac atc acc gtt ctg tca atg gat gtt gcc aat gag gat tca gtc<br>Asp Ile Thr Val Leu Ser Met Asp Val Ala Asn Glu Asp Ser Val<br>2195                    2200                      2205 | 6624 |
| gat gct ggc ctt ggc aag ctt gtc gat atg aag ttg cca cct gtt<br>Asp Ala Gly Leu Gly Lys Leu Val Asp Met Lys Leu Pro Pro Val<br>2210                    2215                      2220 | 6669 |
| gcc ggc atc gcg ttc ggg cct ttg gtg ctg cag gat gtc atg ctg<br>Ala Gly Ile Ala Phe Gly Pro Leu Val Leu Gln Asp Val Met Leu<br>2225                    2230                      2235 | 6714 |
| aag aac atg gac cac cag atg atg gac atg gtg ttg aag ccc aag<br>Lys Asn Met Asp His Gln Met Met Asp Met Val Leu Lys Pro Lys<br>2240                    2245                      2250 | 6759 |
| gta caa gga gca cgc att ctt cat gaa cgg ttc tcc gaa cag acg<br>Val Gln Gly Ala Arg Ile Leu His Glu Arg Phe Ser Glu Gln Thr<br>2255                    2260                      2265 | 6804 |
| ggc agc aag gcg ctc gac ttc ttc atc atg ttt tcg tcc att gtt<br>Gly Ser Lys Ala Leu Asp Phe Phe Ile Met Phe Ser Ser Ile Val<br>2270                    2275                      2280 | 6849 |
| gca gtt att ggc aat cct ggc cag tcc aac tat ggc gct gcg aat<br>Ala Val Ile Gly Asn Pro Gly Gln Ser Asn Tyr Gly Ala Ala Asn<br>2285                    2290                      2295 | 6894 |
| gcc tac cta cag gct ctg gcc cag caa cgg tgc gcc aga gga ttg<br>Ala Tyr Leu Gln Ala Leu Ala Gln Gln Arg Cys Ala Arg Gly Leu<br>2300                    2305                      2310 | 6939 |
| gcg gga tca acc atc gat att ggt gcc gtt tac ggt gta ggg ttt<br>Ala Gly Ser Thr Ile Asp Ile Gly Ala Val Tyr Gly Val Gly Phe<br>2315                    2320                      2325 | 6984 |
| gtc acg agg gcc gag atg gag gag gac ttt gat gct atc cgt ttc<br>Val Thr Arg Ala Glu Met Glu Glu Asp Phe Asp Ala Ile Arg Phe<br>2330                    2335                      2340 | 7029 |
| atg ttt gac tca gtt gaa gag cat gag ctg cac acg ctt ttc gcc<br>Met Phe Asp Ser Val Glu Glu His Glu Leu His Thr Leu Phe Ala<br>2345                    2350                      2355 | 7074 |
| gaa gcg gtc gtg tct gac cag cgt gcc cgg cag caa cca cag cgc<br>Glu Ala Val Val Ser Asp Gln Arg Ala Arg Gln Gln Pro Gln Arg<br>2360                    2365                      2370 | 7119 |
| aag acg gtc att gac atg gcg gac ctt gag ctt acc acg ggt atc<br>Lys Thr Val Ile Asp Met Ala Asp Leu Glu Leu Thr Thr Gly Ile<br>2375                    2380                      2385 | 7164 |
| cca gat ctt gac cct gcg ctt caa gat cga att att tac ttc aac<br>Pro Asp Leu Asp Pro Ala Leu Gln Asp Arg Ile Ile Tyr Phe Asn<br>2390                    2395                      2400 | 7209 |
| gac cct cgt ttc gga aac ttc aaa att ccc ggt caa cgc gga gac<br>Asp Pro Arg Phe Gly Asn Phe Lys Ile Pro Gly Gln Arg Gly Asp<br>2405                    2410                      2415 | 7254 |
| ggt ggc gac aat gga tca ggg tct aaa ggc tcc att gcc gac cag<br>Gly Gly Asp Asn Gly Ser Gly Ser Lys Gly Ser Ile Ala Asp Gln<br>2420                    2425                      2430 | 7299 |
| ctc aaa caa gca aca act tta gac caa gtt cgg caa atc gtg att<br>Leu Lys Gln Ala Thr Thr Leu Asp Gln Val Arg Gln Ile Val Ile<br>2435                    2440                      2445 | 7344 |
| gat ggt cta tct gag aaa ctc cgt gtt acc ctc caa gtt tcg gac<br>Asp Gly Leu Ser Glu Lys Leu Arg Val Thr Leu Gln Val Ser Asp<br>2450                    2455                      2460 | 7389 |
| ggg gag agc gtg gac cca acc att cct ctc att gat caa ggt gtc<br>Gly Glu Ser Val Asp Pro Thr Ile Pro Leu Ile Asp Gln Gly Val<br>2465                    2470                      2475 | 7434 |
| gac tcc ttg ggt gca gtg act gtc ggc tca tgg ttc tca aag caa<br>Asp Ser Leu Gly Ala Val Thr Val Gly Ser Trp Phe Ser Lys Gln<br>2480                    2485                      2490 | 7479 |

```
                                    -continued ctc tac ctt gac ctc cca ctc ttg agg gta ctt ggc ggt gct tct        7524
Leu Tyr Leu Asp Leu Pro Leu Leu Arg Val Leu Gly Gly Ala Ser
    2495                2500                2505 gtc gct gat ctt gcc gac gac gcg gcc acc cga ctc cca gct aca        7569
Val Ala Asp Leu Ala Asp Asp Ala Ala Thr Arg Leu Pro Ala Thr
2510                2515                2520 tcc att ccg ctg ctg ttg caa att ggt gat tcc acg gga acc tcg        7614
Ser Ile Pro Leu Leu Leu Gln Ile Gly Asp Ser Thr Gly Thr Ser
    2525                2530                2535 gac agc ggg gct tct ccg aca cca aca gac agc cat gat gaa gca        7659
Asp Ser Gly Ala Ser Pro Thr Pro Thr Asp Ser His Asp Glu Ala
2540                2545                2550 agc tct gct acc agc aca gat gcg tcg tca gcc gaa gag gat gaa        7704
Ser Ser Ala Thr Ser Thr Asp Ala Ser Ser Ala Glu Glu Asp Glu
    2555                2560                2565 gag caa gag gac gat aat gag cag gga ggc cgt aag att ctt cgt        7749
Glu Gln Glu Asp Asp Asn Glu Gln Gly Gly Arg Lys Ile Leu Arg
2570                2575                2580 cgc gag agg ttg tcc ctt ggc cag gag tat tcc tgg agg cag caa        7794
Arg Glu Arg Leu Ser Leu Gly Gln Glu Tyr Ser Trp Arg Gln Gln
    2585                2590                2595 caa atg gta aaa gat cat acc atc ttc aac aac act att ggc atg        7839
Gln Met Val Lys Asp His Thr Ile Phe Asn Asn Thr Ile Gly Met
2600                2605                2610 ttc atg aag ggt acc att gac ctc gac cgg ttg agg cgg gct ctg        7884
Phe Met Lys Gly Thr Ile Asp Leu Asp Arg Leu Arg Arg Ala Leu
    2615                2620                2625 aaa gcc tca ttg cgc cgt cac gag atc ttc cgt acg tgc ttt gtt        7929
Lys Ala Ser Leu Arg Arg His Glu Ile Phe Arg Thr Cys Phe Val
2630                2635                2640 act ggc gat gac tat agc agc gat tta aat ggt ccc gtc caa gtg        7974
Thr Gly Asp Asp Tyr Ser Ser Asp Leu Asn Gly Pro Val Gln Val
    2645                2650                2655 gtt ctc aag aac ccg gag aac aga gtg cac ttt gtt cag gtg aac        8019
Val Leu Lys Asn Pro Glu Asn Arg Val His Phe Val Gln Val Asn
2660                2665                2670 aac gct gcg gag gca gag gaa gag tac cgg aaa ctc gag aag aca        8064
Asn Ala Ala Glu Ala Glu Glu Glu Tyr Arg Lys Leu Glu Lys Thr
    2675                2680                2685 aac tat agc atc tcc aca ggt gac act ctc aga ctc gtt gat ttc        8109
Asn Tyr Ser Ile Ser Thr Gly Asp Thr Leu Arg Leu Val Asp Phe
2690                2695                2700 tac tgg ggc aca gat gac cac ctg ttg gta atc ggc tac cac aga        8154
Tyr Trp Gly Thr Asp Asp His Leu Leu Val Ile Gly Tyr His Arg
    2705                2710                2715 tta gtt ggt gat ggc tca aca aca gaa aac ctg ttc aat gag atc        8199
Leu Val Gly Asp Gly Ser Thr Thr Glu Asn Leu Phe Asn Glu Ile
2720                2725                2730 ggg cag att tac agc ggg gtg aaa atg cag cga cca tcg acc caa        8244
Gly Gln Ile Tyr Ser Gly Val Lys Met Gln Arg Pro Ser Thr Gln
    2735                2740                2745 ttc tct gat cta gcc gtc caa cag cgg gaa aac ctg gaa aat ggg        8289
Phe Ser Asp Leu Ala Val Gln Gln Arg Glu Asn Leu Glu Asn Gly
2750                2755                2760 cga atg ggg gac gat atc gcg ttc tgg aag tcc atg cat agc aaa        8334
Arg Met Gly Asp Asp Ile Ala Phe Trp Lys Ser Met His Ser Lys
    2765                2770                2775 gtc tcg tca tct gcg cca acc gtg ctt ccc atc atg aat ctg atc        8379
Val Ser Ser Ser Ala Pro Thr Val Leu Pro Ile Met Asn Leu Ile
```

-continued

| | | |
|---|---|---|
| aat gac cct gct gcc aat tca gag cag cag caa ata cag cca ttc<br>Asn Asp Pro Ala Ala Asn Ser Glu Gln Gln Gln Ile Gln Pro Phe<br>2795                              2800                       2805 | | 8424 |
| acg tgg cag cag tat gaa gca att gct cgt tta gat ccc atg gtc<br>Thr Trp Gln Gln Tyr Glu Ala Ile Ala Arg Leu Asp Pro Met Val<br>2810                              2815                       2820 | | 8469 |
| gcc ttc cga atc aaa gag cgg agc cgc aag cac aag gca acc ccc<br>Ala Phe Arg Ile Lys Glu Arg Ser Arg Lys His Lys Ala Thr Pro<br>2825                              2830                       2835 | | 8514 |
| atg cag ttc tac ctg gcc gcc tac cac gtt ttg ttg gcg cgt ctt<br>Met Gln Phe Tyr Leu Ala Ala Tyr His Val Leu Leu Ala Arg Leu<br>2840                              2845                       2850 | | 8559 |
| acc ggc agc aaa gac ata acc atc ggc ctc gcc gaa acc aac cga<br>Thr Gly Ser Lys Asp Ile Thr Ile Gly Leu Ala Glu Thr Asn Arg<br>2855                              2860                       2865 | | 8604 |
| tcc acc atg gaa gaa att tcg gcg atg ggc ttt ttc gct aac gtg<br>Ser Thr Met Glu Glu Ile Ser Ala Met Gly Phe Phe Ala Asn Val<br>2870                              2875                       2880 | | 8649 |
| ctt ccc ctg cgc ttt gat gag ttc gtc ggc agc aag aca ttc ggc<br>Leu Pro Leu Arg Phe Asp Glu Phe Val Gly Ser Lys Thr Phe Gly<br>2885                              2890                       2895 | | 8694 |
| gag cac ctt gta gcc acc aag gac agt gtg cgt gag gcc atg caa<br>Glu His Leu Val Ala Thr Lys Asp Ser Val Arg Glu Ala Met Gln<br>2900                              2905                       2910 | | 8739 |
| cac gcg cgg gtg ccg tat ggc gtc atc ctc gac tgt cta ggc ctg<br>His Ala Arg Val Pro Tyr Gly Val Ile Leu Asp Cys Leu Gly Leu<br>2915                              2920                       2925 | | 8784 |
| aat ctc cct acc tca ggc gag gaa ccc aag act cag aca cac gcc<br>Asn Leu Pro Thr Ser Gly Glu Glu Pro Lys Thr Gln Thr His Ala<br>2930                              2935                       2940 | | 8829 |
| ccc ttg ttc cag gct gtc ttt gat tac aag cag ggt caa gcg gag<br>Pro Leu Phe Gln Ala Val Phe Asp Tyr Lys Gln Gly Gln Ala Glu<br>2945                              2950                       2955 | | 8874 |
| agt ggc tca att ggc aat gcc aaa atg acg agt gtt ctc gct tcc<br>Ser Gly Ser Ile Gly Asn Ala Lys Met Thr Ser Val Leu Ala Ser<br>2960                              2965                       2970 | | 8919 |
| cgt gag cgc act cct tat gac atc gtt ctc gag atg tgg gat gac<br>Arg Glu Arg Thr Pro Tyr Asp Ile Val Leu Glu Met Trp Asp Asp<br>2975                              2980                       2985 | | 8964 |
| cct acc aag gac cca ctc att cat gtc aaa ctt cag agc tcg ctg<br>Pro Thr Lys Asp Pro Leu Ile His Val Lys Leu Gln Ser Ser Leu<br>2990                              2995                       3000 | | 9009 |
| tat ggc cct gag cac gct cag gcc ttt gta gac cac ttt tct tca<br>Tyr Gly Pro Glu His Ala Gln Ala Phe Val Asp His Phe Ser Ser<br>3005                              3010                       3015 | | 9054 |
| atc ctc act atg ttc tcg atg aac ccg gct ctg aag ttg gcc tag<br>Ile Leu Thr Met Phe Ser Met Asn Pro Ala Leu Lys Leu Ala<br>3020                              3025                       3030 | | 9099 |

<210> SEQ ID NO 44
<211> LENGTH: 3032
<212> TYPE: PRT
<213> ORGANISM: Penicillium citrinum

<400> SEQUENCE: 44

Met Asp Gln Ala Asn Tyr Pro Asn Glu Pro Ile Val Val Val Gly Ser
1               5                   10                  15

Gly Cys Arg Phe Pro Gly Gly Val Asn Thr Pro Ser Lys Leu Trp Glu
              20                   25                   30

```
Leu Leu Lys Glu Pro Arg Asp Val Gln Thr Lys Ile Pro Lys Glu Arg
         35                  40                  45

Phe Asp Val Asp Thr Phe Tyr Ser Pro Asp Gly Thr His Pro Gly Arg
     50                  55                  60

Thr Asn Ala Pro Phe Ala Tyr Leu Leu Gln Glu Asp Leu Arg Gly Phe
 65                  70                  75                  80

Asp Ala Ser Phe Phe Asn Ile Gln Ala Gly Glu Ala Glu Thr Ile Asp
                 85                  90                  95

Pro Gln Gln Arg Leu Leu Leu Glu Thr Val Tyr Glu Ala Val Ser Asn
                100                 105                 110

Ala Gly Leu Arg Ile Gln Gly Leu Gln Gly Ser Ser Thr Ala Val Tyr
            115                 120                 125

Val Gly Met Met Thr His Asp Tyr Glu Thr Ile Val Thr Arg Glu Leu
        130                 135                 140

Asp Ser Ile Pro Thr Tyr Ser Ala Thr Gly Val Ala Val Ser Val Ala
145                 150                 155                 160

Ser Asn Arg Val Ser Tyr Phe Phe Asp Trp His Gly Pro Ser Met Thr
                165                 170                 175

Ile Asp Thr Ala Cys Ser Ser Ser Leu Ala Ala Val His Leu Ala Val
                180                 185                 190

Gln Gln Leu Arg Thr Gly Glu Ser Thr Met Ala Val Ala Ala Gly Ala
            195                 200                 205

Asn Leu Ile Leu Gly Pro Met Thr Phe Val Met Glu Ser Lys Leu Asn
            210                 215                 220

Met Leu Ser Pro Asn Gly Arg Ser Arg Met Trp Asp Ala Ala Ala Asp
225                 230                 235                 240

Gly Tyr Ala Arg Gly Glu Gly Val Cys Ser Ile Val Leu Lys Thr Leu
                245                 250                 255

Ser Gln Ala Leu Arg Asp Gly Asp Ser Ile Glu Cys Val Ile Arg Glu
            260                 265                 270

Thr Gly Ile Asn Gln Asp Gly Arg Thr Thr Gly Ile Thr Met Pro Asn
            275                 280                 285

His Ser Ala Gln Glu Ala Leu Ile Arg Ala Thr Tyr Ala Lys Ala Gly
    290                 295                 300

Leu Asp Ile Thr Asn Pro Gln Glu Arg Cys Gln Phe Phe Glu Ala His
305                 310                 315                 320

Gly Thr Gly Thr Pro Ala Gly Asp Pro Gln Glu Ala Glu Ala Ile Ala
                325                 330                 335

Thr Ala Phe Phe Gly His Lys Asp Gly Thr Ile Asp Ser Asp Gly Glu
            340                 345                 350

Lys Asp Glu Leu Phe Val Gly Ser Ile Lys Thr Val Leu Gly His Thr
            355                 360                 365

Glu Gly Thr Ala Gly Ile Ala Gly Leu Met Lys Ala Ser Phe Ala Val
        370                 375                 380

Arg Asn Gly Val Ile Pro Pro Asn Leu Leu Phe Glu Lys Ile Ser Pro
385                 390                 395                 400

Arg Val Ala Pro Phe Tyr Thr His Leu Lys Ile Ala Thr Glu Ala Thr
                405                 410                 415

Glu Trp Pro Ile Val Ala Pro Gly Gln Pro Arg Arg Val Ser Val Asn
            420                 425                 430

Ser Phe Gly Phe Gly Gly Thr Asn Ala His Ala Ile Ile Glu Glu Tyr
        435                 440                 445
```

```
Met Ala Pro His Lys Pro Thr Ala Val Thr Glu Val Thr Ser
    450             455             460

Asp Ala Asp Ala Cys Ser Leu Pro Leu Val Leu Ser Ser Lys Ser Gln
465             470             475             480

Arg Ser Met Lys Ala Thr Leu Glu Asn Met Leu Gln Phe Leu Glu Thr
            485             490             495

His Asp Asp Val Asp Met His Asp Ile Ala Tyr Thr Leu Leu Glu Lys
            500             505             510

Arg Ser Ile Leu Pro Phe Arg Arg Ala Ile Ala His Asn Lys Glu
            515             520             525

Val Ala Arg Ala Ala Leu Glu Ala Ile Ala Asp Gly Glu Val Val
    530             535             540

Thr Asp Phe Arg Thr Asp Ala Asn Asp Asn Pro Arg Val Leu Gly Val
545             550             555             560

Phe Thr Gly Gln Gly Ala Gln Trp Pro Gly Met Leu Lys Lys Leu Met
                565             570             575

Val Gly Met Pro Phe Val Arg Gly Ile Leu Glu Glu Leu Asp Asn Ser
            580             585             590

Leu Gln Thr Leu Pro Glu Lys Tyr Arg Pro Thr Trp Thr Leu Tyr Asp
    595             600             605

Gln Leu Met Leu Glu Gly Asp Ala Ser Asn Val Arg Leu Ala Ser Phe
    610             615             620

Ser Gln Pro Leu Cys Cys Ala Val Gln Ile Val Leu Val Arg Leu Leu
625             630             635             640

Ala Ala Ala Gly Ile Glu Phe Ser Ala Ile Val Gly His Ser Ser Gly
                645             650             655

Glu Ile Ala Cys Ala Phe Ala Ala Gly Phe Ile Ser Ala Thr Gln Ala
            660             665             670

Ile Arg Ile Ala His Leu Arg Gly Val Val Ser Ala Glu His Ala Ser
        675             680             685

Ser Pro Ser Gly Gln Thr Gly Ala Met Leu Ala Ala Gly Met Ser Tyr
    690             695             700

Asp Asp Ala Lys Glu Leu Cys Glu Leu Glu Ala Phe Glu Gly Arg Val
705             710             715             720

Cys Val Ala Ala Ser Asn Ser Pro Asp Ser Val Thr Phe Ser Gly Asp
                725             730             735

Met Asp Ala Ile Gln His Val Glu Gly Val Leu Glu Asp Glu Ser Thr
            740             745             750

Phe Ala Arg Ile Leu Arg Val Asp Lys Ala Tyr His Ser His His Met
        755             760             765

His Pro Cys Ala Ala Pro Tyr Val Lys Ala Leu Leu Glu Cys Asp Cys
    770             775             780

Ala Val Ala Asp Gly Gln Gly Asn Asp Ser Val Ala Trp Phe Ser Ala
785             790             795             800

Val His Glu Thr Ser Lys Gln Met Thr Val Gln Asp Val Met Pro Ala
            805             810             815

Tyr Trp Lys Asp Asn Leu Val Ser Pro Val Leu Phe Ser Gln Ala Val
            820             825             830

Gln Lys Ala Val Ile Thr His Arg Leu Ile Asp Val Ala Ile Glu Ile
        835             840             845

Gly Ala His Pro Ala Leu Lys Gly Pro Cys Leu Ala Thr Ile Lys Asp
    850             855             860

Ala Leu Ala Gly Val Glu Leu Pro Tyr Thr Gly Cys Leu Ala Arg Asn
```

-continued

```
            865                 870                 875                 880
Val Asp Asp Val Asp Ala Phe Ala Gly Gly Leu Gly Tyr Ile Trp Glu
                    885                 890                 895
Arg Phe Gly Val Arg Ser Ile Asp Ala Glu Gly Phe Val Gln Gln Val
                900                 905                 910
Arg Pro Asp Arg Ala Val Gln Asn Leu Ser Lys Ser Leu Pro Thr Tyr
            915                 920                 925
Ser Trp Asp His Thr Arg Gln Tyr Trp Ala Glu Ser Arg Ser Thr Arg
    930                 935                 940
Gln His Leu Arg Gly Gly Ala Pro His Leu Leu Leu Gly Lys Leu Ser
945                 950                 955                 960
Ser Tyr Ser Thr Ala Ser Thr Phe Gln Trp Thr Asn Phe Ile Arg Pro
                965                 970                 975
Arg Asp Leu Glu Trp Leu Asp Gly His Ala Leu Gln Gly Gln Thr Val
            980                 985                 990
Phe Pro Ala Ala Gly Tyr Ile Ile Met Ala Met Glu Ala Ala Met Lys
            995                 1000                1005
Val Ala Gly Glu Arg Ala Ala Gln Val Gln Leu Leu Glu Ile Leu
    1010                1015                1020
Asp Met Ser Ile Asn Lys Ala Ile Val Phe Glu Asp Glu Asn Thr
    1025                1030                1035
Ser Val Glu Leu Asn Leu Thr Ala Glu Val Thr Ser Asp Asn Asp
    1040                1045                1050
Ala Asp Gly Gln Val Thr Val Lys Phe Val Ile Asp Ser Cys Leu
    1055                1060                1065
Ala Lys Glu Ser Glu Leu Ser Thr Ser Ala Lys Gly Gln Ile Val
    1070                1075                1080
Ile Thr Leu Gly Glu Ala Ser Pro Ser Ser Gln Leu Leu Pro Pro
    1085                1090                1095
Pro Glu Glu Glu Tyr Pro Gln Met Asn Asn Val Asn Ile Asp Phe
    1100                1105                1110
Phe Tyr Arg Glu Leu Asp Leu Leu Gly Tyr Asp Tyr Ser Lys Asp
    1115                1120                1125
Phe Arg Arg Leu Gln Thr Met Arg Arg Ala Asp Ser Lys Ala Ser
    1130                1135                1140
Gly Thr Leu Ala Phe Leu Pro Leu Lys Asp Glu Leu Arg Asn Glu
    1145                1150                1155
Pro Leu Leu Leu His Pro Ala Pro Leu Asp Ile Ala Phe Gln Thr
    1160                1165                1170
Val Ile Gly Ala Tyr Ser Ser Pro Gly Asp Arg Arg Leu Arg Ser
    1175                1180                1185
Leu Tyr Val Pro Thr His Val Asp Arg Val Thr Leu Ile Pro Ser
    1190                1195                1200
Leu Cys Ile Ser Ala Gly Asn Ser Gly Glu Thr Glu Leu Ala Phe
    1205                1210                1215
Asp Thr Ile Asn Thr His Asp Lys Gly Asp Phe Leu Ser Gly Asp
    1220                1225                1230
Ile Thr Val Tyr Asp Ser Lys Thr Thr Leu Phe Gln Val Asp
    1235                1240                1245
Asn Ile Val Phe Lys Pro Phe Ser Pro Pro Thr Ala Ser Thr Asp
    1250                1255                1260
His Arg Ile Phe Ala Lys Trp Val Trp Gly Pro Leu Thr Pro Glu
    1265                1270                1275
```

-continued

```
Lys Leu Leu Glu Asp Pro Ala Thr Leu Ile Ile Ala Arg Asp Lys
    1280            1285                1290

Glu Asp Ile Leu Thr Ile Glu Arg Ile Val Tyr Phe Tyr Ile Lys
    1295            1300                1305

Ser Phe Leu Ala Gln Ile Thr Pro Asp Asp Arg Gln Asn Ala Asp
    1310            1315                1320

Leu His Ser Gln Lys Tyr Ile Glu Trp Cys Asp Gln Val Gln Ala
    1325            1330                1335

Asp Ala Arg Ala Gly His His Gln Trp Tyr Gln Glu Ser Trp Glu
    1340            1345                1350

Glu Asp Thr Ser Val His Ile Glu Gln Met Cys Glu Ser Asn Ser
    1355            1360                1365

Ser His Pro His Val Arg Leu Ile Gln Arg Val Gly Lys Glu Leu
    1370            1375                1380

Ile Ser Ile Val Arg Gly Asn Gly Asp Pro Leu Asp Ile Met Asn
    1385            1390                1395

Arg Asp Gly Leu Phe Thr Glu Tyr Tyr Thr Asn Lys Leu Ala Phe
    1400            1405                1410

Gly Ser Ala Ile His Val Val Gln Asp Leu Val Ser Gln Ile Ala
    1415            1420                1425

His Arg Tyr Gln Ser Ile Asp Ile Leu Glu Ile Gly Leu Gly Thr
    1430            1435                1440

Gly Ile Ala Thr Lys Arg Val Leu Ala Ser Pro Gln Leu Gly Phe
    1445            1450                1455

Asn Ser Tyr Thr Cys Thr Asp Ile Ser Ala Asp Val Ile Gly Lys
    1460            1465                1470

Ala Arg Glu Gln Leu Ser Glu Phe Asp Gly Leu Met Gln Phe Glu
    1475            1480                1485

Ala Leu Asp Ile Asn Arg Ser Pro Ala Glu Gln Gly Phe Lys Pro
    1490            1495                1500

His Ser Tyr Asp Leu Ile Ile Ala Ser Asp Val Leu His Ala Ser
    1505            1510                1515

Ser Asn Phe Glu Glu Lys Leu Ala His Ile Arg Ser Leu Leu Lys
    1520            1525                1530

Pro Gly Gly His Leu Val Thr Phe Gly Val Thr His Arg Glu Pro
    1535            1540                1545

Ala Arg Leu Ala Phe Ile Ser Gly Leu Phe Ala Asp Arg Trp Thr
    1550            1555                1560

Gly Glu Asp Glu Thr Arg Ala Leu Ser Ala Ser Gly Ser Val Asp
    1565            1570                1575

Gln Trp Glu His Thr Leu Lys Arg Val Gly Phe Ser Gly Val Asp
    1580            1585                1590

Ser Arg Thr Leu Asp Arg Glu Asp Asp Leu Ile Pro Ser Val Phe
    1595            1600                1605

Ser Thr His Ala Val Asp Ala Thr Val Glu Arg Leu Tyr Asp Pro
    1610            1615                1620

Leu Ser Ala Pro Leu Lys Asp Ser Tyr Pro Pro Leu Val Val Ile
    1625            1630                1635

Gly Gly Glu Ser Thr Lys Thr Glu Arg Ile Leu Asn Asp Met Lys
    1640            1645                1650

Ala Ala Leu Pro His Arg His Ile His Ser Val Lys Arg Leu Glu
    1655            1660                1665
```

-continued

| | | | | | | | | | |
|---|---|---|---|---|---|---|---|---|---|
| Ser | Val | Leu | Asp | Asp | Pro | Ala | Leu | Gln | Pro | Lys | Ser | Thr | Phe | Val |
| | 1670 | | | | 1675 | | | | 1680 | | | | | |
| Ile | Leu | Ser | Glu | Leu | Asp | Asp | Glu | Val | Phe | Cys | Asn | Leu | Glu | Glu |
| | 1685 | | | | 1690 | | | | 1695 | | | | | |
| Asp | Lys | Phe | Glu | Ala | Val | Lys | Ser | Leu | Leu | Phe | Tyr | Ala | Gly | Arg |
| | 1700 | | | | 1705 | | | | 1710 | | | | | |
| Met | Met | Trp | Leu | Thr | Glu | Asn | Ala | Trp | Ile | Asp | His | Pro | His | Gln |
| | 1715 | | | | 1720 | | | | 1725 | | | | | |
| Ala | Ser | Thr | Ile | Gly | Met | Leu | Arg | Thr | Ile | Lys | Leu | Glu | Asn | Pro |
| | 1730 | | | | 1735 | | | | 1740 | | | | | |
| Asp | Leu | Gly | Thr | His | Val | Phe | Asp | Val | Asp | Thr | Val | Glu | Asn | Leu |
| | 1745 | | | | 1750 | | | | 1755 | | | | | |
| Asp | Thr | Lys | Phe | Phe | Val | Glu | Gln | Leu | Leu | Arg | Phe | Glu | Glu | Ser |
| | 1760 | | | | 1765 | | | | 1770 | | | | | |
| Asp | Asp | Gln | Leu | Leu | Glu | Ser | Ile | Thr | Trp | Thr | His | Glu | Pro | Glu |
| | 1775 | | | | 1780 | | | | 1785 | | | | | |
| Val | Tyr | Trp | Cys | Lys | Gly | Arg | Ala | Trp | Val | Pro | Arg | Leu | Lys | Gln |
| | 1790 | | | | 1795 | | | | 1800 | | | | | |
| Asp | Ile | Ala | Arg | Asn | Asp | Arg | Met | Asn | Ser | Ser | Arg | Arg | Pro | Ile |
| | 1805 | | | | 1810 | | | | 1815 | | | | | |
| Phe | Gly | Asn | Phe | Asn | Ser | Ser | Lys | Thr | Ala | Ile | Ala | Leu | Lys | Glu |
| | 1820 | | | | 1825 | | | | 1830 | | | | | |
| Ala | Arg | Gly | Ala | Ser | Ser | Ser | Met | Tyr | Tyr | Leu | Glu | Ser | Thr | Glu |
| | 1835 | | | | 1840 | | | | 1845 | | | | | |
| Thr | Cys | Asp | Ser | Leu | Glu | Asp | Ala | Arg | His | Ala | Gly | Lys | Ala | Thr |
| | 1850 | | | | 1855 | | | | 1860 | | | | | |
| Val | Arg | Val | Arg | Tyr | Ala | Leu | Pro | Gln | Ala | Ile | Arg | Val | Gly | His |
| | 1865 | | | | 1870 | | | | 1875 | | | | | |
| Leu | Gly | Tyr | Phe | His | Val | Val | Gln | Gly | Ser | Ile | Leu | Glu | Asn | Thr |
| | 1880 | | | | 1885 | | | | 1890 | | | | | |
| Cys | Glu | Val | Pro | Val | Val | Ala | Leu | Ala | Glu | Lys | Asn | Gly | Ser | Ile |
| | 1895 | | | | 1900 | | | | 1905 | | | | | |
| Leu | His | Val | Pro | Arg | Asn | Tyr | Met | His | Ser | Leu | Pro | Asp | Asn | Met |
| | 1910 | | | | 1915 | | | | 1920 | | | | | |
| Ala | Glu | Gly | Glu | Asp | Ser | Ser | Phe | Leu | Leu | Ser | Thr | Ala | Ala | Ala |
| | 1925 | | | | 1930 | | | | 1935 | | | | | |
| Leu | Leu | Ala | Glu | Thr | Ile | Leu | Ser | Ser | Ala | Gln | Ser | Phe | Gly | Ser |
| | 1940 | | | | 1945 | | | | 1950 | | | | | |
| Asp | Ala | Ser | Ile | Leu | Ile | Met | Glu | Pro | Pro | Ile | Phe | Cys | Val | Lys |
| | 1955 | | | | 1960 | | | | 1965 | | | | | |
| Ala | Ile | Leu | Glu | Ser | Ala | Lys | Thr | Tyr | Gly | Val | Gln | Val | His | Leu |
| | 1970 | | | | 1975 | | | | 1980 | | | | | |
| Ala | Thr | Thr | Leu | Ser | Asp | Val | Lys | Thr | Ile | Pro | Ala | Pro | Trp | Ile |
| | 1985 | | | | 1990 | | | | 1995 | | | | | |
| Arg | Leu | His | Ala | Lys | Glu | Thr | Asp | Ala | Arg | Leu | Lys | His | Ser | Leu |
| | 2000 | | | | 2005 | | | | 2010 | | | | | |
| Pro | Thr | Asn | Met | Met | Ala | Phe | Phe | Asp | Leu | Ser | Thr | Asp | Arg | Thr |
| | 2015 | | | | 2020 | | | | 2025 | | | | | |
| Ala | Ala | Gly | Ile | Thr | Asn | Arg | Leu | Ala | Lys | Leu | Leu | Pro | Pro | Ser |
| | 2030 | | | | 2035 | | | | 2040 | | | | | |
| Cys | Phe | Met | Tyr | Ser | Gly | Asp | Tyr | Leu | Ile | Arg | Ser | Thr | Ala | Ser |
| | 2045 | | | | 2050 | | | | 2055 | | | | | |
| Thr | Tyr | Lys | Val | Ser | His | Val | Glu | Asp | Ile | Pro | Ile | Leu | Glu | His |

-continued

```
                2060                2065                2070
Ser Val Ala Met Ala Lys Asn Thr Val Ser Ala Ser Thr Val Asp
    2075                2080                2085
Asp Thr Glu Lys Val Ile Thr Ala Thr Gln Ile Leu Leu Pro Gly
    2090                2095                2100
Gln Leu Ser Val Asn His Asn Asp Gln Arg Phe Asn Leu Ala Thr
    2105                2110                2115
Val Ile Asp Trp Lys Glu Asn Glu Val Ser Ala Arg Ile Cys Pro
    2120                2125                2130
Ile Asp Ser Gly Asn Leu Phe Ser Asn Lys Lys Thr Tyr Leu Leu
    2135                2140                2145
Val Gly Leu Thr Gly Asp Leu Gly Arg Ser Leu Cys Arg Trp Met
    2150                2155                2160
Ile Leu His Gly Ala Arg His Val Val Leu Thr Ser Arg Asn Pro
    2165                2170                2175
Arg Leu Asp Pro Lys Trp Ile Ala Asn Met Glu Ala Leu Gly Gly
    2180                2185                2190
Asp Ile Thr Val Leu Ser Met Asp Val Ala Asn Glu Asp Ser Val
    2195                2200                2205
Asp Ala Gly Leu Gly Lys Leu Val Asp Met Lys Leu Pro Pro Val
    2210                2215                2220
Ala Gly Ile Ala Phe Gly Pro Leu Val Leu Gln Asp Val Met Leu
    2225                2230                2235
Lys Asn Met Asp His Gln Met Met Asp Met Val Leu Lys Pro Lys
    2240                2245                2250
Val Gln Gly Ala Arg Ile Leu His Glu Arg Phe Ser Glu Gln Thr
    2255                2260                2265
Gly Ser Lys Ala Leu Asp Phe Phe Ile Met Phe Ser Ser Ile Val
    2270                2275                2280
Ala Val Ile Gly Asn Pro Gly Gln Ser Asn Tyr Gly Ala Ala Asn
    2285                2290                2295
Ala Tyr Leu Gln Ala Leu Ala Gln Gln Arg Cys Ala Arg Gly Leu
    2300                2305                2310
Ala Gly Ser Thr Ile Asp Ile Gly Ala Val Tyr Gly Val Gly Phe
    2315                2320                2325
Val Thr Arg Ala Glu Met Glu Glu Asp Phe Asp Ala Ile Arg Phe
    2330                2335                2340
Met Phe Asp Ser Val Glu Glu His Glu Leu His Thr Leu Phe Ala
    2345                2350                2355
Glu Ala Val Val Ser Asp Gln Arg Ala Arg Gln Gln Pro Gln Arg
    2360                2365                2370
Lys Thr Val Ile Asp Met Ala Asp Leu Glu Leu Thr Thr Gly Ile
    2375                2380                2385
Pro Asp Leu Asp Pro Ala Leu Gln Asp Arg Ile Ile Tyr Phe Asn
    2390                2395                2400
Asp Pro Arg Phe Gly Asn Phe Lys Ile Pro Gly Gln Arg Gly Asp
    2405                2410                2415
Gly Gly Asp Asn Gly Ser Gly Ser Lys Gly Ser Ile Ala Asp Gln
    2420                2425                2430
Leu Lys Gln Ala Thr Thr Leu Asp Gln Val Arg Gln Ile Val Ile
    2435                2440                2445
Asp Gly Leu Ser Glu Lys Leu Arg Val Thr Leu Gln Val Ser Asp
    2450                2455                2460
```

-continued

```
Gly Glu Ser Val Asp Pro Thr Ile Pro Leu Ile Asp Gln Gly Val
    2465                2470                2475

Asp Ser Leu Gly Ala Val Thr Val Gly Ser Trp Phe Ser Lys Gln
    2480                2485                2490

Leu Tyr Leu Asp Leu Pro Leu Leu Arg Val Leu Gly Gly Ala Ser
    2495                2500                2505

Val Ala Asp Leu Ala Asp Asp Ala Ala Thr Arg Leu Pro Ala Thr
    2510                2515                2520

Ser Ile Pro Leu Leu Leu Gln Ile Gly Asp Ser Thr Gly Thr Ser
    2525                2530                2535

Asp Ser Gly Ala Ser Pro Thr Pro Thr Asp Ser His Asp Glu Ala
    2540                2545                2550

Ser Ser Ala Thr Ser Thr Asp Ala Ser Ser Ala Glu Glu Asp Glu
    2555                2560                2565

Glu Gln Glu Asp Asp Asn Glu Gln Gly Gly Arg Lys Ile Leu Arg
    2570                2575                2580

Arg Glu Arg Leu Ser Leu Gly Gln Glu Tyr Ser Trp Arg Gln Gln
    2585                2590                2595

Gln Met Val Lys Asp His Thr Ile Phe Asn Asn Thr Ile Gly Met
    2600                2605                2610

Phe Met Lys Gly Thr Ile Asp Leu Asp Arg Leu Arg Arg Ala Leu
    2615                2620                2625

Lys Ala Ser Leu Arg Arg His Glu Ile Phe Arg Thr Cys Phe Val
    2630                2635                2640

Thr Gly Asp Asp Tyr Ser Ser Asp Leu Asn Gly Pro Val Gln Val
    2645                2650                2655

Val Leu Lys Asn Pro Glu Asn Arg Val His Phe Val Gln Val Asn
    2660                2665                2670

Asn Ala Ala Glu Ala Glu Glu Glu Tyr Arg Lys Leu Glu Lys Thr
    2675                2680                2685

Asn Tyr Ser Ile Ser Thr Gly Asp Thr Leu Arg Leu Val Asp Phe
    2690                2695                2700

Tyr Trp Gly Thr Asp Asp His Leu Leu Val Ile Gly Tyr His Arg
    2705                2710                2715

Leu Val Gly Asp Gly Ser Thr Thr Glu Asn Leu Phe Asn Glu Ile
    2720                2725                2730

Gly Gln Ile Tyr Ser Gly Val Lys Met Gln Arg Pro Ser Thr Gln
    2735                2740                2745

Phe Ser Asp Leu Ala Val Gln Gln Arg Glu Asn Leu Glu Asn Gly
    2750                2755                2760

Arg Met Gly Asp Asp Ile Ala Phe Trp Lys Ser Met His Ser Lys
    2765                2770                2775

Val Ser Ser Ser Ala Pro Thr Val Leu Pro Ile Met Asn Leu Ile
    2780                2785                2790

Asn Asp Pro Ala Ala Asn Ser Glu Gln Gln Gln Ile Gln Pro Phe
    2795                2800                2805

Thr Trp Gln Gln Tyr Glu Ala Ile Ala Arg Leu Asp Pro Met Val
    2810                2815                2820

Ala Phe Arg Ile Lys Glu Arg Ser Arg Lys His Lys Ala Thr Pro
    2825                2830                2835

Met Gln Phe Tyr Leu Ala Ala Tyr His Val Leu Leu Ala Arg Leu
    2840                2845                2850
```

```
Thr Gly Ser Lys Asp Ile Thr  Ile Gly Leu Ala Glu  Thr Asn Arg
    2855             2860             2865

Ser Thr Met Glu Glu Ile Ser  Ala Met Gly Phe Phe  Ala Asn Val
    2870             2875             2880

Leu Pro Leu Arg Phe Asp Glu  Phe Val Gly Ser Lys  Thr Phe Gly
    2885             2890             2895

Glu His Leu Val Ala Thr Lys  Asp Ser Val Arg Glu  Ala Met Gln
    2900             2905             2910

His Ala Arg Val Pro Tyr Gly  Val Ile Leu Asp Cys  Leu Gly Leu
    2915             2920             2925

Asn Leu Pro Thr Ser Gly Glu  Glu Pro Lys Thr Gln  Thr His Ala
    2930             2935             2940

Pro Leu Phe Gln Ala Val Phe  Asp Tyr Lys Gln Gly  Gln Ala Glu
    2945             2950             2955

Ser Gly Ser Ile Gly Asn Ala  Lys Met Thr Ser Val  Leu Ala Ser
    2960             2965             2970

Arg Glu Arg Thr Pro Tyr Asp  Ile Val Leu Glu Met  Trp Asp Asp
    2975             2980             2985

Pro Thr Lys Asp Pro Leu Ile  His Val Lys Leu Gln  Ser Ser Leu
    2990             2995             3000

Tyr Gly Pro Glu His Ala Gln  Ala Phe Val Asp His  Phe Ser Ser
    3005             3010             3015

Ile Leu Thr Met Phe Ser Met  Asn Pro Ala Leu Lys  Leu Ala
    3020             3025             3030
```

<210> SEQ ID NO 45
<211> LENGTH: 7692
<212> TYPE: DNA
<213> ORGANISM: Penicillium citrinum
<220> FEATURE:
<221> NAME/KEY: CDS
<222> LOCATION: (1)..(7692)

<400> SEQUENCE: 45

```
atg aac aat acc ccc gcc gta acc gca acc gca acc gca acc gca acc      48
Met Asn Asn Thr Pro Ala Val Thr Ala Thr Ala Thr Ala Thr Ala Thr
1               5                   10                  15 gca acc gca atg gca ggc tcg gct tgc tct aac aca tcc acg ccc att      96
Ala Thr Ala Met Ala Gly Ser Ala Cys Ser Asn Thr Ser Thr Pro Ile
            20                  25                  30 gcc ata gtt gga atg gga tgt cga ttt gct gga gat gca acg agt cca     144
Ala Ile Val Gly Met Gly Cys Arg Phe Ala Gly Asp Ala Thr Ser Pro
        35                  40                  45 cag aag ctt tgg gaa atg gtt gaa aga gga ggc agt gcc tgg tct aag     192
Gln Lys Leu Trp Glu Met Val Glu Arg Gly Gly Ser Ala Trp Ser Lys
    50                  55                  60 gtc ccc tcc tcg cga ttc aat gtg aga gga gta tac cac ccg aat ggc     240
Val Pro Ser Ser Arg Phe Asn Val Arg Gly Val Tyr His Pro Asn Gly
65                  70                  75                  80 gaa agg gtc ggg tcc acc cac gta aag ggt gga cac ttc atc gac gag     288
Glu Arg Val Gly Ser Thr His Val Lys Gly Gly His Phe Ile Asp Glu
                85                  90                  95 gat cct gct tta ttt gac gcc gcg ttc ttc aac atg acc aca gag gtc     336
Asp Pro Ala Leu Phe Asp Ala Ala Phe Phe Asn Met Thr Thr Glu Val
            100                 105                 110 gcc agc tgc atg gat ccg cag tat cgg ctt atg ctt gag gtg gtc tac     384
Ala Ser Cys Met Asp Pro Gln Tyr Arg Leu Met Leu Glu Val Val Tyr
        115                 120                 125
```

-continued

| | |
|---|---|
| gaa tcg ctg gag agt gcc ggt atc acc atc gat ggt atg gca ggc tct<br>Glu Ser Leu Glu Ser Ala Gly Ile Thr Ile Asp Gly Met Ala Gly Ser<br>130                            135                     140 | 432 |
| aat acg tcg gtg ttt ggg ggt gtc atg tac cac gac tat cag gat tcg<br>Asn Thr Ser Val Phe Gly Gly Val Met Tyr His Asp Tyr Gln Asp Ser<br>145                      150                     155                  160 | 480 |
| ctc aat cgt gac ccc gag aca gtt ccg cgt tat ttc ata act ggc aac<br>Leu Asn Arg Asp Pro Glu Thr Val Pro Arg Tyr Phe Ile Thr Gly Asn<br>               165                     170                  175 | 528 |
| tca gga aca atg ctt tcg aac cgg ata tca cac ttc tac gac tta cgt<br>Ser Gly Thr Met Leu Ser Asn Arg Ile Ser His Phe Tyr Asp Leu Arg<br>             180                     185                  190 | 576 |
| ggt ccc agc gtg acg gtt gac acg gcc tgt tcg aca aca ttg acc gca<br>Gly Pro Ser Val Thr Val Asp Thr Ala Cys Ser Thr Thr Leu Thr Ala<br>195                            200                     205 | 624 |
| ctg cac ttg gcg tgc cag agc tta cgt act ggg gag tca gat aca gcc<br>Leu His Leu Ala Cys Gln Ser Leu Arg Thr Gly Glu Ser Asp Thr Ala<br>210                            215                     220 | 672 |
| atc gtt atc ggt gca aat ctt ctc aat ccc gat gtt ttt gtt acg<br>Ile Val Ile Gly Ala Asn Leu Leu Asn Pro Asp Val Phe Val Thr<br>225                            230                     235                  240 | 720 |
| atg tca aac ctg gga ttt ttg tcc ccg gat ggt atc tcg tac tct ttt<br>Met Ser Asn Leu Gly Phe Leu Ser Pro Asp Gly Ile Ser Tyr Ser Phe<br>                     245                     250                  255 | 768 |
| gat cct cga gcg aat gga tat ggt cgc ggg gaa gga att gcc gct ctg<br>Asp Pro Arg Ala Asn Gly Tyr Gly Arg Gly Glu Gly Ile Ala Ala Leu<br>             260                     265                  270 | 816 |
| gta ata aag gcc ctc cct aac gcg ttg cga gac caa gac cct atc cga<br>Val Ile Lys Ala Leu Pro Asn Ala Leu Arg Asp Gln Asp Pro Ile Arg<br>          275                     280                  285 | 864 |
| gcc gtc att cga gag aca gcg ctg aac cag gat ggc aaa aca ccc gca<br>Ala Val Ile Arg Glu Thr Ala Leu Asn Gln Asp Gly Lys Thr Pro Ala<br>290                            295                     300 | 912 |
| att act gcg ccg agt gat gtg gcg cag aaa agt ctg atc cag gag tgt<br>Ile Thr Ala Pro Ser Asp Val Ala Gln Lys Ser Leu Ile Gln Glu Cys<br>305                            310                     315                  320 | 960 |
| tac gat aag gct ggg cta gat atg tcg ttg acc tcg tac gtg gag gcc<br>Tyr Asp Lys Ala Gly Leu Asp Met Ser Leu Thr Ser Tyr Val Glu Ala<br>                    325                     330                  335 | 1008 |
| cac gga act gga aca cca act ggt gac ccc ctt gaa atc tca gca att<br>His Gly Thr Gly Thr Pro Thr Gly Asp Pro Leu Glu Ile Ser Ala Ile<br>             340                     345                  350 | 1056 |
| tca gca gct ttt aaa gga cat cct ctg cac ctt ggc tct gtg aaa gca<br>Ser Ala Ala Phe Lys Gly His Pro Leu His Leu Gly Ser Val Lys Ala<br>          355                     360                  365 | 1104 |
| aat att ggc cat aca gaa gcc gcc agt ggc ctg gcc agt ata atc aag<br>Asn Ile Gly His Thr Glu Ala Ala Ser Gly Leu Ala Ser Ile Ile Lys<br>370                            375                     380 | 1152 |
| gtg gcc ttg gcc ttg gag aag ggc ttg att ccc cct aat gcg cgg ttc<br>Val Ala Leu Ala Leu Glu Lys Gly Leu Ile Pro Pro Asn Ala Arg Phe<br>385                            390                     395                  400 | 1200 |
| ctg caa aag aac agc aag ctg atg ctt gac caa aag aac atc aag atc<br>Leu Gln Lys Asn Ser Lys Leu Met Leu Asp Gln Lys Asn Ile Lys Ile<br>                    405                     410                  415 | 1248 |
| ccc atg tct gct caa gac tgg cct gtg aaa gat ggg act cgt cgc gca<br>Pro Met Ser Ala Gln Asp Trp Pro Val Lys Asp Gly Thr Arg Arg Ala<br>             420                     425                  430 | 1296 |
| tct gtc aat aac ttc ggc ttt ggt ggt tcg aat gct cac gtc att ttg<br>Ser Val Asn Asn Phe Gly Phe Gly Gly Ser Asn Ala His Val Ile Leu<br>435                            440                     445 | 1344 |

-continued

| | |
|---|---|
| gaa tca tat gat cgc gca tca ttg gcc ctg cca gag gat caa gtg cat<br>Glu Ser Tyr Asp Arg Ala Ser Leu Ala Leu Pro Glu Asp Gln Val His<br>450                                 455                           460 | 1392 |
| gtc aat ggt aac tct gag cat ggt agg gtt gag gat ggt tcc aaa cag<br>Val Asn Gly Asn Ser Glu His Gly Arg Val Glu Asp Gly Ser Lys Gln<br>465                       470                       475                       480 | 1440 |
| agc cgc ata tac gtt gtg cgt gcc aag gac gag caa gct tgt cgg cga<br>Ser Arg Ile Tyr Val Val Arg Ala Lys Asp Glu Gln Ala Cys Arg Arg<br>                       485                       490                       495 | 1488 |
| acg ata gca agc ctg cga gac tac att aaa tcc gtc gct gac att gac<br>Thr Ile Ala Ser Leu Arg Asp Tyr Ile Lys Ser Val Ala Asp Ile Asp<br>500                                 505                           510 | 1536 |
| ggg gaa ccc ttc ctc gcc agc ctc gcc tat aca cta ggc tct cgc cgt<br>Gly Glu Pro Phe Leu Ala Ser Leu Ala Tyr Thr Leu Gly Ser Arg Arg<br>               515                       520                       525 | 1584 |
| tcc att ctg cca tgg acg tca gtg tat gta gca gac agc ctt ggc ggc<br>Ser Ile Leu Pro Trp Thr Ser Val Tyr Val Ala Asp Ser Leu Gly Gly<br>530                                 535                           540 | 1632 |
| ctt gtt tct gcc ctc agc gat gag tcc aat caa cca aaa cga gcg aat<br>Leu Val Ser Ala Leu Ser Asp Glu Ser Asn Gln Pro Lys Arg Ala Asn<br>545                                 550                       555                       560 | 1680 |
| gag aaa gta cgg ctc gga ttt gta ttc acc ggt cag ggg gcg cag tgg<br>Glu Lys Val Arg Leu Gly Phe Val Phe Thr Gly Gln Gly Ala Gln Trp<br>               565                       570                       575 | 1728 |
| cat gca atg ggc aga gag ctg gtc aat aca ttc cca gta ttc aaa cag<br>His Ala Met Gly Arg Glu Leu Val Asn Thr Phe Pro Val Phe Lys Gln<br>                    580                       585                       590 | 1776 |
| gcg att ctt gaa tgt gat ggc tac atc aag caa ctg ggc gcg agt tgg<br>Ala Ile Leu Glu Cys Asp Gly Tyr Ile Lys Gln Leu Gly Ala Ser Trp<br>               595                       600                       605 | 1824 |
| aat ttt atg gag gag ctc cac cgt gat gag ctg acg act cgg gta aat<br>Asn Phe Met Glu Glu Leu His Arg Asp Glu Leu Thr Thr Arg Val Asn<br>610                                 615                       620 | 1872 |
| gat gcc gaa tac agt cta cca ctg tca acc gct atc caa att gca ctt<br>Asp Ala Glu Tyr Ser Leu Pro Leu Ser Thr Ala Ile Gln Ile Ala Leu<br>625                                 630                       635                       640 | 1920 |
| gtg cgt ctc ctt tgg tca tgg gga att cgg cca acg ggg ata acc agt<br>Val Arg Leu Leu Trp Ser Trp Gly Ile Arg Pro Thr Gly Ile Thr Ser<br>                       645                       650                       655 | 1968 |
| cac tca agt gga gag gct gct gct gcc tac gca gct ggg gct tta tcc<br>His Ser Ser Gly Glu Ala Ala Ala Ala Tyr Ala Ala Gly Ala Leu Ser<br>                    660                       665                       670 | 2016 |
| gcg cgg tcg gcc att ggg atc act tat ata cgc ggt gta ttg acc act<br>Ala Arg Ser Ala Ile Gly Ile Thr Tyr Ile Arg Gly Val Leu Thr Thr<br>               675                       680                       685 | 2064 |
| aag ccc aag ccc gca ttg gca gcc aaa gga gga atg atg gcg gtg ggt<br>Lys Pro Lys Pro Ala Leu Ala Ala Lys Gly Gly Met Met Ala Val Gly<br>690                                 695                       700 | 2112 |
| ctt ggt cgc agt gag acc aat gtt tac att tcg cgt ctc aac cag gag<br>Leu Gly Arg Ser Glu Thr Asn Val Tyr Ile Ser Arg Leu Asn Gln Glu<br>705                                 710                       715                       720 | 2160 |
| gac ggc tgt gtg gtg gtt gga tgt atc aac agt caa tgt agt gtg acg<br>Asp Gly Cys Val Val Val Gly Cys Ile Asn Ser Gln Cys Ser Val Thr<br>                       725                       730                       735 | 2208 |
| gtg tcg gga gat ttg ggt gca atc gag aaa ctt gaa aag ttg tta cac<br>Val Ser Gly Asp Leu Gly Ala Ile Glu Lys Leu Glu Lys Leu Leu His<br>                    740                       745                       750 | 2256 |
| gcc gat ggc atc ttt acc agg aaa ctg aaa gtc act gaa gcc ttc cat<br>Ala Asp Gly Ile Phe Thr Arg Lys Leu Lys Val Thr Glu Ala Phe His | 2304 |

-continued

|     |     | 755 |     |     | 760 |     |     | 765 |     |     |     |     |      |
|-----|-----|-----|-----|-----|-----|-----|-----|-----|-----|-----|-----|-----|------|
| tca | agc | cac | atg | cga | cca | atg | gca | gat | gcc | ttt | ggg | gcg tca ctg aga | 2352 |
| Ser | Ser | His | Met | Arg | Pro | Met | Ala | Asp | Ala | Phe | Gly | Ala Ser Leu Arg | |
|     | 770 |     |     |     | 775 |     |     |     | 780 |     |     | | |

```
gat ctg ttc aac tcg gat aac aac aac gac aat ccc aat gct gac acc      2400
Asp Leu Phe Asn Ser Asp Asn Asn Asn Asp Asn Pro Asn Ala Asp Thr
785                 790                 795                 800 tca aag ggt gta tta tat tca tca cct aag act ggt agt cgc atg acc      2448
Ser Lys Gly Val Leu Tyr Ser Ser Pro Lys Thr Gly Ser Arg Met Thr
                805                 810                 815 gat ctt aaa ttg cta ttg gat ccc aca cac tgg atg gat agt atg cta      2496
Asp Leu Lys Leu Leu Leu Asp Pro Thr His Trp Met Asp Ser Met Leu
        820                 825                 830 cag ccg gta gag ttc gag tcc tca ctc cgc gag atg tgc ttt gat ccc      2544
Gln Pro Val Glu Phe Glu Ser Ser Leu Arg Glu Met Cys Phe Asp Pro
            835                 840                 845 aac acc aaa gag aaa gcc gtc gat gtg att att gaa ata ggg cct cac      2592
Asn Thr Lys Glu Lys Ala Val Asp Val Ile Ile Glu Ile Gly Pro His
850                 855                 860 gga gcg ctt ggt ggt cca atc aac caa gtc atg cag gat ctg ggt ctg      2640
Gly Ala Leu Gly Gly Pro Ile Asn Gln Val Met Gln Asp Leu Gly Leu
865                 870                 875                 880 aaa gga aca gat ata aac tat ctc agt tgc ctt tct cgc ggc aga agc      2688
Lys Gly Thr Asp Ile Asn Tyr Leu Ser Cys Leu Ser Arg Gly Arg Ser
                885                 890                 895 tcg ttg gag aca atg tat cgt gct gct acg gag ttg ata agc aag ggt      2736
Ser Leu Glu Thr Met Tyr Arg Ala Ala Thr Glu Leu Ile Ser Lys Gly
            900                 905                 910 tat ggg ctc aaa atg gac gct ata aac ttt cct cat gga aga aaa gag      2784
Tyr Gly Leu Lys Met Asp Ala Ile Asn Phe Pro His Gly Arg Lys Glu
        915                 920                 925 ccc aga gtg aag gta ctg agc gat ttg ccg gcg tac ccg tgg aat cac      2832
Pro Arg Val Lys Val Leu Ser Asp Leu Pro Ala Tyr Pro Trp Asn His
930                 935                 940 caa acc cgt tat tgg aga gag cct cgc ggc agt cgt gag tcc aaa cag      2880
Gln Thr Arg Tyr Trp Arg Glu Pro Arg Gly Ser Arg Glu Ser Lys Gln
945                 950                 955                 960 aga acc cat ccg cct cac act ttg ata ggc tca cgg gaa tct ctc tct      2928
Arg Thr His Pro Pro His Thr Leu Ile Gly Ser Arg Glu Ser Leu Ser
                965                 970                 975 cct cat ttc gcg cct aaa tgg aaa cat gtt ctc cgt ctg tca gat att      2976
Pro His Phe Ala Pro Lys Trp Lys His Val Leu Arg Leu Ser Asp Ile
            980                 985                 990 cca tgg ata cga gat cac gtc gtt  ggt tcg agc atc atc  ttt ccg gga    3024
Pro Trp Ile Arg Asp His Val Val  Gly Ser Ser Ile Ile  Phe Pro Gly
        995                  1000                 1005 gct ggc  ttc atc agc atg gcc  atc gag ggg ttt tca  caa gtc tgc       3069
Ala Gly  Phe Ile Ser Met Ala  Ile Glu Gly Phe Ser  Gln Val Cys
1010                 1015                 1020 cca cca  gtt gcg ggg gct agc  atc aac tac aac ttg  cgt gac gtt       3114
Pro Pro  Val Ala Gly Ala Ser  Ile Asn Tyr Asn Leu  Arg Asp Val
1025                 1030                 1035 gaa ctc  gcg cag gct ctc ata  ata ccc gct gat gca  gaa gca gag       3159
Glu Leu  Ala Gln Ala Leu Ile  Ile Pro Ala Asp Ala  Glu Ala Glu
1040                 1045                 1050 gtt gac  ctg cgc cta acg atc  cgt tca tgt gag gaa  agg tcc ctc       3204
Val Asp  Leu Arg Leu Thr Ile  Arg Ser Cys Glu Glu  Arg Ser Leu
1055                 1060                 1065 ggc aca  aag aac tgg cat caa  ttt tct gtg cac tca  att tcg ggc       3249
```

|  |  |  |  |  |  |  |  |  |  |  |  |  |  |  |  |
|---|---|---|---|---|---|---|---|---|---|---|---|---|---|---|---|
| Gly | Thr | Lys | Asn | Trp | His | Gln | Phe | Ser | Val | His | Ser | Ile | Ser | Gly | |
| | 1070 | | | | 1075 | | | | 1080 | | | | | | |
| gaa | aat | aat | acc | tgg | aca | gaa | cac | tgc | acc | gga | tta | ata | cgt | tcg | 3294 |
| Glu | Asn | Asn | Thr | Trp | Thr | Glu | His | Cys | Thr | Gly | Leu | Ile | Arg | Ser | |
| | 1085 | | | | 1090 | | | | 1095 | | | | | | |
| gag | agc | gaa | aga | agc | cac | ctt | gac | tgt | tca | act | gtg | gaa | gcc | tca | 3339 |
| Glu | Ser | Glu | Arg | Ser | His | Leu | Asp | Cys | Ser | Thr | Val | Glu | Ala | Ser | |
| | 1100 | | | | 1105 | | | | 1110 | | | | | | |
| cgc | agg | ttg | aat | cta | ggc | tca | gat | aac | cgg | agc | att | gat | ccc | aac | 3384 |
| Arg | Arg | Leu | Asn | Leu | Gly | Ser | Asp | Asn | Arg | Ser | Ile | Asp | Pro | Asn | |
| | 1115 | | | | 1120 | | | | 1125 | | | | | | |
| gat | ctc | tgg | gag | tcc | tta | cac | gcg | aat | ggg | ata | tgc | cac | gga | ccc | 3429 |
| Asp | Leu | Trp | Glu | Ser | Leu | His | Ala | Asn | Gly | Ile | Cys | His | Gly | Pro | |
| | 1130 | | | | 1135 | | | | 1140 | | | | | | |
| att | ttt | cag | aac | att | cag | cga | att | caa | aac | aat | gga | cag | ggc | tcg | 3474 |
| Ile | Phe | Gln | Asn | Ile | Gln | Arg | Ile | Gln | Asn | Asn | Gly | Gln | Gly | Ser | |
| | 1145 | | | | 1150 | | | | 1155 | | | | | | |
| ttt | tgc | aga | ttt | tcc | att | gct | gac | act | gcc | tcg | gct | atg | cct | cac | 3519 |
| Phe | Cys | Arg | Phe | Ser | Ile | Ala | Asp | Thr | Ala | Ser | Ala | Met | Pro | His | |
| | 1160 | | | | 1165 | | | | 1170 | | | | | | |
| tcg | tac | gag | aat | cga | cac | atc | gtc | cat | cct | act | act | ctg | gac | tcg | 3564 |
| Ser | Tyr | Glu | Asn | Arg | His | Ile | Val | His | Pro | Thr | Thr | Leu | Asp | Ser | |
| | 1175 | | | | 1180 | | | | 1185 | | | | | | |
| gtg | atc | cag | gcg | gca | tac | acg | gtg | tta | ccc | tac | gcg | gga | aca | cgt | 3609 |
| Val | Ile | Gln | Ala | Ala | Tyr | Thr | Val | Leu | Pro | Tyr | Ala | Gly | Thr | Arg | |
| | 1190 | | | | 1195 | | | | 1200 | | | | | | |
| atg | aaa | acg | gcc | atg | gta | cca | agg | agg | cta | aga | aat | gtc | aaa | ata | 3654 |
| Met | Lys | Thr | Ala | Met | Val | Pro | Arg | Arg | Leu | Arg | Asn | Val | Lys | Ile | |
| | 1205 | | | | 1210 | | | | 1215 | | | | | | |
| tcc | tct | agc | ctg | gct | gac | ttg | gag | gct | ggt | gat | gct | ctg | gac | gca | 3699 |
| Ser | Ser | Ser | Leu | Ala | Asp | Leu | Glu | Ala | Gly | Asp | Ala | Leu | Asp | Ala | |
| | 1220 | | | | 1225 | | | | 1230 | | | | | | |
| cag | gcc | agc | atc | aag | gat | cgc | aac | tct | caa | tcc | ttc | tct | acc | gac | 3744 |
| Gln | Ala | Ser | Ile | Lys | Asp | Arg | Asn | Ser | Gln | Ser | Phe | Ser | Thr | Asp | |
| | 1235 | | | | 1240 | | | | 1245 | | | | | | |
| ttg | gca | gtg | ttt | gat | gac | tat | gat | agc | ggt | tct | tct | ccc | tcg | gac | 3789 |
| Leu | Ala | Val | Phe | Asp | Asp | Tyr | Asp | Ser | Gly | Ser | Ser | Pro | Ser | Asp | |
| | 1250 | | | | 1255 | | | | 1260 | | | | | | |
| gga | atc | cca | gtc | ata | gag | att | gaa | ggc | ctt | gtt | ttc | cag | tcg | gtt | 3834 |
| Gly | Ile | Pro | Val | Ile | Glu | Ile | Glu | Gly | Leu | Val | Phe | Gln | Ser | Val | |
| | 1265 | | | | 1270 | | | | 1275 | | | | | | |
| gga | agc | agc | ttc | tct | gac | caa | aag | tca | gac | tcc | aac | gac | aca | gaa | 3879 |
| Gly | Ser | Ser | Phe | Ser | Asp | Gln | Lys | Ser | Asp | Ser | Asn | Asp | Thr | Glu | |
| | 1280 | | | | 1285 | | | | 1290 | | | | | | |
| aat | gcc | tgc | agc | tcc | tgg | gtt | tgg | gcc | cct | gac | atc | agc | ttg | ggt | 3924 |
| Asn | Ala | Cys | Ser | Ser | Trp | Val | Trp | Ala | Pro | Asp | Ile | Ser | Leu | Gly | |
| | 1295 | | | | 1300 | | | | 1305 | | | | | | |
| gac | tcc | act | tgg | ctc | aaa | gaa | aag | ttg | agc | act | gag | gct | gag | acg | 3969 |
| Asp | Ser | Thr | Trp | Leu | Lys | Glu | Lys | Leu | Ser | Thr | Glu | Ala | Glu | Thr | |
| | 1310 | | | | 1315 | | | | 1320 | | | | | | |
| aaa | gaa | acg | gaa | ctc | atg | atg | gac | ctc | cga | aga | tgc | acg | atc | aac | 4014 |
| Lys | Glu | Thr | Glu | Leu | Met | Met | Asp | Leu | Arg | Arg | Cys | Thr | Ile | Asn | |
| | 1325 | | | | 1330 | | | | 1335 | | | | | | |
| ttt | ata | cag | gag | gct | gtc | act | gat | ttg | aca | aat | tct | gat | atc | caa | 4059 |
| Phe | Ile | Gln | Glu | Ala | Val | Thr | Asp | Leu | Thr | Asn | Ser | Asp | Ile | Gln | |
| | 1340 | | | | 1345 | | | | 1350 | | | | | | |
| cat | ctg | gat | ggc | cac | ctt | cag | aag | tat | ttc | gat | tgg | atg | aat | gtc | 4104 |
| His | Leu | Asp | Gly | His | Leu | Gln | Lys | Tyr | Phe | Asp | Trp | Met | Asn | Val | |
| | 1355 | | | | 1360 | | | | 1365 | | | | | | |

| | | | | | | | | | | | |
|---|---|---|---|---|---|---|---|---|---|---|---|
| caa | ttg | gac | ctt | gcg | aga | caa | aac | aag | ctc | agc | cca | gcc | agt | tgc | 4149 |
| Gln | Leu | Asp | Leu | Ala | Arg | Gln | Asn | Lys | Leu | Ser | Pro | Ala | Ser | Cys | |
| | 1370 | | | | 1375 | | | | 1380 | | | | | | |

| gac | tgg | cta | agt | gac | gat | gct | gag | cag | aag | aaa | tgc | cta | cag | gcc | 4194 |
| Asp | Trp | Leu | Ser | Asp | Asp | Ala | Glu | Gln | Lys | Lys | Cys | Leu | Gln | Ala | |
| 1385 | | | | | 1390 | | | | | 1395 | | | | | |

| aga | gtc | gct | gga | gaa | agc | gtc | aat | ggc | gag | atg | att | tct | cgt | cta | 4239 |
| Arg | Val | Ala | Gly | Glu | Ser | Val | Asn | Gly | Glu | Met | Ile | Ser | Arg | Leu | |
| 1400 | | | | | 1405 | | | | | 1410 | | | | | |

| gga | cct | cag | tta | ata | gca | atg | cta | cgc | cgc | gaa | aca | gag | cca | ctt | 4284 |
| Gly | Pro | Gln | Leu | Ile | Ala | Met | Leu | Arg | Arg | Glu | Thr | Glu | Pro | Leu | |
| 1415 | | | | | 1420 | | | | | 1425 | | | | | |

| gag | ttg | atg | atg | caa | gat | cag | ctg | cta | agc | aga | tac | tac | gtc | aac | 4329 |
| Glu | Leu | Met | Met | Gln | Asp | Gln | Leu | Leu | Ser | Arg | Tyr | Tyr | Val | Asn | |
| 1430 | | | | | 1435 | | | | | 1440 | | | | | |

| gca | atc | aaa | tgg | agc | cga | tca | aac | gca | caa | gcc | agc | gag | ctg | atc | 4374 |
| Ala | Ile | Lys | Trp | Ser | Arg | Ser | Asn | Ala | Gln | Ala | Ser | Glu | Leu | Ile | |
| 1445 | | | | | 1450 | | | | | 1455 | | | | | |

| cga | ctt | tgc | gcc | cac | aag | aac | ccg | cgt | tct | cgc | att | ttg | gag | att | 4419 |
| Arg | Leu | Cys | Ala | His | Lys | Asn | Pro | Arg | Ser | Arg | Ile | Leu | Glu | Ile | |
| 1460 | | | | | 1465 | | | | | 1470 | | | | | |

| ggc | gga | ggc | acg | ggc | ggc | tgc | aca | aag | ctt | att | gtc | aat | gca | ttg | 4464 |
| Gly | Gly | Gly | Thr | Gly | Gly | Cys | Thr | Lys | Leu | Ile | Val | Asn | Ala | Leu | |
| 1475 | | | | | 1480 | | | | | 1485 | | | | | |

| gga | aac | acc | aag | ccg | atc | gat | cgt | tat | gac | ttc | acc | gat | gtg | tct | 4509 |
| Gly | Asn | Thr | Lys | Pro | Ile | Asp | Arg | Tyr | Asp | Phe | Thr | Asp | Val | Ser | |
| 1490 | | | | | 1495 | | | | | 1500 | | | | | |

| gcc | ggg | ttt | ttc | gag | tcg | gcg | cgt | gag | caa | ttt | gcg | gat | tgg | caa | 4554 |
| Ala | Gly | Phe | Phe | Glu | Ser | Ala | Arg | Glu | Gln | Phe | Ala | Asp | Trp | Gln | |
| 1505 | | | | | 1510 | | | | | 1515 | | | | | |

| gac | gtg | atg | act | ttc | aaa | aaa | ttg | gat | att | gaa | agc | gat | ccc | gag | 4599 |
| Asp | Val | Met | Thr | Phe | Lys | Lys | Leu | Asp | Ile | Glu | Ser | Asp | Pro | Glu | |
| 1520 | | | | | 1525 | | | | | 1530 | | | | | |

| caa | caa | ggg | ttt | gaa | tgt | gcc | acc | tac | gat | gtg | gtc | gtg | gct | tgc | 4644 |
| Gln | Gln | Gly | Phe | Glu | Cys | Ala | Thr | Tyr | Asp | Val | Val | Val | Ala | Cys | |
| 1535 | | | | | 1540 | | | | | 1545 | | | | | |

| cag | gtc | ctg | cat | gca | act | cga | tgc | atg | aaa | cga | aca | ctg | agt | aac | 4689 |
| Gln | Val | Leu | His | Ala | Thr | Arg | Cys | Met | Lys | Arg | Thr | Leu | Ser | Asn | |
| 1550 | | | | | 1555 | | | | | 1560 | | | | | |

| gtt | cga | aaa | ttg | ctc | aag | cct | ggg | ggc | aac | ttg | att | ttg | gtt | gag | 4734 |
| Val | Arg | Lys | Leu | Leu | Lys | Pro | Gly | Gly | Asn | Leu | Ile | Leu | Val | Glu | |
| 1565 | | | | | 1570 | | | | | 1575 | | | | | |

| act | acc | agg | gat | cag | ctc | gat | ttg | ttc | ttt | acc | ttc | gga | ctg | ttg | 4779 |
| Thr | Thr | Arg | Asp | Gln | Leu | Asp | Leu | Phe | Phe | Thr | Phe | Gly | Leu | Leu | |
| 1580 | | | | | 1585 | | | | | 1590 | | | | | |

| cca | ggt | tgg | tgg | ctc | agt | gag | gag | cct | gag | cgg | aag | tcg | acg | cca | 4824 |
| Pro | Gly | Trp | Trp | Leu | Ser | Glu | Glu | Pro | Glu | Arg | Lys | Ser | Thr | Pro | |
| 1595 | | | | | 1600 | | | | | 1605 | | | | | |

| tcg | ctc | act | acc | gat | ctt | tgg | aac | acc | atg | ttg | gac | acg | agc | ggt | 4869 |
| Ser | Leu | Thr | Thr | Asp | Leu | Trp | Asn | Thr | Met | Leu | Asp | Thr | Ser | Gly | |
| 1610 | | | | | 1615 | | | | | 1620 | | | | | |

| ttc | aac | ggt | gtg | gaa | ttg | gag | gtt | cgt | gat | tgt | gaa | gac | gat | gag | 4914 |
| Phe | Asn | Gly | Val | Glu | Leu | Glu | Val | Arg | Asp | Cys | Glu | Asp | Asp | Glu | |
| 1625 | | | | | 1630 | | | | | 1635 | | | | | |

| ttt | tac | atg | atc | agc | aca | atg | cta | tcg | acg | gct | aga | aaa | gag | aat | 4959 |
| Phe | Tyr | Met | Ile | Ser | Thr | Met | Leu | Ser | Thr | Ala | Arg | Lys | Glu | Asn | |
| 1640 | | | | | 1645 | | | | | 1650 | | | | | |

| aca | acc | ccg | gat | aca | gtg | gca | gaa | tcg | gag | gtg | ctt | ttg | ctg | cac | 5004 |
| Thr | Thr | Pro | Asp | Thr | Val | Ala | Glu | Ser | Glu | Val | Leu | Leu | Leu | His | |
| 1655 | | | | | 1660 | | | | | 1665 | | | | | |

-continued

| | | |
|---|---|---|
| gga gcg ctc cga cct cct tca tct tgg ctg gaa agt ctc cag gca<br>Gly Ala Leu Arg Pro Pro Ser Ser Trp Leu Glu Ser Leu Gln Ala<br>1670                          1675                        1680 | 5049 |
| gca att tgt gaa aag acc agt tct agc cca tcg atc aac gct ctg<br>Ala Ile Cys Glu Lys Thr Ser Ser Ser Pro Ser Ile Asn Ala Leu<br>1685                          1690                        1695 | 5094 |
| ggc gag gta gat acc act gga agg aca tgc att ttt ctt ggg gaa<br>Gly Glu Val Asp Thr Thr Gly Arg Thr Cys Ile Phe Leu Gly Glu<br>1700                          1705                        1710 | 5139 |
| atg gag tcc tcg ctc ctt gga gag gtg gga agc gag acc ttc aaa<br>Met Glu Ser Ser Leu Leu Gly Glu Val Gly Ser Glu Thr Phe Lys<br>1715                          1720                        1725 | 5184 |
| tcc atc acc gcg atg ctg aat aac tgc aac gca ctt ctc tgg gtg<br>Ser Ile Thr Ala Met Leu Asn Asn Cys Asn Ala Leu Leu Trp Val<br>1730                          1735                        1740 | 5229 |
| tct aga gga gca gcc atg agc tcc gag gat cca tgg aaa gct cta<br>Ser Arg Gly Ala Ala Met Ser Ser Glu Asp Pro Trp Lys Ala Leu<br>1745                          1750                        1755 | 5274 |
| cat att ggt ctg ctg cgt acc atc cgc aac gaa aat aac ggg aag<br>His Ile Gly Leu Leu Arg Thr Ile Arg Asn Glu Asn Asn Gly Lys<br>1760                          1765                        1770 | 5319 |
| gaa tat gta tcg ttg gat ctc gat cct tct cga aac gca tac acc<br>Glu Tyr Val Ser Leu Asp Leu Asp Pro Ser Arg Asn Ala Tyr Thr<br>1775                          1780                        1785 | 5364 |
| cac gag tcc ctg tat gct atc tgc aat atc ttc aat ggc cgc ctc<br>His Glu Ser Leu Tyr Ala Ile Cys Asn Ile Phe Asn Gly Arg Leu<br>1790                          1795                        1800 | 5409 |
| ggc gac ctt tcc gaa gac aag gag ttt gaa ttt gca gag aga aac<br>Gly Asp Leu Ser Glu Asp Lys Glu Phe Glu Phe Ala Glu Arg Asn<br>1805                          1810                        1815 | 5454 |
| ggc gtc atc cac gta ccg cga ctt ttc aat gac ccg cac tgg aag<br>Gly Val Ile His Val Pro Arg Leu Phe Asn Asp Pro His Trp Lys<br>1820                          1825                        1830 | 5499 |
| gac caa gaa gcg gtt gag gtc aca ctg cag ccg ttc gag caa ccc<br>Asp Gln Glu Ala Val Glu Val Thr Leu Gln Pro Phe Glu Gln Pro<br>1835                          1840                        1845 | 5544 |
| ggg cgt cgt ctg cgg atg gag gtt gag acg cca ggg ctc tta gac<br>Gly Arg Arg Leu Arg Met Glu Val Glu Thr Pro Gly Leu Leu Asp<br>1850                          1855                        1860 | 5589 |
| tcc ctg caa ttt cga gac gac gaa gga cgt gaa ggc aag gat ctt<br>Ser Leu Gln Phe Arg Asp Asp Glu Gly Arg Glu Gly Lys Asp Leu<br>1865                          1870                        1875 | 5634 |
| ccg gat gat tgg gta gaa atc gaa ccc aaa gct ttc ggt ctc aat<br>Pro Asp Asp Trp Val Glu Ile Glu Pro Lys Ala Phe Gly Leu Asn<br>1880                          1885                        1890 | 5679 |
| ttt cgg gat gtc atg gtt gcc atg ggt caa ttg gag gcc aac cgt<br>Phe Arg Asp Val Met Val Ala Met Gly Gln Leu Glu Ala Asn Arg<br>1895                          1900                        1905 | 5724 |
| gtg atg ggc ttc gaa tgc gcc gga gtg atc aca aag ctc ggt gga<br>Val Met Gly Phe Glu Cys Ala Gly Val Ile Thr Lys Leu Gly Gly<br>1910                          1915                        1920 | 5769 |
| gct gct gcc gct agc caa ggc ctc aga tta ggg gac cgc gta tgt<br>Ala Ala Ala Ala Ser Gln Gly Leu Arg Leu Gly Asp Arg Val Cys<br>1925                          1930                        1935 | 5814 |
| gca cta ctg aaa ggc cat tgg gcg acc aga aca cag acg ccg tac<br>Ala Leu Leu Lys Gly His Trp Ala Thr Arg Thr Gln Thr Pro Tyr<br>1940                          1945                        1950 | 5859 |
| act aat gtc gtc cgt att ccg gac gaa atg ggc ttc cca gaa gcc<br>Thr Asn Val Val Arg Ile Pro Asp Glu Met Gly Phe Pro Glu Ala | 5904 |

|  |  |  |  |  |  |  |  |  |  |  |  |  |  |  |
|---|---|---|---|---|---|---|---|---|---|---|---|---|---|---|
| gct | tcg | gtc | ccc | ctg | gct | ttc | act | acc | gca | tat | att | gcg | ctt | tat | 5949 |
| Ala | Ser | Val | Pro | Leu | Ala | Phe | Thr | Thr | Ala | Tyr | Ile | Ala | Leu | Tyr | |
| | 1970 | | | | 1975 | | | | | 1980 | | | | | |
| acc | acg | gca | aag | cta | cga | cga | ggc | gaa | aga | gtc | ttg | atc | cac | agt | 5994 |
| Thr | Thr | Ala | Lys | Leu | Arg | Arg | Gly | Glu | Arg | Val | Leu | Ile | His | Ser | |
| | 1985 | | | | | 1990 | | | | | 1995 | | | | |
| gga | gct | gga | ggc | gtc | ggt | caa | gca | gcg | atc | att | ttg | tcc | cag | ctt | 6039 |
| Gly | Ala | Gly | Gly | Val | Gly | Gln | Ala | Ala | Ile | Ile | Leu | Ser | Gln | Leu | |
| 2000 | | | | | 2005 | | | | | 2010 | | | | | |
| gcg | ggt | gcc | gag | gtc | ttc | gtc | aca | gcg | gga | act | caa | gcc | aag | cgt | 6084 |
| Ala | Gly | Ala | Glu | Val | Phe | Val | Thr | Ala | Gly | Thr | Gln | Ala | Lys | Arg | |
| 2015 | | | | | 2020 | | | | | 2025 | | | | | |
| gac | ttt | gtc | ggc | gat | aaa | ttc | ggc | atc | aat | ccg | gat | cat | atc | ttc | 6129 |
| Asp | Phe | Val | Gly | Asp | Lys | Phe | Gly | Ile | Asn | Pro | Asp | His | Ile | Phe | |
| 2030 | | | | | 2035 | | | | | 2040 | | | | | |
| tcg | agc | agg | aat | gac | tta | ttc | gtc | gac | ggc | atc | aaa | gcc | tac | acg | 6174 |
| Ser | Ser | Arg | Asn | Asp | Leu | Phe | Val | Asp | Gly | Ile | Lys | Ala | Tyr | Thr | |
| 2045 | | | | | 2050 | | | | | 2055 | | | | | |
| ggc | gga | ctt | ggc | gtt | cat | gtc | gtt | cta | aac | tca | ttg | gca | ggt | caa | 6219 |
| Gly | Gly | Leu | Gly | Val | His | Val | Val | Leu | Asn | Ser | Leu | Ala | Gly | Gln | |
| 2060 | | | | | 2065 | | | | | 2070 | | | | | |
| ctc | ctc | caa | gca | agc | ttt | gac | tgc | atg | gcc | gaa | ttc | ggc | aga | ttt | 6264 |
| Leu | Leu | Gln | Ala | Ser | Phe | Asp | Cys | Met | Ala | Glu | Phe | Gly | Arg | Phe | |
| 2075 | | | | | 2080 | | | | | 2085 | | | | | |
| gtt | gag | att | gga | aaa | aag | gac | ctg | gag | caa | aac | agc | aga | ctt | gac | 6309 |
| Val | Glu | Ile | Gly | Lys | Lys | Asp | Leu | Glu | Gln | Asn | Ser | Arg | Leu | Asp | |
| | 2090 | | | | | 2095 | | | | | 2100 | | | | |
| atg | ctg | cca | ttc | acc | cgg | gac | gtc | tct | ttc | aca | tca | att | gat | ctt | 6354 |
| Met | Leu | Pro | Phe | Thr | Arg | Asp | Val | Ser | Phe | Thr | Ser | Ile | Asp | Leu | |
| | 2105 | | | | | 2110 | | | | | 2115 | | | | |
| ctc | tcg | tgg | caa | aga | gcc | aaa | agt | gaa | gaa | gta | tcc | gaa | gcg | ttg | 6399 |
| Leu | Ser | Trp | Gln | Arg | Ala | Lys | Ser | Glu | Glu | Val | Ser | Glu | Ala | Leu | |
| | 2120 | | | | | 2125 | | | | | 2130 | | | | |
| aac | cat | gtc | aca | aaa | ctc | ctc | gag | aca | aaa | gcg | att | ggc | ttg | att | 6444 |
| Asn | His | Val | Thr | Lys | Leu | Leu | Glu | Thr | Lys | Ala | Ile | Gly | Leu | Ile | |
| | 2135 | | | | | 2140 | | | | | 2145 | | | | |
| ggt | cca | atc | cag | cag | cac | tcc | ttg | tca | aac | atc | gag | aag | gcc | ttc | 6489 |
| Gly | Pro | Ile | Gln | Gln | His | Ser | Leu | Ser | Asn | Ile | Glu | Lys | Ala | Phe | |
| | 2150 | | | | | 2155 | | | | | 2160 | | | | |
| cgt | acg | atg | cag | agt | ggt | cag | cat | gtt | ggc | aaa | gtt | gtg | gtc | aat | 6534 |
| Arg | Thr | Met | Gln | Ser | Gly | Gln | His | Val | Gly | Lys | Val | Val | Val | Asn | |
| | 2165 | | | | | 2170 | | | | | 2175 | | | | |
| gta | tct | ggg | gac | gaa | ctg | gtc | cca | gtc | ggc | gat | gga | ggg | ttc | tcg | 6579 |
| Val | Ser | Gly | Asp | Glu | Leu | Val | Pro | Val | Gly | Asp | Gly | Gly | Phe | Ser | |
| | 2180 | | | | | 2185 | | | | | 2190 | | | | |
| ctg | aag | ctg | aag | cct | gac | agt | tct | tac | cta | gtt | gct | ggt | ggg | ctg | 6624 |
| Leu | Lys | Leu | Lys | Pro | Asp | Ser | Ser | Tyr | Leu | Val | Ala | Gly | Gly | Leu | |
| | 2195 | | | | | 2200 | | | | | 2205 | | | | |
| ggg | gga | att | gga | aag | cag | atc | tgt | cag | tgg | ctt | gtt | gat | cat | ggc | 6669 |
| Gly | Gly | Ile | Gly | Lys | Gln | Ile | Cys | Gln | Trp | Leu | Val | Asp | His | Gly | |
| | 2210 | | | | | 2215 | | | | | 2220 | | | | |
| gcg | aag | cac | ttg | att | atc | cta | tcg | aga | agt | gca | aag | gcc | agt | cca | 6714 |
| Ala | Lys | His | Leu | Ile | Ile | Leu | Ser | Arg | Ser | Ala | Lys | Ala | Ser | Pro | |
| | 2225 | | | | | 2230 | | | | | 2235 | | | | |
| ttc | ata | acc | agc | ttg | caa | aat | caa | cag | tgc | gct | gtc | tat | cta | cac | 6759 |
| Phe | Ile | Thr | Ser | Leu | Gln | Asn | Gln | Gln | Cys | Ala | Val | Tyr | Leu | His | |
| | 2240 | | | | | 2245 | | | | | 2250 | | | | |
| gca | tgt | gac | atc | tca | gat | caa | gat | cag | gtc | acc | aag | gtg | ctc | cgg | 6804 |

|     |     |     |     |     |     |     |     |     |     |     |     |     |     |      |
|-----|-----|-----|-----|-----|-----|-----|-----|-----|-----|-----|-----|-----|-----|------|
| Ala | Cys | Asp | Ile | Ser | Asp | Gln | Asp | Gln | Val | Thr | Lys | Val | Leu | Arg  |
| 2255 |    |     |     | 2260 |    |     |     | 2265 |    |     |     |     |     |      |

| ttg | tgc | gaa | gaa | gca | cat | gca | ccg | cca | att | cga | ggt | atc | ata | caa | 6849 |
|-----|-----|-----|-----|-----|-----|-----|-----|-----|-----|-----|-----|-----|-----|-----|------|
| Leu | Cys | Glu | Glu | Ala | His | Ala | Pro | Pro | Ile | Arg | Gly | Ile | Ile | Gln |      |
| 2270 |   |     |     | 2275 |   |     |     | 2280 |   |     |     |     |     |     |      |

| ggt | gcc | atg | gtt | ctc | aag | gac | gcg | ctt | cta | tcg | cga | atg | aca | ttg | 6894 |
|-----|-----|-----|-----|-----|-----|-----|-----|-----|-----|-----|-----|-----|-----|-----|------|
| Gly | Ala | Met | Val | Leu | Lys | Asp | Ala | Leu | Leu | Ser | Arg | Met | Thr | Leu |      |
| 2285 |   |     |     | 2290 |   |     |     | 2295 |   |     |     |     |     |     |      |

| gat | gaa | ttt | aat | gca | gca | aca | cgc | cca | aaa | gta | cag | ggt | agt | tgg | 6939 |
|-----|-----|-----|-----|-----|-----|-----|-----|-----|-----|-----|-----|-----|-----|-----|------|
| Asp | Glu | Phe | Asn | Ala | Ala | Thr | Arg | Pro | Lys | Val | Gln | Gly | Ser | Trp |      |
| 2300 |   |     |     | 2305 |   |     |     | 2310 |   |     |     |     |     |     |      |

| tat | ctt | cac | aag | atc | gca | cag | gat | gtt | gac | ttc | ttc | gtg | atg | ctc | 6984 |
|-----|-----|-----|-----|-----|-----|-----|-----|-----|-----|-----|-----|-----|-----|-----|------|
| Tyr | Leu | His | Lys | Ile | Ala | Gln | Asp | Val | Asp | Phe | Phe | Val | Met | Leu |      |
| 2315 |   |     |     | 2320 |   |     |     | 2325 |   |     |     |     |     |     |      |

| tca | tcc | ctt | gtt | ggg | gtc | atg | ggt | ggg | gca | ggc | cag | gcc | aat | tac | 7029 |
|-----|-----|-----|-----|-----|-----|-----|-----|-----|-----|-----|-----|-----|-----|-----|------|
| Ser | Ser | Leu | Val | Gly | Val | Met | Gly | Gly | Ala | Gly | Gln | Ala | Asn | Tyr |      |
| 2330 |   |     |     | 2335 |   |     |     | 2340 |   |     |     |     |     |     |      |

| gca | gct | gct | ggt | gca | ttc | cag | gac | gca | ctt | gcg | cac | cac | cgg | aga | 7074 |
|-----|-----|-----|-----|-----|-----|-----|-----|-----|-----|-----|-----|-----|-----|-----|------|
| Ala | Ala | Gly | Ala | Phe | Gln | Asp | Ala | Leu | Ala | His | His | Arg | Arg |     |      |
| 2345 |   |     |     | 2350 |   |     |     | 2355 |   |     |     |     |     |     |      |

| gcc | cat | ggc | atg | ccg | gct | gtc | acc | att | gac | ttg | ggc | atg | gtc | aag | 7119 |
|-----|-----|-----|-----|-----|-----|-----|-----|-----|-----|-----|-----|-----|-----|-----|------|
| Ala | His | Gly | Met | Pro | Ala | Val | Thr | Ile | Asp | Leu | Gly | Met | Val | Lys |      |
| 2360 |   |     |     | 2365 |   |     |     | 2370 |   |     |     |     |     |     |      |

| tct | gtt | gga | tac | gtg | gct | gaa | act | ggc | cgt | ggt | gtg | gcc | gac | cgg | 7164 |
|-----|-----|-----|-----|-----|-----|-----|-----|-----|-----|-----|-----|-----|-----|-----|------|
| Ser | Val | Gly | Tyr | Val | Ala | Glu | Thr | Gly | Arg | Gly | Val | Ala | Asp | Arg |      |
| 2375 |   |     |     | 2380 |   |     |     | 2385 |   |     |     |     |     |     |      |

| ctc | gct | aga | ata | ggt | tac | aag | cct | atg | cat | gaa | aag | gac | gtc | atg | 7209 |
|-----|-----|-----|-----|-----|-----|-----|-----|-----|-----|-----|-----|-----|-----|-----|------|
| Leu | Ala | Arg | Ile | Gly | Tyr | Lys | Pro | Met | His | Glu | Lys | Asp | Val | Met |      |
| 2390 |   |     |     | 2395 |   |     |     | 2400 |   |     |     |     |     |     |      |

| gat | gtg | ttg | gag | aag | gca | atc | ctg | tgt | tct | tcc | cct | caa | ttt | cca | 7254 |
|-----|-----|-----|-----|-----|-----|-----|-----|-----|-----|-----|-----|-----|-----|-----|------|
| Asp | Val | Leu | Glu | Lys | Ala | Ile | Leu | Cys | Ser | Ser | Pro | Gln | Phe | Pro |      |
| 2405 |   |     |     | 2410 |   |     |     | 2415 |   |     |     |     |     |     |      |

| tca | cct | ccc | gca | gct | gtg | gtt | aca | gga | atc | aac | aca | tcc | ccg | ggt | 7299 |
|-----|-----|-----|-----|-----|-----|-----|-----|-----|-----|-----|-----|-----|-----|-----|------|
| Ser | Pro | Pro | Ala | Ala | Val | Val | Thr | Gly | Ile | Asn | Thr | Ser | Pro | Gly |      |
| 2420 |   |     |     | 2425 |   |     |     | 2430 |   |     |     |     |     |     |      |

| gct | cac | tgg | acc | gag | gca | aac | tgg | ata | cag | gaa | cag | cgg | ttt | gtg | 7344 |
|-----|-----|-----|-----|-----|-----|-----|-----|-----|-----|-----|-----|-----|-----|-----|------|
| Ala | His | Trp | Thr | Glu | Ala | Asn | Trp | Ile | Gln | Glu | Gln | Arg | Phe | Val |      |
| 2435 |   |     |     | 2440 |   |     |     | 2445 |   |     |     |     |     |     |      |

| gga | ctt | aaa | tac | cgc | caa | gtc | ctt | cat | gca | gac | caa | tcc | ttt | gtc | 7389 |
|-----|-----|-----|-----|-----|-----|-----|-----|-----|-----|-----|-----|-----|-----|-----|------|
| Gly | Leu | Lys | Tyr | Arg | Gln | Val | Leu | His | Ala | Asp | Gln | Ser | Phe | Val |      |
| 2450 |   |     |     | 2455 |   |     |     | 2460 |   |     |     |     |     |     |      |

| tct | tcg | cat | aaa | aaa | gga | cca | gat | ggc | gtg | cgg | gcc | caa | cta | agc | 7434 |
|-----|-----|-----|-----|-----|-----|-----|-----|-----|-----|-----|-----|-----|-----|-----|------|
| Ser | Ser | His | Lys | Lys | Gly | Pro | Asp | Gly | Val | Arg | Ala | Gln | Leu | Ser |      |
| 2465 |   |     |     | 2470 |   |     |     | 2475 |   |     |     |     |     |     |      |

| agg | gtc | acc | tct | cac | gac | gag | gcc | att | tct | atc | gtc | ctc | aaa | gca | 7479 |
|-----|-----|-----|-----|-----|-----|-----|-----|-----|-----|-----|-----|-----|-----|-----|------|
| Arg | Val | Thr | Ser | His | Asp | Glu | Ala | Ile | Ser | Ile | Val | Leu | Lys | Ala |      |
| 2480 |   |     |     | 2485 |   |     |     | 2490 |   |     |     |     |     |     |      |

| atg | acg | gaa | aag | ctg | atg | cga | atg | ttt | ggt | ctg | gca | gaa | gac | gac | 7524 |
|-----|-----|-----|-----|-----|-----|-----|-----|-----|-----|-----|-----|-----|-----|-----|------|
| Met | Thr | Glu | Lys | Leu | Met | Arg | Met | Phe | Gly | Leu | Ala | Glu | Asp | Asp |      |
| 2495 |   |     |     | 2500 |   |     |     | 2505 |   |     |     |     |     |     |      |

| atg | tcc | tcg | tcc | aaa | aac | ctg | gca | ggt | gtc | ggc | gta | gac | tca | ctc | 7569 |
|-----|-----|-----|-----|-----|-----|-----|-----|-----|-----|-----|-----|-----|-----|-----|------|
| Met | Ser | Ser | Ser | Lys | Asn | Leu | Ala | Gly | Val | Gly | Val | Asp | Ser | Leu |      |
| 2510 |   |     |     | 2515 |   |     |     | 2520 |   |     |     |     |     |     |      |

| gtc | gcc | att | gaa | ctt | cga | aac | tgg | atc | aca | tct | gaa | atc | cat | gtt | 7614 |
|-----|-----|-----|-----|-----|-----|-----|-----|-----|-----|-----|-----|-----|-----|-----|------|
| Val | Ala | Ile | Glu | Leu | Arg | Asn | Trp | Ile | Thr | Ser | Glu | Ile | His | Val |      |
| 2525 |   |     |     | 2530 |   |     |     | 2535 |   |     |     |     |     |     |      |

| gat | gtg | tcg | atc | ttt | gag | ctc | atg | aat | ggt | aac | acc | atc | gcc | ggc | 7659 |
|-----|-----|-----|-----|-----|-----|-----|-----|-----|-----|-----|-----|-----|-----|-----|------|
| Asp | Val | Ser | Ile | Phe | Glu | Leu | Met | Asn | Gly | Asn | Thr | Ile | Ala | Gly |      |
| 2540 |   |     |     | 2545 |   |     |     | 2550 |   |     |     |     |     |     |      |

```
ctc gtc gag tta gtt gtg gcg aaa tgc agt taa                    7692
Leu Val Glu Leu Val Val Ala Lys Cys Ser
    2555                2560
```

<210> SEQ ID NO 46
<211> LENGTH: 2563
<212> TYPE: PRT
<213> ORGANISM: Penicillium citrinum

<400> SEQUENCE: 46

```
Met Asn Asn Thr Pro Ala Val Thr Ala Thr Ala Thr Ala Thr
1               5                  10                  15

Ala Thr Ala Met Ala Gly Ser Ala Cys Ser Asn Thr Ser Pro Ile
                20                  25                  30

Ala Ile Val Gly Met Gly Cys Arg Phe Ala Gly Asp Ala Thr Ser Pro
            35                  40                  45

Gln Lys Leu Trp Glu Met Val Glu Arg Gly Ser Ala Trp Ser Lys
        50                  55                  60

Val Pro Ser Ser Arg Phe Asn Val Arg Gly Val Tyr His Pro Asn Gly
65                  70                  75                  80

Glu Arg Val Gly Ser Thr His Val Lys Gly Gly His Phe Ile Asp Glu
                85                  90                  95

Asp Pro Ala Leu Phe Asp Ala Ala Phe Phe Asn Met Thr Thr Glu Val
            100                 105                 110

Ala Ser Cys Met Asp Pro Gln Tyr Arg Leu Met Leu Glu Val Val Tyr
        115                 120                 125

Glu Ser Leu Glu Ser Ala Gly Ile Thr Ile Asp Gly Met Ala Gly Ser
    130                 135                 140

Asn Thr Ser Val Phe Gly Gly Val Met Tyr His Asp Tyr Gln Asp Ser
145                 150                 155                 160

Leu Asn Arg Asp Pro Glu Thr Val Pro Arg Tyr Phe Ile Thr Gly Asn
                165                 170                 175

Ser Gly Thr Met Leu Ser Asn Arg Ile Ser His Phe Tyr Asp Leu Arg
            180                 185                 190

Gly Pro Ser Val Thr Val Asp Thr Ala Cys Ser Thr Thr Leu Thr Ala
        195                 200                 205

Leu His Leu Ala Cys Gln Ser Leu Arg Thr Gly Glu Ser Asp Thr Ala
    210                 215                 220

Ile Val Ile Gly Ala Asn Leu Leu Asn Pro Asp Val Phe Val Thr
225                 230                 235                 240

Met Ser Asn Leu Gly Phe Leu Ser Pro Asp Gly Ile Ser Tyr Ser Phe
                245                 250                 255

Asp Pro Arg Ala Asn Gly Tyr Gly Arg Gly Glu Gly Ile Ala Ala Leu
            260                 265                 270

Val Ile Lys Ala Leu Pro Asn Ala Leu Arg Asp Gln Asp Pro Ile Arg
        275                 280                 285

Ala Val Ile Arg Glu Thr Ala Leu Asn Gln Asp Gly Lys Thr Pro Ala
    290                 295                 300

Ile Thr Ala Pro Ser Asp Val Ala Gln Lys Ser Leu Ile Gln Glu Cys
305                 310                 315                 320

Tyr Asp Lys Ala Gly Leu Asp Met Ser Leu Thr Ser Tyr Val Glu Ala
                325                 330                 335

His Gly Thr Gly Thr Pro Thr Gly Asp Pro Leu Glu Ile Ser Ala Ile
            340                 345                 350

Ser Ala Ala Phe Lys Gly His Pro Leu His Leu Gly Ser Val Lys Ala
```

```
                355                 360                 365
Asn Ile Gly His Thr Glu Ala Ala Ser Gly Leu Ala Ser Ile Ile Lys
370                 375                 380
Val Ala Leu Ala Leu Glu Lys Gly Leu Ile Pro Pro Asn Ala Arg Phe
385                 390                 395                 400
Leu Gln Lys Asn Ser Lys Leu Met Leu Asp Gln Lys Asn Ile Lys Ile
                405                 410                 415
Pro Met Ser Ala Gln Asp Trp Pro Val Lys Asp Gly Thr Arg Arg Ala
                420                 425                 430
Ser Val Asn Asn Phe Gly Phe Gly Ser Asn Ala His Val Ile Leu
                435                 440                 445
Glu Ser Tyr Asp Arg Ala Ser Leu Ala Leu Pro Glu Asp Gln Val His
450                 455                 460
Val Asn Gly Asn Ser Glu His Gly Arg Val Glu Asp Gly Ser Lys Gln
465                 470                 475                 480
Ser Arg Ile Tyr Val Val Arg Ala Lys Asp Glu Gln Ala Cys Arg Arg
                485                 490                 495
Thr Ile Ala Ser Leu Arg Asp Tyr Ile Lys Ser Val Ala Asp Ile Asp
                500                 505                 510
Gly Glu Pro Phe Leu Ala Ser Leu Ala Tyr Thr Leu Gly Ser Arg Arg
                515                 520                 525
Ser Ile Leu Pro Trp Thr Ser Val Tyr Val Ala Asp Ser Leu Gly Gly
                530                 535                 540
Leu Val Ser Ala Leu Ser Asp Glu Ser Asn Gln Pro Lys Arg Ala Asn
545                 550                 555                 560
Glu Lys Val Arg Leu Gly Phe Val Phe Thr Gly Gln Gly Ala Gln Trp
                565                 570                 575
His Ala Met Gly Arg Glu Leu Val Asn Thr Phe Pro Val Phe Lys Gln
                580                 585                 590
Ala Ile Leu Glu Cys Asp Gly Tyr Ile Lys Gln Leu Gly Ala Ser Trp
                595                 600                 605
Asn Phe Met Glu Glu Leu His Arg Asp Glu Leu Thr Thr Arg Val Asn
                610                 615                 620
Asp Ala Glu Tyr Ser Leu Pro Leu Ser Thr Ala Ile Gln Ile Ala Leu
625                 630                 635                 640
Val Arg Leu Leu Trp Ser Trp Gly Ile Arg Pro Thr Gly Ile Thr Ser
                645                 650                 655
His Ser Ser Gly Glu Ala Ala Ala Tyr Ala Ala Gly Ala Leu Ser
                660                 665                 670
Ala Arg Ser Ala Ile Gly Ile Thr Tyr Ile Arg Gly Val Leu Thr Thr
                675                 680                 685
Lys Pro Lys Pro Ala Leu Ala Ala Lys Gly Gly Met Met Ala Val Gly
690                 695                 700
Leu Gly Arg Ser Glu Thr Asn Val Tyr Ile Ser Arg Leu Asn Gln Glu
705                 710                 715                 720
Asp Gly Cys Val Val Gly Cys Ile Asn Ser Gln Cys Ser Val Thr
                725                 730                 735
Val Ser Gly Asp Leu Gly Ala Ile Glu Lys Leu Glu Lys Leu Leu His
                740                 745                 750
Ala Asp Gly Ile Phe Thr Arg Lys Leu Lys Val Thr Glu Ala Phe His
                755                 760                 765
Ser Ser His Met Arg Pro Met Ala Asp Ala Phe Gly Ala Ser Leu Arg
770                 775                 780
```

```
Asp Leu Phe Asn Ser Asp Asn Asn Asp Asn Pro Asn Ala Asp Thr
785                 790                 795                 800

Ser Lys Gly Val Leu Tyr Ser Ser Pro Lys Thr Gly Ser Arg Met Thr
                805                 810                 815

Asp Leu Lys Leu Leu Asp Pro Thr His Trp Met Asp Ser Met Leu
            820                 825                 830

Gln Pro Val Glu Phe Glu Ser Ser Leu Arg Glu Met Cys Phe Asp Pro
        835                 840                 845

Asn Thr Lys Glu Lys Ala Val Asp Val Ile Ile Glu Ile Gly Pro His
    850                 855                 860

Gly Ala Leu Gly Gly Pro Ile Asn Gln Val Met Gln Asp Leu Gly Leu
865                 870                 875                 880

Lys Gly Thr Asp Ile Asn Tyr Leu Ser Cys Leu Ser Arg Gly Arg Ser
                885                 890                 895

Ser Leu Glu Thr Met Tyr Arg Ala Ala Thr Glu Leu Ile Ser Lys Gly
            900                 905                 910

Tyr Gly Leu Lys Met Asp Ala Ile Asn Phe Pro His Gly Arg Lys Glu
        915                 920                 925

Pro Arg Val Lys Val Leu Ser Asp Leu Pro Ala Tyr Pro Trp Asn His
    930                 935                 940

Gln Thr Arg Tyr Trp Arg Glu Pro Arg Gly Ser Arg Glu Ser Lys Gln
945                 950                 955                 960

Arg Thr His Pro Pro His Thr Leu Ile Gly Ser Arg Glu Ser Leu Ser
                965                 970                 975

Pro His Phe Ala Pro Lys Trp Lys His Val Leu Arg Leu Ser Asp Ile
            980                 985                 990

Pro Trp Ile Arg Asp His Val Val  Gly Ser Ser Ile Ile  Phe Pro Gly
        995                 1000                1005

Ala Gly  Phe Ile Ser Met Ala  Ile Glu Gly Phe Ser  Gln Val Cys
    1010                 1015                1020

Pro Pro  Val Ala Gly Ala Ser  Ile Asn Tyr Asn Leu  Arg Asp Val
    1025                 1030                1035

Glu Leu  Ala Gln Ala Leu Ile  Ile Pro Ala Asp Ala  Glu Ala Glu
    1040                 1045                1050

Val Asp  Leu Arg Leu Thr Ile  Arg Ser Cys Glu Glu  Arg Ser Leu
    1055                 1060                1065

Gly Thr  Lys Asn Trp His Gln  Phe Ser Val His Ser  Ile Ser Gly
    1070                 1075                1080

Glu Asn  Asn Thr Trp Thr Glu  His Cys Thr Gly Leu  Ile Arg Ser
    1085                 1090                1095

Glu Ser  Glu Arg Ser His Leu  Asp Cys Ser Thr Val  Glu Ala Ser
    1100                 1105                1110

Arg Arg  Leu Asn Leu Gly Ser  Asp Asn Arg Ser Ile  Asp Pro Asn
    1115                 1120                1125

Asp Leu  Trp Glu Ser Leu His  Ala Asn Gly Ile Cys  His Gly Pro
    1130                 1135                1140

Ile Phe  Gln Asn Ile Gln Arg  Ile Gln Asn Asn Gly  Gln Gly Ser
    1145                 1150                1155

Phe Cys  Arg Phe Ser Ile Ala  Asp Thr Ala Ser Ala  Met Pro His
    1160                 1165                1170

Ser Tyr  Glu Asn Arg His Ile  Val His Pro Thr Thr  Leu Asp Ser
    1175                 1180                1185
```

-continued

```
Val Ile Gln Ala Ala Tyr Thr Val Leu Pro Tyr Ala Gly Thr Arg
1190                1195                1200

Met Lys Thr Ala Met Val Pro Arg Arg Leu Arg Asn Val Lys Ile
1205                1210                1215

Ser Ser Ser Leu Ala Asp Leu Glu Ala Gly Asp Ala Leu Asp Ala
1220                1225                1230

Gln Ala Ser Ile Lys Asp Arg Asn Ser Gln Ser Phe Ser Thr Asp
1235                1240                1245

Leu Ala Val Phe Asp Asp Tyr Asp Ser Gly Ser Ser Pro Ser Asp
1250                1255                1260

Gly Ile Pro Val Ile Glu Ile Glu Gly Leu Val Phe Gln Ser Val
1265                1270                1275

Gly Ser Ser Phe Ser Asp Gln Lys Ser Asp Ser Asn Asp Thr Glu
1280                1285                1290

Asn Ala Cys Ser Ser Trp Val Trp Ala Pro Asp Ile Ser Leu Gly
1295                1300                1305

Asp Ser Thr Trp Leu Lys Glu Lys Leu Ser Thr Glu Ala Glu Thr
1310                1315                1320

Lys Glu Thr Glu Leu Met Met Asp Leu Arg Arg Cys Thr Ile Asn
1325                1330                1335

Phe Ile Gln Glu Ala Val Thr Asp Leu Thr Asn Ser Asp Ile Gln
1340                1345                1350

His Leu Asp Gly His Leu Gln Lys Tyr Phe Asp Trp Met Asn Val
1355                1360                1365

Gln Leu Asp Leu Ala Arg Gln Asn Lys Leu Ser Pro Ala Ser Cys
1370                1375                1380

Asp Trp Leu Ser Asp Asp Ala Glu Gln Lys Lys Cys Leu Gln Ala
1385                1390                1395

Arg Val Ala Gly Glu Ser Val Asn Gly Glu Met Ile Ser Arg Leu
1400                1405                1410

Gly Pro Gln Leu Ile Ala Met Leu Arg Arg Glu Thr Glu Pro Leu
1415                1420                1425

Glu Leu Met Met Gln Asp Gln Leu Leu Ser Arg Tyr Tyr Val Asn
1430                1435                1440

Ala Ile Lys Trp Ser Arg Ser Asn Ala Gln Ala Ser Glu Leu Ile
1445                1450                1455

Arg Leu Cys Ala His Lys Asn Pro Arg Ser Arg Ile Leu Glu Ile
1460                1465                1470

Gly Gly Gly Thr Gly Gly Cys Thr Lys Leu Ile Val Asn Ala Leu
1475                1480                1485

Gly Asn Thr Lys Pro Ile Asp Arg Tyr Asp Phe Thr Asp Val Ser
1490                1495                1500

Ala Gly Phe Phe Glu Ser Ala Arg Glu Gln Phe Ala Asp Trp Gln
1505                1510                1515

Asp Val Met Thr Phe Lys Lys Leu Asp Ile Glu Ser Asp Pro Glu
1520                1525                1530

Gln Gln Gly Phe Glu Cys Ala Thr Tyr Asp Val Val Val Ala Cys
1535                1540                1545

Gln Val Leu His Ala Thr Arg Cys Met Lys Arg Thr Leu Ser Asn
1550                1555                1560

Val Arg Lys Leu Leu Lys Pro Gly Gly Asn Leu Ile Leu Val Glu
1565                1570                1575

Thr Thr Arg Asp Gln Leu Asp Leu Phe Phe Thr Phe Gly Leu Leu
```

-continued

```
         1580                1585                1590
Pro Gly  Trp Trp Leu Ser Glu  Glu Pro Glu Arg Lys  Ser Thr Pro
    1595                1600                1605

Ser Leu  Thr Thr Asp Leu Trp  Asn Thr Met Leu Asp  Thr Ser Gly
    1610                1615                1620

Phe Asn  Gly Val Glu Leu Glu  Val Arg Asp Cys Glu  Asp Asp Glu
    1625                1630                1635

Phe Tyr  Met Ile Ser Thr Met  Leu Ser Thr Ala Arg  Lys Glu Asn
    1640                1645                1650

Thr Thr  Pro Asp Thr Val Ala  Glu Ser Glu Val Leu  Leu Leu His
    1655                1660                1665

Gly Ala  Leu Arg Pro Pro Ser  Ser Trp Leu Glu Ser  Leu Gln Ala
    1670                1675                1680

Ala Ile  Cys Glu Lys Thr Ser  Ser Ser Pro Ser Ile  Asn Ala Leu
    1685                1690                1695

Gly Glu  Val Asp Thr Thr Gly  Arg Thr Cys Ile Phe  Leu Gly Glu
    1700                1705                1710

Met Glu  Ser Ser Leu Leu Gly  Glu Val Gly Ser Glu  Thr Phe Lys
    1715                1720                1725

Ser Ile  Thr Ala Met Leu Asn  Asn Cys Asn Ala Leu  Leu Trp Val
    1730                1735                1740

Ser Arg  Gly Ala Ala Met Ser  Ser Glu Asp Pro Trp  Lys Ala Leu
    1745                1750                1755

His Ile  Gly Leu Leu Arg Thr  Ile Arg Asn Glu Asn  Asn Gly Lys
    1760                1765                1770

Glu Tyr  Val Ser Leu Asp Leu  Asp Pro Ser Arg Asn  Ala Tyr Thr
    1775                1780                1785

His Glu  Ser Leu Tyr Ala Ile  Cys Asn Ile Phe Asn  Gly Arg Leu
    1790                1795                1800

Gly Asp  Leu Ser Glu Asp Lys  Glu Phe Glu Phe Ala  Glu Arg Asn
    1805                1810                1815

Gly Val  Ile His Val Pro Arg  Leu Phe Asn Asp Pro  His Trp Lys
    1820                1825                1830

Asp Gln  Glu Ala Val Glu Val  Thr Leu Gln Pro Phe  Glu Gln Pro
    1835                1840                1845

Gly Arg  Arg Leu Arg Met Glu  Val Glu Thr Pro Gly  Leu Leu Asp
    1850                1855                1860

Ser Leu  Gln Phe Arg Asp Asp  Glu Gly Arg Glu Gly  Lys Asp Leu
    1865                1870                1875

Pro Asp  Asp Trp Val Glu Ile  Glu Pro Lys Ala Phe  Gly Leu Asn
    1880                1885                1890

Phe Arg  Asp Val Met Val Ala  Met Gly Gln Leu Glu  Ala Asn Arg
    1895                1900                1905

Val Met  Gly Phe Glu Cys Ala  Gly Val Ile Thr Lys  Leu Gly Gly
    1910                1915                1920

Ala Ala  Ala Ala Ser Gln Gly  Leu Arg Leu Gly Asp  Arg Val Cys
    1925                1930                1935

Ala Leu  Leu Lys Gly His Trp  Ala Thr Arg Thr Gln  Thr Pro Tyr
    1940                1945                1950

Thr Asn  Val Val Arg Ile Pro  Asp Glu Met Gly Phe  Pro Glu Ala
    1955                1960                1965

Ala Ser  Val Pro Leu Ala Phe  Thr Thr Ala Tyr Ile  Ala Leu Tyr
    1970                1975                1980
```

```
Thr Thr Ala Lys Leu Arg Arg Gly Glu Arg Val Leu Ile His Ser
    1985            1990            1995

Gly Ala Gly Gly Val Gly Gln Ala Ala Ile Ile Leu Ser Gln Leu
    2000            2005            2010

Ala Gly Ala Glu Val Phe Val Thr Ala Gly Thr Gln Ala Lys Arg
    2015            2020            2025

Asp Phe Val Gly Asp Lys Phe Gly Ile Asn Pro Asp His Ile Phe
    2030            2035            2040

Ser Ser Arg Asn Asp Leu Phe Val Asp Gly Ile Lys Ala Tyr Thr
    2045            2050            2055

Gly Gly Leu Gly Val His Val Val Leu Asn Ser Leu Ala Gly Gln
    2060            2065            2070

Leu Leu Gln Ala Ser Phe Asp Cys Met Ala Glu Phe Gly Arg Phe
    2075            2080            2085

Val Glu Ile Gly Lys Lys Asp Leu Glu Gln Asn Ser Arg Leu Asp
    2090            2095            2100

Met Leu Pro Phe Thr Arg Asp Val Ser Phe Thr Ser Ile Asp Leu
    2105            2110            2115

Leu Ser Trp Gln Arg Ala Lys Ser Glu Glu Val Ser Glu Ala Leu
    2120            2125            2130

Asn His Val Thr Lys Leu Leu Glu Thr Lys Ala Ile Gly Leu Ile
    2135            2140            2145

Gly Pro Ile Gln Gln His Ser Leu Ser Asn Ile Glu Lys Ala Phe
    2150            2155            2160

Arg Thr Met Gln Ser Gly Gln His Val Gly Lys Val Val Val Asn
    2165            2170            2175

Val Ser Gly Asp Glu Leu Val Pro Val Gly Asp Gly Gly Phe Ser
    2180            2185            2190

Leu Lys Leu Lys Pro Asp Ser Ser Tyr Leu Val Ala Gly Gly Leu
    2195            2200            2205

Gly Gly Ile Gly Lys Gln Ile Cys Gln Trp Leu Val Asp His Gly
    2210            2215            2220

Ala Lys His Leu Ile Ile Leu Ser Arg Ser Ala Lys Ala Ser Pro
    2225            2230            2235

Phe Ile Thr Ser Leu Gln Asn Gln Gln Cys Ala Val Tyr Leu His
    2240            2245            2250

Ala Cys Asp Ile Ser Asp Gln Asp Gln Val Thr Lys Val Leu Arg
    2255            2260            2265

Leu Cys Glu Glu Ala His Ala Pro Pro Ile Arg Gly Ile Ile Gln
    2270            2275            2280

Gly Ala Met Val Leu Lys Asp Ala Leu Leu Ser Arg Met Thr Leu
    2285            2290            2295

Asp Glu Phe Asn Ala Ala Thr Arg Pro Lys Val Gln Gly Ser Trp
    2300            2305            2310

Tyr Leu His Lys Ile Ala Gln Asp Val Asp Phe Phe Val Met Leu
    2315            2320            2325

Ser Ser Leu Val Gly Val Met Gly Gly Ala Gly Gln Ala Asn Tyr
    2330            2335            2340

Ala Ala Ala Gly Ala Phe Gln Asp Ala Leu Ala His His Arg Arg
    2345            2350            2355

Ala His Gly Met Pro Ala Val Thr Ile Asp Leu Gly Met Val Lys
    2360            2365            2370
```

-continued

```
Ser Val Gly Tyr Val Ala Glu  Thr Gly Arg Gly Val  Ala Asp Arg
    2375             2380             2385

Leu Ala Arg Ile Gly Tyr Lys  Pro Met His Glu Lys  Asp Val Met
    2390             2395             2400

Asp Val Leu Glu Lys Ala Ile  Leu Cys Ser Ser Pro  Gln Phe Pro
    2405             2410             2415

Ser Pro Pro Ala Ala Val Val  Thr Gly Ile Asn Thr  Ser Pro Gly
    2420             2425             2430

Ala His Trp Thr Glu Ala Asn  Trp Ile Gln Glu Gln  Arg Phe Val
    2435             2440             2445

Gly Leu Lys Tyr Arg Gln Val  Leu His Ala Asp Gln  Ser Phe Val
    2450             2455             2460

Ser Ser His Lys Lys Gly Pro  Asp Gly Val Arg Ala  Gln Leu Ser
    2465             2470             2475

Arg Val Thr Ser His Asp Glu  Ala Ile Ser Ile Val  Leu Lys Ala
    2480             2485             2490

Met Thr Glu Lys Leu Met Arg  Met Phe Gly Leu Ala  Glu Asp Asp
    2495             2500             2505

Met Ser Ser Lys Asn Leu Ala  Gly Val Gly Val Asp  Ser Leu
    2510             2515             2520

Val Ala Ile Glu Leu Arg Asn  Trp Ile Thr Ser Glu  Ile His Val
    2525             2530             2535

Asp Val Ser Ile Phe Glu Leu  Met Asn Gly Asn Thr  Ile Ala Gly
    2540             2545             2550

Leu Val Glu Leu Val Val Ala  Lys Cys Ser
    2555             2560
```

```
<210> SEQ ID NO 47
<211> LENGTH: 1557
<212> TYPE: DNA
<213> ORGANISM: Penicillium citrinum
<220> FEATURE:
<221> NAME/KEY: CDS
<222> LOCATION: (1)..(1557)

<400> SEQUENCE: 47 atg ctc ggc cag gtt ctt ctg acc gtc gaa tcg tac caa tgg gta tcg      48
Met Leu Gly Gln Val Leu Leu Thr Val Glu Ser Tyr Gln Trp Val Ser
1               5                   10                  15 acc cct caa gcc ctt gtg gcg gtc gca gtg ctt ctt agt ctc atc gcc      96
Thr Pro Gln Ala Leu Val Ala Val Ala Val Leu Leu Ser Leu Ile Ala
            20                  25                  30 tac cgt ttg cgg ggg cgc cag tcc gaa ctg caa gtc tat aat ccc aaa     144
Tyr Arg Leu Arg Gly Arg Gln Ser Glu Leu Gln Val Tyr Asn Pro Lys
        35                  40                  45 aaa tgg tgg gag ttg acg acc atg agg gct agg cag gac ttc gat acg     192
Lys Trp Trp Glu Leu Thr Thr Met Arg Ala Arg Gln Asp Phe Asp Thr
    50                  55                  60 tat ggt ccg agc tgg atc gaa gct tgg ttc tcg aaa aac gac aag ccc     240
Tyr Gly Pro Ser Trp Ile Glu Ala Trp Phe Ser Lys Asn Asp Lys Pro
65                  70                  75                  80 ctg cgc ttc att gtt gat tcc ggc tat tgc acc atc ctc cca tcg tcc     288
Leu Arg Phe Ile Val Asp Ser Gly Tyr Cys Thr Ile Leu Pro Ser Ser
                85                  90                  95 atg gcc gac gag ttt cgg aaa atc aaa gat atg tgc atg tac aag ttt     336
Met Ala Asp Glu Phe Arg Lys Ile Lys Asp Met Cys Met Tyr Lys Phe
            100                 105                 110 ttg gcg gat gac ttt cac tct cat ctc cct gga ttc gac ggg ttc aag     384
```

```
                                                                                -continued Leu Ala Asp Asp Phe His Ser His Leu Pro Gly Phe Asp Gly Phe Lys
        115                 120                 125 gaa atc tgc cag gat gca cat ctt gtc aac aaa gtt gtt ttg aac cag        432
Glu Ile Cys Gln Asp Ala His Leu Val Asn Lys Val Val Leu Asn Gln
130                 135                 140 tta caa acc caa gcc ccc aag tac aca aag cca ttg gct acc ttg gcc        480
Leu Gln Thr Gln Ala Pro Lys Tyr Thr Lys Pro Leu Ala Thr Leu Ala
145                 150                 155                 160 gac gct act att gcc aag ttg ttc ggt aaa agc gag gag tgg caa acc        528
Asp Ala Thr Ile Ala Lys Leu Phe Gly Lys Ser Glu Glu Trp Gln Thr
                165                 170                 175 gca cct gtc tat tcc aat gga ttg gac ctt gtc aca cga aca gtc aca        576
Ala Pro Val Tyr Ser Asn Gly Leu Asp Leu Val Thr Arg Thr Val Thr
                180                 185                 190 ctc att atg gtc ggc gac aaa atc tgc cac aat gag gag tgg ctg gat        624
Leu Ile Met Val Gly Asp Lys Ile Cys His Asn Glu Glu Trp Leu Asp
            195                 200                 205 att gca aag aac cat gcc gtg agt gtg gcg gta caa gct cgc caa ctt        672
Ile Ala Lys Asn His Ala Val Ser Val Ala Val Gln Ala Arg Gln Leu
210                 215                 220 cgc gta tgg ccc atg cta ctg cga ccg ctc gct cac tgg ttt caa ccg        720
Arg Val Trp Pro Met Leu Leu Arg Pro Leu Ala His Trp Phe Gln Pro
225                 230                 235                 240 caa gga cgc aaa ttg cgt gac caa gtg cgc cgc gca cga aag atc att        768
Gln Gly Arg Lys Leu Arg Asp Gln Val Arg Arg Ala Arg Lys Ile Ile
                245                 250                 255 gat cct gag att cag cga cga cgt gct gaa aag gcc gca tgt gta gcg        816
Asp Pro Glu Ile Gln Arg Arg Arg Ala Glu Lys Ala Ala Cys Val Ala
                260                 265                 270 aag ggc gtg cag ccg ccc cag tac gtc gat acc atg caa tgg ttt gaa        864
Lys Gly Val Gln Pro Pro Gln Tyr Val Asp Thr Met Gln Trp Phe Glu
                275                 280                 285 gac acc gcc gac ggc cgc tgg tac gat gtg gcg ggt gct cag ctc gct        912
Asp Thr Ala Asp Gly Arg Trp Tyr Asp Val Ala Gly Ala Gln Leu Ala
290                 295                 300 atg gat ttc gcc ggc atc tac gcc tcg acg gat ctt ttc gtc ggt gcc        960
Met Asp Phe Ala Gly Ile Tyr Ala Ser Thr Asp Leu Phe Val Gly Ala
305                 310                 315                 320 ctt gtg gac att gcc agg cac cca gac ctt att cag cct ctc cgc caa       1008
Leu Val Asp Ile Ala Arg His Pro Asp Leu Ile Gln Pro Leu Arg Gln
                325                 330                 335 gag atc cgc act gta atc gga gaa ggg ggc tgg acg cct gcc tct ctg       1056
Glu Ile Arg Thr Val Ile Gly Glu Gly Gly Trp Thr Pro Ala Ser Leu
                340                 345                 350 ttc aag ctg aag ctc ctc gac agc tgc atg aaa gag acg cag cga atc       1104
Phe Lys Leu Lys Leu Leu Asp Ser Cys Met Lys Glu Thr Gln Arg Ile
            355                 360                 365 aag ccg gtc gag tgc gcc act atg cgc agt acc gct ctc aga gac atc       1152
Lys Pro Val Glu Cys Ala Thr Met Arg Ser Thr Ala Leu Arg Asp Ile
            370                 375                 380 act cta tcc aat ggc ctc ttc att ccc aag ggc gag ttg gcc gct gtg       1200
Thr Leu Ser Asn Gly Leu Phe Ile Pro Lys Gly Glu Leu Ala Ala Val
385                 390                 395                 400 gct gca gac cgc atg aac aac cct gat gtg tgg gaa aac ccc gaa aat       1248
Ala Ala Asp Arg Met Asn Asn Pro Asp Val Trp Glu Asn Pro Glu Asn
                405                 410                 415 tat gat ccc tac cga ttt atg cgc atg cgc gag gat cca gac aag gcc       1296
Tyr Asp Pro Tyr Arg Phe Met Arg Met Arg Glu Asp Pro Asp Lys Ala
                420                 425                 430
```

```
ttc acc gct caa ttg gag aat acc aac ggt gat cac atc ggc ttc ggc      1344
Phe Thr Ala Gln Leu Glu Asn Thr Asn Gly Asp His Ile Gly Phe Gly
        435                 440                 445 tgg aac cca cgc gct tgt ccc ggg cgg ttc ttc gcc tcg aag gaa atc      1392
Trp Asn Pro Arg Ala Cys Pro Gly Arg Phe Phe Ala Ser Lys Glu Ile
450                 455                 460 aag att ctc ctc gct cat ata ctg att cag tat gat gtg aag cct gta      1440
Lys Ile Leu Leu Ala His Ile Leu Ile Gln Tyr Asp Val Lys Pro Val
465                 470                 475                 480 cca gga gac gat gac aaa tac tac cgt cac gct ttt agc gtt cgt atg      1488
Pro Gly Asp Asp Asp Lys Tyr Tyr Arg His Ala Phe Ser Val Arg Met
                485                 490                 495 cat cca acc aca aag ctc atg gta cgc cgg cgc aac gag gac atc ccg      1536
His Pro Thr Thr Lys Leu Met Val Arg Arg Arg Asn Glu Asp Ile Pro
            500                 505                 510 ctc cct cat gac cgg tgc taa                                           1557
Leu Pro His Asp Arg Cys
        515

<210> SEQ ID NO 48
<211> LENGTH: 518
<212> TYPE: PRT
<213> ORGANISM: Penicillium citrinum

<400> SEQUENCE: 48

Met Leu Gly Gln Val Leu Leu Thr Val Glu Ser Tyr Gln Trp Val Ser
1               5                   10                  15

Thr Pro Gln Ala Leu Val Ala Val Ala Val Leu Leu Ser Leu Ile Ala
            20                  25                  30

Tyr Arg Leu Arg Gly Arg Gln Ser Glu Leu Gln Val Tyr Asn Pro Lys
        35                  40                  45

Lys Trp Trp Glu Leu Thr Thr Met Arg Ala Arg Gln Asp Phe Asp Thr
    50                  55                  60

Tyr Gly Pro Ser Trp Ile Glu Ala Trp Phe Lys Asn Asp Lys Pro
65                  70                  75                  80

Leu Arg Phe Ile Val Asp Ser Gly Tyr Cys Thr Ile Leu Pro Ser Ser
                85                  90                  95

Met Ala Asp Glu Phe Arg Lys Ile Lys Asp Met Cys Met Tyr Lys Phe
            100                 105                 110

Leu Ala Asp Asp Phe His Ser His Leu Pro Gly Phe Asp Gly Phe Lys
        115                 120                 125

Glu Ile Cys Gln Asp Ala His Leu Val Asn Lys Val Leu Asn Gln
    130                 135                 140

Leu Gln Thr Gln Ala Pro Lys Tyr Thr Lys Pro Leu Ala Thr Leu Ala
145                 150                 155                 160

Asp Ala Thr Ile Ala Lys Leu Phe Gly Lys Ser Glu Glu Trp Gln Thr
                165                 170                 175

Ala Pro Val Tyr Ser Asn Gly Leu Asp Leu Val Thr Arg Thr Val Thr
            180                 185                 190

Leu Ile Met Val Gly Asp Lys Ile Cys His Asn Glu Glu Trp Leu Asp
        195                 200                 205

Ile Ala Lys Asn His Ala Val Ser Val Ala Val Gln Ala Arg Gln Leu
    210                 215                 220

Arg Val Trp Pro Met Leu Leu Arg Pro Leu Ala His Trp Phe Gln Pro
225                 230                 235                 240

Gln Gly Arg Lys Leu Arg Asp Gln Val Arg Arg Ala Arg Lys Ile Ile
                245                 250                 255
```

```
Asp Pro Glu Ile Gln Arg Arg Ala Glu Lys Ala Ala Cys Val Ala
            260                 265                 270

Lys Gly Val Gln Pro Pro Gln Tyr Val Asp Thr Met Gln Trp Phe Glu
        275                 280                 285

Asp Thr Ala Asp Gly Arg Trp Tyr Asp Val Ala Gly Ala Gln Leu Ala
        290                 295                 300

Met Asp Phe Ala Gly Ile Tyr Ala Ser Thr Asp Leu Phe Val Gly Ala
305                 310                 315                 320

Leu Val Asp Ile Ala Arg His Pro Asp Leu Ile Gln Pro Leu Arg Gln
                325                 330                 335

Glu Ile Arg Thr Val Ile Gly Glu Gly Gly Trp Thr Pro Ala Ser Leu
            340                 345                 350

Phe Lys Leu Lys Leu Leu Asp Ser Cys Met Lys Glu Thr Gln Arg Ile
        355                 360                 365

Lys Pro Val Glu Cys Ala Thr Met Arg Ser Thr Ala Leu Arg Asp Ile
    370                 375                 380

Thr Leu Ser Asn Gly Leu Phe Ile Pro Lys Gly Glu Leu Ala Ala Val
385                 390                 395                 400

Ala Ala Asp Arg Met Asn Asn Pro Asp Val Trp Glu Asn Pro Glu Asn
                405                 410                 415

Tyr Asp Pro Tyr Arg Phe Met Arg Met Arg Glu Asp Pro Asp Lys Ala
            420                 425                 430

Phe Thr Ala Gln Leu Glu Asn Thr Asn Gly Asp His Ile Gly Phe Gly
        435                 440                 445

Trp Asn Pro Arg Ala Cys Pro Gly Arg Phe Phe Ala Ser Lys Glu Ile
    450                 455                 460

Lys Ile Leu Leu Ala His Ile Leu Ile Gln Tyr Asp Val Lys Pro Val
465                 470                 475                 480

Pro Gly Asp Asp Asp Lys Tyr Tyr Arg His Ala Phe Ser Val Arg Met
                485                 490                 495

His Pro Thr Thr Lys Leu Met Val Arg Arg Asn Glu Asp Ile Pro
            500                 505                 510

Leu Pro His Asp Arg Cys
        515

<210> SEQ ID NO 49
<211> LENGTH: 3522
<212> TYPE: DNA
<213> ORGANISM: Penicillium citrinum
<220> FEATURE:
<221> NAME/KEY: CDS
<222> LOCATION: (1)..(3522)

<400> SEQUENCE: 49 atg gtc gct tcg ttg cta ccc tct cgc ttt cgc ggt agg gaa tca atg       48
Met Val Ala Ser Leu Leu Pro Ser Arg Phe Arg Gly Arg Glu Ser Met
1               5                   10                  15 aat cag cag cac cct cta cgc tcg gga aat cgg gca ttg acc tcc aca       96
Asn Gln Gln His Pro Leu Arg Ser Gly Asn Arg Ala Leu Thr Ser Thr
            20                  25                  30 ctc caa ttt cta tcc aaa acg gcg tgt cta cac ccg atc cat acc gtt      144
Leu Gln Phe Leu Ser Lys Thr Ala Cys Leu His Pro Ile His Thr Val
        35                  40                  45 tgc acc ata gct att cta gct agt acc aca tac gtt gga cta ctc aaa      192
Cys Thr Ile Ala Ile Leu Ala Ser Thr Thr Tyr Val Gly Leu Leu Lys
    50                  55                  60
```

```
-continued gac agc ttc ttc cat ggc ccc gca aac gtt gat aaa gca gaa tgg ggc       240
Asp Ser Phe Phe His Gly Pro Ala Asn Val Asp Lys Ala Glu Trp Gly
 65              70                  75                  80 tct ttg gtc gaa gga agt cga agc ttg atc acc ggc cca cag aat ggc       288
Ser Leu Val Glu Gly Ser Arg Ser Leu Ile Thr Gly Pro Gln Asn Gly
                 85                  90                  95 tgg aag tgg cag agc ttc gac ggg gat gca gat gtt ctc gga gat ttc       336
Trp Lys Trp Gln Ser Phe Asp Gly Asp Ala Asp Val Leu Gly Asp Phe
            100                 105                 110 aac cat caa gca cta atg acc ttg gta ttc ccg ggg tca tat ggg gtt       384
Asn His Gln Ala Leu Met Thr Leu Val Phe Pro Gly Ser Tyr Gly Val
        115                 120                 125 gca tct caa gca gcc tca cca ttc ctt gct ccc ctc cct gtg aac cta       432
Ala Ser Gln Ala Ala Ser Pro Phe Leu Ala Pro Leu Pro Val Asn Leu
130                 135                 140 tct gtg att gac ctt ccc tca acg tcg agc cct tta acc gcc tat tcg       480
Ser Val Ile Asp Leu Pro Ser Thr Ser Ser Pro Leu Thr Ala Tyr Ser
145                 150                 155                 160 aaa gat aaa gtt ttc gcc ttc tct gtg gaa tac agc agc gcg ccg gaa       528
Lys Asp Lys Val Phe Ala Phe Ser Val Glu Tyr Ser Ser Ala Pro Glu
                165                 170                 175 ctc gtg gct gct gtt caa gaa atc ccc aac aac agt gcc gac ctg aaa       576
Leu Val Ala Ala Val Gln Glu Ile Pro Asn Asn Ser Ala Asp Leu Lys
            180                 185                 190 ttg cag gag acg caa ttg atc gag atg gaa cgc cag atg tgg atc atg       624
Leu Gln Glu Thr Gln Leu Ile Glu Met Glu Arg Gln Met Trp Ile Met
        195                 200                 205 aag gct gcc agg gct cac aca aaa cgc agc ctt gct caa tgg gtg cac       672
Lys Ala Ala Arg Ala His Thr Lys Arg Ser Leu Ala Gln Trp Val His
210                 215                 220 gat acc tgg aca gag tct ctt gat ctt atc aag agc gct caa acg ctc       720
Asp Thr Trp Thr Glu Ser Leu Asp Leu Ile Lys Ser Ala Gln Thr Leu
225                 230                 235                 240 gac gtg gtt gtc atg gtg cta ggt tat ata tca atg cac ttg act ttc       768
Asp Val Val Val Met Val Leu Gly Tyr Ile Ser Met His Leu Thr Phe
                245                 250                 255 gtc tca ctc ttc ctc agc atg aaa aaa ttg gga tcg aag gtt tgg ctg       816
Val Ser Leu Phe Leu Ser Met Lys Lys Leu Gly Ser Lys Val Trp Leu
            260                 265                 270 gct aca agc gtc ctt ttg tcg tca aca ttt gcc ttt ctc ctc ggt ctc       864
Ala Thr Ser Val Leu Leu Ser Ser Thr Phe Ala Phe Leu Leu Gly Leu
        275                 280                 285 gac gtg gcc ata aga cta ggg gtt ccg atg agc atg agg ttg cta tcc       912
Asp Val Ala Ile Arg Leu Gly Val Pro Met Ser Met Arg Leu Leu Ser
290                 295                 300 gaa ggc ctc ccc ttc ttg gtg gtg atc gtt ggc ttt gag aag agc atc       960
Glu Gly Leu Pro Phe Leu Val Val Ile Val Gly Phe Glu Lys Ser Ile
305                 310                 315                 320 act ctg acc agg gct gtt ttg tcc tat gct gtg cag cac cga aag ccc      1008
Thr Leu Thr Arg Ala Val Leu Ser Tyr Ala Val Gln His Arg Lys Pro
                325                 330                 335 cag aag ata cag tct gac cag ggt agc gtg aca gcc att gct gaa agt      1056
Gln Lys Ile Gln Ser Asp Gln Gly Ser Val Thr Ala Ile Ala Glu Ser
            340                 345                 350 acc atc aat tac gcc gta cga agc gcc att cgg gag aag ggt tac aat      1104
Thr Ile Asn Tyr Ala Val Arg Ser Ala Ile Arg Glu Lys Gly Tyr Asn
        355                 360                 365 atc gtg tgc cac tac gtg gtc gag atc ctg ctc cta gtt atc ggt gct      1152
Ile Val Cys His Tyr Val Val Glu Ile Leu Leu Leu Val Ile Gly Ala
370                 375                 380
```

-continued

```
gtc tta ggc atc caa ggt ggg cta cag cac ttc tgt gtt cta gct gca    1200
Val Leu Gly Ile Gln Gly Gly Leu Gln His Phe Cys Val Leu Ala Ala
385                 390                 395                 400 ttg atc ctg ttc ttt gac tgt ctg ctg ctg ttt aca ttc tac act gcg    1248
Leu Ile Leu Phe Phe Asp Cys Leu Leu Leu Phe Thr Phe Tyr Thr Ala
            405                 410                 415 att ctg tct atc aag ctc gag gta aac cgc ctc aaa cgt cat atc aac    1296
Ile Leu Ser Ile Lys Leu Glu Val Asn Arg Leu Lys Arg His Ile Asn
        420                 425                 430 atg cgg tac gcg ttg gaa gat gag ggt ctc agt cag cgg acg gcg gag    1344
Met Arg Tyr Ala Leu Glu Asp Glu Gly Leu Ser Gln Arg Thr Ala Glu
    435                 440                 445 agt gtc gcg acc agc aat gat gcc caa gac agt gca cgt aca tat ctg    1392
Ser Val Ala Thr Ser Asn Asp Ala Gln Asp Ser Ala Arg Thr Tyr Leu
450                 455                 460 ttt ggc aat gat atg aaa ggc agc agt gtt ccg aag ttc aaa ttc tgg    1440
Phe Gly Asn Asp Met Lys Gly Ser Ser Val Pro Lys Phe Lys Phe Trp
465                 470                 475                 480 atg gtc gtt ggt ttc ctt atc gtc aac ctc gtc aac atc ggc tcc acc    1488
Met Val Val Gly Phe Leu Ile Val Asn Leu Val Asn Ile Gly Ser Thr
            485                 490                 495 ctt ttc caa gcc tct tct agt gga tcg ttg tcc agt ata tca tct tgg    1536
Leu Phe Gln Ala Ser Ser Ser Gly Ser Leu Ser Ser Ile Ser Ser Trp
        500                 505                 510 acc gaa agt ctg agc gga tcg gcc att aaa ccc ccg ctt gag ccc ttc    1584
Thr Glu Ser Leu Ser Gly Ser Ala Ile Lys Pro Pro Leu Glu Pro Phe
    515                 520                 525 aag gta gct gga agt gga cta gat gaa cta ctt ttc cag gca aga ggg    1632
Lys Val Ala Gly Ser Gly Leu Asp Glu Leu Leu Phe Gln Ala Arg Gly
530                 535                 540 cgc ggt caa tcg act atg gtc act gtc ctc gcc ccc atc aag tac gaa    1680
Arg Gly Gln Ser Thr Met Val Thr Val Leu Ala Pro Ile Lys Tyr Glu
545                 550                 555                 560 cta gag tat cct tcc att cac cgt ggt acc tcg cag cta cac gag tat    1728
Leu Glu Tyr Pro Ser Ile His Arg Gly Thr Ser Gln Leu His Glu Tyr
            565                 570                 575 gga gtt ggt gga aaa atg gtc ggt agc ctg ctc acc agc ctg gaa gat    1776
Gly Val Gly Gly Lys Met Val Gly Ser Leu Leu Thr Ser Leu Glu Asp
        580                 585                 590 ccc gtc ctc tcc aaa tgg gtg ttt gtg gca ctt gcc cta agt gtc gct    1824
Pro Val Leu Ser Lys Trp Val Phe Val Ala Leu Ala Leu Ser Val Ala
    595                 600                 605 ctg aac agc tat ctg ttc aag gcc gcc aga ctg gga atc aaa gat cct    1872
Leu Asn Ser Tyr Leu Phe Lys Ala Ala Arg Leu Gly Ile Lys Asp Pro
610                 615                 620 aat ctc ccg agt cac cca gtt gat cca gtt gag ctt gac cag gcc gaa    1920
Asn Leu Pro Ser His Pro Val Asp Pro Val Glu Leu Asp Gln Ala Glu
625                 630                 635                 640 agc ttc aac gct gcc cag aac cag acc cct cag att caa tca agt ctc    1968
Ser Phe Asn Ala Ala Gln Asn Gln Thr Pro Gln Ile Gln Ser Ser Leu
            645                 650                 655 caa gct cct cag acc aga gtg ttc act cct acc acc acc gac agt gac    2016
Gln Ala Pro Gln Thr Arg Val Phe Thr Pro Thr Thr Thr Asp Ser Asp
        660                 665                 670 agt gat gcc tca tta gtc tta att aaa gca tct cta aag gtc act aag    2064
Ser Asp Ala Ser Leu Val Leu Ile Lys Ala Ser Leu Lys Val Thr Lys
    675                 680                 685 cga gca gaa gga aag aca gcc act agt gaa ctt ccc gtg tct cgc aca    2112
Arg Ala Glu Gly Lys Thr Ala Thr Ser Glu Leu Pro Val Ser Arg Thr
```

-continued

```
          690                 695                 700
caa atc gaa ctg gac aat ttg ctg aag cag aac aca atc agc gag ttg     2160
Gln Ile Glu Leu Asp Asn Leu Leu Lys Gln Asn Thr Ile Ser Glu Leu
705                 710                 715                 720 aac gat gag gat gtc gtt gcc ttg tct ttg cgg gga aag gtt ccc ggg     2208
Asn Asp Glu Asp Val Val Ala Leu Ser Leu Arg Gly Lys Val Pro Gly
                725                 730                 735 tat gcc cta gag aag agt ctc aaa gac tgc act cgt gcc gtc aag gtt     2256
Tyr Ala Leu Glu Lys Ser Leu Lys Asp Cys Thr Arg Ala Val Lys Val
            740                 745                 750 cgc cgc tct atc att tcg agg aca ccg gct acc gca gag ctt aca agt     2304
Arg Arg Ser Ile Ile Ser Arg Thr Pro Ala Thr Ala Glu Leu Thr Ser
        755                 760                 765 atg ctg gag cac tcg aag ctg ccg tac gaa aac tac gcc tgg gaa cgc     2352
Met Leu Glu His Ser Lys Leu Pro Tyr Glu Asn Tyr Ala Trp Glu Arg
    770                 775                 780 gtg ctc ggt gca tgt tgc gag aac gtt att ggc tat atg cca gtc cct     2400
Val Leu Gly Ala Cys Cys Glu Asn Val Ile Gly Tyr Met Pro Val Pro
785                 790                 795                 800 gtt ggc gtc gcc ggt cct att gtt atc gac ggc aag agt tat ttc att     2448
Val Gly Val Ala Gly Pro Ile Val Ile Asp Gly Lys Ser Tyr Phe Ile
                805                 810                 815 cct atg gca acc acc gag ggc gtc ctc gtc gct agt gct agc cgt ggc     2496
Pro Met Ala Thr Thr Glu Gly Val Leu Val Ala Ser Ala Ser Arg Gly
            820                 825                 830 agt aag gca atc aac ctc ggt ggc ggt gcc gtg aca gtc ctg act ggc     2544
Ser Lys Ala Ile Asn Leu Gly Gly Gly Ala Val Thr Val Leu Thr Gly
        835                 840                 845 gac ggt atg aca cga ggc ccg tgt gtg aag ttt gat gtc ctt gaa cga     2592
Asp Gly Met Thr Arg Gly Pro Cys Val Lys Phe Asp Val Leu Glu Arg
850                 855                 860 gct ggt gct gct aag atc tgg ctc gat tcg gac gtc ggc cag acc gta     2640
Ala Gly Ala Ala Lys Ile Trp Leu Asp Ser Asp Val Gly Gln Thr Val
865                 870                 875                 880 atg aaa gaa gcc ttc aat tca acc agc aga ttt gcg cgc tta caa agt     2688
Met Lys Glu Ala Phe Asn Ser Thr Ser Arg Phe Ala Arg Leu Gln Ser
                885                 890                 895 atg cgg aca act atc gcc ggt act cac tta tat att cga ttt aag act     2736
Met Arg Thr Thr Ile Ala Gly Thr His Leu Tyr Ile Arg Phe Lys Thr
            900                 905                 910 act act ggc gac gct atg gga atg aat atg att tct aag ggc gtg gag     2784
Thr Thr Gly Asp Ala Met Gly Met Asn Met Ile Ser Lys Gly Val Glu
        915                 920                 925 cat gca ctg aat gtt atg gcg aca gag gca ggt ttc agc gat atg aat     2832
His Ala Leu Asn Val Met Ala Thr Glu Ala Gly Phe Ser Asp Met Asn
    930                 935                 940 att att acc cta tca gga aat tac tgt acg gat aag aaa cct tca gct     2880
Ile Ile Thr Leu Ser Gly Asn Tyr Cys Thr Asp Lys Lys Pro Ser Ala
945                 950                 955                 960 ttg aat tgg atc gat gga cgg ggc aag ggc att gtg gcc gaa gcc atc     2928
Leu Asn Trp Ile Asp Gly Arg Gly Lys Gly Ile Val Ala Glu Ala Ile
                965                 970                 975 ata ccg gcg aac gtt gtc agg gat gtc tta aag agc gat gtg gat agc     2976
Ile Pro Ala Asn Val Val Arg Asp Val Leu Lys Ser Asp Val Asp Ser
            980                 985                 990 atg gtt cag ctc aac ata tcg aaa  aat ctg att ggg tcc  gct atg gct  3024
Met Val Gln Leu Asn Ile Ser Lys  Asn Leu Ile Gly Ser  Ala Met Ala
        995                 1000                1005 ggc tca  gtt ggc ggc ttc aac  gcc caa gct gcc aat  ctt gcg gca      3069
```

-continued

| | | | | | | | | | | | | |
|---|---|---|---|---|---|---|---|---|---|---|---|---|
| Gly | Ser | Val | Gly | Gly | Phe | Asn | Ala | Gln | Ala | Ala | Asn | Leu Ala Ala |
| | 1010 | | | | 1015 | | | | 1020 | | | |

```
gcc att ttc att gcc aca ggt cag gat ccg gcg caa gtt gtg gag      3114
Ala Ile Phe Ile Ala Thr Gly Gln Asp Pro Ala Gln Val Val Glu
    1025            1030                1035 agc gct aac tgc atc act ctc atg aac aat ctt cgc gga tcg ctt      3159
Ser Ala Asn Cys Ile Thr Leu Met Asn Asn Leu Arg Gly Ser Leu
    1040            1045                1050 caa atc tct gtc tcc atg ccg tct att gag gtt gga acg ttg ggc      3204
Gln Ile Ser Val Ser Met Pro Ser Ile Glu Val Gly Thr Leu Gly
    1055            1060                1065 ggt ggt acg att ctg gag ccc cag ggc gca atg ctt gac atg ctt      3249
Gly Gly Thr Ile Leu Glu Pro Gln Gly Ala Met Leu Asp Met Leu
    1070            1075                1080 ggt gtc cgc gga tca cac ccg acc act ccc ggt gag aat gca cgt      3294
Gly Val Arg Gly Ser His Pro Thr Thr Pro Gly Glu Asn Ala Arg
    1085            1090                1095 caa ctt gcg cgc atc atc gga agc gct gtt ttg gct ggg gag ctc      3339
Gln Leu Ala Arg Ile Ile Gly Ser Ala Val Leu Ala Gly Glu Leu
    1100            1105                1110 tcg cta tgt gct gcc cta gcc gcc ggt cac ctg gtc aag gcg cac      3384
Ser Leu Cys Ala Ala Leu Ala Ala Gly His Leu Val Lys Ala His
    1115            1120                1125 atg gcg cac aac cgt tct gcc ccg gca tct tca gcc cct tct cga      3429
Met Ala His Asn Arg Ser Ala Pro Ala Ser Ser Ala Pro Ser Arg
    1130            1135                1140 agt gtc tcc ccg tca ggc gga acc agg aca gtc cct gtt cct aac      3474
Ser Val Ser Pro Ser Gly Gly Thr Arg Thr Val Pro Val Pro Asn
    1145            1150                1155 aat gca ctg agg ccg agt gct gca gct act gat cgg gct cga cgc      3519
Asn Ala Leu Arg Pro Ser Ala Ala Ala Thr Asp Arg Ala Arg Arg
    1160            1165                1170 tga                                                               3522
```

<210> SEQ ID NO 50
<211> LENGTH: 1173
<212> TYPE: PRT
<213> ORGANISM: Penicillium citrinum

<400> SEQUENCE: 50

```
Met Val Ala Ser Leu Leu Pro Ser Arg Phe Arg Gly Arg Glu Ser Met
1               5                   10                  15

Asn Gln Gln His Pro Leu Arg Ser Gly Asn Arg Ala Leu Thr Ser Thr
            20                  25                  30

Leu Gln Phe Leu Ser Lys Thr Ala Cys Leu His Pro Ile His Thr Val
        35                  40                  45

Cys Thr Ile Ala Ile Leu Ala Ser Thr Thr Tyr Val Gly Leu Leu Lys
    50                  55                  60

Asp Ser Phe Phe His Gly Pro Ala Asn Val Asp Lys Ala Glu Trp Gly
65                  70                  75                  80

Ser Leu Val Glu Gly Ser Arg Ser Leu Ile Thr Gly Pro Gln Asn Gly
                85                  90                  95

Trp Lys Trp Gln Ser Phe Asp Gly Asp Ala Asp Val Leu Gly Asp Phe
            100                 105                 110

Asn His Gln Ala Leu Met Thr Leu Val Phe Pro Gly Ser Tyr Gly Val
        115                 120                 125

Ala Ser Gln Ala Ala Ser Pro Phe Leu Ala Pro Leu Pro Val Asn Leu
    130                 135                 140
```

```
Ser Val Ile Asp Leu Pro Ser Thr Ser Ser Pro Leu Thr Ala Tyr Ser
145                 150                 155                 160

Lys Asp Lys Val Phe Ala Phe Ser Val Glu Tyr Ser Ser Ala Pro Glu
            165                 170                 175

Leu Val Ala Ala Val Gln Glu Ile Pro Asn Asn Ser Ala Asp Leu Lys
            180                 185                 190

Leu Gln Glu Thr Gln Leu Ile Glu Met Glu Arg Gln Met Trp Ile Met
            195                 200                 205

Lys Ala Ala Arg Ala His Thr Lys Arg Ser Leu Ala Gln Trp Val His
210                 215                 220

Asp Thr Trp Thr Glu Ser Leu Asp Leu Ile Lys Ser Ala Gln Thr Leu
225                 230                 235                 240

Asp Val Val Val Met Val Leu Gly Tyr Ile Ser Met His Leu Thr Phe
                245                 250                 255

Val Ser Leu Phe Leu Ser Met Lys Lys Leu Gly Ser Lys Val Trp Leu
            260                 265                 270

Ala Thr Ser Val Leu Leu Ser Ser Thr Phe Ala Phe Leu Leu Gly Leu
            275                 280                 285

Asp Val Ala Ile Arg Leu Gly Val Pro Met Ser Met Arg Leu Leu Ser
290                 295                 300

Glu Gly Leu Pro Phe Leu Val Val Ile Val Gly Phe Glu Lys Ser Ile
305                 310                 315                 320

Thr Leu Thr Arg Ala Val Leu Ser Tyr Ala Val Gln His Arg Lys Pro
            325                 330                 335

Gln Lys Ile Gln Ser Asp Gln Gly Ser Val Thr Ala Ile Ala Glu Ser
            340                 345                 350

Thr Ile Asn Tyr Ala Val Arg Ser Ala Ile Arg Glu Lys Gly Tyr Asn
            355                 360                 365

Ile Val Cys His Tyr Val Val Glu Ile Leu Leu Leu Val Ile Gly Ala
            370                 375                 380

Val Leu Gly Ile Gln Gly Gly Leu Gln His Phe Cys Val Leu Ala Ala
385                 390                 395                 400

Leu Ile Leu Phe Phe Asp Cys Leu Leu Leu Phe Thr Phe Tyr Thr Ala
                405                 410                 415

Ile Leu Ser Ile Lys Leu Glu Val Asn Arg Leu Lys Arg His Ile Asn
            420                 425                 430

Met Arg Tyr Ala Leu Glu Asp Glu Gly Leu Ser Gln Arg Thr Ala Glu
            435                 440                 445

Ser Val Ala Thr Ser Asn Asp Ala Gln Asp Ser Ala Arg Thr Tyr Leu
450                 455                 460

Phe Gly Asn Asp Met Lys Gly Ser Ser Val Pro Lys Phe Lys Phe Trp
465                 470                 475                 480

Met Val Val Gly Phe Leu Ile Val Asn Leu Val Asn Ile Gly Ser Thr
                485                 490                 495

Leu Phe Gln Ala Ser Ser Ser Gly Ser Leu Ser Ser Ile Ser Ser Trp
            500                 505                 510

Thr Glu Ser Leu Ser Gly Ser Ala Ile Lys Pro Pro Leu Glu Pro Phe
            515                 520                 525

Lys Val Ala Gly Ser Gly Leu Asp Glu Leu Leu Phe Gln Ala Arg Gly
            530                 535                 540

Arg Gly Gln Ser Thr Met Val Thr Val Leu Ala Pro Ile Lys Tyr Glu
545                 550                 555                 560
```

-continued

```
Leu Glu Tyr Pro Ser Ile His Arg Gly Thr Ser Gln Leu His Glu Tyr
            565                 570                 575
Gly Val Gly Gly Lys Met Val Gly Ser Leu Leu Thr Ser Leu Glu Asp
        580                 585                 590
Pro Val Leu Ser Lys Trp Val Phe Val Ala Leu Ala Leu Ser Val Ala
            595                 600                 605
Leu Asn Ser Tyr Leu Phe Lys Ala Ala Arg Leu Gly Ile Lys Asp Pro
610                 615                 620
Asn Leu Pro Ser His Pro Val Asp Pro Val Glu Leu Asp Gln Ala Glu
625                 630                 635                 640
Ser Phe Asn Ala Ala Gln Asn Gln Thr Pro Gln Ile Gln Ser Ser Leu
                645                 650                 655
Gln Ala Pro Gln Thr Arg Val Phe Thr Pro Thr Thr Thr Asp Ser Asp
            660                 665                 670
Ser Asp Ala Ser Leu Val Leu Ile Lys Ala Ser Leu Lys Val Thr Lys
        675                 680                 685
Arg Ala Glu Gly Lys Thr Ala Thr Ser Glu Leu Pro Val Ser Arg Thr
    690                 695                 700
Gln Ile Glu Leu Asp Asn Leu Lys Gln Asn Thr Ile Ser Glu Leu
705                 710                 715                 720
Asn Asp Glu Asp Val Val Ala Leu Ser Leu Arg Gly Lys Val Pro Gly
                725                 730                 735
Tyr Ala Leu Glu Lys Ser Leu Lys Asp Cys Thr Arg Ala Val Lys Val
            740                 745                 750
Arg Arg Ser Ile Ile Ser Arg Thr Pro Ala Thr Ala Glu Leu Thr Ser
        755                 760                 765
Met Leu Glu His Ser Lys Leu Pro Tyr Glu Asn Tyr Ala Trp Glu Arg
    770                 775                 780
Val Leu Gly Ala Cys Cys Glu Asn Val Ile Gly Tyr Met Pro Val Pro
785                 790                 795                 800
Val Gly Val Ala Gly Pro Ile Val Ile Asp Gly Lys Ser Tyr Phe Ile
                805                 810                 815
Pro Met Ala Thr Thr Glu Gly Val Leu Val Ala Ser Ala Ser Arg Gly
            820                 825                 830
Ser Lys Ala Ile Asn Leu Gly Gly Gly Ala Val Thr Val Leu Thr Gly
        835                 840                 845
Asp Gly Met Thr Arg Gly Pro Cys Val Lys Phe Asp Val Leu Glu Arg
    850                 855                 860
Ala Gly Ala Ala Lys Ile Trp Leu Asp Ser Asp Val Gly Gln Thr Val
865                 870                 875                 880
Met Lys Glu Ala Phe Asn Ser Thr Ser Arg Phe Ala Arg Leu Gln Ser
                885                 890                 895
Met Arg Thr Thr Ile Ala Gly Thr His Leu Tyr Ile Arg Phe Lys Thr
            900                 905                 910
Thr Thr Gly Asp Ala Met Gly Met Asn Met Ile Ser Lys Gly Val Glu
        915                 920                 925
His Ala Leu Asn Val Met Ala Thr Glu Ala Gly Phe Ser Asp Met Asn
    930                 935                 940
Ile Ile Thr Leu Ser Gly Asn Tyr Cys Thr Asp Lys Lys Pro Ser Ala
945                 950                 955                 960
Leu Asn Trp Ile Asp Gly Arg Gly Lys Gly Ile Val Ala Glu Ala Ile
                965                 970                 975
Ile Pro Ala Asn Val Val Arg Asp Val Leu Lys Ser Asp Val Asp Ser
```

```
                    980             985             990
Met Val Gln Leu Asn Ile Ser Lys Asn Leu Ile Gly Ser Ala Met Ala
                995             1000            1005

Gly Ser Val Gly Gly Phe Asn Ala Gln Ala Ala Asn Leu Ala Ala
    1010            1015            1020

Ala Ile Phe Ile Ala Thr Gly Gln Asp Pro Ala Gln Val Val Glu
    1025            1030            1035

Ser Ala Asn Cys Ile Thr Leu Met Asn Asn Leu Arg Gly Ser Leu
    1040            1045            1050

Gln Ile Ser Val Ser Met Pro Ser Ile Glu Val Gly Thr Leu Gly
    1055            1060            1065

Gly Gly Thr Ile Leu Glu Pro Gln Gly Ala Met Leu Asp Met Leu
    1070            1075            1080

Gly Val Arg Gly Ser His Pro Thr Thr Pro Gly Glu Asn Ala Arg
    1085            1090            1095

Gln Leu Ala Arg Ile Ile Gly Ser Ala Val Leu Ala Gly Glu Leu
    1100            1105            1110

Ser Leu Cys Ala Ala Leu Ala Ala Gly His Leu Val Lys Ala His
    1115            1120            1125

Met Ala His Asn Arg Ser Ala Pro Ala Ser Ser Ala Pro Ser Arg
    1130            1135            1140

Ser Val Ser Pro Ser Gly Gly Thr Arg Thr Val Pro Val Pro Asn
    1145            1150            1155

Asn Ala Leu Arg Pro Ser Ala Ala Ala Thr Asp Arg Ala Arg Arg
    1160            1165            1170

<210> SEQ ID NO 51
<211> LENGTH: 20
<212> TYPE: DNA
<213> ORGANISM: Penicillium citrinum

<400> SEQUENCE: 51
gcaagctctg ctaccagcac                                              20

<210> SEQ ID NO 52
<211> LENGTH: 20
<212> TYPE: DNA
<213> ORGANISM: Penicillium citrinum

<400> SEQUENCE: 52
ctaggccaac ttcagagccg                                              20

<210> SEQ ID NO 53
<211> LENGTH: 20
<212> TYPE: DNA
<213> ORGANISM: Penicillium citrinum

<400> SEQUENCE: 53
agtcatgcag gatctgggtc                                              20

<210> SEQ ID NO 54
<211> LENGTH: 20
<212> TYPE: DNA
<213> ORGANISM: Penicillium citrinum

<400> SEQUENCE: 54
gcagacacat cggtgaagtc                                              20
```

```
<210> SEQ ID NO 55
<211> LENGTH: 20
<212> TYPE: DNA
<213> ORGANISM: Penicillium citrinum

<400> SEQUENCE: 55
aaaccgcacc tgtctattcc                                              20

<210> SEQ ID NO 56
<211> LENGTH: 20
<212> TYPE: DNA
<213> ORGANISM: Penicillium citrinum

<400> SEQUENCE: 56
ctttgtggtt ggatgcatac                                              20

<210> SEQ ID NO 57
<211> LENGTH: 20
<212> TYPE: DNA
<213> ORGANISM: Penicillium citrinum

<400> SEQUENCE: 57
cgctctatca tttcgaggac                                              20

<210> SEQ ID NO 58
<211> LENGTH: 20
<212> TYPE: DNA
<213> ORGANISM: Penicillium citrinum

<400> SEQUENCE: 58
tcaatagacg gcatggagac                                              20

<210> SEQ ID NO 59
<211> LENGTH: 20
<212> TYPE: DNA
<213> ORGANISM: Penicillium citrinum

<400> SEQUENCE: 59
atgtcagaac ctctacccccc                                             20

<210> SEQ ID NO 60
<211> LENGTH: 20
<212> TYPE: DNA
<213> ORGANISM: Penicillium citrinum

<400> SEQUENCE: 60
tcaagcatca gtctcaggca                                              20

<210> SEQ ID NO 61
<211> LENGTH: 20
<212> TYPE: DNA
<213> ORGANISM: Penicillium citrinum

<400> SEQUENCE: 61
atgtccctgc cgcatgcaac                                              20

<210> SEQ ID NO 62
<211> LENGTH: 20
<212> TYPE: DNA
<213> ORGANISM: Penicillium citrinum

<400> SEQUENCE: 62
ctaagcaata ttgtgtttct                                              20
```

METHODS FOR PRODUCING ML-236B, A PRAVASTATIN PRECURSOR, USING A HOST CELL TRANSFORMED WITH MLCR, A TRANSCRIPTION FACTOR

FIELD OF THE INVENTION

The present invention relates to a gene cluster, and more particularly to genes from a gene cluster.

More particularly the invention relates to polynucleotides, such as DNA, which accelerate the biosynthesis of a HMG-CoA reductase inhibitor. ML-236B, in an ML-236 producing micro-organism when introduced in the ML-236B producing micro-organism. The invention further relates to vectors into which said polynucleotides are incorporated, host cells transformed by said vectors, proteins expressed by said vectors, a method for producing ML-236B using said polynucleotides and/or proteins where the method comprises recovering ML-236B from the culture of said host cell, and the invention further relates to other associated aspects.

BACKGROUND OF THE INVENTION

Pravastatin is an HMG-CoA reductase inhibitor. Pravastatin sodium has been used in the treatment of hyperlipemia or hyperlipidaemia and has the useful pharmacological effect of being able to reduce serum cholesterol. Pravastatin can be obtained using *Streptomyces carbophilus* by microbial conversion of ML-236B produced by *Penicillium citrinum* [described in Endo, A., et al., J. Antibiot., 29 1346 (1976): Matsuoka, T., et al., Eur. J. Biochem., 184, 707 (1989), and in Japanese Patent Application Publication No 57-2240].

It has been shown that both ML-236B, a precursor of pravastatin, and lovastatin, a HMG-CoA inhibitor, share the same partial structure. They are synthesized biologicals via polyketides [described in Moore, R. N., at al., J. Am. Chem. Soc., 107, 3694(1985); Shiao, M, and Don, H. S., Proc. Natl. Sci. Counc. Repub. China B. 11, 223(1987)].

Polyketides are compounds derived from a β-keto carbon chains that result from a continuous condensation reaction of low-molecular weight carboxylic acids, such as acetic acid, propionic acid, butyric acid or the like. Various structures may be derived depending on the pathway of condensation or reduction of each of the β-keto carbonyl groups [described in Hopwood, D. A, and Sherman, D. H., Annu. Rev. Genet., 24, 37–66 (1990): Hutchinson, C. R. and Fujii, I., Annu. Re. Microbiol., 49, 201–238(1995)].

Polyketide Synthases (hereinafter referred to as PKSs) that contribute to the synthesis of polyketides are enzymes known to be present in filamentous fungi and bacteria. The enzymes of filamentous fungi have been studied using molecular biological techniques [as described in Feng, G. H, and Leonard, T. J., J. Bacteriol., 177, 6246 (1995); Takano, Y., et al. Mol. Gen. Genet. 249, 162 (1995)]. In *Aspergillus terreus*, which is a lovastatin producing micro-organism, a PKS gene related to the biosynthesis of lovastatin has been analyzed [described in International application laid-open in Japan (KOHYO) No.9-504436, and see corresponding WO 9512661 which claims DNA encoding a triol polyketide synthase].

Genes related to biosynthesis of secondary metabolites of filamentous fungi often form a cluster on the genome. In the pathways of the biosynthesis of polyketides, gene clusters participating in said pathway are known to exist. In the biosynthesis of Aflatoxin, which is a polyketide produced by *Aspergillus flavus* and *Aspergillus parasiticus*, genes encoding enzyme proteins participating in said biosynthesis (such as PKS) have been known to form a cluster structure. Genomic analysis and a comparison of the genes participating in the biosynthesis of Aflatoxin in each of the micro-organisms has been carried out [see Yu, J., et al., Appl. Environ. Microbiol., 61, 2365 (1995)]. It has been reported that genes participating in biosynthesis of Sterigmatocystin produced by *Aspergillus nidulans* form a cluster structure in about 60 kb of a continuous region on its genome [described in Brown, D. W, et al., Proc. Natl. Acad. Sci. USA, 93, 1418 (1996)].

The modulation of polyketide synthase activity by accessory proteins during lovastatin synthesis has been investigated [see Kennedy, J, et al. Science Vol 284, 1368 (1999)].

However, to date, there has been insufficient molecular biological analysis into the biosynthesis of ML-236B, and factors regulating it. The present invention sets out to address this problem

SUMMARY OF INVENTION

According to the present invention, there is provided a polynucleotide which is suitable for use in accelerating the biosynthesis of ML-236B.

The polynucleotide is typically a polynucleotide encoding a protein including or consisting of the amino acid sequence of SEQ ID NO38, 42,44, 46, 48 or 50. Polynucleotide variants thereof are also provided which encode a modified amino acid sequence having at least one deletion, addition, substitution or alteration.

TABULATION FOR SEQUENCE LISTING

A sequence listing forms part of this patent specification. As an aid to understanding, we give the following tabulation of the listed sequences.

| SEQ ID NO | identity |
| --- | --- |
| 1 | pML48 insert |
| 2 | complementary to SEQ ID NO 1 |
| 3 | PCR primer for Example 4 |
| 4 | PCR primer for Example 4 |
| 5 | oligonucleotide DNA (1) for 5'-RACE, Example 8 |
| 6 | oligonucleotide DNA (1) for 5'-RACE, Example 8 |
| 7 | oligonucleotide DNA (1) for 5'-RACE, Example 8 |
| 8 | oligonucleotide DNA (1) for 5'-RACE, Example 8 |
| 9 | oligonucleotide DNA (1) for 5'-RACE, Example 8 |
| 10 | oligonucleotide DNA (1) for 5'-RACE, Example 8 |
| 11 | oligonucleotide DNA (2) for 5'-RACE, Example 8 |
| 12 | oligonucleotide DNA (2) for 5'-RACE, Example 8 |
| 13 | oligonucleotide DNA (2) for 5'-RACE, Example 8 |
| 14 | oligonucleotide DNA (2) for 5'-RACE, Example 8 |
| 15 | oligonucleotide DNA (2) for 5'-RACE, Example 8 |
| 16 | oligonucleotide DNA (2) for 5'-RACE, Example 8 |
| 17 | 5'-end cDNA fragment, Example 8 |
| 18 | 5'-end cDNA fragment, Example 8 |
| 19 | 5'-end cDNA fragment, Example 8 |
| 20 | 5'-end cDNA fragment, Example 8 |
| 21 | 5'-end cDNA fragment, Example 8 |
| 22 | 5'-end cDNA fragment, Example 8 |
| 23 | oligonucleotide DNA (3) for 3'-RACE, Example 8 |
| 24 | oligonucleotide DNA (3) for 3'-RACE, Example 8 |
| 25 | oligonucleotide DNA (3) for 3'-RACE, Example 8 |
| 26 | oligonucleotide DNA (3) for 3'-RACE, Example 8 |
| 27 | oligonucleotide DNA (3) for 3'-RACE, Example 8 |
| 28 | oligonucleotide DNA (3) for 3'-RACE, Example 8 |
| 29 | 3'-end cDNA fragment, Example 8 |
| 30 | 3'-end cDNA fragment, Example 8 |
| 31 | 3'-end cDNA fragment, Example 8 |

-continued

| SEQ ID NO | identity |
|---|---|
| 32 | 3'-end cDNA fragment, Example 8 |
| 33 | 3'-end cDNA fragment, Example 8 |
| 34 | 3'-end cDNA fragment, Example 8 |
| 35 | RT-PCR primer, Example 9 |
| 36 | RT-PCR primer, Example 9 |
| 37 | mlcE; cDNA nucleotide sequence and deduced amino acid sequence |
| 38 | deduced mlcE polypeptide |
| 39 | RT-PCR primer, Example 12 |
| 40 | RT-PCR primer, Example 12 |
| 41 | mlcR: cDNA nucleotide sequence and deduced amino acid sequence |
| 42 | deduced mlcR polypeptide |
| 43 | mlcA: cDNA nucleotide sequence and deduced amino acid sequence |
| 44 | deduced mlcA polypeptide |
| 45 | mlcB; cDNA nucleotide sequence and deduced amino acid sequence |
| 46 | deduced mlcB polypeptide |
| 47 | mlcC: cDNA nucleotide sequence and deduced amino acid sequence |
| 48 | deduced mlcC polypeptide |
| 49 | mlcD: cDNA nucleotide sequence and deduced amino acid sequence |
| 50 | deduced mlcD polypeptide |
| 51 | RT-PCR primer, Example 17 |
| 52 | RT-PCR primer, Example 17 |
| 53 | RT-PCR primer, Example 17 |
| 54 | RT-PCR primer, Example 17 |
| 55 | RT-PCR primer, Example 17 |
| 56 | RT-PCR primer, Example 17 |
| 57 | RT-PCR primer, Example 17 |
| 58 | RT-PCR primer, Example 17 |
| 59 | RT-PCR primer, Example 17 |
| 60 | RT-PCR primer, Example 17 |
| 61 | RT-PCR primer, Example 17 |
| 62 | RT-PCR primer, Example 17 |

PREFERRED EMBODIMENTS

The polynucleotides encoding the amino acid sequences of SEQ ID NO 38, 42, 44, 46, 48 or 50 can be cDNA, genomic DNA or mRNA. The genomic DNA encoding each of these six sequences are referred to as structural genes mlcE, mlcR, mlcA, mlcB, mlcC and mlcD, respectively. Without being tied to these assignments, we believe that the structural genes encode proteins with the following functions:

| | |
|---|---|
| mlcA | polyketide synthase |
| mlcB | polyketide synthase |
| mlcC | P450 monooxygenase |
| mlcD | HMG-CoA reductase |
| mlcE | efflux pump |
| mlcR | transcriptional factor |

We have discovered that the incorporation of mlcE or cDNA corresponding to mlcE can accelerate the biosynthesis of ML-236B, and the incorporation of mlcR or cDNA corresponding to mlcR can accelerate the biosynthesis of ML-236B. Furthermore, mlcR stimulates transcriptional expression of mlcA to D, mlcA, B, C and D are involved in the production of ML-236B, independently or in combination, as shown by gene disruption studies.

Variants of mlcA, B and/or C obtainably by natural or artificial change will be useful to produce derivatives of ML-236B, including statins such as pravastatin or lovastatin. In this respect, it may be possible to produce pravastatin directly by using such variants with only the one fermentation step and without the need for microbial conversion of ML-236B to pravastatin currently performed with *Streptomyces carbophilus*.

A preferred polynucleotide includes a sequence comprising SEQ ID NO 37, or comprising a mutant or variant thereof capable of accelerating the biosynthesis of ML-236B. Such a DNA polynucleotide is obtainable from transformed *Escherichia coli* pSAKexpE SANK 72499 (FERM BP-7005).

Another preferred polynucleotide includes a sequence comprising SEQ ID NO 41, or comprising a mutant or variant thereof capable of accelerating the biosynthesis of ML-236B. Such a DNA polynucleotide is obtainable from transformed *Escherichia coli* pSAKexpR SANK 72599 (FERM BP-7006).

The polynucleotides of this invention can be employed in operative combination with one or more polynucleotides. Preferred combinations are suitable for use in enhancing the production of ML236B in an ML-236B producing microorganism.

Examples of such combinations include the polynucleotide of SEQ ID NO 37, o variant thereof having similar function, in combination with one or more sequences selected from SEQ ID NO 37 itself, 41, 43, 45, 47 or 49; as well as the polynucleotide of SEQ ID NO 41, or variant thereof having similar function, in combination with one or more sequences selected from SEQ ID NO 37, 41 itself, 43, 45, 47 or 49.

In one aspect, the polynucleotide is preferably a polynucleotide encoding a protein including or consisting of the amino acid sequence of SEQ ID NO 38, 42, 44, 46, 48 or 50 and capable of accelerating the biosynthesis of ML-236B alone or in conjunction with the polynucleotide of SEQ ID NO 37, SEQ ID NO 41 or a variant thereof having a similar function.

The present invention further extends to polynucleotides which are capable of hybridizing under stringent conditions with a polynucleotide of this invention. Such polynucleotides extend to polynucleotides suitable for accelerating the biosynthesis of ML-236B in a ML-236B producing microorganism when introduced in the ML-236B producing micro-organism.

The polynucleotide is typically DNA, cDNA or genomic DNA, or RNA, and can be sense or antisense. The polynucleotide is typically a purified polynucleotide, such as a polynucleotide free from other cellular components.

The present invention extends to polynucleotide variants encoding amino acid sequences of the indicated SEQ ID NO 38, 42, 44, 46, 48 or 50, where one or more nucleotides has been changed. The changes may be naturally occuring, and can be made within the redundancy or degeneracy of the triplets of the genetic code. Such degeneratively changed polynucleotides thus encode the same amino acid sequence. Within these polynucleotide variants, we include genomic DNA having extrons and introns, rather than simply the cDNA sequence.

The present invention further extends to polynucleotide variants encoding amino acid sequences of the indicated SEQ ID NO 38, 42, 44, 46, 48 or 50, which encode a modified amino acid sequence having at least one deletion, addition, substitution or alteration. Thus, the invention extends to polynucleotide variants of the indicated sequences which encode amino acid sequences which are shorter, longer or the same length as that encoded by the indicated sequences. Preferably the variant polypeptides retain an ability to accelerate the synthesis of ML-236B, and preferably have activity substantially similar to or better than the parent sequence giving rise to the variant sequence.

The polynucleotide variants retain a degree of identity with the parent sequence. Suitably the degree of identity is at least 60%, at least 80%, at least 90% or at least 95% or 100%. The degree of identity of a variant is preferably assessed by computer software, such as the BLAST program which uses an algorithm for performing homology searches.

In one aspect, the preferred polynucleotide of this invention is DNA selected from the group consisting of:

(a) DNA which comprises one or more of nucleotide sequence shown in nucleotide No. 1 to 1662 of SEQ ID No. 37 of the Sequence Listing, and which is characterized in accelerating the biosynthesis of ML-236B in a ML-236B producing micro-organism when being introduced in said ML-236B producing micro-organism;

(b) DNA which hybridizes with the DNA described in (a) under the stringent condition, and which is characterized in accelerating the biosynthesis of ML-236B in a ML-236B producing micro-organism when being introduced in said ML-236B producing micro-organism:

(c) DNA which comprises one or more of nucleotide sequence shown in nucleotide No. 1 to 1380 of SEQ ID No. 41 of the Sequence Listing, and which is characterized in accelerating the biosynthesis of ML-236B in a ML-236B producing micro-organism when being introduced in said ML-236B producing micro-organism:

(d) DNA which hybridizes with the DNA described in (c) under the stringent condition, and which is characterized in accelerating the biosynthesis of ML-236B in a ML-236B producing micro-organism when being introduced in said ML-236B producing micro-organism.

The polynucleotides of this invention accelerate the biosynthesis of ML-236B in a micro-organism which produces ML-236B. Examples of ML-236B producing micro-ogranisms include *Penicillium* species, such as *Penicillium citrinum*, *Penicillium brevicompactum* [described in Brown, A. G., et al., J. Chem. Soc. Perkin-1 . . . 1165(1976)]. *Penicillium cyclopium* [described in Doss, S. L., et al., J. Natl. Prod., 49, 357 (1986)] or the like. Other examples include: *Eupenicillium* sp.M6603 [described in Endo, A., et al., J. Antibiot.-Tokyo, 39, 1609(1986)]. *Paecilomyces viridis* FERM P-6236 [described in Japanese Patent Application Publication No.58-98092]. *Paecilomyces* sp.M2016 [described in Endo, A., et al., J. Antibiot.-Tokyo, 39, 1609 (1986)]. *Trichoderma longibrachiatum* M6735 [described in Endo, A., et al., J. Antibiot.-Tokyo, 39, 1609(1986)]. *Hypomyces chrysospermus* IFO 7798 [described in Endo, A., et al. J. Antibiot.-Tokyo, 39, 1609(1986)]. *Gliocladium* sp. YJ-9515 [described in WO 9806867]. *Trichorderma viride* IFO 5836 [described in Japanese Patent Publication No.62-19159]. *Eupenicillium reticulisporum* IFO 9022 [described in Japanese Patent Publication No. 62-19159], or any other suitable organism.

Among these ML-236B producing micro-organisms, *Penicillium citrinum* is preferred, and the *Penicillium citrinum* strain SANK 13380 is more preferred. *Penicillium citrinum* SANK 13380 strain was deposited at the Research Institute of Life Science and Technology of the Agency of Industrial Science and Technology on Dec. 22, 1992 under the deposit Nos. FERM BP-4129, in accordance with the Budapest Treaty on the Deposition of Micro-organisms. Examples of ML-236B producing micro-organisms also include those isolated from natural sources and those mutated naturally or artificially.

The invention further provides vectors comprising a polynucleotide of this invention, such as the vector obtainable from *Escherichia coli* pSAKexpE SANK 72499 (FERM BP-7005) or *Escherichia coli* pSAKexpR SANK 72599 (FERM BP-7006). Such vectors of this invention include expression vectors.

Host cells transformed by a vector of this invention are also provided, including ML-236B producing micro-organisms. Host cells of this invention include *Penicillium citrinum* and *Escherichia coli*, such as *Escherichia coli* pSAKexpE SANK 72499 (FERM BP-7005) or *Escherichia coli* pSAKexpR SANK 72599 (FERM BP-7006).

Additionally the invention extends to polypeptides encoded by a polynucleotide of this invention. Examples of polypeptides of this invention include the sequence of SEQ ID NO 38 or 42, or a variant thereof which has at a specified degree of identity to SEQ ID NO 38 or 42 and which is capable of accelerating ML236B production in an ML236B producing organism. Other polypeptides are those encoded by the other polynucleotide sequences of this invention and variants which retain a degree of identity.

Suitably the degree of identity of polypeptide variants to SEQ ID NO 38 or 42 is at least 80%, at least 90% or at least 95% or 100%. The degree of identity of a variant is preferably assessed by computer software, such as the BLAST program which uses an algorithm for performing homology searches.

The polypeptides of this invention include shorter or longer sequences of SEQ ID NO 38 or 42 or variants. Shorter polypeptides comprise partial amino acid sequences of SEQ ID NO 38, 42 or variants thereof and preferably retain the ability to accelerate the biosynthesis of ML236B. Longer polypeptides comprise all or partial amino acid sequences of SEQ ID NO 38, 42 or variants thereof and preferably retain the ability to accelerate the biosynthesis of ML236B. Longer polypeptides include fusion proteins such as Fc-fused protein.

Polypeptides of this invention include one having the sequence of SEQ ID NO 38. SEQ ID NO 42, SEQ ID NO 44, SEQ ID NO 46, SEQ ID NO 48, or a varinat thereof having the similar function. Antibody to polypeptides of this invention are also provided. Both polyclonal antibody and monoclonal antibody are provided by this invention. Said antibody is useful for regulating ML-236B production and for producing derivatives of ML-236B such as statins including pravastatin and lovastatin. Furthermore, said antibody can be preferably used for analysis of ML-236B biosynthesis and regulatory mechanisms thereof. Such analysis is useful for modulating ML-236B production and for producing derivatives of ML-236B.

The host cells of this invention which have a vector of this invention can be used in a method for producing ML-236B, comprising culturing such a host cell and then recovering ML-236B from the culture. In one method, the vector comprises mlcE or mlcR, and no additional genes such as mlcA, mlcB, mlcC or mlcD.

Production by a method of this invention can occur in the absence of recombinant mlcA, mlcB, mlcC and/or mlcD (polypeptides) corresponding to SEQ ID NO 44, SEQ ID NO 46, SEQ ID NO 48 or SEQ ID NO 50.

DESCRIPTION OF SPECIFIC EMBODIMENTS

The present invention will be hereinafter described in more detail,

The inventors of the present invention have cloned genomic DNA comprising genes participating in the biosynthesis of ML-236B in *Pencillium citrinum*. The genomic DNA is hereinafter referred to as ML-236B biosynthesis related genomic DNA, and was cloned from a genomic DNA library of a ML-236B producing micro-organism. The genomic DNA was analyzed to find structural genes on said genomic DNA, then cDNAs corresponding to said structural genes were obtained by reverse transcription—polymerase chain reaction (hereinafter referred to as a "RT-PCR") using total RNA which contains mRNA of *Penicillium citrinum* as a template. It was found that the biosynthesis of ML-236B in a ML-236B producing micro-organism was accelerated when the ML-236B producing micro-organism was transformed by a recombined DNA vector containing said cDNAs.

The present invention relates particularly to cDNAs (hereinafter referred to as ML- 236B biosynthesis accelerating cDNA) that accelerate the biosynthesis of ML-236B in a ML-236B producing micro-organism when introduced into said ML-236B producing micro-organism.

An ML-236B biosynthesis accelerating polynucleotide of the present invention, such as ML-236B biosynthesis acclerating cDNA, includes, by way of example:

(I) DNA obtainable by synthesis using, as a template, a transcribed product (messenger RNA, hereinafter referred to as mRNA) of a structural gene which participates in the biosynthesis of ML-236B and which exists in the genomic DNA of a ML-236B-producing micro-organism;

(II) double stranded DNA formed as a result of association of a DNA (I) and the second strand DNA synthesized using the DNA (I) as a first strand;

(III) double stranded DNA formed by replicating or amplifying the double stranded DNA (II), for example by a method of cloning or the like;

(IV) DNA which can hybridize with one of the above DNA's or mRNA under stringent conditions.

The DNA (IV) can be those shown in any of the structural gene sequences herein, for example nucleotide No. to 1662 of SEQ ID No.37 of the Sequence Listing or nucleotide numbers 1 to 1380 of SEQ ID No 41, wherein one or more nucleotides is optionally substituted, deleted and/or added, and which can accelerate the biosynthesis of ML-236B in an ML-236B producing micro-organism when introduced in the ML-236B producing micro-organism.

When two single stranded nucleic acids hybridize they form a double-stranded molecule in a region in which they are complementary or highly complementary with each other, and "stringent conditions" suitably refers to the case in which the hybridization solution is 6×SSC [1×SSC has a composition of 150 mM NaCl, 15 mM of sodium citrate], and the temperature for the hybridization is 55° C.

ML-236B biosynthesis accelerating cDNA can be obtained, for example, by isolating a clone containing the cDNA from a cDNA library of a ML-236B producing micro-organism. As an alternative, RT-PCR can be used employing a pair of primers designed on the basis of the nucleotide sequence of an ML-236B biosynthesis-related genomic DNA together with mRNA or total RNA of a ML-236B producing micro-organism.

An ML-236B producing micro-organism is a micro-organism inherently having an ability to produce ML-236B. As indicated previously, examples of ML-236B producing micro-organisms include *Penicillium* species, such as *Penicillium citrinum, Penicillium brevicompactum, Penicillium cyclopium* or the like, and other examples include: *Eupenicillium* sp.M6603, *Paecilomyces viridis* FERM P-6236, *Paecilomyces* sp.M2016, *Trichoderma longibrachiaium* M6735, *Hypomyces chryospermus* IFO 7798, *Gliocladium* sp. YJ-9515, *Trichorderma viride* IFO 5836, *Eupenicillium reticulisporum* IFO 9022, and any other suitable organisms Among these ML-236B producing micro-organisms, *Penicillium citrinum* is preferred, and the *Penicillium citrinum* strain SANK 13380 is more preferred. *Penicillium citrinum* SANK 13380 strain was deposited at the Research Institute of Life Science and Technology of the Agency of Industrial Science and Technology on Dec. 22, 1992 under the deposit Nos. FERM BP4129, in accordance with the Budapest Treaty on the Deposition of Micro-organisms. Examples of ML-236B producing micro-organisms also include both those isolated from natural sources and those mutated naturally or artificially.

ML-236B biosynthesis related genomic DNA can be obtained by screening a genomic DNA library of an ML-236B producing micro-organism with a suitable probe. Suitably the probe is designed on the basis of a DNA sequence predicted to have a role in ML-236B biosynthesis, suitably originating from a filamentous fungus.

The choice of methods for creating a genomic DNA library are not limited, and any suitable method may be used, preferably being a general method for constructing a genomic DNA library of a eukaryotic organism. Examples thereof include the method of Maniatis et at. [Maniatis, T., et al, Molecular cloning, a laboratory manual, 2nd ed., Cold Spring Harbor Laboratory. Cold Spring Harbor, N.Y. (1989)]. Other suitable methods are known in the art.

In outline, genomic DNA from an ML-236B producing micro-organism can be obtained by recovering cells from a culture of said ML-236B producing micro-organism, physically breaking the cells extracting DNA present in the nuclei thereof and purifing said DNA.

Culturing of a ML-236B producing micro-organism can be performed under conditions suitable for the particular ML-236B producing micro-organisms. For example, culturing of *Penicillium citrinum*, a preferred ML-236B producing micro-organism, can be performed by inoculating the cells in MBG3–8 medium [composition: 7% (w/v) glycerin, 3% (w/v) glucose, 1% (w/v) soybean powder, 1% (w/v) peptone (manufactured by Kyokuto Seiyaku Kogyo corporation), 1% (w/v) Corn steep liqueur (manufactured by Honen corporation), 0.5% (w/v) sodium nitrate, 0.1% (w/v) magnesium sulfate heptahydrate (pH 6.5)], and incubating at 22 to 28° C. with shaking for 3 to 7 days. A slant for storage of the bacterium can be prepared by pouring melted PGA agar medium [composition: 200 g/L potato extract, 15% (w/v) glycerin, 2% (w/v) agar] into a test tube, and allowing the agar to solidify at an angle. *Penicillium citrinum* may then be inoculating into the slant using a platinum needle, followed by incubation at 22 to 28° C. for 7 to 15 days. Micro-organisms or bacteria grown in this way can be continuously maintained on the slant by reserving the slant at 0 to 4° C.

Cells of an ML-236B producing micro-organism cultured in a liquid medium can be recovered by centrifugation, and those cultured on a solid medium can be recovered by scraping from the solid media with a cell scraper or the like.

Physical breaking of cells can be performed by grinding the cells using a pestle and a mortar, after freezing them with liquid nitrogen or the like. DNA in the nuclei of the broken cell can be extracted using a surfactant such as sodium dodecylsulfate (hereinafter referred to as SDS) or other suitable surfactant. The extracted genomic DNA is suitably treated with phenol-chloroform to remove protein, and recovered as a precipitate by performing an ethanol precipitation.

The resulting genomic DNA is fragmented by digestion with a suitable restriction enzyme. There is no limitation on the restriction enzymes that can be used for the restriction digest, with generally available restriction enzymes preferred. Examples thereof include Sau3AI. Other suitable enzymes are known in the art. Digested DNA is then subjected to gel electrophoresis, and genomic DNA having a suitable size is recovered from the gel. The size of DNA fragment is not particularly limited, but is preferably 20 kb or more.

There is likewise no limitation on the choice of DNA vector used in construction of the genomic DNA library, as long as the vector has a DNA sequence necessary for replication in the host cell which is to be transformed by the vector. Examples of suitable vectors include a plasmid vector, a phage vector, a cosmid vector, a BAC vector or the like, with a cosmid vector being preferred. The DNA vector is preferably an expression vector. More preferably, the DNA vector comprises a DNA or nucleotide sequence which confers a selective phenotype onto the host cell transformed by the vector.

The DNA vector is suitably a vector that can be used in both cloning and expression. Preferably the vector is a shuttle vector which can be used for transformation of more than one micro-organism host. The shuttle vector suitably has a DNA sequence which permits replication in a host cell, and preferably a sequence or sequences which permit replication in a number of different host cells from different micro-organism groups such as bacteria and fungi. Furthermore, the shuttle vector preferably comprises a DNA sequence which can provides a selectable phenotype for a range of different host cells, such as cells from different micro-organism groups.

The choice of combination of a micro-organism groups and host cells transformed by the shuttle vector is not particularly limited, provided that one of the micro-organism groups can be used in cloning and the other has ML-236B producing ability. Such combination can be, for example, a combination of a bacterium and filamentous fungi, a combination of yeast and filamentous fungi, with a combination of a bacterium and filamentous fungi being preferred. The choice of bacterium is not particularly limited as long as it can be generally used in biotechnology, such as for example *Escherichia coli, Bacillus subtilis* or the like. *Escherichia coli* is preferred, and *Escherichia coli* XL1-Blue MR is more preferred. Similarly there is no restriction on yeast species as long as it can be generally used in biotechnology, such as for example. *Saccharomyces cerevisiae* or the like. Examples of filamentous fungi include ML-236B producing micro-organisms described above. Other suitable examples of micro-organisms are known in the art.

In the present invention, the micro-organism group can be selected from bacteria, filamentous fungi and yeast.

Examples of the above-mentioned shuttle vector include a cosmid vector having a suitable marker gene for selecting a phenotype and a cos site. Other suitable vectors are known in the art. The preferred vector is pSAKcos1, constructed by inserting a cos site from cosmid vector pWE15 (manufactured by STRATAGENE) into plasmid pSAK333, which comprises the sequence of *Escherichia coli* hygromycin B phosphotransferase gene [described in Japanese Patent Application Publication No.3-262486]. A method for constructing pSAKcos1 is shown in FIG. 1. The present invention is not limited to this vector.

A genomic DNA library can be prepared by introducing a shuttle vector into a host cell, the vector containing a genomic DNA fragment from an ML-236B producing micro-organism. The host cell to be used is preferably *Escherichia coli*, more preferably *Escherichia coli* XL1-Blue MR. When the host cell is *Escherichia coli*, introduction can be performed by in vitro packaging. In the present invention, transformation also covers the introduction of foreign DNA by in vitro packaging, and a transformed cell also covers a cell to which foreign DNA is introduced by in vitro packaging.

A genomic library can be screened to identify a desired clone using an antibody or a nucleic acid probe, with a nucleic acid probe being preferred. Preferably the nucleic acid probe is prepared based on the nucleotide sequence of a gene or DNA related to polyketide biosynthesis, preferably being a sequence derived from a filamentous fungus. The choice of particular gene is not limited as long as it is involved in biosynthesis of polyketides and the nucleotide sequence thereof is known. Examples of such genes include the Aflatoxin PKS gene of *Aspergillus flavus* and *Aspergillus parasiticus*, the Sterigmatocystin PKS gene of *Aspergillus nidulans* or the like.

Suitable nucleic acid probes can be obtained, for example by synthesizing an oligonucleotide probe comprising part of a known genomic DNA sequence as described above, or by preparing oligonucleotide primers and amplifying the target DNA using the polymerase chain reaction [hereinafter referred to as "PCR" described in Saiki, R. K., et al. Science, 239, 487 (1988)] and genomic DNA as a template or by RT-PCR using mRNA as a template. Other suitable methods for obtaining such probes are well known in the art.

A nucleic acid probe can be obtained from a ML-236B producing micro-organism using, for example, PCR or RT-PCR. Design of the primers used for PCR or RT-PCR (hereinafter referred to as "primer for PCR") is preferably carried out based on the nucleotide sequence of a gene related to polyketide biosynthesis for which the nucleotide sequence is known. Preferably the gene is the aflatoxin PKS gene of *Aspergillus flavus, Aspergillus parasiticus*, or the Sterigmatocystin PKS gene of *Aspergillus nidulans*.

The primer for PCR are suitably designed to comprise nucleotide sequences which encode amino acid sequences that are highly conserved within PKS genes. Methods to identify nucleotide sequences corresponding to a given amino acid sequence include deduction on the basis of the codon usage of the host cell, and methods of making mixed oligonucleotide sequences using multiple codons (hereinafter referred to as a 'degenerate oligonucleotides'). In the latter case, the multiplicity of oligonucleotides can be reduced by introducing hypoxanthine to their nucleotide sequences.

Primer for PCR may comprise a nucleotide sequence designed to anneal with a template chain, the primer being joined to an additional 5' sequence. The choice of such an additional 5' nucleotide sequence is not particularly limited, as long as the primer can be used for PCR or RT-PCR. Such an additional 5' sequence can be, for example, a nucleotide sequence convenient for the cloning operation of a PCR product. Such a nucleotide sequence can be, for example, a restriction enzyme cleavage site or a nucleotide sequence containing a restriction enzyme cleavage site.

Furthermore, in designing of the primer for PCR, it is preferred that the sum of the number of guanine (G) and the number of cytosine (C) bases is 40 to 60% of the total number of bases. Furthermore, preferably there is little or no self-annealling for a given primer and, in the case of a pair of primers, preferably little or no annealing between the primers.

The number of nucleotides making up the primer for PCR is not particularly limited, as long as it can be used for PCR. The lower limit of the number is generally 10 to 14 nucleotides, with the upper limit 40 to 60 nucleotides. Preferably, primers are 14 to 40 oligonucleotides in length.

The primer for PCR is preferably DNA. Nucleosides in the primer can be deoxy adenosine, deoxy cytidine, deoxy thymidine, and deoxy guanosine, and additionally deoxy inosine. The 5'-position of the nucleoside at the 5'-end of the primer for PCR is suitably a hydroxyl group or a hydroxy group to which one phosphoric acid is bonded by an ester link.

Synthesis of primer for PCR can be performed by methods generally used for synthesis of nucleic acids, for example, the phosphoamidite method. An automated DNA synthesizer can be preferably used in such a method.

Genomic DNA and mRNA from an ML-236B producing micro-organism can be used as a template for PCR or RT-PCR respectively. Total RNA can also be used as a template for RT-PCR instead of mRNA.

The PCR product or RT-PCR product can be cloned by incorporation into a suitable DNA vector. The choice of DNA vector used for the cloning step is not generally limited. Kits for the easy cloning of PCR and RT-PCR products are commercially available. By way of example, the Original TA Cloning Kit (manufactured by Invitrogen: using pCR2.1 as DNA vector) is suitable for such cloning.

In order to obtain a cloned PCR product, transformed host cells containing plasmids comprising the desired PCR product are cultured, and then the plasmids extracted from the cells and purified. The inserted DNA fragment is then recovered from the resulting plasmid.

Culturing of the transformed host cells is suitably performed under conditions appropriate for the host cells. A preferred host cell. Escherichia coli, can be cultured in LB medium [1% (w/v) trypton, 0.5% (w/v) yeast extract, 0.5% (w/v) sodium chloride] at 30 to 37° C. for 18 hours to two days with shaking.

Preparation of plasmids from a culture of the transformed host cells can be performed by recovering the host cells and isolating plasmids free from other cellular components such as genomic DNA or host protein. Preparation of plasmid DNA from a culture of Escherichia coli can be performed according to the alkaline method of Maniatis [described in Maniatis, T., et al. Molecular cloning, a laboratory manual, 2nd ed., Cold Spring Harbor Laboratory, Cold Spring Harbor, N.Y. (1989)]. Kits for obtaining a plasmid having higher purity are commercially available. The Plasmid Mini Kit [manufactured by QIAGEN AG] is preferred. Furthermore., a kit for mass-production of a plasmid is commercially available. The Plasmid Maxi Kit (manufactured by QIAGEN AG) is preferred.

The concentration of the resulting plasmid DNA can be determined by measuring absorbance at a wavelength of 260 nm after adequate dilution of DNA sample, and calculating on the basis that a solution with an absorbance $OD_{260}$ of 1 contains 50 μg/ml DNA (described in Maniatis, T., et al., supra).

Purity of DNA can be calculated from a ratio of absorbance at a wavelength of 280 and 260 nm (described in Maniatis, T., et al., supra).

Methods for labeling of nucleic acid probes can be generally classified as radiolabeling and non-radiolabeling. The choice of radionucleotide for radio-labeling is not generally limited, and can be, for example. $^{32}P$. $^{35}S$. $^{14}C$ or the like. The use of $^{32}P$ in labeling is preferred. The choice of agent for non-radiolabeling is also not generally limited, so long as it may be generally used for labeling nucleic acid, and can be, for example, digoxgenin, biotin, or the like, with digoxigenin preferred.

Methods for the labeling of nucleic acid probe are also not generally limited. Preferred are commonly used methods, such as, for example, methods incorporating the label into the product by PCR or RT-PCR using labeled nucleotide substrates, nick translation, use of random primers, terminal labeling, and methods for synthesizing oligonucleotide DNA using labeled nucleotide substrates. A suitable method can be selected from these methods depending on the kind of nucleic acid probe.

The presence in the genome of a ML-236B producing micro-organism of a nucleotide sequence that is the same as the nucleotide sequence of a particular nucleic acid probe can be confirmed by Southern blot hybridization with the genomic DNA of said ML-236B producing micro-organism.

Southern blot hybridization can be performed according to the method of Maniatis [described in Maniatis, T., et al., supra].

A labeled nucleic acid probe, prepared as described above, can be used to screen a genomic DNA library. The choice of screening method is not particularly limited, as long as it is generally appropriate for gene cloning, but it is preferably the colony hybridization method [described in Maniatis, T., et al., supra].

Culturing of the colonies used for colony hybridization is suitably performed under conditions appropriate for the host cells. Culturing of Escherichia coli, a preferred host, can be performed by incubation in LB agar medium [1% (w/v) trypton, 0.5% (w/v) yeast extract, 0.5% (w/v) sodium chloride, 1.5% (w/v) agarose] at 30 to 37° C. for 18 hours to two days.

Preparation of recombinant DNA vector from the positive clone obtained by colony hybridization is generally performed by extracting the plasmid from the culture of the positive clone and purifying it.

A transformed Escherichia coli strain. Escherichia coli pML48 SANK71199 representing a positive clone obtained according to the present invention, was deposited at the Research Institute of Life Science and Technology of the Agency of Industrial Science and Technology on Jul. 7, 1999, in accordance with the Budapest Treaty on the Deposition of Micro-organisms, and was accorded the accession number FERM BP-6780.

A typical DNA vector carried by Escherichia coli pML48 SANK71199 was designated as pML48.

Confirmation that the recombinant DNA vector present in the positive clone contains ML-236B biosynthesis-related genomic DNA can be suitably assessed by determining the nucleotide sequence of the recombinant DNA vector insert. Southern blot hybridization or expression of the insert to determine function.

The nucleotide sequence of DNA can be determined according to the Maxam and Gilbert chemical modification technique [described in Maxam, A. M. M. and Gilbert, W., Methods in Enzymology, 65, 499 (1980)] or the dideoxy chain termination method [described in Messing, J, and Vieira, J., Gene, 19, 269 (1982)]. Other suitable methods are well known in the art. Plasmid DNA used for determination of nucleotide sequence is preferably a high purity sample, as described above.

The nucleotide sequence of the pML48 insert is shown in SEQ ID No. 1 of the Sequence Listing. The nucleotide sequence shown in SEQ ID No. 2 of the Sequence Listing is completely complementary to the nucleotide sequence shown in SEQ ID No. 1. Generally, a nucleotide sequence of a genomic DNA can have genetic polymorphisms within a species, that is, allogenic differences. Furthermore, in the process of DNA cloning and sequencing, it is known that nucleotide substitutions, or other alterations, can occur at a certain frequency. Accordingly, the ML-236B biosynthesis-related genomic DNA of the present invention also includes genomic and other DNAs that can be hybridized to DNA of nucleotide No. 1 to 34203 of SEQ ID No. 1 or 2 of the Sequence Listing. Preferred are genomic or other DNAs that can be hybridized under stringent condition to DNA of nucleotide No. 1 to 34203 of SEQ ID No. 1 or 2 of the Sequence Listing. These DNAs include the DNA of nucleotide No. 1 to 34203 of SEQ ID No. 1 or 2 of the Sequence Listing, wherein one or more nucleotides are substituted, deleted and/or added. Additionally these hybridizing genomic or other DNAs can include DNA originating from ML-236B producing micro-organisms other than *Penicillium citrinum* SANK13380, preferably being those capable of improving the production of ML-236B when introduced into an ML-236B producing micro-organism.

ML-236B biosynthesis related genomic DNA is suitably analyzed in accordance with the following methods 1) to 3).

1) Analysis with Gene Analyzing Software

Genes within genomic DNA can be located using a program for finding genes (hereinafter referred to as "GRAIL"), and a program for searching homologous sequences (BLASTN and BLASTX).

GRAIL is a program which searches for structural genes in genomic DNA by separating the genomic sequence into seven parameters for evaluation of the appearance of a gene sequence, and integration of the results using a neural net method [described in Uberbacher, E. C. & Mural, R. J. Proc. Natl. Acad. Sci. USA., 88, 11261 (1991)]. By way of example, the ApoCom GRAIL Toolkit [produced by Apocom corporation] can be used.

BLAST is a program using an algorithm for performing homology searches of nucleotide sequences and amino acid sequences [described in Altschul, S. F., Madden, T. L., et al., Nucl. Acids Res., 25, 3389 (1997)].

The position and direction of a structural gene on a sample genomic DNA sequence can be predicted by dividing the DNA sequence into suitable lengths and performing a homology search of a genetic data base using BLASTN. The position and direction of structural gene on a DNA sequence to be tested can also be predicted by translating the divided genomic DNA sequences into the six translation frames (three on the sense strand and the other three on the antisense strand) and performing a homology search of the derived amino acid sequences in a peptide data base using BLASTX.

Coding regions for structural genes in genomic DNA are sometimes split with introns in eukaryotic organisms. For analysis of structural genes having such gaps, the BLAST program for sequences containing gaps is more effective, with Gapped-BLAST program (installed in BLAST2: WISCONSIN GCG package ver. 10.0) being preferred.

2) Analysis According to Northern Blot Hybridization Method

Expression of a structural gene predicted by the analysis methods described in paragraph 1) can be studied using the Northern blot hybridization method.

Suitably, total RNA from a ML-236B producing micro-organism is obtained from a culture of the micro-organism. A culture of the preferred ML-236B producing micro-organism *Penicillium citrinum* can be obtained by inoculating said micro-organism from a slant into MGB3–8 medium, followed by incubation with shaking, incubating at 22 to 28° C. for one to four days.

The choice of method of extraction of RNA from an ML-236B producing micro-organism is not limited, and preferred is the guanidine thiocyanate-hot phenol method, guanidine thiocyanate-guanidine hydrochloric acid method or the like. Examples of a commercially available kit for preparing higher purity total RNA include RNeasy Plant Mini Kit (manufactured by Qiagen AG). Furthermore, mRNA can be obtained by applying total RNA to an oligo (dT) column, and recovering the fraction adsorbed in the column.

Transfer of RNA to a membrane, preparation of a probe, hybridization and detection of a signal can be performed in a similar manner to the above mentioned Southern blot hybridization method.

3) Analysis of 5'-end and 3'-end of Transcript.

Analysis of the 5'-end and 3'-end of each transcript can be performed according to the 'RACE' (rapid amplification of cDNA ends) method. RACE is a method for obtaining a cDNA comprising a known nucleotide region and an unknown region at the 5'-end or 3'-end of a gene, using RT-PCR with mRNA as a template [described in Frohman, M. A., Methods Enzymol. 218, 340 (1998)].

5'-RACE can be performed according to the following method. The first strand of a cDNA is synthesized according to a reverse transcriptase reaction using mRNA as a template. As a primer, antisense oligonucleotides (1) are used which are designed to a known part of a nucleotide sequence. A homopolymeric nucleotide chain (consisting of one kind of base) is added to the 3'-end of the first strand of the cDNA using terminal deoxynucleotidyl transferase. Then, double stranded cDNA in 5'-end region is amplified by PCR using the first strand of the cDNA as a template. For amplification, 2 primers are used; a DNA oligonucleotide from the sense strand containing a sequence complementary to the homopolymeric sequence, and an oligonucleotide (2) on the antisense strand and on the 3'-end side of the oligonucleotide DNA (1) [described in Frohman, M. A. Methods in Enzymol., 218, 340 (1993]. A kit for 5' RACE is commercially available, suitably the 5' RACE System for Rapid Amplification of cDNA ends. Version 2.0 (manufactured by GIBCO corporation).

3' RACE is a method using the polyA region existing at the 3'-end of mRNA. Specifically, the first strand of cDNA is synthesized through a reverse transcriptase reaction using mRNA as a template and an oligo d(T) adapter as a primer. Then, double stranded cDNA in 3'-end region is amplified by PCR using the first strand of the cDNA as a template. As primers, a DNA oligonucleotide (3) on the sense strand designed to a known part of the nucleotide sequence of the sense strand, and the oligo d(T) adapter on the antisense strand are used. A kit for 3' RACE is commercially available, suitably the Ready-To-Go T-primed First-Strand Kit (Pharmacia corporation).

The results of analysis 1) and 2) above are preferable used in the RACE procedure, in the design of the primers based upon a known part of the nucleotide sequence of interest.

Using the methods of the analysis described in 1) to 3) above, the direction of a structural gene on a genomic DNA sequence, the location of transcription initiation site in the structural gene, the position of the translation initiation codon, and translation termination codon and position thereof can be deduced. Based on the above information, each structural gene, and cDNA thereof namely. ML-236B biosynthesis accelerating cDNAs can be obtained.

Six structural genes are assumed to be present on the incorporated sequence in a recombinant DNA vector pML48 obtained according to the present invention. They are named mlcA mlcB, mlcC, mlcD, mlcE, and mlcR, respectively. Among them, mlcA mlcB, mlcE and mlcR are assumed to have a coding region on the nucleotide sequence shown in SEQ ID No. 2 of the Sequence Listing, mlcC and mlcD are assumed to have a coding region on the nucleotide sequence shown in SEQ ID No. 1 of the Sequence Listing.

Examples of a method for obtaining the specific ML-236B biosynthesis accelerating cDNAs corresponding to the above-mentioned structural genes include: cloning with RT-PCR using primers designed to the sequence of each of the structural genes and flanking DNA thereof and cloning from a cDNA library using appropriate DNA probes designed to known nucleotide sequences. Other suitable methods are well known in the art. In order to express functionally the cDNA obtained according to these methods, it is preferable to obtain a full length cDNA.

A method for obtaining ML-236B biosynthesis accelerating cDNA using RT-PCR is explained below.

A pair of primers for RT-PCR and for obtaining ML-236B biosynthesis accelerating cDNA needs to be designed so that it selectively anneals with each template chain, to allow cDNA to be obtained. However, it is not essential that the primers for RT-PCR are completely complementary to a part of each template chain, provided that they satisfy the condition described above. Suitable primers for RT-PCR that can anneal with the antisense chain (hereinafter referred to as "sense primer") are sense primers that are completely complementary to a part of the antisense chain (hereinafter referred to as "unsubstituted sense primer") or sense primers that are not completely complementary to a part of the antisense chain (hereinafter referred to as "partially substituted sense primer"). The other suitable primers for RT-PCR that can anneal with the sense chain (hereinafter referred to as "antisense primer") are antisense primers that are completely complementary to a part of the sense chain (hereinafter referred to as "unsubstituted antisense primer") or antisense primers that are not completely complementary to a part of the sense chain (hereinafter referred to as "partially substituted antisense primer").

A sense primer is suitably designed so that the RT-PCR product obtained using it contains the codon ATG at the original position of translation initiation. Suitably the RT-PCR product also only contains the correct translation termination codon in the reading frame having the original ATG start site, and no additional (spurious) translational stop sites. The position of the translation initiation codon of those structural genes predicted in the present invention is shown in Table 5 for genes located in SEQ ID No. 1 and SEQ ID No. 2 of the Sequence Listing.

The 5'-end of the unsubstituted sense primer is suitably the nucleotide 'A' of the translation initiation codon ATG, or a base existing on the 5'-end side thereof.

A partially substituted sense primer selectively anneals with a specific region in SEQ ID No. 1 or SEQ ID No. 2 of the Sequence Listing, the nucleotide sequence of SEQ ID No. 2 of the Sequence Listing being completely complementary to SEQ ID No. 1 of the Sequence Listing.

When a partially substituted sense primer contains a nucleotide sequence present on the 3'-side of the translation initiation codon ATG, it suitably does not contain nucleotide sequences in this region that are termination codons (TAA, TAG or TGA) in the same reading frame as the ATG.

A partially substituted sense primer may contain nucleotide "A", nucleotide sequence "AT" or "ATG" (hereinafter referred to as "nucleotide or nucleotide sequence m") which correspond to nucleotide "A", nucleotide sequence "AT" or "ATG" of the translation initiation codon (hereinafter referred to as "nucleotide or nucleotide sequence m). Where the nucleotide m' is "A", corresponding to the "A" of sequence "m", we prefer that the m' "A" is located at 3'-end of the partially substituted sense primer. Similarly, where m' is "AT", we prefer that this m' "AT" sequence is located at 3'-end of the partially substituted sense primer. When the nucleotide or nucleotide sequence m is "ATG", corresponding to the m' "ATG", we prefer that those trinucleotides which are 3' to the ATG in the primer are not stop codons. In other words, for trinucleotides whose 5'-end nucleotide is the (3×n+1)th nucleotide (n represents an integer of one or more) counted from A of the m' "ATG" in the direction of the 3'-end, the nucleotide sequence of the trinucleotide is preferably neither TAA, TAG nor TGA. Primers described above can be used to obtain cDNA having a methionine codon at the position corresponding to the translational initiation codon of mRNA used as an RT-PCT template.

Where the 3'-end of a partially substituted sense primer is nucleotide position (3×n+1), preferably the trinucleotide which begins at this position is not TAA, TAG or TGA in the RT-PCR product obtained using the partially substituted sense primer as one of the primers, and RNA or mRNA of the ML-236B producing micro-organism as a template, or in the PCR products obtained by using genomic DNA or cDNA as a template. The nucleotide position is counted from the 'A' of the translation initiation codon "ATG" in the direction of 3'-end, and where 'n' represents an integer of one or more.

Where the 3'-end of a partially substituted sense primer is nucleotide position (3×n+2), the triplet for which position 3×n+2 is the central nucleotide is preferably none of the sequences TAA, TAG or TGA for a PCR or RT-PCR product obtained as above.

Where the 3'-end of a partially substituted sense primer is nucleotide position (3×n+3), the triplet for which position (3×n+3) is the 3' nucleotide is preferably none of the sequences TAA, TAG or TGA.

The requirements for the sense primer are as discussed above.

An antisense primer is designed so that, when paired together with the sense primer, cDNA encoding each of structural genes (mlcA, mlcB, mlcC, mlcD, mlcE and mlcR) can be amplified using RT-PCR in a direction equivalent to the N-terminus to C-terminus of the corresponding peptides.

The choice of unsubstituted antisense primer is not limited, as long as it is an antisense primer having a nucleotide sequence complementary to a nucleotide sequence located in the region of the translational termination site of the cDNA. However, a primer having a 5'-end base which is complementary to the base at 3'-end of translation termination codon, or having a base on the 5'-end side of said primer base, is preferred. A primer containing three bases complementary to a translation termination codon is more preferred. Tables 8 to 10 show the translation termination codon of each structural gene, the sequence complementary to the translation termination codon, an amino acid residue at C-terminal of the peptide encoded by each structural gene, the nucleotide sequence encoding the amino acid residue, and position thereof in SEQ ID No. 1 or SEQ ID No. 2.

Partially substituted antisense primers selectively anneal with a specific region in the nucleotide sequence of SEQ ID No. 1 or SEQ ID No. 2 of the Sequence Listing.

The above are requirements for an antisense primer.

It is possible to add suitable nucleotide sequences to the 5'-end of the partially substituted sense primers and the partially substituted antisense primers, as long as the abovementioned requirements are satisfied. The choice of such a nucleotide sequence is not particularly limited, as long as the primer can be used for PCR. Examples of suitable sequences include nucleotide sequences convenient for the cloning of PCR products, such as restriction enzyme cleavage sites and nucleotide sequence containing suitable restriction enzyme cleavage sites.

In addition, the sense primer and the antisense primer are suitably desioned according to the above description and in accordance with the general design of primer for PCR.

As described above, mRNA or total RNA from a ML-236B producing micro-organism may be used as a template for RT-PCR. In the present invention an ML-236B biosynthesis-accelerating cDNA corresponding to the structural gene mlcE was obtained be designing and synthesizing a pair of primers suitable to amplify all of coding region of the structural gene mlcE in the pML48 insert sequence and then performing RT-PCR using total RNA of SANK13380 as a template [primers represented by nucleotide sequences SEQ ID Nos. 35 and 36 of the Sequence Listing respectively].

An ML-236B biosynthesis-accelerating cDNA corresponding to the structural gene mlcR was obtained in a similar way using primers represented by nucleotide sequences SEQ ID Nos. 39 and 40 of the Sequence Listing respectively.

As described above, the RT-PCR product can be cloned by incorporation into a suitable DNA vector. The choice of DNA vector used for such cloning is not limited, and is suitably a DNA vector generally used for cloning of DNA fragments. Kits for easily performing cloning of an RT-PCR product are commercially available, and the Original TA Cloning Kit [manufactured by Invitrogen: using pCR2.1 as DNA vector] is preferred.

Confirmation of functional expression of the ML-236B biosynthesis accelerating cDNAs obtained using the above methods in an ML-236B producing micro-organism can be obtained by cloning the cDNA into a DNA vector suitable for functional expression in an ML-236B producing micro-organism. Suitable cells are then transformed with the recombinant DNA vector, and the ML-236B biosynthesis ability of the transformed cells and non transformed host cells compared. If ML-236B biosynthesis accelerating cDNA is functionally expressed in the transformed cell, then the ML-236B biosynthesis ability of the transformed cell is improved compared with that of a host cell.

The choice of DNA vector suitable for expression in an ML-236B producing micro-organism [hereinafter referred to as a functional expression vector] is not particularly limited, as long as it can be used to transform the ML-236B producing micro-organism and can functionally express the polypeptide encoded by the ML-236B biosynthesis accelerating cDNA in that organism. Preferably the vector is stable in the host cell, and has a nucleotide sequence which allows replication in the host cell.

The vector for functional expression can contain one or more than one of ML-236B biosynthesis accelerating cDNAs, for example cDNAs corresponding to the structural genes mlcE and/or mlcR.

A vector for functional expression may contain one or more than one kind of DNA, other than cDNA corresponding to the structural genes mlcE and/or mlcR, that accelerate biosynthesis of ML-236B when introduced into ML-236B producing micro-organism. Examples of such DNA include: cDNAs corresponding to structural genes mlcA, mlcB, mlcC, or mlcD, ML-236B biosynthesis related genomic DNA. DNA encoding expression regulatory factors of ML-236B biosynthesis accelerating cDNA of the present invention, or the like.

A vector for functional expression preferably comprises a nucleotide sequence providing a selective phenotype for the plasmid in a host cell, and is preferably a shuttle vector.

Furthermore, the selective phenotype may be a drug resistance phenotype or the like, is preferably antibiotic resistance, and more preferably resistance to ampicillin or resistance to hygromycin B.

In the case that the expression vector is a shuttle vector, the vector suitably comprises a nucleotide sequence which allows the vector to replicate in a host cell of one of the micro-organism groups, and a nucleotide sequence necessary for the expression of polypeptide encoded by the vector insert in another host cell type. It is preferable that the vector affords a different selective phenotpe for each host cell of the different micro-organism groups transformed. The requirements for combinations of micro-organism groups is similar to the requirement for the shuttle vector used for cloning and expression of ML-236B biosynthesis related genomic DNA described in the present specification.

In the present invention, a suitable shuttle vector DNA vector is pSAK700. constructed by combining the 3-phosphoglycerate kinase (hereinafter referred to as "pgk") promoter originating from *Aspergillus nidulans* existing in the DNA vector pSAK333 (described in Japanese Patent Application Publication No.3-262486), an adapter for incorporating a foreign gene, and pgk terminator existing in the DNA, in this order (see FIG. 4).

A polypeptide can be expressed in an ML-236B producing micro-organism by incorporating the cDNA corresponding to the strutural gene mlcE, described above, into the expression vector described above. In the present invention, a recombinant cDNA expression vector pSAKexpE has been obtained by incorporating cDNA corresponding to the strutural gene mlcE into an adopter site of pSAK700. The incorporated sequence in pSAKexpE, namely the nucleotide sequence of cDNA corresponding to the strutural gene mlcE is shown in SEQ ID No.37 of the Sequence Listing. Similarly a recombinant cDNA expression vector pSAKexpR has been obtained by incorporating cDNA corresponding to the strutural gene mlcR into an adapter site of pSAK700. The incorporated sequence in pSAKexpR, namely the nucleotide sequence of cDNA corresponding to the strutural gene mlcR is shown in SEQ ID No. 41 of the Sequence Listing.

*Escherichia coil* pSAKexpE SANK 72499 that is an *Escherichia coil* strain transformed by pSAKexpE was deposited at the Research Institute of Life Science and Technology of the Agency of Industrial Science and Technology (located at 1–3. Higashi 1-chome, Tsukuba-shi, Ibaraki-ken, 305–8566 Japan) on Jan. 25, 2000 under the Deposit No. FERM BP-7005, in accordance with the Budapest Treaty on the Deposition of Micro-organisms. *Escherichia coil* pSAKexpR SANK 72599 that is an *Escherichia coil* strain transformed by pSAKexpR was deposited at the Research Institute of Life Science and Technology of the Agency of Industrial Science and Technology (located at 1–3, Higashi 1-chome, Tsukuba-shi, Ibaraki-ken, 305–8566 Japan) on Jan. 25, 2000 under the Deposit No. FERM BP-7006, in accordance with the Budapest Treaty on the Deposition of Micro-organisms.

Suitable methods of transformation can be appropriately selected, depending on the host cell, to obtain expression of ML-236B biosynthesis accelerating cDNA. ML-236B biosynthesis related genomic DNA or fragments thereof. Transformation of *Penicillium citrinum*, a preferred ML-236B producing micro-organism, can be performed by preparing protoplasts from spores of *Penicillium citrinum*, then introducing recombinant DNA vector into the protoplast [described in Nara, F., et al., Curr. Genet. 23, 28 (1993)].

Suitably spores from a slant of culture of *Penicillium citrinum* are inoculated on a plate of PGA agar medium and incubated at 22 to 28° C. for 10 to 14 days. The spores are then harvested from the plate and $1\times10^7$–$1\times10^9$ spores inoculated into 50 to 100 ml of YPL-20 culture medium [composition: 0.1% (w/v) yeast extract (manufactured by Difco corporation), 0.5% (w/v) polypeptone (manufactured by Nihon Seiyaku corporation), 20% (w/v) of lactose, pH5.0], then incubated at 22 to 28° C. for 18 hours to two days. The germinating spores are recovered from the culture, and treated with cell wall degrading enzymes to yield protoplasts. The choice of cell wall degrading enzyme is not particularly limited, as long as it can degrade the cell wall of *Penicillium citrinum* and does not have a harmful effect on the micro-organism. Example thereof include: zymolyase, chitinase or the like.

Mixing of a recombinant DNA vector comprising an ML-236B biosynthesis accelerating cDNA and ML-236B producing micro-organism, or the protoplast thereof, under suitable conditions allows introduction of the recombinant DNA vector into said protoplast, to provide a transformant.

Culturing of transformants of ML-236B producing micro-organism is suitably performed under conditions suitable for each of the host-cell. Culturing of a transformant of *Penicillium citrinum*, a preferred ML-236B producing micro-organism, can be performed by culturing the previous transformed protoplast under conditions appropriate to regenerate a cell wall, and then culturing. Namely, the transformed protoplast of *Penicillium citrinum* may be introduced into VGS middle layer agar medium [composition: Vogel minimum medium, 2% (w/v) glucose, 1M glucitol, 2% (w/v) agar], the VGS middle layer agar then sandwiched between VGS lower layer agar medium [composition: Vogel minimum medium, 2% (w/v) glucose, 1M glucitol, 2.7% (w/v) agar] and VGS upper layer agar medium [composition: Vogel minimum medium, 2% (w/v) glucose, 1M glucitol, 1.5% (w/v) agar] containing 800 µg/ml hygromycin B, then incubated at 22 to 28° C. for 7 to 15 days. The resultant strain is subcultured with incubation at 22 to 28° C. on PGA medium. The strain is inoculated with a platinum needle to a slant prepared of PGA medium, incubated at 22 to 28° C. for 10 to 14 days, and then reserved at 0 to 4° C.

As described above. ML-236B can be efficiently produced by inoculating a *Penicillium citrinum* transformant obtained from a slant as above, and having a regenerated cell wall, into MBG 3–8 medium, followed by incubation at 22 to 28° C. for 7 to 12 days with shaking. *Penicillium citrinum* as a host can be cultured in liquid medium as well to produce ML-236B.

Purification of ML-236B from culture of a transformant of ML-236B producing micro-organism can be performed by combining various methods generally used for purification of natural products. The choice of such methods is not particularly limited, and can be, for example, by centrifugation, separation of solids and liquids by filtration, treatment with alkali or acid, extraction with organic solvents, dissolution, chromatography methods such as adsorption chromatography, partition chromatography or the like, and crstallization or the like. ML-236B can be in either hydroxy acid or lactone form, which may be reciprocally converted. The hydroxy acid is convertible to a salt thereof that is more stable. Using such physical properties, the ML-236B hydroxy acid form (hereinafter referred to as free hydroxy acid), salts of ML-236B hydroxy acid (hereinafter referred to as a salt of hydroxy acid), or the ML236B lactone form (hereinafter referred to as lactone) can be obtained.

The culture is subjected to alkaline hydrolysis at raised temperature or room temperature for ring opening and conversion to a salt of hydroxy acid, and then the reaction solution is acidified, followed by filtration. The filtrate is extracted with an organic solvent that separates from water to provide an intended product as a free hydroxy acid. The choice of organic solvent is not particularly limited. Examples thereof include: aliphatic hydrocarbons such as hexane, heptane or the like; aromatic hydrocarbons such as benzene, toluene or the like; halogenated hydrocarbons such as methylene chloride, chloroform or the like; ethers such as diethyl ether or the like; esters such as ethyl formate, ethyl acetate or the like; or a mixture consisting of two or more solvents.

The intended compound can be obtained as a hydroxy acid salt by dissolving the free hydroxy acid in an aqueous solution of an alkaline metal salt such as sodium hydroxide.

Furthermore, the intended compound can be obtained as lactone through ring closure by heating the free hydroxy acid in an organic solvent to be dehydrated, or by other suitable methods.

It is possible to purify and isolate the free hydroxy acid, hydroxy acid or lactone thus obtained using column chromatography or the like. The support for the column used in chromatography is not particularly limited. Examples thereof include: Sephadex LH-20 (produced by Pharmacia corporation). Diaion HP-20 (produced by Mitsubishi Kagaku corporation), silica gel, reversed phase supports or the like, with supports of the C18 series preferred.

The choice of a method for quantification of ML-236B are not particularly limited, preferably being a method generally used for quantification of organic compounds. Examples thereof include: reversed phase high performance liquid chromatography (hereinafter referred to as "reverse phase HPLC") or the like. Quantification according to the reverse phase HPLC can be performed by subjecting a culture of an ML-236B producing micro-organism to alkaline hydrolysis, subjecting the soluble fraction to reverse phase HPLC using a C18 column, measuring UV absorption, and converting the absorption value to an amount of ML-236B. Choice of C18 column is not particularly limited, preferably being a C18 column used for general reverse phase HPLC. Examples thereof include: SSC-ODS-262 (diameter of 6 mm, length of 100 mm manufactured by Senshu Kagaku corporation) or the like. The choice of solvent for the moving phase is not particularly limited, so long as it is a solvent generally used for reverse phase HPLC. It is, for example, 75% (v/v) methanol-0.1% (v/v) triethyl amine-0.1% (v/v) acetic acid or the like. When ML-236B is added at room temperature to an SSC-ODS-262 column, where 75% (v/v) methanol-0.1% (v/v) triethyl amine-0.1% (X/v) acetic acid is used as moving phase at a rate of 2 ml/minute. ML-236B is eluted after 4.0 minutes. ML-236B can be detected using a UV detector for HPLC. The absorbed wave length for UV detection is 220 to 280 nm, preferably 220 to 260 nm, more preferably 236 nm.

Pharmaceutical compositions are provided containing ML-236B obtained using the present invention, together with a pharmaceutical carrier.

Pharmaceutical compositions are also provided containing pravastatin prepared from ML-236B obtained using the present invention, together with a pharmaceutical carrier.

The pharmaceutical compositions of this invention can be conventional and the same as those employed for existing formulations of ML-236B or pravastatin.

Methods of treatment are also part of this invention and employ the compounds or compositions to treat hyperlipemia and other conditions.

The invention is now illustrated in more detail with reference to the following Figures and Examples. The Examples are illustrative of, but not binding upon, the present invention.

EXAMPLES OF THE INVENTION

Example 1

Construction of pSAKcos1 Vector

Plasmid pSAK333 containing the hygromycin B phosphotransferase gene (hereinafter referred to as "HPT") originating from *Escherichia coli* (Japanese Patent Application Publication No. 3-262486) was digested with restriction enzyme BamHI (manufactured by Takara Shuzo Co., Ltd., Japan), and was treated to form blunt ends with T4DNA polymerase (manufactured by Takara Shuzo Co., Ltd., Japan).

The DNA fragment obtained as above was self-ligated into a circular form using DNA ligation kit Ver.2 (manufactured by Takara Shuzo Co., Ltd., Japan), and competent cells JM 109 of *Escherichia coli* (manufactured by Takara Shuzo Co., Ltd., Japan) were then transformed therewith. A strain having a plasmid in which the BamHI site was deleted was selected from the transformed *Escherichia coli*, and was designated pSAK360.

pSAK 360 was digested with restriction enzyme PvuII, and then treated with alkaline phosphatase to produce a fragment dephosphorylated at 5'-end. A SalI-ScaI fragment (about 3 kb) containing a cos site was obtained from a cosmid vector pWE15 (manufactured by STRATAGENE) and was treated to form blunt ends with T4 DNA polymerase. It was subsequently ligated to the PvuII site of pSAK360. JM109 was transformed with this DNA. Those strains having a plasmid into which SalI-ScaI fragment (about 3 kb) was inserted at the PvuII site were selected from the transformed *Escherichia coli*, and the plasmid carried by the strain was designated pSAKcos1, pSAKcos1 contains a cleavage site for the restriction enzymes BamHI, EcoRI and NotI, each site originating from pWE15. The pSAKcos1 has an ampicillin resistance gene and a hygromycin resistance gene as selection markers.

In the following examples, where *Escherichia coli* was used as a host, selection of pSAKcos1 transformants, or transformants of pSAKcos1 comprising a foreign gene-insert, was performed by adding 40 µg/ml ampicillin (Ampicillin: manufactured by Sigma corporation) to the relevant medium. Where *Penicillium citrinum* SANK13380 was used as a host, selection of pSAKcos1 transformants, or transformants of pSAKcos1 comprising a foreign gene-insert, was performed by adding 200 µg/ml hygromycin (Hygromycin B: manufactured by Sigma corporation) to the relevant medium.

Figure 1:
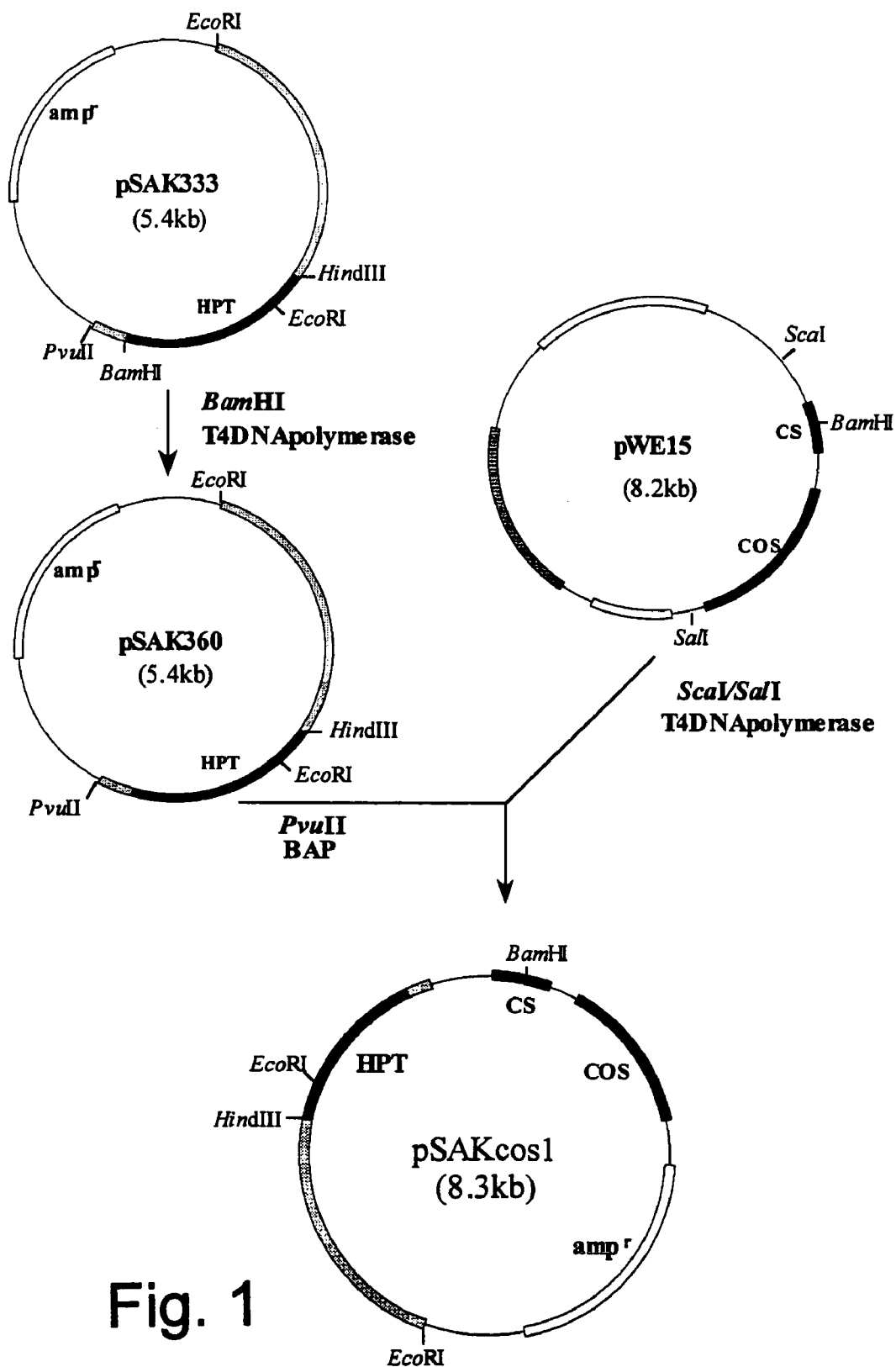
FIG. 1 is a diagram depicting the construction of DNA vector pSAKcos1.

The method of construction of pSAKcos1 is shown in FIG. 1

Example 2

Preparation of Genomic DNA of *Penicillium citrinum* SANK 13380

1) Culture of *Penicillium citrinum* SANK 13380

A seed culture of *Penicillium citrinum* SANK 13380 was made on a slant of PGA agar medium. Namely, the agar was inoculated with *Penicillium citrinum* SANK 13380 using a platinum needle, and kept at 26° C. for 14 days. The slant was kept at 4° C.

Main culturing was performed by liquid aeration culture. Cells from a 5 mm square of the above-mentioned slant were inoculated in 50 ml of MBG3–8 medium in 500 ml conical flask, and incubated at 26° C. with shaking at 210 rpm for five days.

2) Preparation of Genomic DNA from *Penicillium citrinum* SANK 13380

The culture obtained in step 1) was centrifuged at 10000×G at room temperature for 10 minutes and cells were harvested, 3 g (wet weight) of cells were broken in a mortar cooled with dry ice so as to be in the form of a powder. The broken cells were put in a centrifuge tube filled with 20 ml of 62.5 mM EDTA.2Na (manufactured by Wako Pure Chemical Industries, Ltd.)-5% (w/v) SDS-5 mM Tris hydrochloric acid (manufactured by Wako Pure Chemical Industries, Ltd.) buffer (pH8.0), and were mixed gently, then allowed to stand at 0° C. for one hour. 10 ml of phenol saturated with 10 mM Tris hydrochloric acid-0.1 mM EDTA.2Na (pH 8.0, hereinafter referred to as "TE") were added thereto, and the mix stirred gently at 50° C. for one hour.

After centrifugation at room temperature at 10000×G for 10 minutes, 15 ml of the upper layer (water phase) was placed into another centrifuge tube. To the solution were added 0.5 times by volume of TE saturated phenol and 0.5 times by volume of chloroform solution. The mixture was stirred for two minutes and centrifuged at room temperature at 10000×G for 10 minutes (hereinafter referred to as "phenol chloroform extraction"). To 10 ml of the upper layer (water phase) was added 10 ml of 8M ammonium acetate (pH 7.5) and 25 ml of 2-propanol (manufactured by Wako Pure Chemical Industries, Ltd.), followed by cooling at –80° C. for 15 minutes, and centrifugation at 4° C. at 10000×G for 10 minutes.

After precipitation, the precipitates were dissolved in 5 ml of TE, after which 20 µl of 10 mg/ml ribonuclease A (manufactured by Sigma corporation) and 250 units of ribonuclease T1 (manufactured by GIBCO corporation) were added thereto, followed by incubation at 37° C. for 20 minutes, 20 ml of 2-propanol was added thereto, and mixed gently. Subsequently, threads of genomic DNA were spooled at the tip of a Pasteur pipette, and dissolved in one ml of TE.

Next, 0.1 times by volume of 3 M sodium acetate (pH6.5) and 2.5 times by volume of ethanol were added to the DNA solution. The solution was cooled at −80° C. for 15 minutes, and then centrifuged at 4° C., at 10000×G for five minutes (herein after referred to as "ethanol precipitation"). The resultant precipitate was dissolved in 200 μl of TE, and was a genomic DNA fraction.

Example 3

Preparation of Genomic DNA Library of *Penicillium citrinum* SANK13380

1) Preparation of Genomic DNA Fragment 0.25 units of Sau3AI (Takara Shuzo Co., Ltd., Japan) were added to 100 μl of an aqueous solution of genomic DNA (50 μg) of *Penicillium citrinum* SANK13380 obtained in Example 2. After intervals of 10, 30, 60, 90 and 120 seconds, 20 μl samples of the mixture were taken, and 0.5 M EDTA (pH 8.0) was added to each sample to terminate the restriction enzyme reaction. The resulting partially digested DNA fragments were separated by agarose gel electrophoresis, and agarose gel was recovered containing DNA fragments of 30 kb or more The recovered gel was finely crushed, and placed into Ultra Free C3 Centrifuged Filtration Unit (manufactured by Japan Milipore corporation). The gel was cooled at −80° C. for 15 minutes until frozen, and then the gel was melted by incubating it at 37° C. for 10 minutes. It was centrifuged at 5000×G for 5 minutes, to extract DNA. The DNA was subjected to phenol-chloroform extraction and ethanol precipitation. The resulting precipitates were dissolved in a small, appropriate amount of TE.

2) Pretreatment of DNA Vector pSAKcos1 pSAKcos1 was digested with restriction enzyme BamHI (Takara Shuzo Co., Ltd., Japan), and then subjected to alkaline phosphatase (Takara Shuzo Co., Ltd., Japan) treated at 65° C. for 30 minutes. The resultant reaction solution was subjected to phenol-chloroform extraction and ethanol precipitation. The resulting precipitation was dissolved in a small amount of TE.

3) Ligation and in vitro Packaging

The genomic DNA fragment (2 μg) described in the above step 1) and pSAKcos1 (1 μg) subjected to pretreatment as above were mixed, and then ligated at 16° C. for 16 hours using DNA ligation kit Ver.2 (Takara Shuzo Co., Ltd., Japan). The resultant reaction solution was subjected to phenol-chloroform extraction and ethanol precipitation. The resulting precipitates were dissolved in 5 μl of TE. The ligation product solution was subjected to in vitro packaging using the GIGAPAK II Gold kit (manufactured by STRATAGENE corporation) to provide *Escherichia coli* transformants containing a recombinant DNA vector, 3 ml of LB medium were poured onto a plate on which colonies of *Escherichia coli* transformant had formed, and then the colonies on the plate were recovered using a cell scraper (referred to as "recovered solution 1"). The plate was washed with a further 3 ml of LB medium, and cells recovered (referred to as "recovered solution 2"). Glycerol was added to a mixture of recovered solution 1 and 2, to achieve a final concentration of 18% (referred to as *Escherichia coli* cell solution), which was kept at −80° C. as a genomic DNA library of *Penicillium citrinum* SANK13380.

Example 4

Amplification of PKS Gene Fragment by PCR Using Genomic DNA of *Penicillium citrinum* SANK13380 as a Template 1) Design and Synthesis of Primers for PCR.

Based on the amino acid sequence of a PKS gene of *Aspergillus flavus* (described in Brown, D. W., et al., Proc. Natl. Acad. Sci. USA, 93, 1418 (1996)), degenerate primers shown in SEQ ID Nos. 3 and 4 of the Sequence Listing were designed and synthesized. The synthesis was performed according to the phosphoamidite method.

SEQ ID No. 3 of the Sequence Listing:
gayacngcntgyasttc
SEQ ID No. 4 of the Sequence Listing:
tcnccnknrcwgtgncc In the nucleotide sequence of SEQ ID Nos. 3 and 4, n represents inosine (hypoxanthine), y represents t or c, s represents g or c, k represents g or t, r represents g or a, and w represents a or t.

2) Amplification of DNA Segment by PCR

50 μl of reaction solution was prepared containing the primers for PCR described in the above step 1) (each 100 pmol), genomic DNA of *Penicillium citrinum* SANK13380 obtained in Example 2 (500 ng), 0.2 mM of dCTP, 0.2 mM of dCTP, 0.2 mM of dGTP, 0.2 mM of dTTP, 50 mM of potassium chloride, 2 mM of magnesium chloride and 1.25 units of Ex. Tac DNA polymerase (Takara Shuzo Co., Ltd., Japan). The solution was subjected to a reaction cycle consisting of three consecutive steps as follows: one minute at 94° C. two minutes at 58° C. and 3 minutes at 70° C. The cycle was repeated 30 times to amplify the DNA fragment. PCR was performed using TaKaRa PCR Thermal Cycler MP TP 3000 (manufactured by Takara Shuzo Co., Ltd., Japan).

The amplified DNA fragments were subjected to agarose gel electrophoresis, and then agarose containing DNA fragments having a size of about 1.0 to 2.0 kb were recovered. DNA was recovered from the gel, and subjected to phenol-chloroform extraction and ethanol precipitation. The resulting precipitate was dissolved in a small amount of TE.

3) Ligation and Transformation

The DNA fragment obtained in step 2) was ligated to the plasmid pCR2.1 using the TA cloning system pCR 2.1 (manufactured by Invitrogen corporation), the plasmid being provided as part of the kit. The plasmid was transformed into *Escherichia coli* JM109 to provide transformants.

Several colonies were selected from the resulting transformants, and were cultured according to the method of Maniatis, et al., [described in Maniatis, T., et al., Molecular cloning, a laboratory manual, $2^{nd}$ ed., Cold Spring Harbor Laboratory, Cold Spring Harbor, N.Y. (1989)]. Namely, each of the colonies was inoculated into a 24 ml test tube containing 2 ml of LB medium, and was incubated at 37° C. for 18 hours with shaking.

A recombinant DNA vector was prepared from the culture according to the alkaline method (described in Maniatis, T., et al., supra). Namely, 1.5 ml of the culture solution was centrifuged at room temperature at 10000×G for two minutes. Cells were then recovered from the precipitate. To the cells were added 100 μl of a solution of 50 mM glucose, 25 mM Tris-hydrochloric acid, 10 mM EDTA (pH 8.0), to form a suspension. Thereto was added 200 μl of 0.2 N sodium hydroxide-1% (w/v) SDS. The suspension was stirred gently, to lyse the micro-organisms, 150 μl of 3 M potassium acetate-11.5% (w/v) acetic acid was then added to denature any protein, followed by centrifugation at room temperature at 10000×G for 10 minutes. The supernatant was recovered. The supernatant was subjected to phenol-chloroform extraction and ethanol precipitation. The resulting precipitate was dissolved in 50 μl of TE containing 40 μg/ml of ribonuclease A (manufactured by Sigma corporation).

Each of the recombinant DNA vectors was digested with restriction enzymes, and subjected to electrophoresis. The nucleotide sequences of the DNA inserts in the recombinant DNA vectors were determined using a DNA sequencer (model 377: manufactured by Perkin Elmer Japan) for all inserts having different digestion patterns on electrophoresis.

In this way a strain was identified having a recombinant DNA vector containing a PKS fragment derived from *Penicillium citrinum*.

Example 5

Genomic Southern Blotting Hybridization of *Penicillium citrinum* SANK13380

1) Electrophoresis and Transfer to Membrane

The genomic DNA (10 μg) of *Penicillium citrinum* SANK13380 obtained in Example 2 was digested with restriction enzymes EcoRI, SalI, HindIII or Sac1 (all manufactured by Takara Shuzo Co., Ltd., Japan), and then subjected to agarose gel electrophoresis. The gel was made using agarose L03 "TAKARA" (Takara Shuzo Co., Ltd., Japan). After electrophoresis, the gel was soaked in 0.25 N hydrochloric acid (manufactured by Wako Pure Chemical Industries, Ltd.), and incubated at room temperature for 10 minutes with gentle shaking. The gel was transferred to 0.4 N sodium hydroxide (manufactured by Wako Pure Chemical Industries, Ltd.), and gently incubated at room temperature for 30 minutes. Using the alkaline transfer method of Maniatis et al. (supra). DNA in the gel was transferred onto a nylon membrane Hybond™-N+ (manufactured by Amersham corporation), and fixed thereon. The membrane was washed with 2×SSC (1×SSC contains 150 mM NaCl, 15 mM sodium citrate), and then air-dried.

2) Hybridization and Detection of Signal

The membrane obtained in step 1) was hybridized with the PKS gene fragment obtained in Example 4 as a probe.

For the probe, 1 μg of the PKS gene insert fragment DNA obtained in Example 4 was labeled with a DIG DNA Labeling Kit (manufactured by Boeringer-Mannheim) and was boiled for 10 minutes and then rapidly cooled just prior to use.

The membrane described in step 1) was soaked in hybridization liquid (DIG Easy Hyb: manufactured by Boeringer-Mannheim), and then subjected to prehybridization with shaking at 20 rpm at 42° C. for 2 hours. Then, the above-mentioned labeled probe was added to the hybridization liquid, and hybridization was performed with shaking at 20 rpm at 42° C. for 18 hours using Multishaker Oven HB (manufactured by TAITEC corporation). The membrane subjected to hybridization was then subjected to three washes using 2×SSC at room temperature for 20 minutes, and two washes using 0.1×SSC at 55° C. for 30 minutes.

The washed membrane was treated with DIG Luminescent Detection Kit for Nucleic Acids (manufactured by Boeringer-Mannheim) and exposed to X ray film (Lumifilm, manufactured by Boeringer-Mannheim). Exposure was performed using Fuji medical film processor FPM 800A (manufactured by Fuji Film Corporation).

As a result, it was confirmed that the PKS gene fragment obtained in Example 4 existed on the genome of *Penicillium citrinum*.

Example 6

Screening of Genomic DNA Library of *Penicillium citrinum* SANK13380 Using PKS Gene Fragment as a Probe Cloning of a genomic DNA fragment containing a PKS gene was performed using a colony hybridization method.

1) Preparation of Membrane

The *Escherichia coli* cell solution kept as a genomic DNA library of *Penicillium citrinum* SANK13380 (described in Example 3) was diluted and spread on a LB agar medium plate, such that 5000 to 10000 colonies might grow per plate. The plate was kept at 26° C. for 18 hours, and cooled at 4° C. for one hour. Hybond™-N+ (manufactured by Amasham corporation) was placed on the plate, and brought into contact therewith for one minute. The membrane on which the colony was adhered was carefully removed from the plate. The surface which had been in contact with the colonies was turned upward and soaked in 200 ml of a solution of 1.5 M sodium chloride, 0.5 N sodium hydroxide for 7 minutes, and then soaked in 200 ml of a solution of 1.5 M sodium chloride, 0.5 M Tris hydrochloric acid, 1 mM EDTA (pH 7.5) for three minutes twice, and then washed with 400 ml of 2×SSC. The washed membrane was air-dried for 30 minutes.

2) Hybridization

The PKS gene insert DNA obtained in Example 4 (1 μpg) was used as a probe. The DNA was labeled with using a DIG DNA Labeling Kit (manufactured by Boeringer-Mannheim) and was boiled for 10 minutes and rapidly cooled just prior to use.

The membrane described in step 1) was soaked in hybridization liquid (DIG Easy Hyb: manufactured by Boeringer-Mannheim), and then subjected to a prehybridization wash at 20 rpm at 42° C. for 2 hours. Then, the above-mentioned labeled probe was added to the hybridization liquid, and hybridization was performed at 20 rpm at 42° C. for 18 hours using Multishaker Oven HB (manufactured by TAITEC corporation). The membrane subjected to hybridization was subjected to three washes using 2×SSC at room temperature for 20 minutes, and two washes using 0.1×SSC at 68° C. for 30 minutes.

The washed membrane was treated with DIG Luminescent Detection Kit for Nucleic Acids (manufactured by Boeringer-Mannheim), and exposed to X ray film (Lumifilm, manufactured by Boeringer-Mannheim). Exposure was performed using Fuji medical film processor FPM 800A (manufactured by Fuji Film Corporation).

The above steps 1) and 2) are referred to as Screening.

Colonies on the plate where the positive signal was detected at the first screening was scraped and recovered cells suspended in LB medium. Then, cells were diluted adequately and spread on a suitable plate. Subsequently, a second screening was performed to purify the positive clone.

The positive clone obtained in the present example, namely transformed *Escherichia coli*, *Escherichia coli* pML48 SANK71199 strain was deposited at the Research Institute of Life Science and Technology of the Agency of Industrial Science and Technology on Jul. 7, 1999 under the Deposit Nos FERM BP-6780, in accordance with the Budapest Treaty on the Deposition of Micro-organisms.

Example 7

Analysis of the Inserted Sequence of a Recombinant DNA Vector pML48 (1)

Culturing of *Escherichia coli* pML48 SANK71199 strain obtained in Example 6 and preparation of a recombinant DNA vector from the culture were performed in a similar manner to that described in Example 4.

The obtained DNA vector was designated as pML48. The insert of pML48, which is an ML-236B biosynthesis related genomic DNA, was digested with various restriction enzymes, and resulting fragments subcloned into pUC119 (manufactured by Takara Shizo Co., Ltd., Japan). Using the resultant subclones as probes, Southern blot hybridization was performed by a similar method to that described in Example 5. Namely, the products obtained by digesting pML48 with various restriction enzymes were subjected to electrophoresis, and the DNAs were transferred to a membrane, and subjected to hybridization. As a result, a restriction enzyme cleavage map of the inserted sequence of pML48 was made using techniques standard in the art.

The nucleotide sequence of the inserted sequence of each of the subclones was determined using DNA sequencer model 377 (manufactured by Perkin Elmer Japan Co.Ltd), followed by determination of the entire nucleotide sequence of pML48.

The inserted sequence of pML48 consisted of 34203 bases in total.

The nucleotide sequence of the inserted sequence of pML48 is described in SEQ ID Nos. 1 and 2 of the Sequence Listing. The sequences described in SEQ ID Nos. 1 and 2 of the Sequence Listing are completely complementary with each other.

Existence of structural genes on the pML48 insert sequence was analyzed using a gene searching program GRAIL (ApoCom GRAIL Toolkit; produced by Apocom Corporation) and a homology searching program BLAST (Gapped-BLAST (BLAST2): installed in WISCONSIN GCG package ver.10.0).

As a result, six different structural genes were predicted to exist in the inserted sequence of pML48, and were designated mlcA, mlcB, mlcC, mlcD, mlcE and mlcR respectively. Furthermore, it was predicted that mlcA, mlcB, mlcE and mlcR have a coding region in the nucleotide sequence of SEQ ID NO. 2 of the Sequence Listing, and mlcC and mlcD have a coding region in the nucleotide sequence of SEQ ID NO. 1 of the Sequence Listing. The relative position and length of each of the presumed structure genes of the inserted sequence were also predicted.

Figure 2:
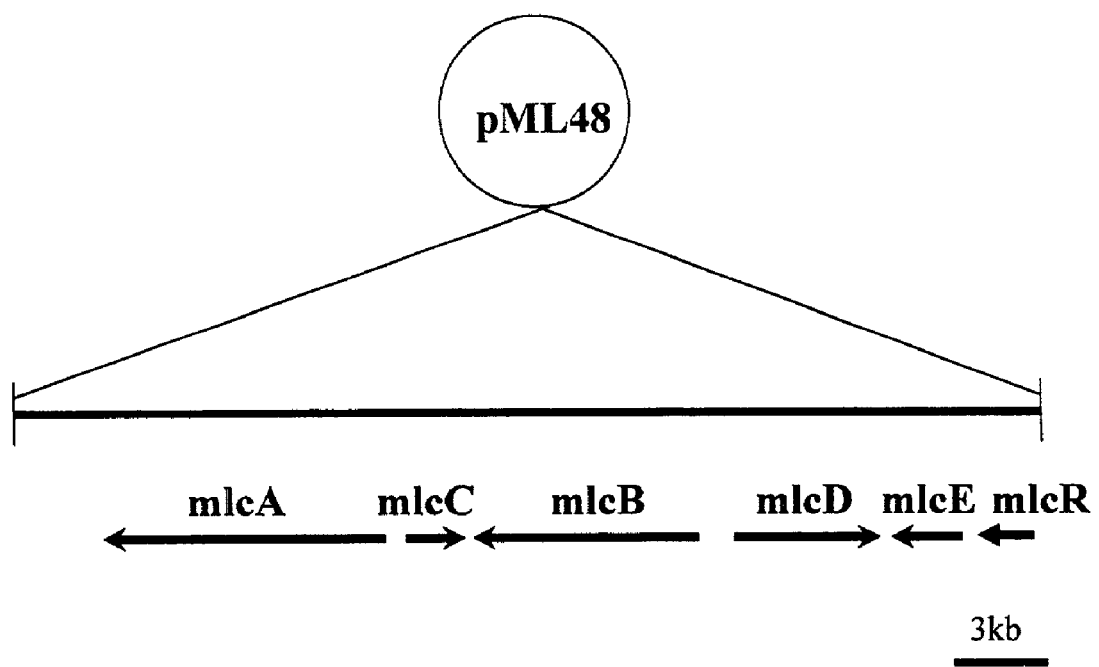
FIG. 2 is the results of structural gene analysis of the inserted sequence of pML48.

The results of the present example are shown in FIG. 2. Each arrow indicates localization., direction and relative size of each structural gene on the pML48 insert. An arrow which points to the left indicates that the coding region of a structural gene exists (mlcA, B, E or R) exists on ID SEQ NO 2. An arrow which points to the right indicates that the coding region of a structural gene (mlcC or D) exists on ID SEQ NO 1.

Example 8

Analysis of the Inserted Sequence of a Recombinant DNA Vector pML48 (2)

Analysis of expression of the structural genes whose existence was predicted in Example 7 was carried out by Northern blot hybridization and RACE. Analysis of 5'- and 3'-end regions was performed. 1) Preparation of Total RNA of *Penicillium citrinum* SANK13380

Cells from a 5 mm square in the *Penicillium citrinum* SANK13380 slant culture (described in Example 2) were inoculated into 10 ml MGB3–8 medium in a 100 ml conical flask, and incubated at 26° C. for 3 days with shaking.

Preparation of total RNA from the culture was performed with the RNeasy Plant Mini Kit (manufactured by Qiagen AG) which uses the guanidine-isothiocyanate method. Namely, the culture was centrifuged at room temperature at 5000×G for 10 minutes to recover cells. Subsequently, 2 g (wet weight) of the cells were frozen with liquid nitrogen and then crushed in a mortar to form a powder. The crushed cells were suspended in 4 ml of buffer for lysis (comprised in the kit), 450 µl of the suspension was poured into each of 10 of QIAshredder spin columns contained in the kit, and then centrifuged at room temperature at 1000×G for 10 minutes. Each of the resultant eluents was recovered and 225 µl of ethanol was added thereto, which was then added to an RNA mini spin column contained in the kit. The column was washed with buffer for washing contained in the kit, followed by elution of adsorbate in each column with 50 µl of ribonuclease free distilled water. The eluent was used as total RNA fraction.

2) Northern Blot Hybridization

An RNA sample was produced by adding 2.25 µl of an aqueous solution containing 20 µg of total RNA of *Penicillium citrinum* SANK13380 to: one µl of 10×MOPS (composition: 200 mM 3-morpholino propane sulfonic acid, 50 mM sodium acetate, 10 mM EDTA.2Na: pH 7.0; used after sterilization at 121° C. for 20 minutes in an autoclave: manufactured by Dojinkagaku Laboratory Co.Ltd.), 1.75 µl of formaldehyde and 5 µl of formamide, followed by mixing. The RNA sample was kept at 65° C. for 10 minutes, then rapidly cooled in ice water, and subjected to agarose gel electrophoresis. The gel for the electrophoresis was prepared by mixing 10 ml of 10×MOPS and one gram of Agarose L03 "TAKARA" (manufactured by Takara Shuzo Co. Ltd., Japan) with 72 ml of pyrocarbonic acid diethyl ester treatment water (manufactured by Sigma Corporation) heated to dissolve the agarose, and then cooled followed by addition of 18 ml of formaldehyde. As the sample buffer, 1×MOPS (prepared by diluting 10×MOPS with 10 times water) was used. RNA in the gel was transferred to Hybond™–N+ (manufactured by Amasham corporation) in 10×SSC.

DNA fragments a, b, c d and e, obtained by digesting the inserted sequence of pML48 with the restriction enzymes 1 and 2 shown in the following Table 1, were used as probes. Localization of each probe on the pML48 insert is shown in the upper panel of FIG. 3.

TABLE 1

Probe for Northern blot hybridization

| Probe | Restriction Enzyme 1 | Nucleotide No. of Restriction Enzyme site * | Restriction Enzyme 2 | Nucleotide No. of Restriction Enzyme site * |
|---|---|---|---|---|
| a | EcoRI | 6319 to 6324 | EcoRI | 15799 to 15804 |
| b | BamHI | 16793 to 16798 | PstI | 18164 to 18169 |
| c | KpnI | 26025 to 26030 | BamHI | 27413 to 27418 |
| d | SalI | 28691 to 28696 | SalI | 29551 to 29556 |
| e | HindIII | 33050 to 33055 | SacI | 34039 to 34044 |

* Each nucleotide No. exists on SEQ ID No. 1 of the Sequence Listing

Labeling of probes, hybridization and detection of signal were performed according to Southern blot hybridization described in Example 5.

Figure 3:
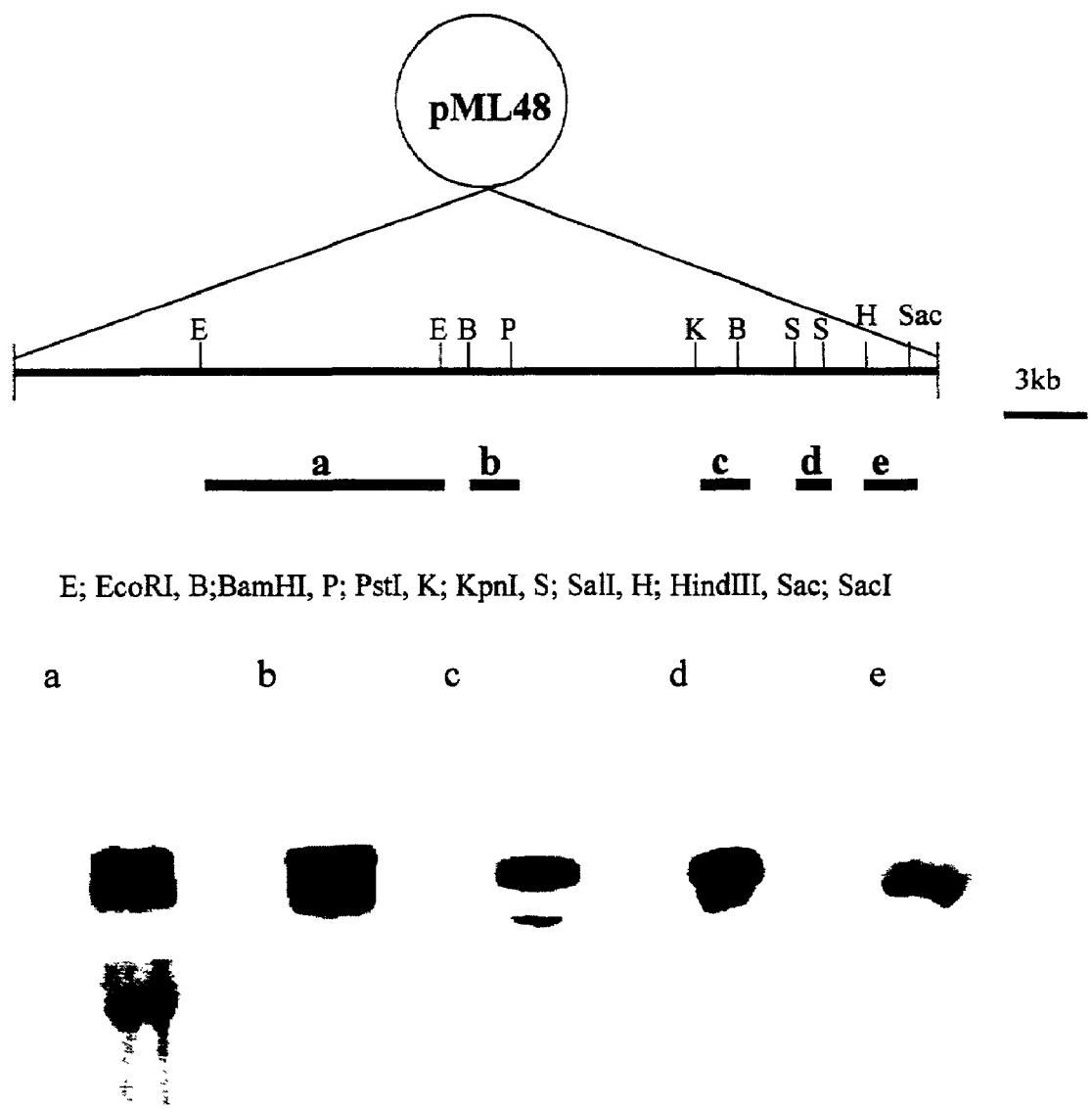
FIG. 3 shows Northern blot hybridization of the inserted sequence of pML48.

The results of the Example are shown in the lower panel of FIG. 3.

Each signal shows the existence of a transcription product homologous to the nucleotide sequence of each probe.

The results suggest that the structural genes predicted to exist in the inserted sequence of pML48 in the present example, namely mlcA mlcB, mlcC mlcD, mlcE and mlcR were transcribed in *Penicillium citrinum* SANK13380.

The position of each signal does not show the relative size of the transcription product.

3) Determination of 5'-end Sequence According to 5'RACE cDNA containing the 5'-end region of each structural gene was obtained using 5' RACE System for Rapid Amplification of cDNA ends, Version 2.0 (manufactured by GIBCO corporation).

Two kinds of antisense oligonucleotide DNAs were produced. The design was based on the nucleotide sequence presumed to be in the coding region and near the 5'-end of each structural gene in the inserted sequence of pML48, as predicted by the results of Example 7 and the item 2) of the present example.

The nucleotide sequence of the antisense oligonucleotide DNA (1) designed based on the nucleotide sequence on the 3'-end side of each structural gene is shown in Table 2. The nucleotide sequence of the antisense oligonucleotide DNA (2), designed based on the nucleotide sequence on the 5'-end side of the each structural gene was shown in Table 3.

TABLE 2

Oligonucleotide DNA (1) used for determination of 5'-end sequence according to 5'RACE

| Gene | SEQ ID No. of Sequence Listing | Nucleotide Sequence |
| --- | --- | --- |
| mlcA | SEQ ID No.5 | Gcatgttcaatttgctctc |
| mlcB | SEQ ID No.6 | Ctggatcagactttctgc |
| mlcC | SEQ ID No.7 | Gtcgcagtagcatgggcc |
| mlcD | SEQ ID No.8 | Gtcagagtgatgctcttctc |
| mlcE | SEQ ID No.9 | Gttgagaggattgtgagggc |
| mlcR | SEQ ID No.10 | Ttgcttgtgttggattgtc |

TABLE 3

Oligonucleotide DNA (2) used for determination of 5'-end sequence according to 5'RACE

| Gene | SEQ ID No. of Sequence Listing | Nucleotide Sequence |
| --- | --- | --- |
| mlcA | SEQ ID No.11 | Catggtactctcgcccgttc |
| mlcB | SEQ ID No.12 | Ctccccagtacgtaagctc |
| mlcC | SEQ ID No.13 | Ccataatgagtgtgactgttc |
| mlcD | SEQ ID No.14 | Gaacatctgcatcccgtc |
| mlcE | SEQ ID No.15 | Ggaaggcaaagaaagtgtac |
| mlcR | SEQ ID No.16 | Agattcattgctgttggcatc |

The first strand of cDNA was synthesized according to a reverse transcription reaction using the oligonucleotide DNA (1) as a primer, and total RNA of *Penicillium citrinum* SANK13380 as a template. Namely, 24 μl of the reaction mixture comprising one μg of total RNA, 2.5 pmol of oligonucleotide DNA (1) and one μl of SUPER SCRIPTTM II reverse transcriptase (contained in the kit) was incubated at 16° C. for one hour, and the reaction product was added to GLASSMAX spin cartridge contained in the kit, to purify the first strand of cDNA.

A poly C chain was added to the 3'-end of the cDNA first strand using terminal deoxyribonucleotidyl transferase contained in the kit.

50 μl of the reaction mixture comprising the first strand of cDNA to which the 3'-end poly C chain had been added, was mixed with 40 pmol of oligonucleotide DNA (2) and 40 pmol of Abriged Anchor Primer (contained in the kit), followed by incubation at 94° C. for two minutes. The incubation cycle of 30 seconds at 94° C., 30 seconds at 55° C. and two minutes at 72° C. was then repeated 35 times, followed by incubation at 72° C. for five minutes and at 4° C. for 18 hours. The resulting product was subjected to agarose gel electrophoresis, and DNA was recovered from the gel. The product was purified by phenol-chloroform extraction and ethanol precipitation, and cloned in the similar manner to a method described in Example 4 using pCR 2.1.

The operation described above is 5'-RACE.

The nucleotide sequence of cDNA fragment containing 5'-end was determined, and position of transcription initiation point and translation initiation codon were predicted.

Table 4 shows the SEQ ID No. in which the nucleotide sequence of the 5'-end cDNA fragment corresponding to each structural gene obtained by 5' RACE was described. Table 5 shows the SEQ ID No. in which the transcription initiation point and translation initiation point of each structural gene exist, and the position of the transcription initiation point and translation initiation point.

TABLE 4

SEQ ID Nos in which nucleotide sequence of 5'-end cDNA fragment is shown

| Gene | SEQ ID NO of SEQUENCE LISTING |
| --- | --- |
| mlcA | SEQ ID No. 17 |
| mlcB | SEQ ID No. 18 |
| mlcC | SEQ ID No. 19 |
| mlcD | SEQ ID No. 20 |
| mlcE | SEQ ID No. 21 |
| mlcR | SEQ ID No. 22 |

TABLE 5

Position of transcription initiation point and translation initiation point of each gene

| | | Nucleotide Number in SEQ ID NO 1 or SEQ ID NO 2 | |
| --- | --- | --- | --- |
| Gene No. | SEQ ID NO where Translation initiation Codon exists | Transcription Initiation Point | Translation initiation codon |
| mlcA | SEQ ID No. 2 | 22913 | 23045 to 23047 |
| mlcB | SEQ ID No. 2 | 11689 | 11748 to 11750 |
| mlcC | SEQ ID No. 1 | 11631 | 11796 to 11798 |
| mlcD | SEQ ID No. 1 | 24066 | 24321 to 24323 |
| mlcE | SEQ ID No. 2 | 3399 | 3545 to 3547 |
| mlcR | SEQ ID No. 2 | 365 | 400 to 402 |

\* nucleotide sequence shown in SEQ ID No. 1 and 2 of Sequence Listing are completely complementary with each other.

4) Determination of 3'-end Sequence According to 3' RACE cDNA containing the 3'-end region of each structural gene was obtained using the Ready To Go: T-Primed First-Strand kit (manufactured by Pharmacia corporation).

One kind of sense oligonucleotide DNA (3) presumed to be in coding region and near the 3'-end in each structural gene in the inserted sequence of pML48 was produced, predicted from the results of Example 7 and the item 2) of the present example.

The nucleotide sequence of the oligonucleotide DNA (3) produced for each structural gene is shown in Table 6.

TABLE 6

Oligonucleotide DNA (3) used for determination of 3'-end sequence according to 3'RACE

| Gene | SEQ ID No. of Sequence Listing | Nucleotide Sequence |
|---|---|---|
| mlcA | SEQ ID No.23 | Atcataccatcttcaacaac |
| mlcB | SEQ ID No.24 | Gctagaataggttacaagcc |
| mlcC | SEQ ID No.25 | Acattgccaggcacccagac |
| mlcD | SEQ ID No.26 | Caacgcccaagctgccaatc |
| mlcE | SEQ ID No.27 | Gtcttttcctactatctacc |
| mlcR | SEQ ID No.28 | Ctttcccagctgctactatc |

The first strand of cDNA was synthesized by a reverse transcription reaction using the NotI-d(T)18 primer (contained in the kit), and total RNA of *Penicillium citrinum* SANK13380 (one μg) as a template.

100 μl of the reaction mixture comprising the first strand of cDNA, 40 pmol of oligonucleotide DNA (3) and NotI-d (T) 18 primer (contained in the kit) was kept at 94° C. for two minutes. An incubation cycle of 30 seconds at 94° C., 30 seconds at 55° C. and two minutes at 72° C. was repeated 35 times, followed by incubation at 72° C. for five minutes and at 4° C. for 18 hours. The resulting product was subjected to agarose gel electrophoresis, and then DNA was recovered from the gel. The product was purified by phenol-chloroform extraction and ethanol precipitation, and cloned in the similar manner to a method described in Example 4 using pCR 2.1.

The operation described above is 3'-RACE.

The nucleotide sequence of cDNA at the 3'-end was determined, and the position of the translation termination codon was predicted.

Table 7 shows the SEQ ID No. of the Sequence Listing in which the nucleotide sequence of the 3'-end cDNA fragment corresponding to each structural gene obtained by 3' RACE is described. Table 8 shows the translation termination codon and position of the codon based on SEQ ID Nos. 1 and 2 of Sequence Listing.

TABLE 7

SEQ ID Nos in which nucleotide sequence of 3'-end cDNA fragment

| Gene | SEQ ID No. of SEQUENCE LISTING |
|---|---|
| mlcA | SEQ ID No. 29 |
| mlcB | SEQ ID No. 30 |
| mlcC | SEQ ID No. 31 |
| mlcD | SEQ ID No. 32 |
| mlcE | SEQ ID No. 33 |
| mlcR | SEQ ID No. 34 |

TABLE 8

Translation termination codon and position of the translation termination codon of each structural gene

| Gene | Translation termination codon | SEQ ID NO where Translation termination Codon exists | Nucleotide No. of translation termination codon in SEQ ID NO 1 or SEQ ID NO 2 |
|---|---|---|---|
| mlcA | tag | SEQ ID No. 2 | 32723 to 32725 |
| mlcB | taa | SEQ ID No. 2 | 19840 to 19842 |
| mlcC | taa | SEQ ID No. 1 | 13479 to 13481 |
| mlcD | tga | SEQ ID No. 1 | 27890 to 27892 |
| mlcE | tga | SEQ ID No. 2 | 5730 to 5732 |
| mlcR | tag | SEQ ID No. 2 | 1915 to 1917 |

* nucleotide sequence shown in SEQ ID No. 1 and 2 of Sequence Listing are completely complementary with each other.

Table 9 shows the C-terminal amino acid residue of the polypeptide predicted to be encoded by each structural gene, the nucleotide sequence of the trinucleotide encoding the amino acid residue and the position of the trinucleotide.

TABLE 9

C-terminal amino acid residue of the polypeptide encoded by each structural gene

| Gene | C-terminal amino acid residue | Nucleotide sequence of tri-nucleotide encoding amino acid | SEQ ID where tri-nucleotide exists | Nucleotide No. of tri-nucleotide in SEQ ID 1 or 2 |
|---|---|---|---|---|
| mlcA | alanine | gcc | SEQ ID No. 2 | 32720 to 32722 |
| mlcB | serine | agt | SEQ ID No. 2 | 19837 to 19839 |
| mlcC | cystein | tgc | SEQ ID No. 1 | 13476 to 13478 |
| mlcD | arginine | cgc | SEQ ID No. 1 | 27887 to 27889 |
| mlcE | alanine | gct | SEQ ID No. 2 | 5727 to 5729 |
| mlcR | alanine | gct | SEQ ID No. 2 | 1912 to 1914 |

* the nucleotide sequence shown in SEQ ID No. 1 and 2 of Sequence Listing are completely complementary with each other.

Table 10 summarizes the sequence complementary, to the translation termination codon shown in Table 8, the SEQ ID where the complementary sequence exists and the position of the complementary sequence

TABLE 10

Sequence complementary to translation termination codon of each structural gene

| Gene | sequence complementary to translation termination codon | SEQ ID NO where the complementary sequence exists | Nucleotide No. of the complementary sequence in SEQ ID NO 1 or SEQ ID NO 2 |
|---|---|---|---|
| mlcA | cta | SEQ ID No. 1 | 1479 to 1481 |
| mlcB | tta | SEQ ID No. 1 | 14362 to 14364 |
| mlcC | tta | SEQ ID No. 2 | 20723 to 20725 |
| mlcD | tca | SEQ ID No. 2 | 6312 to 6314 |
| mlcE | tca | SEQ ID No. 1 | 28472 to 28474 |
| mlcR | cta | SEQ ID No. 1 | 32287 to 32289 |

* the nucleotide sequence shown in SEQ ID No. 1 and 2 of Sequence Listing are completely complementary with each other.

As described above, the position of each structural gene, the direction thereof and position thereof were ascertained. Based on the above information, the transcription product and translation product of each structural gene can be obtained.

Example 9

Obtaining cDNA Corresponding to the Structural Gene mlcE

1) Preparation of Total RNA

Total RNA of *Penicillium citrinum* was prepared according to the method of Example 8.

2) Design of Primer

In order to obtain a full length cDNA corresponding to structural gene mlcE determined in Example 8, the following primers were designed and synthesized:
sense primer 5'-gttaacatgtcagaacctctaccccc-3'(See SEQ ID 35 of Sequence Listing); and
antisense primer 5'-aatatttcaagcatcagtctcaggcac-3': (See SEQ ID 36 of Sequence Listing).

The primers are derived from the sequence on the 5'-end upstream region of structural gene mlcE and from the sequence at the 3'-end downstream region respectively. Synthesis was performed according to the phosphoamidite method.

3) RT-PCR

In order to obtain a full-length cDNA encoding the gene product of mlcE, the Takara RNA LA PCR kit (AMV) Ver. 1.1 was used.

Specifically, 20 µl of a reaction mixture comprising one µg of total RNA, 2.5 pmol of Random 9 mers primer (contained in the kit), and one µl of reverse transcription enzyme (contained in the kit) was incubated at 42° C. for 30 minutes to produce the first strand of cDNA. The reverse transcription enzyme was then deactivated by heating at 99° C. for five minutes.

100 µl of a second reaction mixture comprising the total amount of the reaction mixture of the first strand of cDNA (above), 40 pmol of sense primer and 40 pmol of antisense primer was incubated at 94° C. for two minutes. An incubation cycle of 30 seconds at 94° C. 30 seconds at 60° C. and two minutes at 72° C. was repeated 30 times, followed by incubation at 72° C. for five minutes and at 4° C. for 18 hours. The resulting product was subjected to agarose gel electrophoresis, and DNA was recovered from the gel. The product was purified by phenol-chloroform extraction and ethanol precipitation, and used to transform *Escherichia coli* competent cell JM109 strain (manufactured by Takara Shuzo Co., Ltd., Japan) in the similar manner to a method described in Example 4 using pCR 2.1. A strain carrying a plasmid having the DNA fragment was selected from the transformed *Escherichia coli*, and the plasmid carried by the strain was designated as pCRexpE.

The nucleotide sequence of the inserted DNA of the resulting recombinant DNA vector pCRexpE was determined. The inserted DNA contained full-length cDNA corresponding to structural gene mlcE. The nucleotide sequence thereof and an amino acid sequence of the peptide deduced from the nucleotide sequence are shown in SEQ ID NO.37 and/or SEQ ID NO 38 of the Sequence Listing.

The nearest known sequence for mlc E (polypeptide) was ORF10 on the gene cluster related to biosynthesis of lovastatin, with 70% identity.

Example 10

Construction of the Expression Vector pSAK 700 cDNA expression vector pSAK700 was constructed using the vector pSAK333 and pSAK360 described in Example 1. pSAK333 was digested with both restriction enzymes BamH I and Hind III (manufactured by Takara Shuzo Co., Ltd., Japan), and then subjected to agarose gel electrophoresis. A 4.1 kb fragment was recovered from the gel, and the end of the DNA fragment was blunt-ended with T4-DNA polymerase (manufactured by Takara Shuzo Co., Ltd., Japan).

An EcoRI-NotI-BamHI adapter (manufactured by Takara Shuzo Co., Ltd., Japan) was linked to the above-mentioned DNA fragment using DNA ligation kit Ver.2 (manufactured by Takara Shuzo Co., Ltd., Japan). *Escherichia coli* competent cell JM109 strain (manufactured by Takara Shuzo Co., Ltd., Japan) was transformed with the ligated DNA. A strain carrying the plasmid having the adapter was selected from the transformed *Escherichia coli*, and the plasmid carried by the strain was designated as pSAK410.

pSAK360 was digested with both restriction enzymes Pvu II and Ssp I, and subjected to electrophoresis. A DNA fragment (about 2.9 kb) containing the promoter and terminator of 3-phosphoglycerate kinase (hereinafter referred to as "pgk") gene and HPT originating from *Escherichia coli* was recovered from the gel.

The recovered above-mentioned DNA fragment was linked to the Pvu II site of pSAK410 using DNA ligation kit Ver.2 (manufactured by Takara Shuzo Co., Ltd., Japan). *Escherichia coli* competent cell JM109 strain was transformed with the ligated DNA. A strain carrying the plasmid having the DNA fragment was selected from the transformed *Escherichia coli*, and the plasmid carried by the strain was designated as pSAK700.

Figure 4:
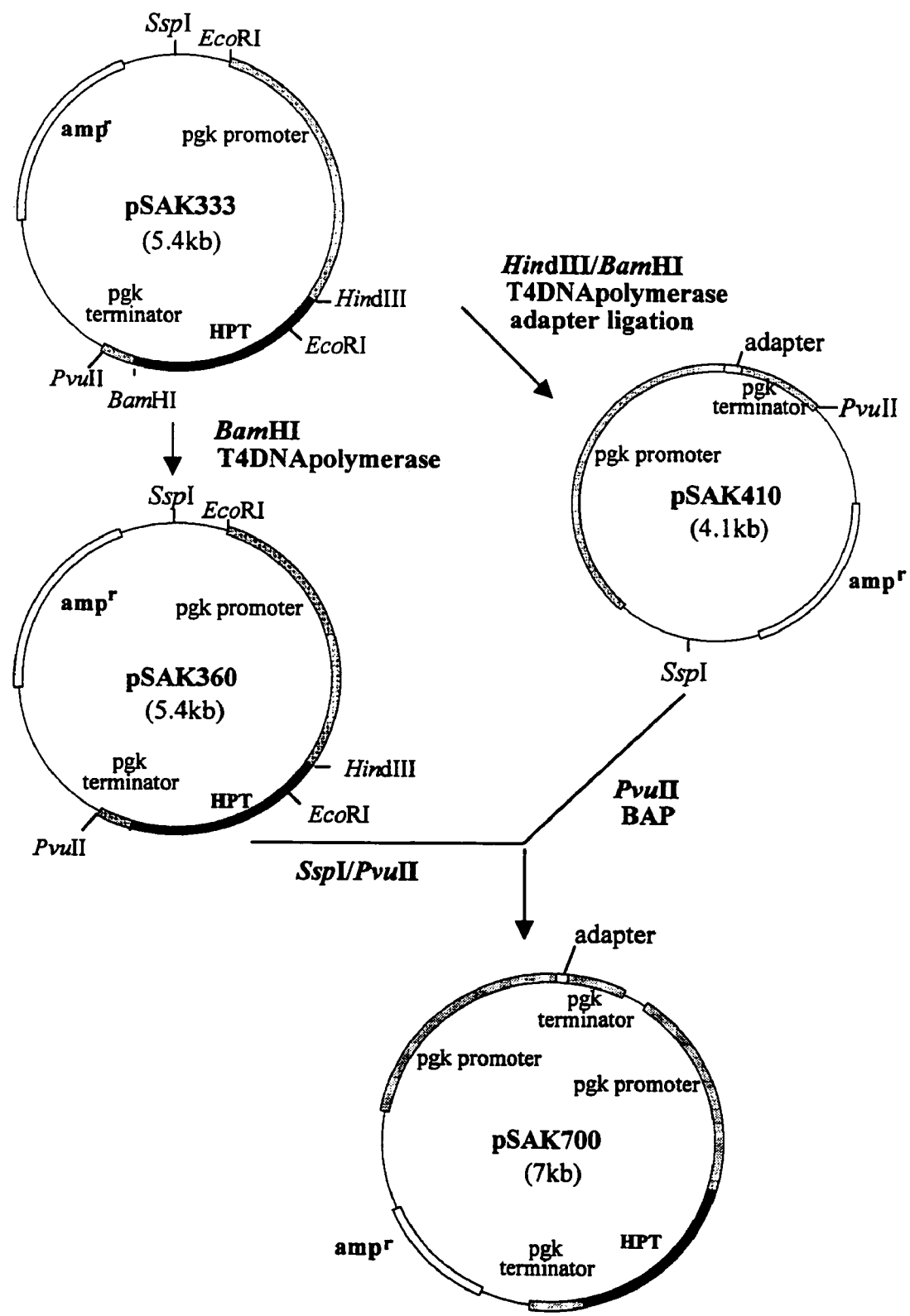
FIG. 4 is a diagram depicting the construction of cDNA expression vector pSAK700.

The construction of pSAK700 is shown in FIG. 4.

pSAK 700 has one restriction enzyme site for each of the enzymes BamHI and NotI, pSAK700 also has an ampicillin resistant gene (hereinafter referred to as "sAmpr") and hygromycin resistance gene HTP as a selection marker. In the following examples when *Escherichia coli* is used as a host selection of cells transformed by pSAK700 or by pSAK700 comprising a foreign DNA insert was performed by adding 40 µg/ml of ampicillin to the relevant medium. When *Penicillium citrinum* SANK13380 is used as a host selection of cells transformed by pSAK700 or by pSAK700 comprising a foreign DNA insert was performed by adding 200 µg/ml of hygromycin to the relevant medium.

Example 11

Construction of cDNA Expression Vector pSAKexpE

Recombinant DNA vector pCRexpE obtained in Example 9 was reacted at 37° C. for 2 hours in the presence of the restriction enzymes HpaI and SspI (manufactured by Takara Shuzo Co., Ltd., Japan), and the reaction product was subjected to agarose gel electrophoresis. A band containing a full-length cDNA of mlcE around 1.7 kb was recovered from the gel.

After reacting pSAK700 with the restriction enzyme Not1 (manufactured by Takara Shuzo Co. Ltd., Japan) at 37° C. for one hour, the end of the vector was blunt-ended with T4 DNA polymerase (Takara Shuzo Co., Ltd., Japan) at 37° C. for 5 minutes. Then, the vector was subjected to phenol chloroform extraction and ethanol precipitation. The precipitate DNA was dissolved in a small amount of TE. Alkaline phosphatase was added thereto and was incubated at 65° C. for 30 minutes, pSAK700, prepared as described above, was ligated to 1.7 kb of DNA fragment obtained in the step 1) using DNA ligation kit Ver.2 (manufactured by Takara Shuzo Co., Ltd., Japan). *Escherichia coli* competent cell JM109 strain was transformed using the ligated DNA. An *Escherichia coli* strain transformed by cDNA expression vector was obtained.

The transformed *Escherichia coli*, termed *Escherichia coli* pSAKexpE SANK 72499, obtained in the present example was deposited at the Research Institute of Life Science and Technology of the Agency of Industrial Science and Technology on Jan. 25, 2000 under the Deposit Nos. FERM BP-7005, in accordance with the Budapest Treaty on the Deposition of Micro-organisms.

Example 12

Obtaining cDNA Corresponding to the Structural Gene mlcR

1) Preparation of Total RNA

Total RNA of *Penicillium citrinum* was prepared according to the method of Example 8.

2) Design of Primer

In order to obtain a full length cDNA corresponding to the structural gene mlcR determined in Example 8, the following primers were designed and synthesized:

sense primer: 5'-ggatccatgtccctgccgcatgcaacgattc-3': (See SEQ ID 39 of Sequence Listing): and antisense primer 5'-ggatccctaagcaatattgtgtttcttcgc-3': (See SEQ ID 40 of Sequence Listing).

The primers were designed from the sequence on 5'-end upstream region of structural gene mlcR and from the sequence at the 3'-end downstream region, respectively. Synthesis was performed according to the phosphoamidite method.

3) RT-PCR

In order to obtain a full-length cDNA encoding the gene product of mlcR, a Takara RNA LA PCR kit (AMV) Ver. 1.1 was used.

Specifically, 20 μl of a reaction mixture comprising one pg of total RNA, 2.5 pmol of Random 9 mers primer (contained in the kit), and one μl of reverse transcription enzyme (contained in the kit) was incubated at 42° C. for 30 minutes to produce the first strand of cDNA. The reverse transcription enzyme was then deactivated by heating at 99° C. for five minutes.

100 μl of a second reaction mixture comprising the total amount of the reaction mixture of the first strand of cDNA (above), 40 pmol of sense primer and 40 pmol of antisense primer was incubated at 94° C. for two minutes. An incubation cycle of 30 seconds at 94° C., 30 seconds at 60° C. and two minutes at 72° C. was repeated 30 times, followed by incubation at 72° C. for five minutes and at 4° C. for 18 hours. The resulting product was subjected to agarose gel electrophoresis, and DNA was recovered from the gel. The product was purified by phenol-chloroform extraction and ethanol precipitation, and used to transform *Escherichia coli* competent cell JM109 strain (manufactured by Takara Shuzo Co., Ltd., Japan) in the similar manner to a method described in Example 4 using pCR 2.1. A strain carrying a plasmid having the DNA fragment was selected from the transformed *Escherichia coli*, and the plasmid carried by the strain was designated as pCRexpR.

The nucleotide sequence of the inserted DNA of the resulting recombinant DNA vector pCRexpR was determined. The inserted DNA contained full-length cDNA corresponding to structural gene mlcR. The nucleotide sequence thereof and an amino acid sequence of the peptide deduced from the nucleotide sequence are shown in SEQ ID NO 41 and/or SEQ ID NO 42 of the Sequence Listing.

The nearest known sequence for mlc R (polypeptide) was lovE on the gene cluster related to biosynthesis of lovastatin, with 34% identity.

Example 13

Construction of cDNA Expression Vector pSAKexpR

Recombinant DNA vector pCRexpR obtained in Example 12 was reacted at 37° C. for 2 hours in the presence of restriction enzyme BamHI (manufactured by Takara Shuzo Co., Ltd., Japan), and the reaction product was subjected to agarose gel electrophoresis. A band containing a full-length cDNA of mlcR around 1.4 kb was recovered from the gel.

After reacting pSAK700 with the restriction enzyme BamHI (manufactured by Takara Shuzo Co., Ltd., Japan) at 37° C. for one hour, alkaline phosphatase (manufactured by Takara Shuzo Co., Ltd., Japan) was added and reacted at 65° C. for 30 minutes, pSAK700 digested with BamHI as described above was ligated to 1.4 kb of DNA fragment obtained in the step 1) using DNA ligation kit Ver.2 (manufactured by Takara Shuzo Co., Ltd., Japan). *Escherichia coli* competent cell JM109 strain was transformed with the ligated DNA. An *Escherichia coli* strain transformed by cDNA expression vector was obtained.

The transformed *Escherichia coli*, termed *Escherichia coli* pSAKexpR SANK 72599, obtained in the present example was deposited at the Research Institute of Life Science and Technology of the Agency of Industrial Science and Technology on Jan. 25, 2000 under the Deposit Nos. FERM BP-7006, in accordance with the Budapest Treaty on the Deposition of Micro-organisms.

Example 14

Transformation of ML-236B Producing Micro-organisms

1) Preparation of Protoplasts

Spores from a slant of a culture of *Penicillium citrinum* SANK 13380 strain were inoculated on a PGA agar medium, then incubated at 26° C. for 14 days. The spores of *Penicillium citrinum* SANK 13380 strain were then recovered from the culture, and $1 \times 10^8$ of the spore were inoculated into 80 ml of YPL-20 culture medium, incubated at 26° C. for one day. After confirming germination of the spores by observation under a microscope, the germinating spores were centrifuged at room temperature at 5000×G for ten minutes, and recovered as a precipitate.

The spores were washed with sterilized water three times, to form protoplasts. Namely, 200 mg of zymolyase 20 T (manufactured by Seikagaku Kogyo corporation) and 100 mg of chitinase (manufactured by Sigma corporation) were dissolved in 10 ml of 0.55 M magnesium chloride solution, and centrifuged at room temperature at 5000×G for 10 minutes. The resultant supernatant was used as an enzyme solution, 20 ml of the enzyme solution and 0.5 g (wet weight) of germinating spores were put into 100 ml conical flask and incubated with gently shaking at 30° C. for 60 minutes. After confirming that the germinating spores became protoplasts using a microscope, the reaction solution was filtered through 3G-2 glass filter (manufactured by HARIO corporation). The filtrate was centrifuged at room temperature at 1000×G for 10 minutes, and then the protoplasts were recovered as a precipitate.

2) Transformation

The protoplasts obtained in step 1) were washed twice with 30 ml of 0.55 M magnesium chloride and once with 30 ml of a solution consisting of 0.55 M magnesium chloride, 50 mM calcium chloride and 10 mM 3-morpholino propane sulfonate (pH 6.3 or lower, hereinafter referred to as MCM solution). Protoplasts were then suspended in 100 μl of a solution of 4% (w/v) polyethylene glycol 8000, 10 mM 3-morpholino propane sulfonate, 0.0025% (w/v) heparin (manufactured by sigma corporation), 50 mM magnesium chloride (pH 6.3 or less, hereinafter referred to as "transformation solution").

96 μl of transformation solution containing about 5×10$^7$ protoplasts and 10 μl of TE containing 120 μg of pSAKexpE, or pSAKexpR, were mixed, and allowed to stand on ice for 30 minutes. Thereto was added 1.2 ml of a solution of 20% (w/v) polyethylene glycol, 50 mM of magnesium chloride, 10 mM of 3-morpholino propane sulfonic acid (pH 6.3). The liquid was then gently pipetted and then allowed to stand at room temperature for 20 minutes. Thereto was added 10 ml of MCM solution, followed by gentle mixing, and centrifugation at room temperature at 1000×G for 10 minutes. The transformed protoplasts were recovered from the precipitate.

3) Regeneration of the Cell Wall of Transformed Protoplasts

The transformed protoplasts obtained in step 2) were suspended in 5 ml of liquid VGS middle layer agar medium, and layered on 10 ml of a solidified VGS lower agar medium plate. The plate was incubated at 26° C. for one day, after which 10 ml of liquid VGS upper agar medium containing 5 mg hygromycin B per plate (final concentration of hygromycin of 200 μg/ml) was layered on top. After incubation at 26° C. for 14 days, both strains (i.e. those strains derived from protoplasts transformed with pSAKexpE, or pSAKexpR ) were subcultured on PGA agar medium containing 200 μg/ml of hygromycin B, and subcultured on a slant prepared with PGA agar medium, incubated at 26° C. for 14 days.

The slants were reserved at 4° C.

TEST Example 1

Comparison of ML-236B Biosynthesis Ability in Transformed and Original Strains

The transformed strains obtained in Example 14 and *Penicillium citrinum* SANK13380 were cultured and the amount of ML-236B in each culture was measured.

A 5 mm square inoculum of spores was cultured from the slants in which the transformed strains were cultured, as described in Example 14, and from the slant described in Example 2, relating to *Penicillium citrinum* SANK 13380. Cells were inoculated in 10 ml of MBG3–8 medium in a 100 ml conical flask, then incubated at 24° C. for two days with shaking, followed by the addition of 3.5 ml of 50% (w/v) glycerin solution. Then, culturing was continued at 24° C. for 10 days with shaking.

To 10 ml of the culture was added 50 ml of 0.2 N sodium hydroxide, followed by incubation at 26° C. for one hour with shaking. The culture was centrifuged at room temperature at 3000×G for two minutes. One ml of the supernatant was recovered, mixed with 9 ml of 75% methanol, and subjected to HPLC.

SSC-ODS-262 (having a diameter of 6 mm, length of 100 mm, manufactured by Senshu Kagaku Co.Ltd.) was used as HPLC column, and 75% (v/v) methanol-0.1% (v/v) triethylamine-0.1% (v/v) acetic acid was used as the mobile phase. Elution was carried out at room temperature at a flow rate of 2 ml/minute. Under these conditions. ML-236B was eluted 4 minutes after addition to the column. Detection was performed with a UV detector at absorption wavelength of 236 nm.

ML-236B biosynthesis ability was increased in three strains among the eight pSAKexpE transformed strains. ML-236B biosynthesis ability of these strains was 10% higher on average compared with the original strain. ML-236B biosynthesis ability of these three strains was also maintained stably after subculture, such as monospore treatment or the like. These results indicate that the insert of pSAKexpE is an ML-236B biosynthesis accelerating cDNA.

ML-236B biosynthesis ability was increased in five strains among the pSAKexpR transformed strains. ML-236B biosynthesis ability of these strains was 15% higher on average compared with the original strain. ML-236B biosynthesis ability of these five strains was also maintained stably after subculture such as monospore treatment or the like. These results indicate that the insert of pSAKexpR is an ML-236B biosynthesis accelerating cDNA.

Thus, ML-236B biosynthesis accelerating cDNA obtained from an ML-236B producing micro-organism according to the present invention accelerates ML-236B biosynthesis in the ML-236B producing micro-organism when introduced in the ML-236B producing micro-organism.

Example 15

Determination of the Sequence of cDNAs Corresponding to the Structural Genes mlc A–D The sequence of the cDNA corresponding to the structural gene mlc A was determined.

The first strand cDNA was synthesized with TAKARA LA PCR kit ver1.1 (Takara Shuzo Co., Ltd.). Several PCRs were carried out for amplification of the full or partial region of the cDNA using the first strand cDNA as a template and several distinct pairs of oligonucleotides as primers.

The cycle of 30 seconds at 94° C. 30 seconds at 60° C. and five minutes at 72° C. was repeated 30 times using The Big Dye Primer/Terminator Cycle Sequencing Kit and The ABI Prism 377 sequence (PE Applied Biosystems).

The product of each reaction was inserted into plasmid pCR2.1 individually.

*Escherichia coli* transformants of each recombinant plasmid were obtained.

The nucleotide sequences of each insert of the recombinant plasmids obtained from said transformants were determined.

The sequences of exons and introns were determined on the basis of a comparison between the nucleotide sequence of several RT-PCR products mentioned above and that of the structural gene mlc A.

Then, the sequence of cDNA corresponding to the structural gene mlc A was determined (SEQ ID NO 43). The corresponding amino acid sequence of polypeptide encoded by said cDNA was predicted (SEQ ID NO 44) and a function of the polypeptide was assumed on the basis of a homology search using the amino acid sequence.

The nearest known sequence for mlc A (polypeptide) was LNKS(lovB) on the gene cluster related to biosynthesis of lovastatin, with 60% identity.

In a simlar way, the sequence of cDNA corresponding to the structural gene mlc B was determined (SEQ ID NO 45). The corresponding amino acid sequence of polypeptide encoded by said cDNA was predicted (SEQ ID NO 46) and a function of the polypeptide was assumed on the basis of a homology search using the amino acid sequence.

The nearest known sequence for mlc B (polypeptide) was LDKS(lovF) on the gene cluster related to biosynthesis of lovastatin, with 61% identity.

Similarly, the sequence of cDNA corresponding to the structural gene mlc C was determined (SEQ ID NO 47). The corresponding amino acid sequence of polypeptide encoded by said cDNA was predicted (SEQ ID NO 48) and a function of the polypeptide was assumed on the basis of a homology search using the amino acid sequence.

The nearest known sequence for mlc C (polypeptide) was lovA on the gene cluster related to biosynthesis of lovastatin, with 72% identity.

Furthermore, the sequence of cDNA corresponding to the structural gene mlc D was determined (SEQ ID NO 49). The corresponding amino acid sequence of polypeptide encoded by said cDNA was predicted (SEQ ID NO 50) and a function of the polypeptide was assumed on the basis of a homology search using the amino acid sequence.

The nearest known sequence for mlc D (polypeptide) was ORF8 on the gene cluster related to biosynthesis of lovastatin, with 63% identity.

the positions of exons of each structural gene on SEQ ID NO 1 or SEQ ID NO 2 were determined as follows:

TABLE 11

The positions of exons of mlcA-D in pML48 inserts

| | SEQ ID where exon exists. | Exon Number | Nucleotide number of SEQ ID NO 1 or SEQ ID NO 2 | | |
|---|---|---|---|---|---|
| MlcA | 2 | 1 | 22913 | to | 22945 |
| | | 2 | 23003 | to | 23846 |
| | | 3 | 23634 | to | 23846 |
| | | 4 | 23918 | to | 24143 |
| | | 5 | 24221 | to | 24562 |
| | | 6 | 24627 | to | 27420 |
| | | 7 | 27479 | to | 27699 |
| | | 8 | 27761 | to | 30041 |
| | | 9 | 30112 | to | 30454 |
| | | 10 | 30514 | to | 30916 |
| | | 11 | 30972 | to | 32910 |
| MlcB | 2 | 1 | 11689 | to | 12002 |
| | | 2 | 12106 | to | 12192 |
| | | 3 | 12247 | to | 12304 |
| | | 4 | 12359 | to | 12692 |
| | | 5 | 12761 | to | 13271 |
| | | 6 | 13330 | to | 13918 |
| | | 7 | 13995 | to | 20052 |
| MlcC | 1 | 1 | 11631 | to | 12140 |
| | | 2 | 12207 | to | 12378 |
| | | 3 | 12442 | to | 13606 |
| mlcD | 1 | 1 | 24066 | to | 24185 |
| | | 2 | 24270 | to | 27463 |
| | | 3 | 27514 | to | 28130 |

Thr positions of transripitionl termination site of each structural gene on SEQ ID NO 1 or SEQ ID NO 2 were determined as follows:

TABLE 12

The positions of transcription termination site of structural genes mlc A–E and R in pML48 inserts

| Gene | SEQ ID NO where transcription termination site exists | Nucleotide number of transcription termination site in SEQ ID NO 1 or SEQ ID NO 2 |
|---|---|---|
| mlcA | SEQ ID NO 2 | 32910 |
| mlcB | SEQ ID NO 2 | 20052 |
| mlcC | SEQ ID NO 1 | 13606 |

TABLE 12-continued

The positions of transcription termination site of structural genes mlc A–E and R in pML48 inserts

| Gene | SEQ ID NO where transcription termination site exists | Nucleotide number of transcription termination site in SEQ ID NO 1 or SEQ ID NO 2 |
|---|---|---|
| mlcD | SEQ ID NO 1 | 28130 |
| mlcE | SEQ ID NO 2 | 5814 |
| mlcR | SEQ ID NO 2 | 1918 |

Example 16

Studies of Gene Disruption

The structural genes mlc A, B or D of *P. citrinum* were disrupted via site directed mutagenics using homologous recombination.

The recombinant plasmid for obtaining the structural gene mlcA-disrupted mutant of *P. citrinum* was constructed using a plasmid, pSAK333.

A 4.1-kb internal KpnI fragment of the mlcA locus on the pML48 insert was recovered, purified, blunt ended with a DNA Blunting Kit (Takara Shuzo Co., Ltd.) was ligated to PuuII-digested pSAK333. The resultant plasmid was designated as pdismlcA.

*P. citrinum* SANK13380 was transformed by pdismlcA.

Southern hybridization of genomic DNA of pdismlcA transformant was carried out to confirm the disruption of the structural gene mlcA.

The resultant mlcA-disrupted mutant did not produce ML-236B or its precursor at all.

The recombinant plasmid for obtaining the structural gene mlcB-disrupted mutant of *P. citrinum* was constructed using a plasmid, pSAK333.

1.4-Kb PsI-BamHI fragment of the mlcB locus on the pML48 insert was recovered, purified, blunt ended with a DNA Blunting Kit (Takara Shuzo Co., Ltd.) and ligated to PuuII-digested pSAK333. The resultant plasmid was designated as pdismlcB.

*P. citrinum* SANK13380 was transformed by pdismlcB.

Southern hybridization of genomic DNA of pdismlcB transformant was carried out to confirm the disruption of the structural gene mlcB.

The resultant mlcB-disrupted mutant produced not ML-236B but ML-236A, the precursor of ML-236B.

The recombinant plasmid for obtaining the structural gene mlcD-disrupted mutant of *P. citrinum* was constructed using a plasmid, pSAK333.

1.4-Kb KpnI-BamHI fragment of the mlcD locus on the pML48 insert was recovered, purified, blunt ended with a DNA Blunting Kit (Takara Shuzo Co. Ltd.) and ligated to PuuII-digested pSAK333. The resultant plasmid was designated as pdismlcD.

*P. citrinum* SANK13380 was transformed by pdismlcD.

Southern hybridization of genomic DNA of pdismlcD transformant was carried out to confirm the disruption of the structural gene mlcD.

The amount of ML-236B produced by resultant mlcD-disrupted mutant was about 30% of that of the untransformed control host.

Example 17

Functional Analysis of mlc R in pSAKexpR Transformants

Two of the pSAKexpR transformants which were obtained in Example 12, designated as TR1 and TR2 respectively, and untransformed host cells *Penicillium citrinum* SANK13380, were inoculated in MBG3–8 medium and incubated individually as described in Example 8.

Total RNA was extracted from each of the cultures described in Example 8.

RT-PCR was carried out using said total RNA as a template and a pair of oligonucleotides designed on the basis of nucleotide sequence of the structural genes mlc A, B, C D E or R as primers.

TABLE 13

Nucleotide sequences of pairs of primers for RT-PCR.

| Target T-PCR | Primer 1 | SEQ ID NO | Primer 2 | SEQ ID NO |
|---|---|---|---|---|
| mlcA | 5'-gcaagctctgctacc agcac-3' | 51 | 5'-ctaggccaacttcaga gccg-3' | 52 |
| mlcB | 5'-agtcatgcaggatct gggtc-3' | 53 | 5'-gcagacacatcggtga agtc-3' | 54 |
| mlcC | 5'-aaaccgcacctgtct attcc-3' | 55 | 5'-ctttgtggttggatgc atac-3' | 56 |
| mlcD | 5'-cgctctatcatttcg aggac-3' | 57 | 5'-tcaatagacggcatgg agac-3' | 58 |
| mlcE | 5'-atgtcagaacctcta ccccc-3' | 59 | 5'-tcaagcatcagtctca ggca-3' | 60 |
| mlcR | 5'-atgtccctgccgcat gcaac-3' | 61 | 5'-ctaagcaatattgtgt ttct-3' | 62 |

Figure 5:
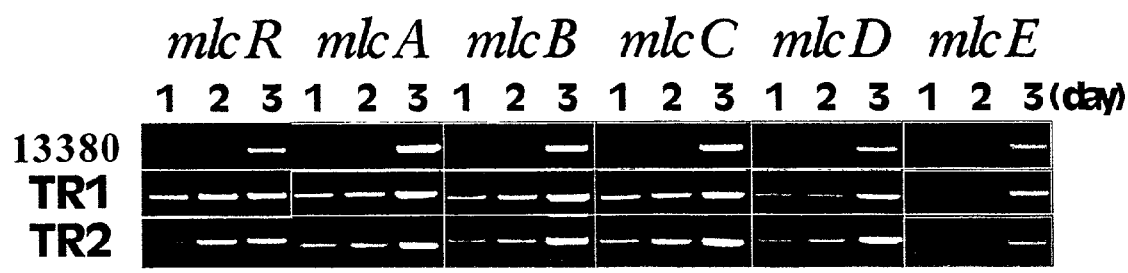
FIG. 5 shows RT-PCR analysis for transcription of mlc A–E and R in a pSAKexpR transformant.

The results of RT-PCR analysis are shown in FIG. 5 for the untransformed *Pencillium citrinum* 13380, and for the two transformants designated TR1. TR2.

The structural genes mlc A, B, C, D and R were expressed at the first, second and third day of cultivation in pSAKexpR transformants.

In contrast, all these structural genes were expressed only at the third day of cultivation in untransformed host cells.

There was no difference in the expression of the structural gene mlcE between pSAKexpR transformants and untranformed host cells.

The results suggests that a protein encoded by cDNA corresponding to a structural gene mlc R induces transcriptions of some of the other structural genes (for example, mlc A, B, C, D) located in the ML-236B biosynthesis related gene cluster.

Example 18

Functional Analysis of mlc E in pSAKexpE Transformants

A pSAKexpE transformant designated as TE1 which was obtained in Example 12, and its untransformed host cells. *Penicillium citrinum* SANK13380, were inoculated in MBG3–8 medium and incubated individually as described in Example 8.

Total RNA was extracted from each of the cultures described in Example 8.

RT-PCR was carried out using said total RNA as a template and a pair of oligonucleotides designed on the basis of nucleotide sequence of the structural genes mlc A, B, C, D, E or R as primers. Primers used for the present example were identical with those in the table of the previous Example.

Figure 6:
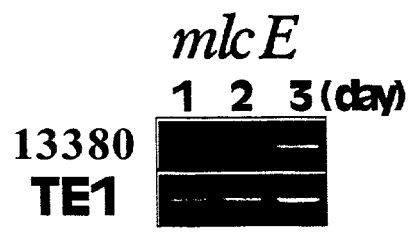
FIG. 6 shows RT-PCR analysis for transcription of mlcE in a pSAKexpE transformant.

The results of RT-PCR analysis are shown in FIG. 6 for the untransformed *Pencillium citrinum* 13380, and for a transformant designated TE1.

The structural gene mlc E was expressed at the first, second and third day of cultivation in pSAKexpE transformants.

In contrast, the structural gene mlc E was expressed only at the third day of cultivation in untransformed host cells.

On the other hand, there was no difference in the expression of the structural genes mlc A, B, C, D and R between pSAKexpE transformant and untranformed host cells (data not shown).

The results suggests that a protein encoded by cDNA corresponding to a structural gene mlc E accelerates ML-236B biosynthesis independently of the structural genes mlc A, B, C, D and R.

---

What is claimed is:

1. A method for producing ML-236B comprising:
   (a) culturing a *Penicillium* host cell having been transformed by a vector comprising a polynucleotide sequence encoding mlcR, wherein said vector does not comprise a polynucleotide sequence encoding at least one of mlcA, mlcB, mlcC, and mlcD and
   (b) recovering ML-236B from the resultant culture;
   wherein said *Penicillium* host cell is selected from the group consisting of *Penicillium citriurm*, *Penicillium brevicompactum* and *Penicillium cyclopium*;
   and wherein mlcR has the amino acid sequence of SEQ ID NO: 42, mlcA has the amino acid sequence of SEQ ID NO: 44, mlcB has the amino acid sequence of SEQ ID NO: 46, mlcC has the amino acid sequence of SEQ ID NO: 48, and mlcD has the amino acid sequence of SEQ ID NO: 50.

2. The method according to claim 1, wherein the host cell is transformed with a vector comprising a polynucleotide having the nucleotide sequence SEQ ID NO: 41.

3. A method of manufacturing pravastatin which comprises carrying out the method according to claim 1 and converting the ML-236B to pravastatin.

4. The method according to claim 1, wherein the polynucleotide encodes a protein consisting of the amino acid sequence of SEQ ID NO: 42.

5. The method according to claim 1, wherein said *Penicillium* host cell is *Penicillium citrinum*.

6. The method according to claim 1, wherein said *Penicillium* host cell is *Penicillium brevicompactum*.

7. The method according to claim 1, wherein said *Penicillium* host cell is *Penicillium cyclopium*.

8. The method according to claim 1, wherein the polynucleotide is a cDNA.

9. The method according to claim 1, wherein the polynucleotide is a genomic DNA.

10. A method for producing ML-236B comprising:
    (a) culturing a *Penicillium* host cell having been transformed by a vector comprising a polynucleotide sequence encoding mlcR, wherein said vector does not comprise a polynucleotide sequence encoding at least one of mlcA, mlcB, mlcC, and mlcD and
    (b) recovering ML236B from the resultant culture;
    wherein said *Penicillium* host cell is selected from the group consisting of *Penicillium citrinum*, *Penicillium brevicompactum* and *Penicillium cyclopium*;
    wherein mlcR has the amino acid sequence of SEQ ID NO: 42;
    and wherein said vector does not comprise at least one nucleotide sequence selected from the group consisting of SEQ ID NO: 43, SEQ ID NO: 45, SEQ ID NO: 47 and SEQ ID NO: 49.

11. The method according to claim 10, wherein said *Penicillium* host cell is *Penicillium citrinum*.

12. The method according to claim 10, wherein said *Penicillium* host cell is *Penicillium brevicompactum*.

13. The method according to claim 10, wherein said *Penicillium* host cell is *Penicillium cyclopium*.

14. A method for producing ML-236B comprising:
    (a) culturing a *Penicillium* host cell having been transformed by a vector comprising a polynucleotide sequence encoding mlcR, and
    (b) recovering ML236B from the resultant culture;
    wherein said *Penicillium* host cell is selected from the group consisting of *Penicillium citrinum*, *Penicillium brevicompactum* and *Penicillium cyclopium*;
    and wherein mlcR has the amino acid sequence of SEQ ID NO: 42, and wherein said producing occurs in the absence of a recombinant polynucleotide sequence encoding at least one of mlcA, mlcB, mlcC, and mlcD and wherein mlcA has the amino acid sequence of SEQ ID NO: 44, mlcB has the amino acid sequence of SEQ ID NO: 46, mlcC has the amino acid sequence of SEQ ID NO: 48, and mlcD has the amino acid sequence of SEQ ID NO: 50.

15. The method according to claim 14, wherein said *Penicillium* host cell is *Penicillium citrinum*.

16. The method according to claim 14, wherein said *Penicillium* host cell is *Penicillium brevicompactum*.

17. The method according to claim 14, wherein said *Penicillium* host cell is *Penicillium cyclopium*.

18. A method for producing ML-236B comprising:
    (a) culturing a *Penicillium* host cell having been transformed by pSAKexpR and
    (b) recovering ML236B from the resultant culture;
    wherein said *Penicillium* host cell is selected from the group consisting of *Penicillium citrinum*, *Penicillium brevicompactum* and *Penicillium cyclopium*.

19. A method of manufacturing pravastatin comprising carrying out the method according to claim 18 and converting the ML-236B to pravastatin.

20. The method according to claim 18, wherein said *Penicillium* host cell is *Penicillium citrinum*.

21. The method according to claim 18, wherein said *Penicillium* host cell is *Penicillium brevicompactum*.

22. The method according to claim 18, wherein said *Penicillium* host cell is *Penicillium cyclopium*.

23. A method for producing ML236B comprising:
    (a) culturing a *Penicillium* host cell having been transformed by a vector comprising a polynucleotide sequence encoding mlcR, and
    (b) recovering ML236B from the resultant culture;
    wherein said *Penicillium* host cell is selected from the group consisting of *Penicillium citrinum*, *Penicillium brevicompactum* and *Penicillium cyclopium*;
    and wherein mlcR has the amino acid sequence of SEQ ID NO: 42, and wherein said producing occurs in the absence of at least one nucleotide sequence from the group consisting of SEQ ID NO: 43, SEQ ID NO: 45, SEQ ID NO: 47 and SEQ ID NO: 49.

24. The method according to claim 23, wherein said *Penicillium* host cell is *Penicillium citrinum*.

25. The method according to claim 23, wherein said *Penicillium* host cell is *Penicillium brevicompactum*.

26. The method according to claim 23, wherein said *Penicillium* host cell is *Penicillium cyclopium*.

* * * * *

UNITED STATES PATENT AND TRADEMARK OFFICE
CERTIFICATE OF CORRECTION

PATENT NO. : 7,056,710 B2
APPLICATION NO. : 09/836705
DATED : June 6, 2006
INVENTOR(S) : Abe et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 218 days Delete the phrase "by 218 days" and insert -- by 296 days--

Signed and Sealed this

Twenty-second Day of May, 2007

JON W. DUDAS
*Director of the United States Patent and Trademark Office*